United States Patent
Schaffer et al.

(10) Patent No.: US 9,233,131 B2
(45) Date of Patent: Jan. 12, 2016

(54) MUTANT ADENO-ASSOCIATED VIRUS VIRIONS AND METHODS OF USE THEREOF

(75) Inventors: David V. Schaffer, Pleasant Hill, CA (US); Brian Kaspar, San Diego, CA (US); Narendra Maheshri, Houston, TX (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 1142 days.

(21) Appl. No.: 12/277,164

(22) Filed: Nov. 24, 2008

(65) Prior Publication Data

US 2009/0202490 A1  Aug. 13, 2009

Related U.S. Application Data

(63) Continuation-in-part of application No. 10/880,297, filed on Jun. 28, 2004.

(60) Provisional application No. 60/484,111, filed on Jun. 30, 2003.

(51) Int. Cl.

| | |
|---|---|
| C12N 15/861 | (2006.01) |
| A61K 39/12 | (2006.01) |
| A61K 35/76 | (2015.01) |
| A61K 31/7088 | (2006.01) |
| A61K 38/17 | (2006.01) |
| C07K 14/005 | (2006.01) |
| C12N 7/00 | (2006.01) |
| C12N 15/86 | (2006.01) |
| A61K 48/00 | (2006.01) |

(52) U.S. Cl.
CPC ............. *A61K 35/76* (2013.01); *A61K 31/7088* (2013.01); *A61K 38/1709* (2013.01); *C07K 14/005* (2013.01); *C12N 7/00* (2013.01); *C12N 15/86* (2013.01); *A61K 48/00* (2013.01); *C12N 2750/14121* (2013.01); *C12N 2750/14122* (2013.01); *C12N 2750/14123* (2013.01); *C12N 2750/14132* (2013.01); *C12N 2750/14143* (2013.01); *C12N 2750/14145* (2013.01); *C12N 2750/14151* (2013.01); *C12N 2750/14161* (2013.01); *C12N 2810/6027* (2013.01)

(58) Field of Classification Search
None
See application file for complete search history.

(56) References Cited

U.S. PATENT DOCUMENTS

| | | | |
|---|---|---|---|
| 6,096,548 A | 8/2000 | Stemmer | |
| 6,491,907 B1 | 12/2002 | Rabinowitz et al. | |
| 6,596,539 B1 | 7/2003 | Stemmer et al. | |
| 6,703,237 B2 | 3/2004 | Samulski et al. | |
| 6,710,036 B2 | 3/2004 | Kurtzman et al. | |
| 6,733,757 B2 | 5/2004 | Patel et al. | |
| 6,943,153 B1 | 9/2005 | Manning, Jr. et al. | |
| 6,962,815 B2 | 11/2005 | Bartlett | |
| 7,252,997 B1 | 8/2007 | Hallek et al. | |
| 7,285,381 B1 | 10/2007 | Hallek et al. | |
| 7,314,912 B1 | 1/2008 | Hallek et al. | |
| 7,556,965 B2 | 7/2009 | Hallek et al. | |
| 7,629,322 B2 | 12/2009 | Kleinschmidt et al. | |
| 7,749,492 B2 | 7/2010 | Bartlett et al. | |
| 7,968,340 B2 | 6/2011 | Hallek et al. | |
| 8,663,624 B2 | 3/2014 | Schaffer et al. | |
| 2002/0136710 A1 | 9/2002 | Samulski et al. | |
| 2002/0192823 A1 | 12/2002 | Bartlett | |
| 2003/0143732 A1 | 7/2003 | Fosnaugh et al. | |
| 2004/0180440 A1 | 9/2004 | Zolotukhin | |
| 2005/0053922 A1 | 3/2005 | Schaffer et al. | |
| 2005/0220766 A1 | 10/2005 | Amalfitano et al. | |
| 2005/0287122 A1 | 12/2005 | Bartlett et al. | |
| 2006/0292117 A1 | 12/2006 | Loiler et al. | |
| 2007/0020624 A1 | 1/2007 | Rubenfield et al. | |
| 2007/0196338 A1 | 8/2007 | Samulski et al. | |

(Continued)

FOREIGN PATENT DOCUMENTS

| | | |
|---|---|---|
| CA | 2379220 | 1/2001 |
| JP | 2002-518050 | 6/2002 |

(Continued)

OTHER PUBLICATIONS den Dunnen, et al. Mutation nomenclature extensions and suggestions to describe complex mutations: a discussion. Human Mutation (2000), 15:7-12, pp. 7-12.

Kwon, et al. Designer gene delivery vectors: molecular engineering and evolution of adeno-associated viral vectors for enhanced gene transfer. (2007), Pharmaceutical Research, vol. 25, No. 3, pp. 489-499.

(Continued)

*Primary Examiner* — Catherine S Hibbert
(74) *Attorney, Agent, or Firm* — Bozicevic Field & Francis, LLP; Paula A. Borden; Kyle A. Gurley

(57) ABSTRACT

The present invention provides mutant adeno-associated virus (AAV) that exhibit altered capsid properties, e.g., reduced binding to neutralizing antibodies in serum and/or altered heparin binding and/or altered infectivity of particular cell types. The present invention further provides libraries of mutant AAV comprising one or more mutations in a capsid gene. The present invention further provides methods of generating the mutant AAV and mutant AAV libraries, and compositions comprising the mutant AAV. The present invention further provides recombinant AAV (rAAV) virions that comprise a mutant capsid protein. The present invention further provides nucleic acids comprising nucleotide sequences that encode mutant capsid proteins, and host cells comprising the nucleic acids. The present invention further provides methods of delivering a gene product to an individual, the methods generally involving administering an effective amount of a subject rAAV virion to an individual in need thereof.

28 Claims, 55 Drawing Sheets

(56) References Cited

U.S. PATENT DOCUMENTS

| | | | |
|---|---|---|---|
| 2008/0269149 A1* | 10/2008 | Bowles et al. | 514/44 |
| 2010/0172871 A1 | 7/2010 | Flannery et al. | |
| 2012/0093772 A1 | 4/2012 | Horsager et al. | |
| 2013/0323302 A1 | 12/2013 | Constable et al. | |
| 2014/0242031 A1 | 8/2014 | Schaffer et al. | |
| 2014/0294771 A1 | 10/2014 | Schaffer et al. | |
| 2014/0364338 A1 | 12/2014 | Schaffer et al. | |

FOREIGN PATENT DOCUMENTS

| | | | | |
|---|---|---|---|---|
| WO | WO 97/38723 A1 | 10/1997 | | |
| WO | WO9967393 A2 | 12/1999 | | |
| WO | WO0028004 A1 | 5/2000 | | |
| WO | WO03023032 A2 | 3/2003 | | |
| WO | WO 03/054197 A2 | 7/2003 | | |
| WO | WO03096436 A2 | 11/2003 | | |
| WO | WO2006/066066 | * | 6/2006 | C12N 15/86 |
| WO | WO 2008/131951 A1 | 11/2008 | | |
| WO | WO 2010/093784 A2 | 8/2010 | | |

OTHER PUBLICATIONS

Girod, et al. Genetic capsid modifications allow efficient re-targeting of adeno-associated virus type 2. (1999) Nat. Med. 5:1052-1056.
Grieger, et al. Separate basic region motifs within the adeno-associated virus capsid proteins are essential for infectivity and assembly. (2006), Journal of Virology, vol. 80, No. 11, pp. 5199-5210.
Loiler, et al. Targeting recombinant adeno-associated virus vectors to enhance gene transfer to pancreatic islets and liver. (2003), Gene Ther. 10:1551-1558.
Nicklin, et al. Efficient and selective AAV2-mediated gene transfer directed to human vascular endothelial cells (2001) Mol. Ther. 4:174-181.
Ried, et al. Adeno-associated virus capsids displaying immunoglobulin-binding domains permit antibody-mediated vector retargeting to specific cell surface receptors. (2002) J. Virol. 76:4559-4566.
Kern, et al. Identification of a heparin-binding motif on adeno-associated virus type 2 capsids. Journal of Virology, (2003) vol. 77, No. 20, pp. 11072-11081.
Shi, et al. Capsid modifications overcome low heterogeneous expression of heparan sulfate proteoglycan that limits AAV2-mediated gene transfer and therapeutic efficacy in human ovarian carcinoma. (2006) Gynecol. Oncol. 103:1054-1062.
Shi and Bartlett. RGD inclusion in VP3 provides adeno-associated virus type 2 (AAV2)-based vectors with a heparan sulfate-independent cell entry mechanism. (2003) Mol. Ther. 7:515-525.
Shi, et al. Insertional mutagenesis at positions 520 and 584 of adeno-associated virus type 2 (AAV2) capsid gene and generation of AAV2 vectors with eliminated heparin-binding ability and introduced novel tropism. (2006) Hum. Gene Ther. 17:353-361.
Sonntag, et al. Adeno-associated virus type 2 capsids with externalized VP1/VP2 trafficking domains are generated prior to passage through the cytoplasm and are maintained until uncoating occurs in the nucleus. Journal of Virology, (2006) vol. 80, No. 22, pp. 11040-11054.
White, et al. Targeted gene delivery to vascular tissue in vivo by tropism-modified adeno-associated virus vectors. (2004) Circulation 109:513-519.
Work, et al. Vascular bed-targeted in vivo gene delivery using tropism-modified adeno-associated viruses. (2006) Mol. Ther. 13:683-693.
Wu, et al. Mutational analysis of the adeno-associated virus type 2 (AAV2) capsid gene and construction of AAV2 vectors with altered tropism. Journal of Virology, (2000) vol. 72, No. 18, pp. 8635-8647.
Blacklow et al. (1971) Am J Epidemiol 94, 359-66. (1971).
Davidson et al. (2000) Proc Natl Acad Sci U S A 97, 3428-32.
Erles et al. (1999) J Med Virol 59, 406-11.
Halbert et al. (2000) J Virol 74, 1524-32.
Moskalenko et al. (2000) J Virol 74, 1761-6.
Nguyen (2001) Neuroreport 12, 1961-4.
Opie et al. (2003) J Virol 77, 6995-7006.
Rabinowitz et al. (1999) Virology 265, 274-85.
Sun et al. (2003) Gene Ther 10, 964-76.
Wobus et al. (2000) J Virol 74, 9281-93.
Huttner, N.A. et al. Genetic Modification of the Adeno-Associated Virus Type-2 Capsid Reduce Affinity to Human Serum Antibodies and Overcome Potential Limitations of Neutralizing Antibodies for the Use in Human Gene Therapy Blood. Nov. 16, 2002 vol. 100, No. 11, pp. Abstract No. 5548, 44th Annual Meeting of the American Society of Hematology, Philadelphia, PA USA, Dec. 6-10, 2000, Society of Hematology.
Paddison, P.J. et al. Stable suppression of gene expression by RNAi in mammalian cells. Proc. Nat'l Acad. Sci. USA. Feb. 5, 2002, vol. 99, No. 3, pp. 1443-1448.
Rabinowitz, J.E. et al. Building a Better Vector: The Manipulation of AAV Virions. Virology. 2000, vol. 278, pp. 301-308.
Shi, W. et al. Insertional Mutagenesis of the Adeno-Associated Virus Type 2 (AAV2) Capsid Gene and Generation of AAV2 Vectors Targeted to Alternative Cell-Surface Receptors. Human Gene Therapy. Sep. 20, 2001, vol. 12, pp. 1697-1711.
Maheshri et al., "Directed evolution of adeno-associated virus yields enhanced gene delivery vectors", Nature Biotechnology, vol. 24, No. 2, Feb. 2006, pp. 198-204.
Opie et al., "Identification of Amino Acid Residues in the Capsid Proteins of Adeno-Associated Virus Type 2 that Contribute to Haparan Sulfate Proteoglycan Binding", Journal of Virology, vol. 77, No. 12, Jun. 2003, pp. 6995-7006.
Perabo et al., "Combinatorial engineering of a gene therapy vector: directed evolution of adeno-associated virus", The Journal of Gene Medicine, vol. 8, No. 2, Feb. 2006, pp. 155-162.
Schaffer et al., "Directed evolution of AAV vector mutants for enhanced gene delivery". Abstracts of Papers American Chemical Society, vol. 227, part 1, Mar. 2004, p. U214.
Tomar et al., "Use of Adeno-Associated Viral Vector for Delivery of Small Interfering RNA", Oncogene, vol. 22, No. 36, Aug. 28, 2003, pp. 5712-5715.
Tal, "Adeno-Associated Virus-Based Vectors in Gene Therapy", Journal of Biomedical Science, vol. 7, No. 4, Jul. 2000, pp. 2790291.
Wu et al., "Mutational Analysis of the Adeno-Associated Virus Type 2 (AAV2) Capsid Gene and Construction of AAV2 Vectors with Altered Tropism", Journal of Virology, vol. 74, No. 18, Sep. 2000, pp. 8635-8647.
Huttner, et al. Blood, vol. 100, No. 11, Abstract No. 5548 (2002).
Attached Score Report Result Per SEQ ID No. 17 per US2002/0192823 to Bartlett Published Dec. 19, 2002.
U.S. Appl. No. 14/444,347, filed Jul. 28, 2014, Schaffer et al.
U.S. Appl. No. 14/606,543, filed Jan. 27, 2015, Schaffer et al.
Allocca, et al.; "Novel adeno-associated virus serotypes efficiently transduce murine photoreceptors"; Journal of Virology; vol. 81, No. 20, pp. 11372-11380 (Oct. 2007).
Asokan, et al., "Reengineering a receptor footprint of adeno-associated virus enables selective and systemic gene transfer to muscle"; Nat Biotechnol; vol. 28, No. 1, pp. 79-82 (Jan. 2010).
Bichsel, et al.; "Bacterial delivery of nuclear proteins into pluripotent and differentiated cells"; PLoS One; vol. 6, No. 1, pp. 1-9 (Jan. 2011).
Boucas, et al.; "Engineering adeno-associated virus serotype 2-based targeting vectors using a new insertion site-position 453-and single point mutations"; J Gene Med.; vol. 11, No. 12, pp. 1103-1113 (Dec. 2009).
Buch, et al., "In Contrast to AAC-Mediated Cntf Expression, AAV-Mediated Gdnf Expression Enhances Gene Replacement Therapy in Rodent Models of Retinal Degeneration"; Molecular Therapy; vol. 14, No. 5, pp. 700-709 (Nov. 2006).
Buning, et al., "Receptor targeting of adeno-associated virus vectors"; Gene Therapy; vol. 10, pp. 1142-1151 (2003).
Choi, et al.; "AAV Hybrid Serotypes: Improved Vectors for Gene Delivery."; Current Gene Therapy; vol. 5, No. 3, pp. 299-310 (Jun. 2005).
Diprimio, et al.; "Surface loop dynamics in adeno-associated virus capsid assembly"; Journal of Virology; vol. 82, No. 11, pp. 5178-5189 (Jun. 2008).

(56) References Cited

OTHER PUBLICATIONS

Excoffon, et al.; "Directed evolution of adeno-associated virus to an infectious respiratory virus"; Proc Natl Acad Sci USA; vol. 106, No. 10, pp. 3865-3870 (Mar. 10, 2009).
Flotte, et al.; "Gene expression from adeno-associated virus vectors in airway epithelial cells"; Am J Respir Cell Mol Biol.; vol. 7, No. 3, pp. 349-356 (Sep. 1992).
GenBank accession No. ABZ10812; AAV13 capsid protein sequence downloaded from NCBI; downloaded on Nov. 3, 2008.
Gray, et al.; "Directed Evolution of a Novel Adeno-associated Virus (AAV) Vector That Crosses the Seizure-compromised Blood-Brain Barrier (BBB)"; Molecular Therapy; vol. 18, No. 3, pp. 570-578 (2010).
Gregory-Evans, et al.; "Ex vivo Gene Therapy Using Intravitreal Injection of GDNF-secreting Mouse Embryonic Stem Cells in a Rat Model of Retinal Degeneration"; Molecular Vision; vol. 15, pp. 962-973 (May 13, 2009).
Grifman, et al.; "Incorporation of tumor-targeting peptides into recombinant adeno-associated virus capsids"; Molecular Therapy; vol. 3, No. 6, pp. 964-975 (Jun. 2001).
Grimm, et al.; "In Vitro and In Vivo Gene Therapy Vector Evolution via Multispecies Interbreeding and Retargeting of Adeno-Associated Viruses"; Journal of Virology; vol. 82, No. 12, pp. 5887-5911 (Jun. 2008).
Hirsch, et al.; "Directed Evolution of the AAV Capsid for Human Embryonic Stem Cell Transduction"; Molecular Therapy; vol. 17, Supp. 1, S177-S178 (May 2009).
Jang, et al.; "An evolved adeno-associated viral variant enhances gene delivery and gene targeting in neural stem cells"; Mol Ther.; vol. 19, No. 4, pp. 667-675 (Apr. 2011).
Karp, et al.; "An in vitro model of differentiated human airway epithelia, Methods for establishing primary cultures"; Methods Mol Biol.; vol. 188, pp. 115-137 (2002).
Klimczak, et al.; "A Novel Adeno-Associated Viral Variant for Efficient and Selective Intravitreal Transduction of Rat Muller Cells"; PLoS ONE; vol. 4, No. 10, pp. 1-10 (Oct. 2009).
Koerber, et al.; "Molecular Evolution of Adeno-associated Virus for Enhanced Glial Gene Delivery", Molecular Therapy; vol. 17, No. 12, pp. 2088-2095 (Dec. 2009).
Lai, et al.; "Long-term evaluation of AAV-mediated sFlt-1 gene therapy for ocular neovascularization in mice and monkeys"; Mol Ther.; vol. 12, No. 4, pp. 659-668 (Oct. 2005).
Li, et al.; "Engineering and Selection of Shuffled AAV Genomes: A New Strategy for Producing Targeted Biological Nanoparticles"; Molecular Therapy; vol. 16, No. 7, pp. 1252-1260 (Jul. 2008).
Li, et al.; "Generation of Novel AAV Variants by Directed Evolution for Improved CFTR Delivery to Human Ciliated Airway Epithelium"; Molecular Therapy; vol. 17, No. 12, pp. 2067-2077 (Dec. 2009).
Limberis, et al.; "Adeno-associated virus serotype 9 vectors transduce murine alveolar and nasal epithelia and can be readministered"; Proc Natl Acad Sci USA; vol. 103, No. 35, pp. 12993-12998 (Aug. 29, 2006).
Maguire, et al.; "Directed evolution of adeno-associated virus for glioma cell transduction"; J. Neurooncol.; vol. 96, pp. 337-347 (2010).
Michelfelder, et al.; "Successful Expansion but Not Complete Restriction of Tropism of Adeno-Associated Virus by In Vivo Biopanning of Random Virus Display Peptide Libraries"; PLoS One; vol. 4, No. 4, pp. 1-13 (Apr. 2009).
Mitchell, et al.; "AAV's anatomy: Roadmap for optimizing vectors for translational success"; Curr Gene Ther.; vol. 10, No. 5, pp. 319-340 (Oct. 2010).

Muller, et al.; "Random peptide libraries displayed on adeno-associated virus to select for targeted gene therapy vectors"; Nat Biotechnol; vol. 21, No. 9, pp. 1040-1046 (Sep. 2003).
Padron, et al.; "Structure of adeno-associated virus type 4"; Journal of Virology; vol. 79, No. 8, pp. 5047-5058 (Apr. 2005).
Park, et al.; "Intravitreal delivery of AAV8 retinoschisin results in cell type-specific gene expression and retinal rescue in the Rs1-KO mouse"; Gene Therapy; vol. 16, pp. 916-926 (2009).
Pechan, et al; "Novel anti-VEGF chimeric molecules delivered by AAV vectors for inhibition of retinal neovascularization."; Gene. Ther.; vol. 16, No. 1, pp. 10-16 (Jan. 2009).
Perabo, et al., "Heparan Sulfate Proteoglycan Binding Properties of Adeno-Associated Virus Retargeting Mutants and Consequences for Their In Vivo Tropism"; Journal of Virology; vol. 80, No. 14, pp. 7265-7269 (Jul. 2006).
Petrs-Silva, et al.; "High-efficiency transduction of the mouse retina by tyrosine-mutant AAV serotype vectors"; Molecular Therapy; vol. 17, No. 3, pp. 463-471 (Mar. 2009).
Ryals, et al.; "Quantifying transduction efficiencies of unmodified and tyrosine capsid mutant AAV vectors in vitro using two ocular cell lines"; Mol Vision; vol. 17, pp. 1090-1102 (Apr. 2011).
Shen, et al.; "Characterization of the relationship of AAV capsid domain swapping to liver transduction efficiency"; Mol Ther.; vol. 15, No. 11, pp. 1955-1962 (Aug. 28, 2007).
Shi, W. et al.; "Insertional Mutagenesis of the Adeno-Associated Virus Type 2 (AAV2) Capsid Gene and Generation of AAV2 Vectors Targeted to Alternative Cell-Surface Receptors"; Human Gene Therapy; vol. 12, pp. 1697-1711 (Sep. 20, 2001).
Steinbach, et al.; "Assembly of adeno-associated virus type 2 capsids in vitro" J of Gen Virology; vol. 78, pp. 1453-1462 (1997).
Van Vliet, et al.; "Proteolytic mapping of the adeno-associated virus capsid"; Mol Ther.; vol. 14, No. 6, pp. 809-821 (Dec. 2006).
Wickham, et al.; "Increased in vitro and in vivo gene transfer by adenovirus vectors containing chimeric fiber proteins"; Journal of Virology; vol. 71, No. 11, pp. 8221-8229 (Nov. 1997).
Wu, et al.; "$\alpha 2,3$ and $\alpha 2,6$ N-linked Sialic Acids Facilitate Efficient Binding and Transduction by Adeno-Associated Virus Types 1 and 6"; Journal of Virology; vol. 80, No. 18, pp. 9093-9103 (Sep. 2006).
Xiao, et al.; "Adenovirus-facilitated nuclear translocation of adeno-associated virus type 2"; Journal of Virology; vol. 76, No. 22, pp. 11505-11517 (Nov. 2002).
Xie, et al.; "The atomic structure of adeno-associated virus (AAV-2), a vector for human gene therapy"; PNAS; vol. 99, No. 16, pp. 10405-10410 (Aug. 6, 2002).
Yang, et al.; "A myocardium tropic adeno-associated virus (AAV) evolved by DNA shuffling and in vivo selection"; PNAS; vol. 106, No. 10, pp. 3946-3951 (Mar. 10, 2009).
Zabner, et al.; "Adeno-associated virus type 5 (AAV5) but not AAV2 binds to the apical surfaces of airway epithelia and facilitates gene transfer"; J Virol.; No. 74, No. 8, pp. 3852-3858 (Apr. 2000).
Zolotukhin, et al.; "Recombinant adeno-associated virus purification using novel methods improves infectious titer and yield"; Gene Therapy; vol. 6, pp. 973-985 (1999).
Michelfelder, et al.; "Vectors selected from adeno-associated viral display peptide libraries for leukemia cell-targeted cytotoxic gene therapy"; Experimental Hematology; vol. 35, pp. 1766-1776 (2007).
Waterkamp, et al.; "Isolation of targeted AAV2 vectors from novel virus display libraries"; J. Gene. Med.; vol. 8, pp. 1307-1319 (Sep. 6, 2006).
Zhao; et al. "Molecular evolution by staggered extension process (StEP) in vitro recombination", Nat Biotechnol (Mar. 1998), 16(3):258-261.

* cited by examiner

FIG. 3A

```
wildtype CAP    1    atggctgccgatggttatcttccagattggctcgaggacactctctctgaaggaataaga  60
AbE 2           1    ATGGCTGCCGATGGTTATCTTCCAGATTGGCTCGAGGACACTCTCTCTGAAGGAATAAGA  60
AbE L           1    ATGGCTGCCGATGGTTATCTTCCAGATTGGCTCGAGGACACTCTCTCTGAAGGAATAAGA  60 wildtype CAP   61    cagtggtggaagctcaaacctggcccaccaccaccaaagcccgcagagcggcataaggac 120
AbE 2          61    CAGTGGTGGAAGCTCAAACCTGGCCCACCACCACCAAAGCCCGCAGAGCGGCATAAGGAC 120
AbE L          61    CAGTGGTGGAAGCTCAAACCTGGCCCACCACCACCAAAGCCCGCAGAGCGGCATAAGGAC 120 wildtype CAP  121    gacagcaggggtcttgtgcttcctgggtacaagtacctcggacccttcaacggactcgac 180
AbE 2         121    GACAGCAGGGGTCTTGTGCTTCCTGGGTACAAGTACCTCGGACCCTTCAACGGACTCGAC 180
AbE L         121    GACAGCAGGGGTCTTGTGCTTCCTGGGTACAAGTACCTCGGACCCTTCAACGGACTCGAC 180 wildtype CAP  181    aagggagagccggtcaacgaggcagacgccgcggccctcgagcacgacaaagcctacgac 240
AbE 2         181    AAGGGAGAGCCGGTCAACGAGGCAGACGCCGCGGCCCTCGAGCACGACAAAGCCTACGAC 240
AbE L         181    AAGGGAGAGCCGGTCAACGAGGCAGACGCCGCGGCCCTCGAGCACGACAAAGCCTACGAC 240 wildtype CAP  241    cggcagctcgacagcggagacaacccgtacctcaagtacaaccacgccgacgcggagttt 300
AbE 2         241    CGGCAGCTCGACAGCGGAGACAACCCGTACCTCAAGTACAACCACGCCGACGCGGAGTTT 300
AbE L         241    CGGCAGCTCGACAGCGGAGACAACCCGTACCTCAAGTACAACCACGCCGACGCGGAGTTT 300 wildtype CAP  301    caggagcgccttaaagaagatacgtcttttgggggcaacctcggacgagcagtcttccag 360
AbE 2         301    CAGGAGCGCCTTAAAGAAGATACGTCTTTTGGGGGCAACCTCGGACGAGCAGTCTTCCAG 360
AbE L         301    CAGGAGCGCCTTAAAGAAGATACGTCTTTTGGGGGCAACCTCGGACGAGCAGTCTTCCAG 360 wildtype CAP  361    gcgaaaaagagggttcttgaacctctgggcctggttgaggaacctgttaagacggctccg 420
AbE 2         361    GCGAAAAAGAGGGTTCTTGAACCTCTGGGCCTGGTTGAGGAACCTGTTAAGACGGCTCCG 420
AbE L         361    GCGAAAAAGAGGGTTCTTGAACCTCTGGGCCTGGTTGAGGAACCTGTTAAGACGGCTCCG 420 wildtype CAP  421    ggaaaaagaggccggtagagcactctcctgtggagccagactcctcctcgggaaccgga 480
AbE 2         421    GGAAAAAGAGGCCGGTAGAGCACTCTCCTGTGGAGCCAGACTCCTCCTCGGGAACCGGA 480
AbE L         421    GGAAAAAGAGGCCGGTAGAGCACTCTCCTGTGGAGCCAGACTCCTCCTCGGGAACCGGA 480 wildtype CAP  481    aaggcgggccagcagcctgcaagaaaaagattgaattttggtcagactggagacgcagac 540
AbE 2         481    AAGGCGGGCCAGCAGCCTGCAAGAAAAAGATTGAATTTTGGTCAGACTGGAGACGCAGAC 540
AbE L         481    AAGGCGGGCCAGCAGCCTGCAAGAAAAAGATTGAATTTTGGTCAGACTGGAGACGCAGAC 540 wildtype CAP  541    tcagtacctgaccccagcctctcggacagccaccagcagcccctctggtctgggaact 600
AbE 2         541    TCAGTACCTGACCCCCAGCCTCTCGGACAGCCACCAGCAGCCCCCTCTGGTCTGGGAACT 600
AbE L         541    TCAGTACCTGACCCCCAGCCTCTCGGACAGCCACCAGCAGCCCCCTCTGGTCTGGGAACT 600 wildtype CAP  601    aatacgatggctacaggcagtggcgcaccaatggcagacaataacgagggcgccgacgga 660
AbE 2         601    AATACGATGGCTACAGGCAGTGGCGCGCCAATGGCAGACAATAACGAGGGCGCCGACGGA 660
AbE L         601    AATACGATGGCTACAGGCAGTGGCGCGCCAATGGCAGACAATAACGAGGGCGCCGACGGA 660 wildtype CAP  661    gtgggtaattcctcgggaaattggcattgcgattccacatggatggcgacagagtcatc 720
AbE 2         661    GTGGGTAATTCCTCGGGAAATTGGCATTGCGATTCCACATGGATGGGCGACAGAGTCATC 720
AbE L         661    GTGGGTAATTCCTCGGGAAATTGGCATTGCGATTCCACATGGATGGGCGACAGAGTCATC 720 wildtype CAP  721    accaccagcacccgaacctgggccctgcccacctacaacaaccacctctacaaacaatt 780
AbE 2         721    ACCACCAGCACCCGAACCTGGGCCCTGCCCACCTACAACAACCACCTCTACAAACAATT 780
AbE L         721    ACCACCAGCACCCGAACCTGGGCCCTGCCCACCTACAACAACCACCTCTACAAACAATT 780 wildtype CAP  781    tccagccaatcaggagcctcgaacgacaatcactactttggctacagcacccccttgggg 840
AbE 2         781    TCCAGCCAATCAGGAGCCTCGAACGACAATCACTACTTTGGCTACAGCACCCCCTTGGGG 840
AbE L         781    TCCAGCCAATCAGGAGCCTCGAACGACAATCACTACTTTGGCTACAGCACCCCCTTGGGG 840 wildtype CAP  841    tattttgacttcaacagattccactgccacttttcaccacgtgactggcaaagactcatc 900
AbE 2         841    TATTTTGACTTCAACAGATTCCACTGCCACTTTTCACCACGTGACTGGCAAAGACTCATC 900
AbE L         841    TATTTTGACTTCAACAGATTCCACTGCCACTTTTCACCACGTGACTGGCAAAGACTCATC 900
```

FIG. 3B

```
wildtype CAP   901  aacaacaactggggattccgacccaagagactcaacttcaagctcttttaacattcaagtc  960
AbE 2          901  AACAACAACTGGGGATTCCGACCCAAGAGACTCAACTTCAAGCTCTTTTAACATTCAAGTC  960
AbE L          901  AACAACAACTGGGGATTCCGACCCAAGAGACTCAACTTCAAGCTCTTTTAACATTCAAGTC  960 wildtype CAP   961  aaagaggtcacgcagaatgacggtacgacgacgattgccaataaccttaccagcacggtt  1020
AbE 2          961  AAAGAGGTCACGCAGAATGACGGTACGACGACGATTGCCAATAACCTTACCAGCACGGTT  1020
AbE L          961  AAAGAGGTCACGCAGAATGACGGTACGACGACGATTGCCAATAACCTTACCAGCACGGTT  1020 wildtype CAP  1021  caggtgtttactgactcggagtaccagctcccgtacgtcctcggctcggcgcatcaagga  1080
AbE 2         1021  CAGGTGTTTACTGACTCGGAGTACCAGCTCCCGTACGTCCTCGGCTCGGCGCATCAAGGA  1080
AbE L         1021  CAGGTGTTTACTGACTCGGAGTACCAGCTCCCGTACGTCCTCGGCTCGGCGCATCAAGGA  1080 wildtype CAP  1081  tgcctcccgccgttcccagcagacgtcttcatggtgccacagtatggatacctcaccctg  1140
AbE 2         1081  TGCCTCCCGCCGTTCCCAGCAGACGTCTTCATGGTGCCACAGTATGGATACCTCACCCTG  1140
AbE L         1081  TGCCTCCCGCCGTTCCCAGCAGACGTCTTCATGGTGCCACAGTATGGATACCTCACCCTG  1140 wildtype CAP  1141  aacaacgggagtcaggcagtaggacgctcttcatttactgcctggagtactttccttct  1200
AbE 2         1141  AACAACGGGAGTCAGGCAGTAGGACGCTCTTCATTTTACTGCCTGGAGTACTTTCCTTCT  1200
AbE L         1141  AACAACGGGAGTCAGGCAGTAGGACGCTCTTCATTTTACTGCCTGGAGTACTTTCCTTCT  1200 wildtype CAP  1201  cagatgctgcgtaccggaaacaactttaccttcagctacacttttgaggacgttcctttc  1260
AbE 2         1201  CAGATGCTGCGTACCGGAAACAACTTTACCTTCAGCTACACTTTTGAGGACCTTCCTTTC  1260
AbE L         1201  CAGATGCTGCGTACCGGAAACAACTTTACCTTCAGCTACACTTTTGAGGACGTTCCTTTC  1260 wildtype CAP  1261  cacagcagctacgctcacagccagagtctggaccgtctcatgaatcctctcatcgaccag  1320
AbE 2         1261  CACAGCAGCTACGCTCACAGCCAGAGTCTGGACCGTCTCATGAATCCTCTCATCGACCAG  1320
AbE L         1261  CACAGCAGCTACGCTCACAGCCAGAGTCTGGACCGTCTCATGAATCCTCTCATCGACCAG  1320 wildtype CAP  1321  tacctgtattacttgagcagaacaaacactccaagtggaaccaccacgcagtcaaggctt  1380
AbE 2         1321  TACCTGTATTACTTGAGCAGAACAAACACTCCAAGTGGAACCACCACGCAGTCAAGGCTT  1380
AbE L         1321  TACCTGTATTACTTGAGCAGAACAAACACTCCAAGTGGAACCACCACGCAGTCAAGGCTT  1380 wildtype CAP  1381  cagttttctcaggccggagcgagtgacattcgggaccagtctaggaactggcttcctgga  1440
AbE 2         1381  CAGTTTTCTCAGGCTGGAGCGAGTGACATTCGGGACCAGTCTAGGAACTGGCTTCCTGGA  1440
AbE L         1381  CAGTTTTCTCAGGCTGGAGCGAGTGACATTCGGGACCAGTCTAGGAACTGGCTTCCTGGA  1440 wildtype CAP  1441  ccctgttaccgccagcagcgagtatcaaagacatctgcggataacaacaacagtgaatac  1500
AbE 2         1441  CCCTGTTACCGCCAGCAGAGAGTATCAAAGACATCTGCGGATAACAACAACAGTGAATAC  1500
AbE L         1441  CCCTGTTACCGCCAGCAGAGAGTATCAAAGACATCTGCGGATAACAACAACAGTGAATAC  1500 wildtype CAP  1501  tcgtggactggagctaccaagtaccacctcaatggcagagactctctggtgaatccgggc  1560
AbE 2         1501  TCGTGGACTGGAGCTACCAAGTACCACCTCAATGGCAGAGACTCTCTGGTGAATCCGGGC  1560
AbE L         1501  TCGTGGACTGGAGCTACCAAGTACCACCTCAATGGCAGAGACTCTCTGGTGAATCCGGGC  1560 wildtype CAP  1561  ccggccatggcaagccacaaggacgatgaagaaaagttttttcctcagagcggggttctc  1620
AbE 2         1561  CCGGCCATGGCAAGCCACAAGGACGATGAAGAAAAGTTTTTTCCTCAGAGCGGGGTTCTC  1620
AbE L         1561  CCGGCCATGGCAAGCCACAAGGACGATGAAGAAAAGTTTTTTCCTCAGAGCGGGGTTCTC  1620 wildtype CAP  1621  atctttgggaagcaaggctcagagaaaacaaatgtggacattgaaaaggtcatgattaca  1680
AbE 2         1621  ATCTTTGGGAAGCAAGGCTCAGAGAAAACAAATGTGGACATTGAAAAGGTCATGATTACA  1680
AbE L         1621  ATCTTTGGGAAGCAAGGCTCAGAGAAAACAAATGTGGACATTGAAAAGGTCATGATTACA  1680 wildtype CAP  1681  gacgaagaggaaatcaggacaaccaatcccgtggctacggagcagtatggttctgtatct  1740
AbE 2         1681  GACGAAGAGGAAATCAGGACAACCAATCCCGTGGCTACGGAGCAGTATGGTTCTGTATCT  1740
AbE L         1681  GACGAAGAGGAAATCAGGACAACCAATCCCGTGGCTACGGAGCAGTATGGTTCTGTATCT  1740 wildtype CAP  1741  accaacctccagagaggcaacagacaagcagctaccgcagatgtcaacacacaaggcgtt  1800
AbE 2         1741  ACCAACCTCCAGAGAGGCAACAGACAAGCAGCTACCGCAGATGTCAACACACAAGGCGTT  1800
AbE L         1741  ACCAACCTCCAGAGAGGCAACAGACAAGCAGCTACCGCAGATGTCAACACACAAGGCGTT  1800
```

FIG. 3C

```
wildtype CAP  1801  cttccaggcatggtctggcaggacagagatgtgtaccttcaggggcccatctgggcaaag  1860
AbE 2         1801  CTTCCAGGCATGGTCTGGCAGGACAGAGATGTGTACCTTCAGGGGCCCATCTGGGCAAAG  1860
AbE L         1801  CTTCCAGGCATGGTCTGGCAGGACAGAGATGTGTACCTTCAGGGGCCCATCTGGGCAAAG  1860 wildtype CAP  1861  attccacacacggacggacattttcacccctctccctcatgggtggattcggacttaaa  1920
AbE 2         1861  ATTCCACACACGGACGGACATTTTCACCCCTCTCCCTCATGGGTGGATTCGGACTTAAA  1920
AbE L         1861  ATTCCACACACGGACGGACATTTTCACCCCTCTCCCCTCATGGGTGGATTCGGACTTAAA  1920 wildtype CAP  1921  caccctcctccacagattctcatcaagaacaccccggtacctgcgaatccttcgaccacc  1980
AbE 2         1921  CACCCTCCTCCACAGATTCTCATCAAGAACACCCCGGTACCTGCGAATCCTTCGACCACC  1980
AbE L         1921  CACCCTCCTCCACAGATTCTCATCAAGAACACCCCGGTACCTGCGAATCCTTCGACCACC  1980 wildtype CAP  1981  ttcagtgcggcaaagtttgcttccttcatcacacagtactccacgggacaggtcagcgtg  2040
AbE 2         1981  TTCAGTGCGGCAAAGTTTGCTTCCTTCATCACACAGTACTCCACGGGACAGGTCAGCGTG  2040
AbE L         1981  TTCAGTGCGGCAAAGTTTGCTTCCTTCATCACACAGTACTCCACGGGACAGGTCAGCGTG  2040 wildtype CAP  2041  gagatcgagtgggagctgcagaaggaaaacagcaaacgctggaatcccgaaattcagtac  2100
AbE 2         2041  GAGATCGAGTGGGAGCTGCAGAAGGAAAACAGCAAACGCTGGAATCCCGAAATTCAGTAC  2100
AbE L         2041  GAGATCGAGTGGGAGCTGCAGAAGGAAAACAGCAAACGCTGGAATCCCGAAATTCAGTAC  2100 wildtype CAP  2101  acttccaactacaacaagtctgttaatgtggacttta ctg tggac a taatggcgtgtat  2160
AbE 2         2101  ACTTCCAACTACAACAAGTCTGTTAATGTGGACTTTA GGA TGGAC G CTAATGGCGTGTAT  2160
AbE L         2101  ACTTCCAACTACAACAAGTCTGTTAATGTGGACTTTA CNG TGGAC G CTAATGGCGTGTAT  2160 wildtype CAP  2161  tcagagcc tcg ccccattggcaccag atacctgactcgtaatctgtaattgcttgcggcc  2220
AbE 2         2161  TCAGAGCC NNN CCCCATTGGCACCAG T------------------------------  2187
AbE L         2161  TCAGAGCC NNG CCCCATTGGCACCAG T------------------------------  2187 wildtype CAP  2221  gcccc  2225  (SEQ ID NO:1)
AbE 2         2187  -----  2187  (SEQ ID NO:2)
AbE L         2187  -----  2187  (SEQ ID NO:3)
```

FIG. 4A

```
                    10        20        30        40        50        60
                ....|....|....|....|....|....|....|....|....|....|....|....|
AAV2 VP1    1   atggctgccgatggttatcttccagattggctcgaggacactctctctgaaggaataaga
rAbE 1      1   ATGGCTGCCGATGGTTATCTTCCAGATTGGCTCGAGGACACTCTCTCTGAAGGAATAAGA
rAbE 2      1   ATGGCTGCCGATGGTTATCTTCCAGATTGGCTCGAGGACACTCTCTCTGAAGGAATAAGA
rAbE 3      1   ATGGCTGCCGATGGTTATCTTCCAGATTGGCTCGAGGACACTCTCTCTGAAGGAATAAGA
rAbE 4      1   ATGGCTGCCGATGGTTATCTTCCAGATTGGCTCGAGGACACTCTCTCTGAAGGAATAAGA
rAbE 5      1   ATGGCTGCCGATGGTTATCTTCCAGATTGGCTCGAGGACACTCTCTCTGAAGGAATAAGA 70        80        90       100       110       120
                ....|....|....|....|....|....|....|....|....|....|....|....|
AAV2 VP1   61   cagtggtggaagctcaaacctggcccaccaccaccaaagcccgcagagcggcataaggac
rAbE 1     61   CAGTGGTGGAAGCTCAAACCTGGCCCACCACCACCAAAGCCCGCAGAGCGGCATAAGGAC
rAbE 2     61   CAGTGGTGGAAGCTCAAACCTGGCCCACCACCACCAAAGCCCGCAGAGCGGCATAAGGAC
rAbE 3     61   CAGTGGTGGAAGCTCAAACCTGGCCCACCACCACCAAAGCCCGCAGAGCGGCATAAGGAC
rAbE 4     61   CAGTGGTGGAAGCTCAAACCTGGCCCACCACCACCAAAGCCCGCAGAGCGGCATAAGGAC
rAbE 5     61   CAGTGGTGGAAGCTCAAACCTGGCCCACCACCACCAAAGCCCGCAGAGCGGCATAAGGAC 130       140       150       160       170       180
                ....|....|....|....|....|....|....|....|....|....|....|....|
AAV2 VP1  121   gacagcagggggtcttgtgcttcctgggtacaagtacctcggacccttcaacggactcgac
rAbE 1    121   GACAGCAGGGGTCTTGTGCTTCCTGGGTACAAGTACCTCGGACCCTTCAACGGACTCGAC
rAbE 2    121   GACAGCAGGGGTCTTGTGCTTCCTGGGTACAAGTACCTCGGACCCTTCAACGGACTCGAC
rAbE 3    121   GACAGCAGGGGTCTTGTGCTTCCTGGGTACAAGTACCTCGGACCCTTCAACGGACTCGAC
rAbE 4    121   GACAGCAGGGGTCTTGTGCTTCCTGGGTACAAGTACCTCGGACCCTTCAACGGACTCGAC
rAbE 5    121   GACAGCAGGGGTCTTGTGCTTCCTGGGTACAAGTACCTCGGACCCTTCAACGGACTCGAC 190       200       210       220       230       240
                ....|....|....|....|....|....|....|....|....|....|....|....|
AAV2 VP1  181   aagggagagccggtcaacgaggcagacgccgcggccctcgagcacgacaaagcctacgac
rAbE 1    181   AAGGGAGAGCCGGTCAACGAGGCAGACGCCGCGGCCCTCGAGCACGACAAAGCCTACGAC
rAbE 2    181   AAGGGAGAGCCGGTCAACGAGGCAGACGCCGCGGCCCTCGAGCACGACAAAGCCTACGAC
rAbE 3    181   AAGGGAGAGCCGGTCAACGAGGCAGACGCCGCGGCCCTCGAGCACGACAAAGCCTACGAC
rAbE 4    181   AAGGGAGAGCCGGTCAACGAGGCAGACGCCGCGGCCCTCGAGCACGACAAAGCCTACGAC
rAbE 5    181   AAGGGAGAGCCGGTCAACGAGGCAGACGCCGCGGCCCTCGAGCACGACAAAGCCTACGAC 250       260       270       280       290       300
                ....|....|....|....|....|....|....|....|....|....|....|....|
AAV2 VP1  241   cggcagctcgacagcggagacaacccgtacctcaagtacaaccacgccgacgcggagttt
rAbE 1    241   CGGCAGCTCGACAGCGGAGACAACCCGTACCTCAAGTACAACCACGCCGACGCGGAGTTT
rAbE 2    241   CGGCAGCTCGACAGCGGAGACAACCCGTACCTCAAGTACAACCACGCCGACGCGGAGTTT
rAbE 3    241   CGGCAGCTCGACAGCGGAGACAACCCGTACCTCAAGTACAACCACGCCGACGCGGAGTTT
rAbE 4    241   CGGCAGCTCGACAGCGGAGACAACCCGTACCTCAAGTACAACCACGCCGACGCGGAGTTT
rAbE 5    241   CGGCAGCTCGACAGCGGAGACAACCCGTACCTCAAGTACAACCACGCCGACGCGGAGTTT 310       320       330       340       350       360
                ....|....|....|....|....|....|....|....|....|....|....|....|
AAV2 VP1  301   caggagcgccttaaagaagatacgtcttttgggggcaacctcggacgagcagtcttccag
rAbE 1    301   CAGGAGCGCCTTAAAGAAGATACGTCTTTTGGGGGCAACCTCGGACGAGCAGTCTTCCAG
rAbE 2    301   CAGGAGCGCCTTAAAGAAGATACGTCTTTTGGGGGCAACCTCGGACGAGCAGTCTTCCAG
rAbE 3    301   CAGGAGCGCCTTAAAgAAGATACGTCTTTTGGGGGCAACCTCGGACGAGCAGTCTTCCAG
rAbE 4    301   CAGGAGCGCCTTAAAGAAGATACGTCTTTTGGGGGCAACCTCGGACGAGCAGTCTTCCAG
rAbE 5    301   CAGGAGCGCCTTAAAGAAGATACGTCTTTTGGGGGCAACCTCGGACGAGCAGTCTTCCAG
```

FIG. 4B

```
              370        380        390        400        410        420
         ....|....|....|....|....|....|....|....|....|....|....|....|
AAV2 VP1 361 gcgaaaaagagggttcttgaacctctgggcctggttgaggaacctgttaagacggctccg
rAbE 1   361 GCGAAAAAGAGGGTTCTTGAACCTCTGGGCCTGGTTGAGGAACCTGTTAAgACGGCTCCG
rAbE 2   361 GCGAAAAAGAGGGTTCTTGAACCTCTGGGCCTGGTTGAGGAACCTGTTAAGACGGCTCCG
rAbE 3   361 GCGAAAAAgAGGGTTCTTGAACCTCTGGGCCTGGTTGAGGAACCTGTTAAgACGGCtCCG
rAbE 4   361 GCGAAAAAGAGGGTTCTTGAACCTCTGGGCCTGGTTGAGGAACCTGTTAAGACGGCTCCG
rAbE 5   361 GCGAAAAAGAGGGTTCTTGAACCTCTGGGCCTGGTTGAGGAACCTGTTAAGACGGCTCCG 430        440        450        460        470        480
         ....|....|....|....|....|....|....|....|....|....|....|....|
AAV2 VP1 421 ggaaaaaagaggccggtagagcactctcctgtggagccagactcctcctcgggaaccgga
rAbE 1   421 GGAAAAAAGAGGCCGGTAGAGCACTCTCCTGtGGAGCCAGACTCCTCCTCGGGAACCGGA
rAbE 2   421 GGAAAAAAGAGGCCGGTAGAGCACTCTCCTGTGGAGCCAGACTCCTCCTCGGGAACCGGA
rAbE 3   421 GGAAAAAAgAGGCCGGTAGAGCACTCTCCTGtGGAGCCAGACTCCTCCTCGGGAACCGGA
rAbE 4   421 GGAAAAAAGAGGCCGGTAGAGCACTCTCCTGTGGAGCCAGACTcCTCCTCGGGAACCGGA
rAbE 5   421 GGAAAAAAGAGGCCGGtAGAGCACTCTCCTGTGGAgCCAGACTCCTCCTCGGGAACCGGA 490        500        510        520        530        540
         ....|....|....|....|....|....|....|....|....|....|....|....|
AAV2 VP1 481 aaggcgggccagcagcctgcaagaaaaagattgaattttggtcagactggagacgcagac
rAbE 1   481 AAGGCGGGCCAgCAgCCTGCAAgAAAAAgATtGAATTTTGGTCAgACTGGAGACGCAGAC
rAbE 2   481 AAGGCGGGCCAGCAGCCTGCAAGAAAAAGATTGAATTTTGGTCAGACTGGAGACGCAGAC
rAbE 3   481 AAGGCGGGCCAGCAGCCTGCAAgAAAAAGATTGAATTTTGGTCAGACTGGAGACGcAgAC
rAbE 4   481 AAGGCGGGCCAgCAGCCTGCAAGAAAAAGATTGAATTTTGGTCAGACTGGAGACGCAAAC
rAbE 5   481 AAGGCGGGCCAGCAGCCTGCAAGAAAAAGATTGAATTTTGGTCAGACTGGAgACGcAgAC 550        560        570        580        590        600
         ....|....|....|....|....|....|....|....|....|....|....|....|
AAV2 VP1 541 tcagtacctgaccccagcctctcggacagccaccagcagcccctctggtctgggaact
rAbE 1   541 TCAGTACCTGACCCCCAGCCTCTCGGACAGCCACCAGCAGCCCCCTCTGGTCTGGGAACT
rAbE 2   541 TCAGTACCTGACCCCCAGCCTCTCGGACAGCCACCAGCAGCCCCCTCTGGTCTGGGAACT
rAbE 3   541 TCAGTACCTGACCCCCAGCCTCTCGGACAGCCACCAGCAGCCCCCTCTGGTCTGGGAACT
rAbE 4   541 TCAGTACCTGACCCCCAGCCTCTCGGACAGCCACCAGCAGCCCCCTCTGGTCTGGGAACT
rAbE 5   541 TCAGTACCTGACCCCCAGCCTCTCGGACAGCCACCAGCAGCCCCCTCTGGTCTGGGAACT 610        620        630        640        650        660
         ....|....|....|....|....|....|....|....|....|....|....|....|
AAV2 VP1 601 aatacgatggctacaggcagtggcgcaccaatggcagacaataacgagggcgccgacgga
rAbE 1   601 AATACGATGGCTACAGGCAGTGGCGCGCCAATGGCAGACAATAACGAGGGCGCCGACGGA
rAbE 2   601 AATACGATGGCTACAGGCAGTGGCGCGCCAATGGCAGACAATAACGAGGGCGCCGACGGA
rAbE 3   601 AATACGATGGCTACAGGCAGTGGCGCGCCAATGGCAGACAATAACGAGGGCGCCGACGGA
rAbE 4   601 AATACGATGGCTACAGGCAGTGGCGCGCCAATGGCAGACAATAACGAGGGCGCCGACGGA
rAbE 5   601 AATACGATGGCTACAGGCAGTGGCGCGCCAATGGCAGACAATAACGAGGGCGCCGACGGA 670        680        690        700        710        720
         ....|....|....|....|....|....|....|....|....|....|....|....|
AAV2 VP1 661 gtgggtaattcctcgggaaattggcattgcgattccacatggatgggcgacagagtcatc
rAbE 1   661 GTGGGTAATTCCTCGGGAAATTGGCATTGCGATTCCACATGGATGGGCGACAGAGTCATC
rAbE 2   661 GTGGGTAATTCCTCGGGAAATTGGCATTGCGATTCCACATGGATGGGCGACAGAGTCATC
rAbE 3   661 GTGGGTAATTCCTCGGGAAATTGGCATTGCGATTCCACATGGATGGGCGACAGAGTCATC
rAbE 4   661 GTGGGTAATTCCTCGGGAAATTGGCATTGCGATTCCACATGGATGGGCGACAGAGTCATC
rAbE 5   661 GTGGGTAATTCCTCGGGAAATTGGCATTGCGATTCCACATGGATGGGCGACAGAGTCATC
```

FIG. 4C

```
             730       740       750       760       770       780
         ....|....|....|....|....|....|....|....|....|....|....|....|
AAV2 VP1 721 accaccagcacccgaacctgggccctgcccacctacaacaaccacctctacaaacaaatt
rAbE 1   721 ACCACCAGCACCCGAACCTGGGCCCTGCCCACCTACAACAACCACCTCTACAAACAAATT
rAbE 2   721 ACCACCAGCACCCGAACCTGGGCCCTGCCCACCTACAACAACCACCTCTACAAACAAATT
rAbE 3   721 ACCACCAGCACCCGAACCTGGGCCCTGCCCACCTACAACAACCACCTCTACAAACAAATT
rAbE 4   721 ACCACCAGCACCCGAACCTGGGCCCTGCCCACCTACAACAACCACCTCTACAAACAAATT
rAbE 5   721 ACCACCAGCACCCGAACCTGGGCCCTGCCCACCTACAACAACCACCTCTACAAACAAATT 790       800       810       820       830       840
         ....|....|....|....|....|....|....|....|....|....|....|....|
AAV2 VP1 781 tccagccaatcaggagcctcgaacgacaatcactactttggctacagcaccccttggggg
rAbE 1   781 TCCAGCCAATCAGGAGCCTCGAACGACAATCACTACTTTGGCTACAGCACCCCTTGGGGG
rAbE 2   781 TCCAGCCAATCAGGAGCCTCGAACGACAATCACTACTTTGGCTACAGCACCCCTTGGGGG
rAbE 3   781 TCCAGCCAATCAGGAGCCTCGAACGACAATCACTACTTTGGCTACAGCACCCCTTGGGGG
rAbE 4   781 TCCAGCCAATCAGGAGCCTCGAACGACAATCACTACTTTGGCTACAGCACCCCTTGGGGG
rAbE 5   781 TCCAGCCAATCAGGAGCCTCGAACGACAATCACTACTTTGGCTACAGCACCCCTTGGGGG 850       860       870       880       890       900
         ....|....|....|....|....|....|....|....|....|....|....|....|
AAV2 VP1 841 tattttgacttcaacagattccactgccacttttcaccacgtgactggcaaagactcatc
rAbE 1   841 TATTTTGACTTCAACAGATTCCACTGCCACTTTTCACCACGTGACTGGCAAAGACTCATC
rAbE 2   841 TATTTTGACTTCAACAGATTCCACTGCCACTTTTCACCACGTGACTGGCAAAGACTCATC
rAbE 3   841 TATTTTGACTTCAACAGATTCCACTGCCACTTTTCACCACGTGACTGGCAAAGACTCATC
rAbE 4   841 TATTTTGACTTCAACAGATTCCACTGCCACTTTTCACCACGTGACTGGCAAAGACTCATC
rAbE 5   841 TATTTTGACTTCAACAGATTCCACTGCCACTTTTCACCACGTGACTGGCAAAGACTCATC 910       920       930       940       950       960
         ....|....|....|....|....|....|....|....|....|....|....|....|
AAV2 VP1 901 aacaacaactggggattccgacccaagagactcaacttcaagctctttaacattcaagtc
rAbE 1   901 AACAACAACTGGGGATTCCGACCCAAGAGACTCAACTTCAAGCTCTTTAACATTCAAGTC
rAbE 2   901 AACAACAACTGGGGATTCCGACCCAAGAGACTCAACTTCAAGCTCTTTAACATTCAAGTC
rAbE 3   901 AACAACAACTGGGGATTCCGACCCAAGAGACTCAACTTCAAGCTCTTTAACATTCAAGTC
rAbE 4   901 AACAACAACTGGGGATTCCGACCCAAGAGACTCAACTTCAAGCTCTTTAACATTCAAGTC
rAbE 5   901 AACAACAACTGGGGATTCCGACCCAAGAGACTCAACTTCAAGCTCTTTAACATTCAAGTC 970       980       990       1000      1010      1020
         ....|....|....|....|....|....|....|....|....|....|....|....|
AAV2 VP1 961 aaagaggtcacgcagaatgacggtacgacgacgattgccaataaccttaccagcacggtt
rAbE 1   961 AAAGAGGTCACGCAgAATGACGGTACGACGACGATTGCCAATAACCTTACCAGCACGGTT
rAbE 2   961 AAAGAGGTCACGCAGAATGACGGTACGACGACGATTGCCAATAACCTTACCAGCACGGTT
rAbE 3   961 AAAGAGGTCACGCAGAATGACGGTACGACGACGATTGCCAATAACCTTACCAGCACGGTT
rAbE 4   961 AAAGAGGTCACGCAGAATGACGGTACGACGACGATTGCCAATAACCTTACCAGCACGGTT
rAbE 5   961 AAAGAGGTCACGCAgAATGACGGTACGACGACGATTGCCAATAACCTTACCAGCACGGTT 1030      1040      1050      1060      1070      1080
         ....|....|....|....|....|....|....|....|....|....|....|....|
AAV2 VP1 1021 caggtgtttactgactcggagtaccagctcccgtacgtcctcggctcggcgcatcaagga
rAbE 1   1021 CAGGTGTTTACTGACTCGGAGTACCAGCTCCCGTACGTCCTCGGCTCGGCGCATCAAGGA
rAbE 2   1021 CAGGTGTTTACTGACTCGGAGTACCAGCTCCCGTACGTCCTCGGCTCGGCGCATCAAGGA
rAbE 3   1021 CAGGTGTTTACTGACTCGGAGTACCAGCTCCCGTACGTCCTCGGCTCGGCGCATCAAGGA
rAbE 4   1021 CAGGTGTTTACTGACTCGGAGTACCAGCTCCCGTACGTCCTCGGCTCGGCGCATCAAGGA
rAbE 5   1021 CAGGTGTTTACTGACTCGGAGTACCAGCTCCCGTACGTCCTCGGCTCGGCGCATCAAGGA
```

FIG. 4D

```
                  1090      1100      1110      1120      1130      1140
             ....|....|....|....|....|....|....|....|....|....|....|....|
AAV2 VP1 1081 tgcctcccgccgttcccagcagacgtcttcatggtgccacagtatggatacctcaccctg
rAbE 1   1081 TGCCTCCCGCCGTTCCCAGCAGACGTCTTCATGGTGCCACAGTATGGATACCTCACCCTG
rAbE 2   1081 TGCCTCCCGCCGTTCCCAGCAGACGTCTTCATGGTGCCACAGTATGGATACCTCACCCTG
rAbE 3   1081 TGCCTCCCGCCGTTCCCAGCAGACGTCTTCATGGTGCCACAGTATGGATACCTCACCCTG
rAbE 4   1081 TGCCTCCCGCCGTTCCCAGCAGACGTCTTCATGGTGCCACAGTATGGATACCTCACCCTG
rAbE 5   1081 TGCCTCCCGCCGTTCCCAGCAGACGTCTTCATGGTGCCACAGTATGGATACCTCACCCTG 1150      1160      1170      1180      1190      1200
             ....|....|....|....|....|....|....|....|....|....|....|....|
AAV2 VP1 1141 aacaacgggagtcaggcagtaggacgctcttcattttactgcctggagtactttccttct
rAbE 1   1141 AACAACGGGAGTCAGGCAGTAGGACGCTCTTCATTTTACTGCCTGGAGTACTTTCCTTCT
rAbE 2   1141 AACAACGGGAGTCAGGCAGTAGGACGCTCTTCATTTTACTGCCTGGAGTACTTTCCTTCT
rAbE 3   1141 AACAACGGGAGTCAGGCAGTAGGACGCTCTTCATTTTACTGCCTGGAGTACTTTCCTTCT
rAbE 4   1141 AACAACGGGAGTCAGGCAGTAGGACGCTCTTCATTTTACTGCCTGGAGTACTTTCCTTCT
rAbE 5   1141 AACAACGGGAGTCAGGCAGTAGGACGCTCTTCATTTTACTGCCTGGAGTACTTTCCTTCT 1210      1220      1230      1240      1250      1260
             ....|....|....|....|....|....|....|....|....|....|....|....|
AAV2 VP1 1201 cagatgctgcgtaccggaaacaactttaccttcagctacacttttgaggacgttcctttc
rAbE 1   1201 CAGATGCTGCGTACCGGAAACAACTTTACCTTCAGCTACACTTTTGAGGACGTTCCTTTC
rAbE 2   1201 CAGATGCTGCGTACCGGAAACAACTTTACCTTCAGCTACACTTTTGAGGACCTTCCTTTC
rAbE 3   1201 CAGATGCTGCGTACCGGAAACAACTTTACCTTCAGCTACACTTTTGAGGACGTTCCTTTC
rAbE 4   1201 CAGATGCTGCGTACCGGAAACAACTTTACCTTCAGCTACACTTTTGAGGACGTTCCTTTC
rAbE 5   1201 CAGATGCTGCGTACCGGAAACAACTTTACCTTCAGCTACACTTTTGAGGACGTTCCTTTC 1270      1280      1290      1300      1310      1320
             ....|....|....|....|....|....|....|....|....|....|....|....|
AAV2 VP1 1261 cacagcagctacgctcacagccagagtctggaccgtctcatgaatcctctcatcgaccag
rAbE 1   1261 CACAGCAGCTACGCTCACAGCCAGAGTCTGGACCGTCTCATGAATCCTCTCATCGACCAG
rAbE 2   1261 CACAGCAGCTACGCTCACAGCCAGAGTCTGGACCGTCTCATGAATCCTCTCATCGACCAG
rAbE 3   1261 CACAGCAGCTACGCTCACAGCCAGAGTCTGGACCGTCTCATGAATCCTCTCATCGACCAG
rAbE 4   1261 CACAGCAGCTACGCTCACAGCCAGAGTCTGGACCGTCTCATGAATCCTCTCATCGACCAG
rAbE 5   1261 CACAGCAGCTACGCTCACAGCCAGAGTCTGGACCGTCTCATGAATCCTCTCATCGACCAG 1330      1340      1350      1360      1370      1380
             ....|....|....|....|....|....|....|....|....|....|....|....|
AAV2 VP1 1321 tacctgtattacttgagcagaacaaacactccaagtggaaccaccacgcagtcaaggctt
rAbE 1   1321 TACCTGTATTACTTGAGCAGAACAAACACTCCAAGTGGAACCACCACGCAGTCAAGGCTT
rAbE 2   1321 TACCTGTATTACTTGAGCAGAACAAACACTCCAAGTGGAACCACCACGCAGTCAAGGCTT
rAbE 3   1321 TACCTGTATTACTTGAGCAGAACAAACACTCCAAGTGGAACCACCACGCAGTCAAGGCTT
rAbE 4   1321 TACCTGTATTACTTGAGCAGAACAAACACTCCAAGTGGAACCACCACGCAGTCAAGGCTT
rAbE 5   1321 TACCTGTATTACTTGAGCAGAACAAACACTCCAAGTGGAACCACCACGCAGTCAAGGCTT 1390      1400      1410      1420      1430      1440
             ....|....|....|....|....|....|....|....|....|....|....|....|
AAV2 VP1 1381 cagttttctcaggccggagcgagtgacattcggaccagtctaggaactggcttcctgga
rAbE 1   1381 CAGTTTTCTCAGGCTGGAGCGAGTGACATTCGGACCAGTCTAGGAACTGGCTTCCTGGA
rAbE 2   1381 CAGTTTTCTCAGGCTGGAGCGAGTGACATTCGGACCAGTCTAGGAACTGGCTTCCTGGA
rAbE 3   1381 CAGTTTTCTCAGGCTGGAGCGAGTGACATTCGGACCAGTCTAGGAACTGGCTTCCTGGA
rAbE 4   1381 CAGTTTTCTCAGGCTGGAGCGAGTGACATTCGGACCAGTCTAGGAACTGGCTTCCTGGA
rAbE 5   1381 CAGTTTTCTCAGGCTGGAGCGAGTGACATTCGGACCAGTCTAGGAACTGGCTTCCTGGA
```

FIG. 4E

```
                   1450       1460       1470       1480       1490       1500
                ....|....|....|....|....|....|....|....|....|....|....|....|
AAV2 VP1  1441  ccctgttaccgccagcagcgagtatcaaagacatctgcggataacaacaacagtgaatac
rAbE 1    1441  CCCTGTTACCGCCAGCAGAGAGTATCAAAGACATCTGCGGATAACAACAACAGTGAATAC
rAbE 2    1441  CCCTGTTACCGCCAGCAGAGAGTATCAAAGACATCTGCGGATAACAACAACAGTGAATAC
rAbE 3    1441  CCCTGTTACCGCCAGCAGAGAGTATCAAAGACATCTGCGGATAACAACAACAGTGAATAC
rAbE 4    1441  CCCTGTTACCGCCAGCAGAGAGTATCAAAGACATCTGCGGATAACAACAACAGTGAATAC
rAbE 5    1441  CCCTGTTACCGCCAGCAGAGAGTATCAAAGACATCTGGGGATAACAACAACAGTGAATAC 1510       1520       1530       1540       1550       1560
                ....|....|....|....|....|....|....|....|....|....|....|....|
AAV2 VP1  1501  tcgtggactggagctaccaagtaccacctcaatggcagagactctctggtgaatccgggc
rAbE 1    1501  TCGTGGACTGGAGCTACCAAGTACCACCTCAATGGCAGAGACTCTCTGGTGAATCCGGGC
rAbE 2    1501  TCGTGGACTGGAGCTACCAAGTACCACCTCAATGGCAGAGACTCTCTGGTGAATCCGGGC
rAbE 3    1501  TCGTGGACTGGAGCTACCAAGTACCACCTCAATGGCAGAGACTCTCTGGTGAATCCGGGC
rAbE 4    1501  TCGTGGACTGGAGCTACCAAGTACCACCTCAATGGCAGAGACTCTCTGGTGAATCCGGGC
rAbE 5    1501  TCGTGGACTGGAGCTACCAAGTACCACCTCAATGGCAGAGACTCTCTGGTGAATCCGGGC 1570       1580       1590       1600       1610       1620
                ....|....|....|....|....|....|....|....|....|....|....|....|
AAV2 VP1  1561  ccggccatggcaagccacaaggacgatgaagaaaagttttttcctcagagcggggttctc
rAbE 1    1561  CCGGCCATGGCAAGCCACAAGGACGATGAAGAAAAGTTTTTTCCTCAGAGCGGGGTTCTC
rAbE 2    1561  CCGGCCATGGCAAGCCACAAGGACGATGAAGAAAAGTTTTTTCCTCAGAGCGGGGTTCTC
rAbE 3    1561  CCGGCCATGGCAAGCCACAAGGACGATGAAGAAAAGTTTTTTCCTCAGAGCGGGGTTCTC
rAbE 4    1561  CCGGCCATGGCAAGCCACAAGGACGATGAAGAAAAGTTTTTTCCTCAGAGCGGGGTTCTC
rAbE 5    1561  CCGGCCATGGCAAGCCACAAGGACGATGAAGAAAAGTTTTTTCCTCAGAGCGGGGTTCTC 1630       1640       1650       1660       1670       1680
                ....|....|....|....|....|....|....|....|....|....|....|....|
AAV2 VP1  1621  atctttgggaagcaaggctcagagaaaacaaatgtggacattgaaaaggtcatgattaca
rAbE 1    1621  ATCTTTGGGAAGCAAGGCTCAGAGAAAACAAATGTGGACATTGAAAAGGTCATGATTACA
rAbE 2    1621  ATCTTTGGGAAGCAAGGCTCAGAGAAAACAAATGTGGACATTGAAAAGGTCATGATTACA
rAbE 3    1621  ATCTTTGGGAAGCAAGGCTCAGAGAAAACAAATGTGGACATTGAAAAGGTCATGATTACA
rAbE 4    1621  ATCTTTGGGAAGCAAGGCTCAGAGAAAACAAATGTGGACATTGAAAAGGTCATGATTACA
rAbE 5    1621  ATCTTTGGGAAGCAAGGCTCAGAGAAAACAAATGTGGACATTGAAAAGGTCATGATTACA 1690       1700       1710       1720       1730       1740
                ....|....|....|....|....|....|....|....|....|....|....|....|
AAV2 VP1  1681  gacgaagaggaaatcaggacaaccaatcccgtggctacggagcagtatggttctgtatct
rAbE 1    1681  GACGAAGAGGAAATCAGGACAACCAATCCCGTGGCTACGGAGCAGTATGGTTCTGTATCT
rAbE 2    1681  GACGAAGAGGAAATCAGGACAACCAATCCCGTGGCTACGGAGCAGTATGGTTCTGTATCT
rAbE 3    1681  GACGAAGAGGAAATCAGGACAACCAATCCCGTGGCTACGGAGCAGTATGGTTCTGTATCT
rAbE 4    1681  GACGAAGAGGAAATCAGGACAACCAATCCCGTGGCTACGGAGCAGTATGGTTCTGTATCT
rAbE 5    1681  GACGAAGAGGAAATCAGGACAACCAATCCCGTGGCTACGGAGCAGTATGGTTCTGTATCT 1750       1760       1770       1780       1790       1800
                ....|....|....|....|....|....|....|....|....|....|....|....|
AAV2 VP1  1741  accaacctccagagaggcaacagacaagcagctaccgcagatgtcaacacacaaggcgtt
rAbE 1    1741  ACCAACCTCCAGAGAGGCAACAGACAAGCAGCTACCGCAGATGTCAACACACAAGGCGTT
rAbE 2    1741  ACCAACCTCCAGAGAGGCAACAGACAAGCAGCTACCGCAGATGTCAACACACAAGGCGTT
rAbE 3    1741  ACCAACCTCCAGAGAGGCAACAGACAAGCAGCTACCGCAGATGTCAACACACAAGGCGTT
rAbE 4    1741  ACCAACCTCCAGAGAGGCAACAGACAAGCAGCTACCGCAGATGTCAACACACAAGGCGTT
rAbE 5    1741  ACCAACCTCCAGAGAGGCAACAGACAAGCAGCTACCGCAGATGTCAACACACAAGGCGTT
```

FIG. 4F

```
                       1810       1820       1830       1840       1850       1860
                  ....|....|....|....|....|....|....|....|....|....|....|....|
AAV2 VP1    1801  cttccaggcatggtctggcaggacagagatgtgtaccttcaggggcccatctgggcaaag
rAbE 1      1801  CTTCCAGGCATGGTCTGGCAGGACAGAGATGTGTACCTTCAGGGGCCCATCTGGGCAAAG
rAbE 2      1801  CTTCCAGGCATGGTCTGGCAGGACAGAGATGTGTACCTTCAGGGGCCCATCTGGGCAAAG
rAbE 3      1801  CTTCCAGGCATGGTCTGGCAGGACAGAGATGTGTACCTTCAGGGGCCCATCTGGGCAAAG
rAbE 4      1801  CTTCCAGGCATGGTCTGGCAGGACAGAGATGTGTACCTTCAGGGGCCCATCTGGGCAAAG
rAbE 5      1801  CTTCCAGGCATGGTCTGGCAGGACAGAGATGTGTACCTTCAGGGGCCCATCTGGGCAAAG 1870       1880       1890       1900       1910       1920
                  ....|....|....|....|....|....|....|....|....|....|....|....|
AAV2 VP1    1861  attccacacacggacggacattttcaccctctccctcatgggtggattcggacttaaa
rAbE 1      1861  ATTCCACACACGGACGGACATTTTCACCCTCTCCCCTCATGGGTGGATTCGGACTTAAA
rAbE 2      1861  ATTCCACACACGGACGGACATTTTCACCCTCTCCCCTCATGGGTGGATTCGGACTTAAA
rAbE 3      1861  ATTCCACACACGGACGGACATTTTCACCCTCTCCCCTCATGGGTGGATTCGGACTTAAA
rAbE 4      1861  ATTCCACACACGGACGGACATTTTCACCCCTCTCCCCTCATGGGTGGATTCGGACTTAAA
rAbE 5      1861  ATTCCACACACGGACGGACATTTTCACCCCTCTCCCCTCATGGGTGGATTCGGACTTAAA 1930       1940       1950       1960       1970       1980
                  ....|....|....|....|....|....|....|....|....|....|....|....|
AAV2 VP1    1921  caccctcctccacagattctcatcaagaacaccccggtacctgcgaatccttcgaccacc
rAbE 1      1921  CACCCTCCTCCACAGATTCTCATCAAGAACACCCCGGTACCTGCGAATCCTTCGACCACC
rAbE 2      1921  CACCCTCCTCCACAGATTCTCATCAAGAACACCCCGGTACCTGCGAATCCTTCGACCACC
rAbE 3      1921  CACCCTCCTCCACAGATTCTCATCAAGAACACCCCGGTACCTGCGAATCCTTCGACCACC
rAbE 4      1921  CACCCTCCTCCACAGATTCTCATCAAGAACACCCCGGTACCTGCGAATCCTTCGACCACC
rAbE 5      1921  CACCCTCCTCCACAGATTCTCATCAAGAACACCCCGGTACCTGCGAATCCTTCGACCACC 1990       2000       2010       2020       2030       2040
                  ....|....|....|....|....|....|....|....|....|....|....|....|
AAV2 VP1    1981  ttcagtgcggcaaagtttgcttccttcatcacacagtactccacgggacaggtcagcgtg
rAbE 1      1981  TTCAGTGCGGCAAAGTTTGCTTCCTTCATCACACAGTACTCCACGGGACAGGTCAGCGTG
rAbE 2      1981  TTCAGTGCGGCAAAGTTTGCTTCCTTCATCACACAGTACTCCACGGGACAGGTCAGCGTG
rAbE 3      1981  TTCAGTGCGGCAAAGTTTGCTTCCTTCATCACACAGTACTCCACGGGACAGGTCAGCGTG
rAbE 4      1981  TTCAGTGCGGCAAAGTTTGCTTCCTTCATCACACAGTACTCCACGGGACAGGTCAGCGTG
rAbE 5      1981  TTCAGTGCGGCAAAGTTTGCTTCCTTCATCACACAGTACTCCACGGGACAGGTCAGCGTG 2050       2060       2070       2080       2090       2100
                  ....|....|....|....|....|....|....|....|....|....|....|....|
AAV2 VP1    2041  gagatcgagtgggagctgcagaaggaaaacagcaaacgctggaatcccgaaattcagtac
rAbE 1      2041  GAGATCGAGTGGGAGCTGCAGAAGGAAAACAGCAAACGCTGGAATCCCGAAATTCAGTAC
rAbE 2      2041  GAGATCGAGTGGGAGCTGCAGAAGGAAAACAGCAAACGCTGGAATCCCGAAATTCAGTAC
rAbE 3      2041  GAgATCGAGTGGGAGCTGCAGAAGGAAAACAGCAAACGCTGGAATCCCGAAATTCAGTAC
rAbE 4      2041  GAGATCGAGTGGGAGCTGCAGAAGGAAAACAGCAAACGCTGGAATCCCGAAATTCAGTAC
rAbE 5      2041  GAgATCGAGTGGGAGCTGCAGAAGGAAAACAGCAAACGCTGGAATCCCGAAATTCAGTAC 2110       2120       2130       2140       2150       2160
                  ....|....|....|....|....|....|....|....|....|....|....|....|
AAV2 VP1    2101  acttccaactacaacaagtctgttaatgtggactttactgtggacactaatggcgtgtat
rAbE 1      2101  ACTTCCAACTACAACAAGTCTGTTAATGTGGACTTTAGGGTGGACGCTAATGGCGTGTAT
rAbE 2      2101  ACTTCCAACTACAACAAGTCTGTTAATGTGGACTTTAGGgTGGACGCTAATGGCGTGTAT
rAbE 3      2101  ACTTCCAACTACAACAAGTCTGTTAATGTGGACTTTAcGGTGGACGCTAATGGCGTGTAT
rAbE 4      2101  ACTTCCAACTACAACAAGTCTGTTAATGTGGACTTTACtGTGGACGCTAATGGCGTGTAT
rAbE 5      2101  ACTTCCAACTACAACAAGTCTGTTAATGTGGACTTTACtGTGGACGCTAATGGCGTGTAT
```

FIG. 4G

```
                   2170       2180       2190       2200
              ....|....|....|....|....|....|....|....|.
AAV2 VP1  2161 tcagagcctcgccccattggcaccagatacctgactcgtaa  (SEQ ID NO:4)
rAbE 1    2161 TCAGAGCCtcgccccattggcaccagatacctgactcgtaa  (SEQ ID NO:6)
rAbE 2    2161 TCAGAGCCtcgccccattggcaccagatacctgactcgtaa  (SEQ ID NO:8)
rAbE 3    2161 TCAGAGCCtcgccccattggcaccagatacctgactcgtaa  (SEQ ID NO:10)
rAbE 4    2161 TCAGAGCCtcgccccattggcaccagatacctgactcgtaa  (SEQ ID NO:12)
rAbE 5    2161 TCAGAGCCtcGcCCCATTGGCACCAGATACCTGACTCGTAA  (SEQ ID NO:14)
```

FIG. 5A

```
                 10         20         30         40         50         60
           ....|....|....|....|....|....|....|....|....|....|....|....|
AAV2 VP1   1   MAADGYLPDWLEDTLSEGIRQWWKLKPGPPPPKPAERHKDDSRGLVLPGYKYLGPFNGLD
rAbE 1     1   MAADGYLPDWLEDTLSEGIRQWWKLKPGPPPPKPAERHKDDSRGLVLPGYKYLGPFNGLD
rAbE 2     1   MAADGYLPDWLEDTLSEGIRQWWKLKPGPPPPKPAERHKDDSRGLVLPGYKYLGPFNGLD
rAbE 3     1   MAADGYLPDWLEDTLSEGIRQWWKLKPGPPPPKPAERHKDDSRGLVLPGYKYLGPFNGLD
rAbE 4     1   MAADGYLPDWLEDTLSEGIRQWWKLKPGPPPPKPAERHKDDSRGLVLPGYKYLGPFNGLD
rAbE 5     1   MAADGYLPDWLEDTLSEGIRQWWKLKPGPPPPKPAERHKDDSRGLVLPGYKYLGPFNGLD 70         80         90        100        110        120
           ....|....|....|....|....|....|....|....|....|....|....|....|
AAV2 VP1   61  KGEPVNEADAAALEHDKAYDRQLDSGDNPYLKYNHADAEFQERLKEDTSFGGNLGRAVFQ
rAbE 1     61  KGEPVNEADAAALEHDKAYDRQLDSGDNPYLKYNHADAEFQERLKEDTSFGGNLGRAVFQ
rAbE 2     61  KGEPVNEADAAALEHDKAYDRQLDSGDNPYLKYNHADAEFQERLKEDTSFGGNLGRAVFQ
rAbE 3     61  KGEPVNEADAAALEHDKAYDRQLDSGDNPYLKYNHADAEFQERLKEDTSFGGNLGRAVFQ
rAbE 4     61  KGEPVNEADAAALEHDKAYDRQLDSGDNPYLKYNHADAEFQERLKEDTSFGGNLGRAVFQ
rAbE 5     61  KGEPVNEADAAALEHDKAYDRQLDSGDNPYLKYNHADAEFQERLKEDTSFGGNLGRAVFQ 130        140        150        160        170        180
           ....|....|....|....|....|....|....|....|....|....|....|....|
AAV2 VP1   121 AKKRVLEPLGLVEEPVKTAPGKKRPVEHSPVEPDSSSGTGKAGQQPARKRLNFGQTGDAD
rAbE 1     121 AKKRVLEPLGLVEEPVKTAPGKKRPVEHSPVEPDSSSGTGKAGQQPARKRLNFGQTGDAD
rAbE 2     121 AKKRVLEPLGLVEEPVKTAPGKKRPVEHSPVEPDSSSGTGKAGQQPARKRLNFGQTGDAD
rAbE 3     121 AKKRVLEPLGLVEEPVKTAPGKKRPVEHSPVEPDSSSGTGKAGQQPARKRLNFGQTGDAD
rAbE 4     121 AKKRVLEPLGLVEEPVKTAPGKKRPVEHSPVEPDSSSGTGKAGQQPARKRLNFGQTGDAN
rAbE 5     121 AKKRVLEPLGLVEEPVKTAPGKKRPVEHSPVEPDSSSGTGKAGQQPARKRLNFGQTGDAD 190        200        210        220        230        240
           ....|....|....|....|....|....|....|....|....|....|....|....|
AAV2 VP1   181 SVPDPQPLGQPPAAPSGLGTNTMATGSGAPMADNNEGADGVGNSSGNWHCDSTWMGDRVI
rAbE 1     181 SVPDPQPLGQPPAAPSGLGTNTMATGSGAPMADNNEGADGVGNSSGNWHCDSTWMGDRVI
rAbE 2     181 SVPDPQPLGQPPAAPSGLGTNTMATGSGAPMADNNEGADGVGNSSGNWHCDSTWMGDRVI
rAbE 3     181 SVPDPQPLGQPPAAPSGLGTNTMATGSGAPMADNNEGADGVGNSSGNWHCDSTWMGDRVI
rAbE 4     181 SVPDPQPLGQPPAAPSGLGTNTMATGSGAPMADNNEGADGVGNSSGNWHCDSTWMGDRVI
rAbE 5     181 SVPDPQPLGQPPAAPSGLGTNTMATGSGAPMADNNEGADGVGNSSGNWHCDSTWMGDRVI 250        260        270        280        290        300
           ....|....|....|....|....|....|....|....|....|....|....|....|
AAV2 VP1   241 TTSTRTWALPTYNNHLYKQISSQSGASNDNHYFGYSTPWGYFDFNRFHCHFSPRDWQRLI
rAbE 1     241 TTSTRTWALPTYNNHLYKQISSQSGASNDNHYFGYSTPWGYFDFNRFHCHFSPRDWQRLI
rAbE 2     241 TTSTRTWALPTYNNHLYKQISSQSGASNDNHYFGYSTPWGYFDFNRFHCHFSPRDWQRLI
rAbE 3     241 TTSTRTWALPTYNNHLYKQISSQSGASNDNHYFGYSTPWGYFDFNRFHCHFSPRDWQRLI
rAbE 4     241 TTSTRTWALPTYNNHLYKQISSQSGASNDNHYFGYSTPWGYFDFNRFHCHFSPRDWQRLI
rAbE 5     241 TTSTRTWALPTYNNHLYKQISSQSGASNDNHYFGYSTPWGYFDFNRFHCHFSPRDWQRLI 310        320        330        340        350        360
           ....|....|....|....|....|....|....|....|....|....|....|....|
AAV2 VP1   301 NNNWGFRPKRLNFKLFNIQVKEVTQNDGTTTIANNLTSTVQVFTDSEYQLPYVLGSAHQG
rAbE 1     301 NNNWGFRPKRLNFKLFNIQVKEVTQNDGTTTIANNLTSTVQVFTDSEYQLPYVLGSAHQG
rAbE 2     301 NNNWGFRPKRLNFKLFNIQVKEVTQNDGTTTIANNLTSTVQVFTDSEYQLPYVLGSAHQG
rAbE 3     301 NNNWGFRPKRLNFKLFNIQVKEVTQNDGTTTIANNLTSTVQVFTDSEYQLPYVLGSAHQG
rAbE 4     301 NNNWGFRPKRLNFKLFNIQVKEVTQNDGTTTIANNLTSTVQVFTDSEYQLPYVLGSAHQG
rAbE 5     301 NNNWGFRPKRLNFKLFNIQVKEVTQNDGTTTIANNLTSTVQVFTDSEYQLPYVLGSAHQG
```

FIG. 5B

```
              370        380        390        400        410        420
              ....|....|....|....|....|....|....|....|....|....|....|....|
AAV2 VP1  361 CLPPFPADVFMVPQYGYLTLNNGSQAVGRSSFYCLEYFPSQMLRTGNNFTFSYTFEDVPF
rAbE 1    361 CLPPFPADVFMVPQYGYLTLNNGSQAVGRSSFYCLEYFPSQMLRTGNNFTFSYTFEDVPF
rAbE 2    361 CLPPFPADVFMVPQYGYLTLNNGSQAVGRSSFYCLEYFPSQMLRTGNNFTFSYTFED PF
rAbE 3    361 CLPPFPADVFMVPQYGYLTLNNGSQAVGRSSFYCLEYFPSQMLRTGNNFTFSYTFEDVPF
rAbE 4    361 CLPPFPADVFMVPQYGYLTLNNGSQAVGRSSFYCLEYFPSQMLRTGNNFTFSYTFEDVPF
rAbE 5    361 CLPPFPADVFMVPQYGYLTLNNGSQAVGRSSFYCLEYFPSQMLRTGNNFTFSYTFEDVPF 430        440        450        460        470        480
              ....|....|....|....|....|....|....|....|....|....|....|....|
AAV2 VP1  421 HSSYAHSQSLDRLMNPLIDQYLYYLSRTNTPSGTTTQSRLQFSQAGASDIRDQSRNWLPG
rAbE 1    421 HSSYAHSQSLDRLMNPLIDQYLYYLSRTNTPSGTTTQSRLQFSQAGASDIRDQSRNWLPG
rAbE 2    421 HSSYAHSQSLDRLMNPLIDQYLYYLSRTNTPSGTTTQSRLQFSQAGASDIRDQSRNWLPG
rAbE 3    421 HSSYAHSQSLDRLMNPLIDQYLYYLSRTNTPSGTTTQSRLQFSQAGASDIRDQSRNWLPG
rAbE 4    421 HSSYAHSQSLDRLMNPLIDQYLYYLSRTNTPSGTTTQSRLQFSQAGASDIRDQSRNWLPG
rAbE 5    421 HSSYAHSQSLDRLMNPLIDQYLYYLSRTNTPSGTTTQSRLQFSQAGASDIRDQSRNWLPG 490        500        510        520        530        540
              ....|....|....|....|....|....|....|....|....|....|....|....|
AAV2 VP1  481 PCYRQQRVSKTSADNNNSEYSWTGATKYHLNGRDSLVNPGPAMASHKDDEEKFFPQSGVL
rAbE 1    481 PCYRQQRVSKTSADNNNSEYSWTGATKYHLNGRDSLVNPGPAMASHKDDEEKFFPQSGVL
rAbE 2    481 PCYRQQRVSKTSADNNNSEYSWTGATKYHLNGRDSLVNPGPAMASHKDDEEKFFPQSGVL
rAbE 3    481 PCYRQQRVSKTSADNNNSEYSWTGATKYHLNGRDSLVNPGPAMASHKDDEEKFFPQSGVL
rAbE 4    481 PCYRQQRVSKTSADNNNSEYSWTGATKYHLNGRDSLVNPGPAMASHKDDEEKFFPQSGVL
rAbE 5    481 PCYRQQRVSKTSGDNNNSEYSWTGATKYHLNGRDSLVNPGPAMASHKDDEEKFFPQSGVL 550        560        570        580        590        600
              ....|....|....|....|....|....|....|....|....|....|....|....|
AAV2 VP1  541 IFGKQGSEKTNVDIEKVMITDEEEIRTTNPVATEQYGSVSTNLQRGNRQAATADVNTQGV
rAbE 1    541 IFGKQGSEKTNVDIEKVMITDEEEIRTTNPVATEQYGSVSTNLQRGNRQAATADVNTQGV
rAbE 2    541 IFGKQGSEKTNVDIEKVMITDEEEIRTTNPVATEQYGSVSTNLQRGNRQAATADVNTQGV
rAbE 3    541 IFGKQGSEKTNVDIEKVMITDEEEIRTTNPVATEQYGSVSTNLQRGNRQAATADVNTQGV
rAbE 4    541 IFGKQGSEKTNVDIEKVMITDEEEIRTTNPVATEQYGSVSTNLQRGNRQAATADVNTQGV
rAbE 5    541 IFGKQGSEKTNVDIEKVMITDEEEIRTTNPVATEQYGSVSTNLQRGNRQAATADVNTQGV 610        620        630        640        650        660
              ....|....|....|....|....|....|....|....|....|....|....|....|
AAV2 VP1  601 LPGMVWQDRDVYLQGPIWAKIPHTDGHFHPSPLMGGFGLKHPPPQILIKNTPVPANPSTT
rAbE 1    601 LPGMVWQDRDVYLQGPIWAKIPHTDGHFHPSPLMGGFGLKHPPPQILIKNTPVPANPSTT
rAbE 2    601 LPGMVWQDRDVYLQGPIWAKIPHTDGHFHPSPLMGGFGLKHPPPQILIKNTPVPANPSTT
rAbE 3    601 LPGMVWQDRDVYLQGPIWAKIPHTDGHFHPSPLMGGFGLKHPPPQILIKNTPVPANPSTT
rAbE 4    601 LPGMVWQDRDVYLQGPIWAKIPHTDGHFHPSPLMGGFGLKHPPPQILIKNTPVPANPSTT
rAbE 5    601 LPGMVWQDRDVYLQGPIWAKIPHTDGHFHPSPLMGGFGLKHPPPQILIKNTPVPANPSTT 670        680        690        700        710        720
              ....|....|....|....|....|....|....|....|....|....|....|....|
AAV2 VP1  661 FSAAKFASFITQYSTGQVSVEIEWELQKENSKRWNPEIQYTSNYNKSVNVDFTVDTNGVY
rAbE 1    661 FSAAKFASFITQYSTGQVSVEIEWELQKENSKRWNPEIQYTSNYNKSVNVDFRVDANGVY
rAbE 2    661 FSAAKFASFITQYSTGQVSVEIEWELQKENSKRWNPEIQYTSNYNKSVNVDFRVDANGVY
rAbE 3    661 FSAAKFASFITQYSTGQVSVEIEWELQKENSKRWNPEIQYTSNYNKSVNVDFTVDANGVY
rAbE 4    661 FSAAKFASFITQYSTGQVSVEIEWELQKENSKRWNPEIQYTSNYNKSVNVDFTVDANGVY
rAbE 5    661 FSAAKFASFITQYSTGQVSVEIEWELQKENSKRWNPEIQYTSNYNKSVNVDFTVDANGVY
```

FIG. 5C

```
                           730
                      ....|....|...
AAV2 VP1   721  SEPRPIGTRYLTR    (SEQ ID NO:5)
rAbE 1     721  SEPRPIGTRYLTR    (SEQ ID NO:7)
rAbE 2     721  SEPRPIGTRYLTR    (SEQ ID NO:9)
rAbE 3     721  SEPRPIGTRYLTR    (SEQ ID NO:11)
rAbE 4     721  SEPRPIGTRYLTR    (SEQ ID NO:13)
rAbE 5     721  SEPRPIGTRYLTR    (SEQ ID NO:15)
```

FIG. 6A

```
                  10        20        30        40        50        60
              ....|....|....|....|....|....|....|....|....|....|....|....|
AAV2 VP1    1 atggctgccgatggttatcttccagattggctcgaggacactctctctgaaggaataaga
S1CM5       1 ATGGCTGCCGATGGTTATCTTCCAGATTGGCTCGAGGACACTCTCTCTGAAGGAATAAGA
S2CM5       1 ATGGCTGCCGATGGTTATCTTCCAGATTGGCTCGAGGACACTCTCTCTGAAGGAGTAAGA
S2CM2       1 ATGGCTGCCGATGGTTATCTTCCAGATTGGCTCGAGGACACTCTCTCTGAAGGAATAAGA
S3CM2       1 ATGGCTGCCGATGGTTATCTTCCAGATTGGCTCGAGGACACTCTCTCTGAAGGAATAAGC
A1CM5       1 ATGGCTGCCGATGGTTATCTTCCAGATTGGCTCGAGGACACTCTCTCTGAAGGAATAAGA
A3CM5       1 ATGGCTGCCGATGGTTATCTTCCAGATTGGCTCGAGGACACTCTCTCTGAAGGAATAAGA
A1CM2       1 ATGGCTGCCGATGGTTATCTTCCAGATTGGCTCGAGGACACTCTCTCTGAAGGAATAAGA
A2CM2       1 ATGGCTGCCGATGGTTATCTTCCAGATTGGCTCGAGGACACTCTCTCTGAAGGAATAAGA
A3CM2       1 ATGGCTGCCGATGGTTATCTTCCAGATTGGCTCGAGGACACTCTCTCTGAGGGAATAAGA 70        80        90       100       110       120
              ....|....|....|....|....|....|....|....|....|....|....|....|
AAV2 VP1   61 cagtggtggaagctcaaacctggcccaccaccaccaaagcccgcagagcggcataaggac
S1CM5      61 CAGTGGTGGAAGCTCAAACCTGGCCCACCACCACCAAAGCCCGCAGAGCGGCATAAGGAC
S2CM5      61 CAGTGGTGGAAGCTCAAACCTGGCCCACCACCACCAAAGCCCGCAGAGCGGCATAAGGAC
S2CM2      61 CAGTGGTGGAAGCTCAAACCTGGCCCACCACCACCAAAGCCCGCAGAGCGGCATAAGGAC
S3CM2      61 CAGTGGTGGAAGCTCAAACCTGGCCCACCACCACCAAAGCCCGCAGAGCGGCATAAGGAC
A1CM5      61 CAGTGGTGGAAGCTCAGACCTGGCCCACCACCACCAAAGCCCGCAGAGCGGCATAAGGAC
A3CM5      61 CAGTGGTGGAAGCTCAAACCTGGCCCACCACCACCAAAGCCCGCAGAGCGGCATAAGGAC
A1CM2      61 CAGTGGTGGGAGCTCAAACCTGGCCCACCACCACCAAAGCCCGCAGAGCGGCATAAGGAC
A2CM2      61 CAGTGGTGGAAGCTCAAACCTGGCCCACCACCACCAAAGCCCGCAGAGCGGCATAAGGAC
A3CM2      61 CAGTGGTGGAAGCTCAAACCTGGCCCACCACTACCAAAGCCCGCAGAGCGGCATAAGGAC 130       140       150       160       170       180
              ....|....|....|....|....|....|....|....|....|....|....|....|
AAV2 VP1  121 gacagcagggggtcttgtgcttcctgggtacaagtacctcggacccttcaacggactcgac
S1CM5     121 GACAGCAGGGGTCTTGTGCTTCCTGGGTACAAGTACCTCGGACCCTTCAACGGACTCGAC
S2CM5     121 GACAGCAGGGGTCTTGTGCTTCCTGGGTACAAGTACCTCGGACCCTTCAACGGACTCGAC
S2CM2     121 GACAGCAGGGGTCTTGTGCTTCCTGGGTACAAGTACCTCGGACCCTTCAACGGACTCGAC
S3CM2     121 GACAGCAGGGGTCTTGTGCTTCCTGGGTACAAGTACCTCGGACCCTTCAGCGGACTCGAC
A1CM5     121 GACAGCAGGGGTCTTGTGCTTCCTGGGTACAAGTACCTCGGACCCTTCAACGGACTCGAC
A3CM5     121 GACAGCAGGGGTCTTGTGCTTCCTGAGTACAAGTACCTCGGACCCTTCAACGGACTCGAC
A1CM2     121 GACAGCAGGGGTCTTGTGCTTCCTGGGTACAAGTACCTCGGACCCTTCAACGGACTCGAC
A2CM2     121 GACAGCAGGGGTCTTGCGCTTCCTGGGTACAAGTACCTCGGACCCTTCAACGGACTCGAC
A3CM2     121 GACAGCAGGGGTCTTGTGCTTCCTGGGTACAAGTACCTCGGACCCTTCAACGGACTCGAC 190       200       210       220       230       240
              ....|....|....|....|....|....|....|....|....|....|....|....|
AAV2 VP1  181 aagggagagccggtcaacgaggcagacgccgcggccctcgagcacgacaaagcctacgac
S1CM5     181 AAGGGAGAGCCGGTCAACGAGGCAGACGCCGCGGCCCTCGAGCACGACAAAGCCTACGAC
S2CM5     181 AAGGGAGAGCCGGTCAACGAGGCAGACGCCGCGGCCCTCGAGCACGACAAAGCCTACGAC
S2CM2     181 AAGGGAGAGCCGGTCAACGAGGCAGACGCCGCGGCCCTCGAGCACGACAAAGCCTACGAC
S3CM2     181 AAGGGAGAGCCGGTCAACGAGGCAGACGCCGCGGCCCTCGAGCACGACAAAGCCTACGAC
A1CM5     181 AAGGGAGAGCCGGTCAACGAGGCAGACGCCGCGGCCCTCGAGCACGACAAAGCCTACGAC
A3CM5     181 AAGGGAGAGCCGGTCAACGAGGCAGACGCCGCGGCCCTCGAGCACGACAAAGCCTACGAC
A1CM2     181 AAGGGAGAGCCGGTCAACGAGGCAGACGCCGCGGCCCTCGAGCACGACAAAGCCTACGAC
A2CM2     181 AAGGGAGAGCCGGTCAACGAGGCAGACGCCGCGGCCCTCGAGCACGACAAAGCCTACGAC
A3CM2     181 AAGGGAGAGCCGGTCAACGAGGCAGACGCCGCGGCCCTCGAGCACGACAAAGCCTACGAC
```

FIG. 6B

```
              250        260        270        280        290        300
              ....|....|....|....|....|....|....|....|....|....|....|....|
AAV2 VP1  241 cggcagctcgacagcggagacaacccgtacctcaagtacaaccacgccgacgcggagttt
S1CM5     241 CGGCAGCTCGACAGCGGAGACAACCCGTACCTCAAGTACAACCACGCCGACGCGGAGTTT
S2CM5     241 CGGCAGCTCGACAGCGGAGACAACCCGTACCTCAAGTACAACCACGCCGACGCGGAGTTT
S2CM2     241 CGGCAGCTCGACAGCGGAGACAACCCGTACCTCAAGTACAACCACGCCGACGCGGAGTTT
S3CM2     241 CGGCAGCTCGACAGCGGAGACAACCCGTACCTCAAGTACAACCACGCCGACGCGGAGTTT
A1CM5     241 CGGCAGCTCGACAGCGGAGACAACCCGTACCTCAAGTACAACCACGCCGACGCGGAGTTT
A3CM5     241 CGGCAGCTCGACAGCGGAGACAACCCGTACCTCAAGTACAACCACGCCGACGCGGAGTTT
A1CM2     241 CGGCAGCTCGACAGCGGAGACAACCCGTACCCAAGTACAACCACGCCGACGCGGAGTTT
A2CM2     241 CGGCAGCTCGACAGCGGAGACAACCCGTACCTCAAGTACAACCACGCCGACGCGGAGTTT
A3CM2     241 CGGCAGCTCGACAGCGGAGACAACCCGTACCTCAAGTACAACCACGCCGACGCGGAGTCT 310        320        330        340        350        360
              ....|....|....|....|....|....|....|....|....|....|....|....|
AAV2 VP1  301 caggagcgccttaaagaagatacgtcttttgggggcaacctcggacgagcagtcttccag
S1CM5     301 CAGGAGCGCCTTAAAGAAGATACGTCTTTTGGGGGCAACCTCGGACGAGCAGTCTTCCAG
S2CM5     301 CAGGAGCGCCTTAAAGAAGATACGTCTTTTGGGGGCAACCTCGGACGAGCAGTCTTCCAG
S2CM2     301 CAGGAGCGCCTTAAAGAAGATACGTCTTTTGGGGGCAACCTCGGACGAGCAGTCTTCCAG
S3CM2     301 CAGGAGCGCCTTAAAGAAGATACGTCTTTTGGGGGCAACCTCGGACGAGCAGTCTTCCAG
A1CM5     301 CAGGAGCGCCTTAAAGAAGATACGTCTTTTGGGGGCAACCTCGGACGAGCAGTCTTCCAG
A3CM5     301 CAGGAGCGCCTTAAAGAAGATACGTCTTTTGGGGGCAACCTCGGACGAGCAGTCTTCCAG
A1CM2     301 CAGGAGCGCCTTAAAGAAGATACGTCTTTTGGGGGCAACCTCGGACGAGCAGTCTTCCAG
A2CM2     301 CAGGAGCGCCTTAAAGAAGATACGTCTTTTGGGGGCAACCTCGGACGAGCAGTCTTCCAG
A3CM2     301 CAGGAGCGCCTTAAAGAAGATACGTCTTTTGGGGGCAACCTCGGACGAGCAGTCTTCCAG 370        380        390        400        410        420
              ....|....|....|....|....|....|....|....|....|....|....|....|
AAV2 VP1  361 gcgaaaaagagggttcttgaacctctgggcctggttgaggaacctgttaagacggctccg
S1CM5     361 GCGAAAAAGAGGGTTCTTGAACCTCTGGGCCTGGTTGAGGAACCTGTTAAGACGGCTCCG
S2CM5     361 GCGAAAAAGAGGGTTCTTGAACCTCTGGGCCTGGTTGAGGAACCTGTTAAGACGGCTCCG
S2CM2     361 GCGAAAAAGAGGGTTCTTGAACCTCTGGGCCTGGTTGAGGAACCTGTTAAGACGGCTCCG
S3CM2     361 GCGAAAAAGAGGGTTCTTGAACCTCTGGGCCTGGTTGAGGAACCTGTTAAGACGGCTCCG
A1CM5     361 GCGAAAAAGAGGGTTCTTGAACCTCTGGGCCTGGTTGAGGAACCTGTTAAGACGGCTCCG
A3CM5     361 GCGAAAAAGAGGGTTCTTGAACCTCTGGGCCTGGTTGAGGAACCTGTTAAGACGGCTCCG
A1CM2     361 GCGAAAAAAGGGTTCTTGAACCTCTGGGCCTGGTTGAGGAACCTGTTACGACGGCTCCG
A2CM2     361 GCGAAAAAGAGGGTTCTTGAACCTCTGGGCCTGGTTGAGGAACCTGTTAAGACGGCTCCG
A3CM2     361 GCGAAAAAGAGGGTTCTTGAACCTCTGGGCCTGGTTGAGGAACCTGTTAAGACGGCTCCG 430        440        450        460        470        480
              ....|....|....|....|....|....|....|....|....|....|....|....|
AAV2 VP1  421 ggaaaaaagaggccggtagagcactctcctgtggagccagactcctcctcgggaaccgga
S1CM5     421 GGAAAAAAGAGGCCGGTAGAGCACTCTCCTGTGGAGCCAGACTCCTCCTCGGGAACCGGA
S2CM5     421 GGAAAAAAGAGGCCGGTAGAGCACTCTCCTGTGGAGCCAGACTCCTCCTCGGGAACCGGA
S2CM2     421 GGAAAAAAGAGGCCGGTAGAGCACTCTCCTGTGGAGCCAGACTCCTCCTCGGGAACCGGA
S3CM2     421 GGAAAAAAGAGGCCGGTAGAGCACTCTCCTGTGGAGCCAGACTCCTCCTCGGGAACCGGA
A1CM5     421 GGAAAAAAGAGGCCGGTAGAGCACTCTCCTGTGGAGCCAGACTCCTCCTCGGGAACCGGA
A3CM5     421 GGAAAAAAGAGGCCGGTAGAGCACTCTCCTGTGGAGCCAGACTCCTCCTCGGGAACCGGA
A1CM2     421 GGAAAAAAGAGGCCGGTAGAGCACTCTCCTGTGGAGCCAGACTCCTCCTCGGGAACCGGA
A2CM2     421 GGAAAAAAGAGGCCGGTAGAGCACTCTCCTGTGGAGCCAGACTCCTCCTCGGGAACCGGA
A3CM2     421 GGAAAAAAGAGGCCGGTAGAGCACTCTCCTGTGGAGCCAGACTCCTCCTCGGGACCCGga
```

FIG. 6C

```
                     490        500        510        520        530        540
                ....|....|....|....|....|....|....|....|....|....|....|....|
AAV2 VP1   481  aaggcgggccagcagcctgcaagaaaaagattgaattttggtcagactggagacgcagac
S1CM5      481  AAGGCAGGCCAGCAGCCTGCAAGAAGAAGATTGAATTTTGGTCAGACTGGAGACGCAGAC
S2CM5      481  AaGGCGGGCCAGCAGCCTGCAAGAAAAAGATTGAATTTTGGTCAGACTGGAGACGCAGAC
S2CM2      481  AAGGCGGGCCAGCAGCCTGCAAGAAAAAGATTGAATTTTGGTCAGACTGGAGACGCAGAC
S3CM2      481  AAGGCGGGCCAGCAGCCTGCAAGAAAAAGATTGAATTTTGGTCAGACTGGAGACGCAGAC
A1CM5      481  AAGGCGGGCCAGCAGCCTGCAAGAAAAAGATTGAATTTTGGTCAGACTGGAGACGCAGAC
A3CM5      481  AAGGCGGGCCAGCAGCCTGCAAGAAAAAGATTGAATTTTGGTCAGACTGGAGACGCAGAC
A1CM2      481  AAGGCGGGCCAGCAGCCTGCAAGAAAAAGATTGAATTTTGGTCAGACTGGAGACGCAGAC
A2CM2      481  AAGGCGGGCCAGCAGCCTGCAAGAAAAAGATTGAATTTTGGTCAGACTGGAGACGCAGAC
A3CM2      481  aaggcgggccagcagcctgcaagaaaaagattgaattttggtcagactggagacgcagac 550        560        570        580        590        600
                ....|....|....|....|....|....|....|....|....|....|....|....|
AAV2 VP1   541  tcagtacctgaccccagcctctcggacagccaccagcagcccctctggtctgggaact
S1CM5      541  CCAGTACCTGACCCCCAGCCTCTCGGACAGCCACCAGCAGCCCCTCTGGTCTGGGAACT
S2CM5      541  TCAGTACCTGACCCCCAGCCTCTCGGACAGCCACCAGCAGCCCCTCTGGTCTGGGAACT
S2CM2      541  TCAGTACCTGACCCCCAGCCTCTCGAACAGCCACCAGCAGCCCCTCTGGTCTGGGAACT
S3CM2      541  TCAGTACCTGACCCCCAGCCTCTCGGACAGCCACCAGCAGCCCCTCTGGTCTGGGAACT
A1CM5      541  TCAGTACCTGACCCCCAGCCTCTCGGACAGCCACCAGCAGCCCCTCTGGTCTGGGAACT
A3CM5      541  TCAGTACCTGACCCCCAGCCTCTCGGACAGCCACCAGCAGCCCCCTGGTCTGGGAACT
A1CM2      541  TCAGTACCTGACCCCCTGCCTCTCGGACAGCCACCAGCAGCCCCTCTGGTCTGGGAACT
A2CM2      541  TCAGTACCTGACCCCCAGCCTCTCGGACAGCCACCAGCAGCCCCCCTGGTCTGGGAACT
A3CM2      541  tcagtacctgaccccagcctctcggacagccaccagcagcccctctggtctgggaact 610        620        630        640        650        660
                ....|....|....|....|....|....|....|....|....|....|....|....|
AAV2 VP1   601  aatacgatggctacaggcagtggcgcaccaatggcagacaataacgagggcgccgacgga
S1CM5      601  AATACGATGGCTACGGCAGTGGCGCACCAATGGCAGACAATAACGAGGGCGCCGACGGA
S2CM5      601  AATACGATGGCTACAGGCAGTGGCGCACCAATGGCAGACAATAACGAGGGCGCCGACGGA
S2CM2      601  AATACGATGGCTACAGGCAGTGGCGCACCAATGGCAGACAATATCGAGGGCGCCGACGGA
S3CM2      601  AATACGATGGCTACAGGCAGTGGCGCACCAATGGCAGACAATAACGAGGGCGCCGACGGA
A1CM5      601  AATACGATGGCTACAGGCAGTGGCGCACCAATGGCAGACAATGACGAGGGCGCCGACGGA
A3CM5      601  AATACGATGGCTACAGGCAGTGGCGCACCAATGGCAGACAATAACGAGGGCGCCGACGGA
A1CM2      601  AATACGATGGCTACAGGCAGTGGCGCACCAATGGCAGACAATAACGAGGGCGCCGACGGA
A2CM2      601  AATACGATGGCTACAGGCAGTGGCGCACCAATGGCAGACAATAACGAGGGCGCCGACGGA
A3CM2      601  aatacgatggctacaggcagtggcgcaccaatggcagacaataacgagggcgccgacgga 670        680        690        700        710        720
                ....|....|....|....|....|....|....|....|....|....|....|....|
AAV2 VP1   661  gtgggtaattcctcgggaaattggcattgcgattccacatggatgggcgacagagtcatc
S1CM5      661  GTGGGTAATTCCTCGGGAAATTGGCATTGCGATTCCACATGGATGGGCGACAGAGTCATC
S2CM5      661  GTGGGTAATTCCTCGGGAAATTGGCATTGCGATTCCACATGGATGGGCGACAGAGTCATC
S2CM2      661  GTGGGTAATTCCTCGGGAAATTGGCATTGCGATTCCACATGGATGGGCGACAGAGTCATC
S3CM2      661  GTGGGTAATTCCTCGGGAAATTGGCATTGCGATTCCACATGGATGGGCGACAGAGTCATC
A1CM5      661  GTGGGTAATTCCTCGGGAAATTGGCATTGCGATTCCACATGGATGGGCGACAGAGTCATC
A3CM5      661  GTGGGTAATTCCTCGGGAAATTGGCATTGCGATTCCACATGGATGGGCGACAGAGTCATC
A1CM2      661  GTGGGTAATTCCTCGGGAAATTGGCATTGCGATTCCACATGGATGGGCGACAGAGTCATC
A2CM2      661  GTGGGTAATTCCTCGGGAAATTGGCATTGCGATTCCACATGGATGGGCGACAGAGTCATC
A3CM2      661  gtgggtaattcctcgggaaattggcattgcgattccacatggatgggcgacagagtcatc
```

FIG. 6D

```
                    730        740        750        760        770        780
                ....|....|....|....|....|....|....|....|....|....|....|....|
AAV2 VP1   721  accaccagcacccgaacctgggccctgcccacctacaacaaccacctctacaaacaaatt
S1CM5      721  ACCACCAGCACCCGAACCTGGGCCCTGCCCACCTACAACAACCACCTCTACAAACAAATT
S2CM5      721  ACCACCAGCACCCGAACCTGGGCCCTGCCCACCTACAACAACCACCTCTACAAACAAATT
S2CM2      721  ACCACCAGCACCCGAACCTGGGCCCTGCCCACCTACAACAACCACCTCTACAAACAAATT
S3CM2      721  ACCACCAGCACCCGAACCTGGGCCCTGCCCACCTACAACAACCACCTCTACAAACAAATT
A1CM5      721  ACCACCAGCACCCGAACCTGGGCCCTGCCCACCTACAACAACCACCTCTACAAGCAAATT
A3CM5      721  ACCACCAGCACCCGAACCTGGGCCCTGCCCACCTACAACAACCACCTCTACAAACAAATT
A1CM2      721  ACCACCAGCACCCGAACCTGGGCCCTGCCCGCCTACAACAACCACCTCTACAAACAAATT
A2CM2      721  ACCACCAGCACCCGAACCTGGGCCCTGCCCACCTACAACAACCACCTCTACAAACAAATT
A3CM2      721  accaCCaGCaCCCGaACCTGGGCCCTGCCCACCTACAACAACCACCTCTACAAACAAACT

790        800        810        820        830        840
                ....|....|....|....|....|....|....|....|....|....|....|....|
AAV2 VP1   781  tccagccaatcaggagcctcgaacgacaatcactactttggctacagcacccccttggggg
S1CM5      781  TCCAGCCAATCAGGAGCCTCGAACGACAATCACTACTTTGGCTACAGCACCCCTTGGGGG
S2CM5      781  TCCAGCCAATCAGGAGCCTCGAACGACAATCACTACTTTGGCTACAGCACCCCTTGGGGG
S2CM2      781  TCCAGCCAATCAGGAGCCTCGAACGACAATCACTACTTTGGCTACAGCACCCCTTGGGGG
S3CM2      781  TCCAGCCAATCAGGAGCCTCGAACGACAATCACTACTTTGGCTACAGCACCCCTTGGGGG
A1CM5      781  TCCAGCCAATCAGGAGCCTCGAACGACAATCACTACTTTGGCTACAGCACCCCTTGGGGG
A3CM5      781  TCCAGCCAATCAGGAGCCTCGAACGACAATCACTACTTTGGCTACAGCACCCCTTGGGGG
A1CM2      781  TCCAGCCAATCAGGAGCCTCGAACGACAATCACTACTTTGGCTACAGCACCCCTTGGGGG
A2CM2      781  TCCAGCCAATCAGGAGCCTCGAACGACAATCACTACTTTGGCTACAGCACCCCTTGGGGG
A3CM2      781  TCCAGCCAATCAGGAGCCTCGAACGACAATCACTACTTTGGCTACAGCACCCCTTGGGGG 850        860        870        880        890        900
                ....|....|....|....|....|....|....|....|....|....|....|....|
AAV2 VP1   841  tattttgacttcaacagattccactgccacttttcaccacgtgactggcaaagactcatc
S1CM5      841  TATTTTGACTTCAACAGATTCCACTGCCACTTTTCACCACGTGACTGGCAAAGACTCATC
S2CM5      841  TATTTTGACTTCAACAGATTCCACTGCCACTTTTCACCACGTGACTGGCAAAGACTCATC
S2CM2      841  TATTTTGACTTCAACAGATTCCACTGCCACTTTTCACCACGTGACTGGCAAAGACTCATC
S3CM2      841  TATTTTGACTTCAACAGATTCCACTGCCACTTTTCACCACGTGACTGGCAAAGACTCATC
A1CM5      841  TATTTTGACTTCAACAGATTCCACTGCCACTTTTCACCACGTGACTGGCAAAGACTCATC
A3CM5      841  TATTTTGACTTCAACAGATTCCACTGCCACTTTTCACCACGTGACTGGCAAAGACTCATC
A1CM2      841  TATTTTGACTTCAACAGATTCCACTGCCTCTTTTCACCACGTGACTGGCAAAGACTCATC
A2CM2      841  TATTTTGACTTCAACAGATTCCACTGCCACTTTTCACCACGTGACTGGCAAAGACTCATC
A3CM2      841  TATTTTGACTTCAACAGGTTCCACTGCCACTTTTCACCACGTGACTGGCAAAGACTCATC 910        920        930        940        950        960
                ....|....|....|....|....|....|....|....|....|....|....|....|
AAV2 VP1   901  aacaacaactggggattccgacccaagagactcaacttcaagctctttaacattcaagtc
S1CM5      901  AACAACAACTGGGGATTCCGACCCAAGAGACTCAACTTCAAGCTCTTTAACATTCAAGTC
S2CM5      901  AACAACAACTGGGGATTCCGACCCAAGAGACTCAACTTCAAGCTCTTTAACATTCAAGTC
S2CM2      901  AACAACAACTGGGGATTCCGACCCAAGAGACTCAACTTCAAGCTCTTTAACATTCAAGTC
S3CM2      901  AACAACAACTGGGGATTCCGACCCAAGAGACTCAACTTCAAGCTCTTTAACATTCAAGTC
A1CM5      901  AACAACAACTGGGGATTCCGACCCAAGAGACTCAACTTCAAGCTCTTTAACATTCAAGTC
A3CM5      901  AACAACAACTGGGGATTCCGACCCAAGAGACTCAACTTCAAGCTCTTTAACATTCAAGTC
A1CM2      901  AACAACAACTGGGGACTCCGACCCAAGAGACTCAACTTCAAGCTCTTTAACATTCAAGTC
A2CM2      901  AACAACAACTGGGGATTCCGACCCAAGAGACTCAACTTCAAGCTCTTTAACATTCAAGTC
A3CM2      901  AACAACAACTGGGGATTCCGACCCAAGAGACTCAACTTCAAGCTCTTTAACATTCAAGTC
```

FIG. 6E

```
              970       980       990      1000      1010      1020
         ....|....|....|....|....|....|....|....|....|....|....|....|
AAV2 VP1  961 aaagaggtcacgcagaatgacggtacgacgacgattgccaataaccttaccagcacggtt
S1CM5     961 AAAGAGGTCACGCAGAATGACGGTACGACGACGATTGTCAATAACCTTACCAGCACGGTT
S2CM5     961 AAAGAGGTCACGCAGAATGACGGTACGACGACGATTGTCAATAACCTTACCAGCACGGTT
S2CM2     961 AAAGAGGTCACGCAGAATGACGGTACGACGACGATTGCCAATAACCTTACCAGCACGGTT
S3CM2     961 AAAGAGGTCACGCAGAATGACGGTACGACGACGATTGCCAATAACCTTACCAGCACGGTT
A1CM5     961 AAAGAGGTCACGCAGAATGACGGTACGACGACGATTGCCAATAACCTTACCAGCACGGTT
A3CM5     961 AAAGAGGTCACGCAGAATGACGGTACGACGACGATTGCCAATAACCTTCCAGCACGGTA
A1CM2     961 AAAGAGGTCACGCAGAATGACGGTACGACGACGATTGCCAATAACCTTACCAGCACGGTT
A2CM2     961 AAAGAGGTCACGCAGAATGACGGTACGACGACGATTGCCAATAACCTTACCAGCACGGTT
A3CM2     961 AAAGAGGTCACGCAGAATGACGGTACGACGACGATTGCCAATAACCTTACCAGCACGGTT 1030      1040      1050      1060      1070      1080
         ....|....|....|....|....|....|....|....|....|....|....|....|
AAV2 VP1 1021 caggtgtttactgactcggagtaccagctcccgtacgtcctcggctcggcgcatcaagga
S1CM5    1021 CAGGTGTTTACTGACTCGGAGTACCAGCTCCCGTACGTCCTCGGCTCGGCGCATCAAGGA
S2CM5    1021 CAGGTGTTTACTGACTCGGAGTACCAGCTCCCGTACGTTCTCGGCTCGGCGCATCAAGGA
S2CM2    1021 CAGGTGTTTACTGACTCGGAGTACCAGCTCCCGTACGTCCTCGGCTCGGCGCATCAAGGA
S3CM2    1021 CAGGTGTTTACTGACTCGGTGTACCAGCTCCCGTACGTCCTCGGCTCGGCGCATCAAGGA
A1CM5    1021 CAGGTGTTTACTGACTCGGAGTACCAGCTCCCGTACGTCCTAGCTCGGCGCATCAAGGA
A3CM5    1021 CAGGTGTTTACTGACTCGGAGTACCAGCTCCCGTACGTCCTCGGCTCGGCGCATCAAGGA
A1CM2    1021 CAGGTGTTTACTGACTCGGAGTACCAGCTCCCGTACGTCCTCGGCTCGGCGCATCAAGGA
A2CM2    1021 CAGGTGTTTACTGACTCGGAGTACCAGCTCCCGTACGTCCTCGGCTCGGCGCATCAAGGA
A3CM2    1021 CAGGTGTTTACTGACTCGGAGTACCAGCTCCCGTACGTCCTCGGCTCGGCGCATCAAGGA 1090      1100      1110      1120      1130      1140
         ....|....|....|....|....|....|....|....|....|....|....|....|
AAV2 VP1 1081 tgcctcccgccgttcccagcagacgtcttcatggtgccacagtatggatacctcaccctg
S1CM5    1081 TGCCTCACGCCGTTCCCAGCAGACGTCTTCATGGTGCCACAGTATGGATACCTCACCCTG
S2CM5    1081 TGCCTCCCGCCGTTCCCAGCAGACGCCTTCATGGTGCCACAGTATGGATACCTCACCCTG
S2CM2    1081 TGCCTCCCGCCGTTCCCAGAAGACGTCTTCATGGTGCCACAGTATGGATACCTCACCCTG
S3CM2    1081 TGCCTCCCGCCGTTCCCAGCGGACGTCTTCATGGTGCCACAGTATGGATACCTCACCCTG
A1CM5    1081 TGCCTCCCGCCGTTCCCAGCAGACGTCTTCATGGTGCCACAGTATGGATACCTCACCCTG
A3CM5    1081 TGCCTCCCGCCGTTCCCAGCAGACGTCTTCATGGTGCCACAGTATGGATACCTCACCCTG
A1CM2    1081 TGCCTCCCGCCGTTCCCAGCAGACGTCTTCATGGTGCCACAGTATGGATACCTCACCCTG
A2CM2    1081 TGCCTCCCGCCGTTCCCAGCAGACGTCTTCATGGTGCCACAGTATGGATACCTCACCCTG
A3CM2    1081 TGCCTCCCGCCGTTCCCAGCAGACGTCTTCATGGTGCCACAGTATGGATACCTCACCCTG 1150      1160      1170      1180      1190      1200
         ....|....|....|....|....|....|....|....|....|....|....|....|
AAV2 VP1 1141 aacaacgggagtcaggcagtaggacgctcttcattttactgcctggagtactttccttct
S1CM5    1141 AACAACGGGAGTCAGGCAGTAGGACGCTCTTCATTTTACTGCCTGGAGTACTTTCCTTCT
S2CM5    1141 AACAACGGGAGTCAGGCAGTAGGACGCTCTTCATTTTACTGCCTGGAGTACTTTCCTTCT
S2CM2    1141 AACAACGGGAGTCAGGCAGTAGGACGCTCTTCATTTTACTGCCTGGAGTACTTTCCTCT
S3CM2    1141 AACAACGGGAGTCAGGCAGTAGGACGCTCTTCATTTTACTGCCTGGAGTACTTTCCTTCT
A1CM5    1141 AACAACGGGAGTCAGGCAGTAGGACGCTCTTCATTTTACTGCCTGGAGTACTTTCCTTCT
A3CM5    1141 AACAACGGGAGTCAGGCAGTAGGACGCTCTTCATTTTACTGCCTGGAGTACTTTCCTTCT
A1CM2    1141 AACAACGGGAGTCAGGCAGTAGGACGCACTTCATTTTACTGCCTGGAGTACTTTCCTTCT
A2CM2    1141 AACAACGGGAGTCAGGCAGTAGGACGCTCTTCATTTTACTGCCTGGAGTACTTTCCTTCT
A3CM2    1141 AACAACGGGAGTCAGGCAGTAGGACGCTCTTCATTTTACTGCCTGGAGTACTTTCCTTCT
```

FIG. 6F

```
                      1210       1220       1230       1240       1250       1260
                 ....|....|....|....|....|....|....|....|....|....|....|....|
AAV2 VP1    1201 cagatgctgcgtaccggaaacaactttaccttcagctacacttttgaggacgttcctttc
S1CM5       1201 CAGATGCTGCGTACCGGAAACAACTTTACCTTCAGCTACACTTTTGAGGACGTTCCTTTC
S2CM5       1201 CAGATGCTGCGTACCGGAAACAACTTTACCTTCAGCTACACTTTTGAGGACGTTCCTTTC
S2CM2       1201 CAGATGCTGCGTACCGGAAACAACTTTACCTTCAGCTACACTTTTGAGGACGTTCCTTTC
S3CM2       1201 CAGATGCTGCGTACCGGAAACAACTTTACCTTCAGCTACACTTTTGAGGACGTTCCTTTC
A1CM5       1201 CAGATGCTGCGTACCGGAAACAACTTTACCTTCAGCTACACTTTTGAGGACGTTCCTTTC
A3CM5       1201 CAGATGCTGCGTACCGGAAGCAACTTTACCTTCAGCTACACTTTTGAGGACGTTCCTTTC
A1CM2       1201 CAGATGCTGCGTACCGGAAACAACTTTACCTTCAGCTACACTTTTGAGGACGTTCCTTTC
A2CM2       1201 CAGATGCTACGTACCGGAAACAACTTTACCTTCAGCTACACTTTTGAGGACGTTCCTTTC
A3CM2       1201 CAGATGCTGCGTACCGGAAACAACTTTACCTTCAGCTACACTTTTGAGGACGTTCCTTTC 1270       1280       1290       1300       1310       1320
                 ....|....|....|....|....|....|....|....|....|....|....|....|
AAV2 VP1    1261 cacagcagctacgctcacagccagagtctggaccgtctcatgaatcctctcatcgaccag
S1CM5       1261 CACAGCAGCTACGCTCACAGCCAGAGTCTGGACCGTCTCATGAATCCTCTCATCGACCAG
S2CM5       1261 CACAGCAGCTACGCTCACAGCCAGAGTCTGGACCGTCTCATGAATCCTCTCATCGACCAG
S2CM2       1261 CACAGCAGCTACGCTCACAGCCAGGGTCTGGACCGTCTCATGAATCCTCTCATCGACCAG
S3CM2       1261 CACAGCAGCTACGCTCACAGCCAGAGTCTGGACCGTCTCATGAATCCTCTCATCGACCAG
A1CM5       1261 CACAGCAGCTACGCTCACAGCCAGAGTCTGGACCGTCTCATGAATCCTCTCATCGACCAG
A3CM5       1261 CACAGCAGCTACGCTCACAGCCAGAGTCTGGACCGTCTCATGAATCCTCTCATCGACCAG
A1CM2       1261 CACAGCAGCTACGCTCACAGCCAGAGTCTGGACCGTCTCATGAATCCTCTCATCGACCAG
A2CM2       1261 CACAGCAGCTACGCTCACAGCCAGAGTCTGGACCGTCTCATGAATCCTCTCATCGACCAG
A3CM2       1261 CACAGCAGCTACGCTCACAGCCAGAGTCTGGACCGTCTCATGAATCCTCTCATCGACCAG 1330       1340       1350       1360       1370       1380
                 ....|....|....|....|....|....|....|....|....|....|....|....|
AAV2 VP1    1321 tacctgtattacttgagcagaacaaacactccaagtggaaccaccacgcagtcaaggctt
S1CM5       1321 TACCTGTATTACTTGAGCAGAACAAACACTCCAAGTGGAACCACCACGCAGTCAAGGCTT
S2CM5       1321 TACCTGTATTACTTGAGCAGAACAAACACTCCAAGTGGAACCACCACGCAGTCAAGGCTT
S2CM2       1321 TACCTGTATTACTTGAGCAGAACAAACACTCCAAGTGGAACCACCACGCAGTCAAGGCTT
S3CM2       1321 TACCTGTATTACTTGAGCAGAACAAACACTCCAAGTGGAACCACCACGCAGTCAAGGCTT
A1CM5       1321 TACCTGTATTACTTGAGCAGAACAAACACTCCAAGTGGAACCACCACGCAGTCAAGGCTT
A3CM5       1321 TACCTGTATTACTTGAGCAGAACAAACACTCCAAGTGGAACCACCACGCAGTCAAGGCTT
A1CM2       1321 TACCTGTATTACTTGAGCAGAACAAACACTCCAAGTGGAACCACCACGCAGTCAAGGCTT
A2CM2       1321 TACCTGTATTACTTGAGCAGAACAAACACTCCAAGTGGAACCACCACGCAGTCAAGGCTT
A3CM2       1321 TACCTGTATTACTTGAGCAGAACAAACACTCCAAGTGGAACCACCACGCAGTCAGGGCTT 1390       1400       1410       1420       1430       1440
                 ....|....|....|....|....|....|....|....|....|....|....|....|
AAV2 VP1    1381 cagttttctcaggccggagcgagtgacattcgggaccagtctaggaactggcttcctgga
S1CM5       1381 CAGTTTTCTCAGGCCGGAGCGAGTGACATTCGGGACCAGTCTAGGAACTGGCTTCCTGGA
S2CM5       1381 CAGTTTTCTCAGGCCGGAGCGAGTGACATTCGGGACCAGTCTAGGAACTGGCTTCCTGGA
S2CM2       1381 CAGTTTTCTCAGGCCGGAGCGAGTGACATTCGGGACCAGTCTAGGAACTGGCTTCCTGGA
S3CM2       1381 CAGTTTTCTCAGGCCGGAGCGAGTGACATTCGGGACCAGTCTAGGAACTGGCTTCCTGGA
A1CM5       1381 CAGTTTTCTCAGGCCGGAGCGAGTGACATTCGGGACCAGTCTAGGAACTGGCTTCCTGGA
A3CM5       1381 CAGTTTTCTCAGGCCGGAGCGAGTGACATTCGGGACCAGTCTAGGAACTGGCTTCCTGGA
A1CM2       1381 CAGTTTTCTCAGGCCGGAGCGAGTGACATTCGGGACCAGTCTAGGAACTGGCTTCCTGGA
A2CM2       1381 CAGTTTTCTCAGGCCGGAGCGAGTGACATTCGGGACCAGTCTAGGAACTGGCTTCCTGGA
A3CM2       1381 CAGTTTTCTCAGGCCGGAGCGAGTGACATTCGGGACCAGTCTAGGAACTGGCTTCCTGGA
```

FIG. 6G

```
                    1450       1460       1470       1480       1490       1500
                ....|....|....|....|....|....|....|....|....|....|....|....|
AAV2 VP1   1441 ccctgttaccgccagcagcgagtatcaaagacatctgcggataacaacaacagtgaatac
S1CM5      1441 CCCTGTTACCGCCAGCAGCGAGTATCAAAGACATCTGAGGATAACAACAACAGTGAATAC
S2CM5      1441 CCCTGTTACCGCCAGCAGCGAGTATCAAAGACATCTGCGGATAACAACAACAGTGAATAC
S2CM2      1441 CCCTGTTACCGCCAGCAGCGAGTATCAAAGACATCTGAGGATAACAACAACAGTGAATAC
S3CM2      1441 CCCTGTTACCGCCAGCAGCGAGTATCAAAGACATCTGAGGATAACAACAACAGTGAATAC
A1CM5      1441 CCCTGTTACCGCCAGCAGCGAGTATCAAAGACATCTGCGGATAACAACAACAGTGAATAC
A3CM5      1441 CCCTGTTACCGCCAGCAGCGAGTATCAAAGACATCTGAGGATAACAACAACAGTGAATAC
A1CM2      1441 CCCTGTTACCGCCAGCAGCGAGTATCAAAGACATCTGAGGATAACAACAACAGTGAATAC
A2CM2      1441 CCCTGTTACCGCCAGCAGCGAGTATCAAAGACATCTGCGGATAACAACAACAGTGAATAC
A3CM2      1441 CCCTGTTACCGCCAGCAGCGAGTATCAAAGACATCTGCGGATAACAACAACAGTGAATAC 1510       1520       1530       1540       1550       1560
                ....|....|....|....|....|....|....|....|....|....|....|....|
AAV2 VP1   1501 tcgtggactggagctaccaagtaccacctcaatggcagagactctctggtgaatccgggc
S1CM5      1501 TCGTGGACTGGAGCTACCAAGTACCACCTCAATGGCAGAGACTCTCTGGTGAATCCGGGC
S2CM5      1501 TCGTGGACTGGAGCTACCAAGTACCACCTCAATGGCAGAGACTCTCTGGTGAATCCGGGC
S2CM2      1501 TCGTGGACTGGAGCTACCAAGTACCACCTCAATGGCAGAGACTCTCTGGTGAATCCGGGC
S3CM2      1501 TCGTGGACTGGAGCTACCAAGTACCACCTCAATGGCAGAGACTCTCTGGTGAATCCGGGC
A1CM5      1501 TCGTGGACTGGAGCTACCAAGTACCACCTCAATGGCAGAGACTCTCTGGTGAATCCGGGC
A3CM5      1501 TCGTGGACTGGAGCTACCAAGTACCACCTCAATGGCAGAGACTCTCTGGTGAATCCGGGC
A1CM2      1501 TCGTGGACTGGAGTTACCAAGTACCACCTCAATGGCAGAGACTCTCTGGTGAATCCGGGC
A2CM2      1501 TCGTGGACTGGAGCTACCAAGTACCACCTCAATGGCAGAGACTCTCTGGTGAATCCGGGC
A3CM2      1501 TCGTGGACTGGAGCTACCAAGTACCACCTCAATGGCAGAGACTCTCTGGTGAATCCGGGC 1570       1580       1590       1600       1610       1620
                ....|....|....|....|....|....|....|....|....|....|....|....|
AAV2 VP1   1561 ccggccatggcaagccacaaggacgatgaagaaaagtttttcctcagagcggggttctc
S1CM5      1561 CCGGCCATGGCAAGCCACAAGGACGATGAAGAAAAGTTTTTTCCTCAGAGCGGGGTTCTC
S2CM5      1561 CCGGCCATGGCAAGCCACAAGGACGATGAAGAAAAGTTTTTTCCTCAGAGCGGGGTTCTC
S2CM2      1561 CCGGCCATGGCAAGCCACAAGGACGATGAAGAAAAGTTTTTTCCTCAGAGCGGGGTTCTC
S3CM2      1561 CCGGCCATGGCAAGCCACAAGGACGATGAAGAAAAGTTTTTTCCTCAGAGCGGGGTTCTC
A1CM5      1561 CCGGCCATGGCAAGCCACAAGGACGATGAAGAAAAGTTTTTTCCTCAGAGCGGGGTTCTC
A3CM5      1561 CCGGCCATGGCAAGCCACAAGGACGATGAAGAAAAGTTTTTTCCTCAGAGCGGGGTTCTC
A1CM2      1561 CCGGCCATGGCAAGCCACAAGGACGATGAAGAAAAGTTTTTTCCTCAGAGCGGGGTTCTC
A2CM2      1561 CCGGCCATGGCAAGCCACAAGGACGATGAAGAAAAGTTTTTTCCTCAGAGCGGGGTTCTC
A3CM2      1561 CCGACCATGGCAAGCCACAAGGACGATGAAGAAAAGTTTTTTCCTCAGAGCGGGGTTCTC 1630       1640       1650       1660       1670       1680
                ....|....|....|....|....|....|....|....|....|....|....|....|
AAV2 VP1   1621 atctttgggaagcaaggctcagagaaaacaaatgtggacattgaaaaggtcatgattaca
S1CM5      1621 ATCTTTGGGAAGCAAGGCTCAGAGAAAACAAATGTGGACATTGAAAAGGTCATGATTACA
S2CM5      1621 ATCTTTGGGAAGCAAGGCTCAGAGAAAACAAATGTGGACATTGAAAAGGTCATGATTACA
S2CM2      1621 ATCTTTGGGAAGCAAGGCTCAGAGAAAACAAATGTGGACATTGAAAAGGTCATGATTACA
S3CM2      1621 ATCTTTGGGAAGCAAGGCTCAGAGAAAACAGATGTGGACATTGAAAAGGTCATGATTACA
A1CM5      1621 ATCTTTGGGAAGCAAGGCTCAGAGAAAACAAATGTGGACATTGAAAAGGTCATGATTACA
A3CM5      1621 ATCTTGGGAAGCAAGGCTCAGAGAAAACAAATGTGGACATTGAAAAGGTCATGATTACA
A1CM2      1621 ATCTTTGGGAAGCAAGGCTCAGAGAAAACAAATGTGGACATTGAAAAGATCATGATTACA
A2CM2      1621 ATCTTTGGGAAGCAAGGCTCAGAGAAAACAAATGTGGACATTGAAAAGGTCATGATTACA
A3CM2      1621 ATCTTTGGGAAGCAAGGCTCAGAGAAAACAAATGTGGACATTGAAAAGGTCATGATTACA
```

FIG. 6H

```
              1690       1700       1710       1720       1730       1740
              ....|....|....|....|....|....|....|....|....|....|....|....|
AAV2 VP1 1681 gacgaagaggaaatcaggacaaccaatcccgtggctacggagcagtatggttctgtatct
S1CM5    1681 GACGAAGAGGAAATCAGGACAACCAATCCCGTGGCTACGGAGCAGTATGGTTCTGTATCT
S2CM5    1681 GACGAAGAGGAAATCAGGACAACCAATCCCGTGGCTACGGAGCAGTATGGTTCTGTATCT
S2CM2    1681 GACGAAGAGGAAATCAGGACAACCAATCCCGTGGCTACGGAGCAGTATGGTTCTGTACCT
S3CM2    1681 GACGAAGAGGAAATCAGGACAACCAATCCCGTGGCTACGGAGCAGTATGGTTCTGTATCT
A1CM5    1681 GACGAAGAGGAAATCAGGACAACCAATCCCGTGGCTACGGAGCAGTATGGTTCTGTATCT
A3CM5    1681 GACGAAGAGGAAATCAGGACAACCAATCCCGTGGCTACGGAGCAGTATGGTTCTGTATCT
A1CM2    1681 GACGAAGAGGAAATCAGGACAACCAATCCCGTGGCTACGGAGCAGTATGGTTCTGTATCT
A2CM2    1681 GACGAAGAGGAAATCAGGACAACCAATCCCGTGGCTACGGAGCAGTATGGTTCTGTATCT
A3CM2    1681 GACGAAGAGGAAATCAGGACAACCAATCCCGTGGCTACGGAGCAGTATGGTTCTGTGTCT 1750       1760       1770       1780       1790       1800
              ....|....|....|....|....|....|....|....|....|....|....|....|
AAV2 VP1 1741 accaacctccagagaggcaacagacaagcagctaccgcagatgtcaacacacaaggcgtt
S1CM5    1741 ACCAACCTCCAGAGGGGCAACAGGCAAGCAGCTACCGCAGATGTCAACACACAAGGCGTT
S2CM5    1741 ACCAACCTCCAGAGAGGCAACAGACAAGCAGCTACCGAAGATGTCAACACTCAAGGCGTT
S2CM2    1741 ACCAACCTCCAGAGAGGCAACAGACAAGCAGCTACCGCAGATGTCAACACACAAGGCGTT
S3CM2    1741 ACCAACCTCCAGAGAGGCAACAGACAAGCAGCTACCGCAGAGGTCAACACACAAGGCGTT
A1CM5    1741 ACCAACCTCCAGAGAGGCAACAGACAAGCAGCTACCGAAGATGTCAACACTCAAGGCGTT
A3CM5    1741 ACCAACCTCCAGAGAGGCAACAGACAAGCAGCTACCGCAGATGTCAACACACAAGGCGTT
A1CM2    1741 ACCAACCTCCAGAGAGGCAACAGACAAGCAGCTACCGCAGATGTCAACACACAAGGCGTT
A2CM2    1741 ACCAACCTCCAGAGAGGCAACAGACAAGCAGCTACCGAAGATGTCAACACTCAAGGCGTT
A3CM2    1741 ACCAACCTCCAGAGAGGCAACAGACAAGCAGCTACCGCAGATGTCAACACACAAGGCGTT 1810       1820       1830       1840       1850       1860
              ....|....|....|....|....|....|....|....|....|....|....|....|
AAV2 VP1 1801 cttccaggcatggtctggcaggacagagatgtgtaccttcaggggcccatctgggcaaag
S1CM5    1801 CTTCCAGGCATGGTCTGGCAGGACAGAGATGTGTACCTTCAGGGGCCCATCTGGGCAAAG
S2CM5    1801 CTTCCAGGCATGGTCTGGCAGGACAGAGATGTGTACCTTCAGGGGCCCATCTGGGCAAAG
S2CM2    1801 CTTCCAGGCATGGTCTGGCAGGACAGAGATGTGTACCTTCAGGGGCCCATCTGGGCAAAG
S3CM2    1801 CTTCCAGGCATGGTCTGGCAGGACAGAGATGTGTACCTTCAGGGGCCCATCTGGGCAAAG
A1CM5    1801 CTTCCAGGCATGGTCTGGCAGGACAGAGATGTGTACCTTCAGGGGCCCATCTGGGCAAAG
A3CM5    1801 CTTCCAGGCATGGTCTGGCAGGACAGAGATGTGTACCTTCAGGGGCCCATCTGGGCAAAG
A1CM2    1801 CTTCCAGGCATGGTCTGGCAGGACAGAGATGTGTACCTTCAGGGGCCCATCTGGGCAAAG
A2CM2    1801 CTTCCAGGCATGGTCTGGCAGGACAGAGATGTGTACCTTCAGGGGCCCATCTGGGCAAAG
A3CM2    1801 CTTCCAGGCATGGTCTGGCAGGACAGAGATGTGTACCTTCAGGGGCCCATCTGGGCAAAG 1870       1880       1890       1900       1910       1920
              ....|....|....|....|....|....|....|....|....|....|....|....|
AAV2 VP1 1861 attccacacacggacggacattttcaccccctctcccctcatgggtggattcggacttaaa
S1CM5    1861 ATTCCACACACGGACGGACATTTTCACCCCTCTCCCCTCATGGGTGGATTCGGACTTAAA
S2CM5    1861 ATTCCACACACGGACGGACATTTTCACCCCTCTCCCCTCATGGGTGGATTCGGACTTAAA
S2CM2    1861 ATTCCACACACGGACGGACATTTTCACCCCTCTCCCCTCATGGGTGGATTCGGACTTAAA
S3CM2    1861 ATTCCACACACGGACGGACATTTTCACCCCTCTCCCCTCATGGGTGGATTCGGACTTAAA
A1CM5    1861 ATTCCACACACGGACGGACATTTTCACCCCTCTCCCCTCATGGGTGGATTCGGACTTAAA
A3CM5    1861 ATTCCACACACGGACGGACATTTTCACCCCTCTCCCCTCATGGGTGGATTCGGACTTAAA
A1CM2    1861 ATTCCACACACGGACGGACATTTTCACCCCTCTCCCCTCATGGGTGGATTCGGACTTAAA
A2CM2    1861 ATTCCACACACGGACGGACATTTTCACCCCTCTCCCCTCATGGGTGGATTCGGACTTAAA
A3CM2    1861 ATTCCACACACGGACGGACATTTTCACCCCTCTCCCCTCATGGGTGGATTCGGACTTAAA
```

FIG. 6I

```
                        1930      1940      1950      1960      1970      1980
                   ....|....|....|....|....|....|....|....|....|....|....|....|
AAV2 VP1   1921    caccctcctccacagattctcatcaagaacaccccggtacctgcgaatccttcgaccacc
S1CM5      1921    CACCCTCCTCCACAGATTCTCATCAAGAACACCCCGGTACCTGCGAATCCTTCGACCACC
S2CM5      1921    CACCCTCCTCCACAGATTCTCATCAAGAACACCCCGGTACCTGCGAATCCTTCGACCACC
S2CM2      1921    CACCCTCTTCCACAGATTCTCATCAAGAACACCCCGGTACCTGCGAATCCTTCGACCACC
S3CM2      1921    CACCCTCCTCCACAGATTCTCATCAAGAACACCCCGGTACCTGCGAATCCTTCGACCACC
A1CM5      1921    CACCCTCCTCCACAGATTCTCATCAAGAACACCCCGGTACCTGCGAATCCTTCGACCACC
A3CM5      1921    CACCCTCCTCCACAGATTCTCATCAAGAACACCCCGGTACCTGCGAATCCTTCGACCACC
A1CM2      1921    CACCCTCCTCCACAGATTCTCATCAAGAACGCCCCGGTACCTGCGAATCCTTCGACCACC
A2CM2      1921    CACCCTCCTCCACAGATTCTCATCAAGAACACCCCGGTACCTGCGAATCCTTCGACCACC
A3CM2      1921    CACCCTCCTCCACAGATTCTCATCAAGAACACCCCGGTACCTGCGAATCCTTCGACCACC 1990      2000      2010      2020      2030      2040
                   ....|....|....|....|....|....|....|....|....|....|....|....|
AAV2 VP1   1981    ttcagtgcggcaaagtttgcttccttcatcacacagtactccacgggacaggtcagcgtg
S1CM5      1981    TTCAGTGCGGCAAAGTTTGCTTCCTTCATCACACAGTACTCCACGGGACAGGTCAGCGTG
S2CM5      1981    TTCAGTGCGGCAAAGTTTGCTTCCTTCATCACACAGTACTCCACGGGACAGGTCAGCGTG
S2CM2      1981    TTCAGTGCGGCAAAGTTTGCTTCCTTCATCACACAGTACTCCACGGGACAGGTCAGCGTG
S3CM2      1981    TTCAGTGCGGCAAAGTTTGCTTCCTTCATCACACAGTACTCCACGGGACAGGTCAGCGTG
A1CM5      1981    TTCAGTGCGGCAAAGTTTGCTTCCTTCATCACACAGTACTCCACGGGACAGGTCAGCGTG
A3CM5      1981    TTCAGTGCGGCAAAGTTTGCTTCCTTCATCACACAGTATTCCACGGGACAGGTCAGCGTG
A1CM2      1981    TTCAGTGCGGCAAAGTTTGCTTCCTTCATCACACAGTACTCCACGGGACAGGTCAGCGTG
A2CM2      1981    TTCAGTGCGGCAAAGTTTGCTTCCTTCATCACACAGTACTCCACGGGACAGGTCAGCGTG
A3CM2      1981    TTCAGTGTGGCAAAGTTTGCTTCCTTCATCACACAGTACTCCACGGGACAGGTCAGCGTG 2050      2060      2070      2080      2090      2100
                   ....|....|....|....|....|....|....|....|....|....|....|....|
AAV2 VP1   2041    gagatcgagtgggagctgcagaaggaaaacagcaaacgctggaatcccgaaattcagtac
S1CM5      2041    GAGATCGAGTGGGAGCTGCAGAAGGAAAACAGCAAACGCTGGAATCCCGAAATTCAGTAC
S2CM5      2041    GAGATCGAGTGGGAGCTACAGAAGGAAAACAGCAAACGCTGGAATCCCGAAATTCAGTAC
S2CM2      2041    GAGATCGAGTGGGTGCTGCAGAAAGAAAACAGCAAACGCTGGAATCCCGAAATTCAGTAC
S3CM2      2041    GAGATCGAGTGGGAGCTGCAGAAGGAAAACAGCAAACGCTGGAATCCCGAAATTCAGTAC
A1CM5      2041    GAGATCGAGTGGGAGCTACAGAAGGAAAACAGCAAACGCTGGAATCCCGAAATTCAGTAC
A3CM5      2041    GAGATCGAGTGGAAGCTGCAGAAGGAAAACAGCAAACGCTGGAATCCCGAAATTCAGTAC
A1CM2      2041    GAGATCGAGTGGGAGCTGCAGAAGGAAAACAGCAAACGCTGGAATCCCGAAATTCAGTAC
A2CM2      2041    GAGATCGAGTGGGAGCTGCAGAAGGAAAACAGCAAACGCTGGAATCCCGAAATTCAGTAC
A3CM2      2041    GGGATCGAGTGGGAGCTGCAGAAGGAAAACAGCAAACGCAGGAATCCCGAAATTCAGTAC 2110      2120      2130      2140      2150      2160
                   ....|....|....|....|....|....|....|....|....|....|....|....|
AAV2 VP1   2101    acttccaactacaacaagtctgttaatgtggactttactgtggacactaatggcgtgtat
S1CM5      2101    ACTTCCAACTACAACAAGTCTGTTAATGTGGACTTTACTGTGGACACTAATGGCGTGTAT
S2CM5      2101    ACTTCCAACTACAACAAGTCTGTTAATGTGGACTTTACTGTGGACACTAATGGCGTGTAT
S2CM2      2101    ACTTCCAACTACAACAAGTCTGTTAATGTGGACTTTACTGTGGACACTAATGGCGTGTAT
S3CM2      2101    ACTTCCAACTACAACAAGTCTGTTAATGTGGACTTTACTgtggacactaatggcgtgtat
A1CM5      2101    ACTTCCAACTACAACAAGTCTGTTAATGTGGACTTTACTGTGGACACTAATGGCGTGTAT
A3CM5      2101    ACTTCCAACTACAACAAGTCTGTTAATGTGGAGTTTACTGTGGACACTAATGGCGTGTAT
A1CM2      2101    ACTTCCAACTACAACAAGTCTGTTAATGTGGACTTTACTGTGGACACTAATGGCGTGTAT
A2CM2      2101    ACTTCTAACTACAACAAGTCTGTTAATGTGGACTTTACTGTGGACACTAATGGCGTGTAT
A3CM2      2101    ACTTCCAACTACAACAAGTCTGTTAATGTGGACTTTACTGTGGACACTAATGGCGTGTAT
```

FIG. 6J

```
             2170      2180      2190      2200
        ....|....|....|....|....|....|....|....|....|...
AAV2 VP1 2161 tcagagcctcgccccattggcaccagatacctgactcgtaatctgtaa (SEQ ID NO:4)
S1CM5    2161 TCAGAGCCTCGCCCCATTGGCACCAGATACCTGACTCGTAATCTGTAA (SEQ ID NO:16)
S2CM5    2161 TCAGAGCCTCGCCCCATTGGCACCAGATACCTGACTAGTAATCTGTAA (SEQ ID NO:18)
S2CM2    2161 TCAGAGCATCGCCCCATTGGCACCAGATACCTGACTCGTAATCTGTAA (SEQ ID NO:20)
S3CM2    2161 tcagagcctcgccccattggcaccagatacctgactcgtaatctgtaa (SEQ ID NO:22)
A1CM5    2161 TCAGAGCCTCGCCCCATTGGCACCAGATACCTGACTCGTAATCTGTAA (SEQ ID NO:24)
A3CM5    2161 TCAGAGCCTCGCCCCATTGGCACCAGATACCTGACTCGTAATCTGTAA (SEQ ID NO:26)
A1CM2    2161 TCAGAGCCTCGCCCCATTGGCACCAGATACCTGACTCGTAATCTGTAA (SEQ ID NO:28)
A2CM2    2161 TCAGAGCCTCGCCCCATTGGCACCAGATACCTGACTCGTAATCTGTAA (SEQ ID NO:30)
A3CM2    2161 TCAGAGCCTCGCCCCATTGGCACCAGATACCTGACTCGTAATCTGTAA (SEQ ID NO:32)
```

FIG. 7A

```
                  10         20         30         40         50         60
                   ....|....|....|....|....|....|....|....|....|....|....|....|
AAV2 VP1    1   MAADGYLPDWLEDTLSEGIRQWWKLKPGPPPPKPAERHKDDSRGLVLPGYKYLGPFNGLD
S1CM5       1   MAADGYLPDWLEDTLSEGIRQWWKLKPGPPPPKPAERHKDDSRGLVLPGYKYLGPFNGLD
S2CM5       1   MAADGYLPDWLEDTLSEGVRQWWKLKPGPPPPKPAERHKDDSRGLVLPGYKYLGPFNGLD
S2CM2       1   MAADGYLPDWLEDTLSEGIRQWWKLKPGPPPPKPAERHKDDSRGLVLPGYKYLGPFNGLD
S3CM2       1   MAADGYLPDWLEDTLSEGISQWWKLKPGPPPPKPAERHKDDSRGLVLPGYKYLGPFSGLD
A1CM5       1   MAADGYLPDWLEDTLSEGIRQWWKLRPGPPPPKPAERHKDDSRGLVLPGYKYLGPFNGLD
A3CM5       1   MAADGYLPDWLEDTLSEGIRQWWKLKPGPPPPKPAERHKDDSRGLVLPEYKYLGPFNGLD
A1CM2       1   MAADGYLPDWLEDTLSEGIRQWWELKPGPPPPKPAERHKDDSRGLVLPGYKYLGPFNGLD
A2CM2       1   MAADGYLPDWLEDTLSEGIRQWWKLKPGPPPPKPAERHKDDSRGLALPGYKYLGPFNGLD
A3CM2       1   MAADGYLPDWLEDTLSEGIRQWWKLKPGPPLPKPAERHKDDSRGLVLPGYKYLGPFNGLD 70         80         90        100        110        120
                   ....|....|....|....|....|....|....|....|....|....|....|....|
AAV2 VP1   61   KGEPVNEADAAALEHDKAYDRQLDSGDNPYLKYNHADAEFQERLKEDTSFGGNLGRAVFQ
S1CM5      61   KGEPVNEADAAALEHDKAYDRQLDSGDNPYLKYNHADAEFQERLKEDTSFGGNLGRAVFQ
S2CM5      61   KGEPVNEADAAALEHDKAYDRQLDSGDNPYLKYNHADAEFQERLKEDTSFGGNLGRAVFQ
S2CM2      61   KGEPVNEADAAALEHDKAYDRQLDSGDNPYLKYNHADAEFQERLKEDTSFGGNLGRAVFQ
S3CM2      61   KGEPVNEADAAALEHDKAYDRQLDSGDNPYLKYNHADAEFQERLKEDTSFGGNLGRAVFQ
A1CM5      61   KGEPVNEADAAALEHDKAYDRQLDSGDNPYLKYNHADAEFQERLKEDTSFGGNLGRAVFQ
A3CM5      61   KGEPVNEADAAALEHDKAYDRQLDSGDNPYLKYNHADAEFQERLKEDTSFGGNLGRAVFQ
A1CM2      61   KGEPVNEADAAALEHDKAYDRQLDSGDNPYPKYNHADAEFQERLKEDTSFGGNLGRAVFQ
A2CM2      61   KGEPVNEADAAALEHDKAYDRQLDSGDNPYLKYNHADAEFQERLKEDTSFGGNLGRAVFQ
A3CM2      61   KGEPVNEADAAALEHDKAYDRQLDSGDNPYLKYNHADAESQERLKEDTSFGGNLGRAVFQ 130        140        150        160        170        180
                   ....|....|....|....|....|....|....|....|....|....|....|....|
AAV2 VP1  121   AKKRVLEPLGLVEEPVKTAPGKKRPVEHSPVEPDSSSGTGKAGQQPARKRLNFGQTGDAD
S1CM5     121   AKKRVLEPLGLVEEPVKTAPGKKRPVEHSPVEPDSSSGTGKAGQQPARRRLNFGQTGDAD
S2CM5     121   AKKRVLEPLGLVEEPVKTAPGKKRPVEHSPVEPDSSSGTGKAGQQPARKRLNFGQTGDAD
S2CM2     121   AKKRVLEPLGLVEEPVKTAPGKKRPVEHSPVEPDSSSGTGKAGQQPARKRLNFGQTGDAD
S3CM2     121   AKKRVLEPLGLVEEPVKTAPGKKRPVEHSPVEPDSSSGTGKAGQQPARKRLNFGQTGDAD
A1CM5     121   AKKRVLEPLGLVEEPVKTAPGKKRPVEHSPVEPDSSSGTGKAGQQPARKRLNFGQTGDAD
A3CM5     121   AKKRVLEPLGLVEEPVKTAPGKKRPVEHSPVEPDSSSGTGKAGQQPARKRLNFGQTGDAD
A1CM2     121   AKKRVLEPLGLVEEPVTTAPGKKRPVEHSPVEPDSSSGTGKAGQQPARKRLNFGQTGDAD
A2CM2     121   AKKRVLEPLGLVEEPVKTAPGKKRPVEHSPVEPDSSSGTGKAGQQPARKRLNFGQTGDAD
A3CM2     121   AKKRVLEPLGLVEEPVKTAPGKKRPVEHSPVEPDSSSGPGKAGQQPARKRLNFGQTGDAD 190        200        210        220        230        240
                   ....|....|....|....|....|....|....|....|....|....|....|....|
AAV2 VP1  181   SVPDPQPLGQPPAAPSGLGTNTMATGSGAPMADNNEGADGVGNSSGNWHCDSTWMGDRVI
S1CM5     181   PVPDPQPLGQPPAAPSGLGTNTMATGSGAPMADNNEGADGVGNSSGNWHCDSTWMGDRVI
S2CM5     181   SVPDPQPLGQPPAAPSGLGTNTMATGSGAPMADNNEGADGVGNSSGNWHCDSTWMGDRVI
S2CM2     181   SVPDPQPLEQPPAAPSGLGTNTMATGSGAPMADNIEGADGVGNSSGNWHCDSTWMGDRVI
S3CM2     181   SVPDPQPLGQPPAAPSGLGTNTMATGSGAPMADNNEGADGVGNSSGNWHCDSTWMGDRVI
A1CM5     181   SVPDPQPLGQPPAAPSGLGTNTMATGSGAPMADNDEGADGVGNSSGNWHCDSTWMGDRVI
A3CM5     181   SVPDPQPLGQPPAAPPGLGTNTMATGSGAPMADNNEGADGVGNSSGNWHCDSTWMGDRVI
A1CM2     181   SVPDPLPLGQPPAAPSGLGTNTMATGSGAPMADNNEGADGVGNSSGNWHCDSTWMGDRVI
A2CM2     181   SVPDPQPLGQPPAAPPGLGTNTMATGSGAPMADNNEGADGVGNSSGNWHCDSTWMGDRVI
A3CM2     181   SVPDPQPLGQPPAAPSGLGTNTMATGSGAPMADNNEGADGVGNSSGNWHCDSTWMGDRVI
```

FIG. 7B

```
              250        260        270        280        290        300
         ....|....|....|....|....|....|....|....|....|....|....|....|
AAV2 VP1 241 TTSTRTWALPTYNNHLYKQISSQSGASNDNHYFGYSTPWGYFDFNRFHCHFSPRDWQRLI
S1CM5    241 TTSTRTWALPTYNNHLYKQISSQSGASNDNHYFGYSTPWGYFDFNRFHCHFSPRDWQRLI
S2CM5    241 TTSTRTWALPTYNNHLYKQISSQSGASNDNHYFGYSTPWGYFDFNRFHCHFSPRDWQRLI
S2CM2    241 TTSTRTWALPTYNNHLYKQISSQSGASNDNHYFGYSTPWGYFDFNRFHCHFSPRDWQRLI
S3CM2    241 TTSTRTWALPTYNNHLYKQISSQSGASNDNHYFGYSTPWGYFDFNRFHCHFSPRDWQRLI
A1CM5    241 TTSTRTWALPTYNNHLYKQISSQSGASNDNHYFGYSTPWGYFDFNRFHCHFSPRDWQRLI
A3CM5    241 TTSTRTWALPTYNNHLYKQISSQSGASNDNHYFGYSTPWGYFDFNRFHCHFSPRDWQRLI
A1CM2    241 TTSTRTWALPAYNNHLYKQISSQSGASNDNHYFGYSTPWGYFDFNRFHCLFSPRDWQRLI
A2CM2    241 TTSTRTWALPTYNNHLYKQISSQSGASNDNHYFGYSTPWGYFDFNRFHCHFSPRDWQRLI
A3CM2    241 TTSTRTWALPTYNNHLYKQTSSQSGASNDNHYFGYSTPWGYFDFNRFHCHFSPRDWQRLI 310        320        330        340        350        360
         ....|....|....|....|....|....|....|....|....|....|....|....|
AAV2 VP1 301 NNNWGFRPKRLNFKLFNIQVKEVTQNDGTTTIANNLTSTVQVFTDSEYQLPYVLGSAHQG
S1CM5    301 NNNWGFRPKRLNFKLFNIQVKEVTQNDGTTTIVNNLTSTVQVFTDSEYQLPYVLGSAHQG
S2CM5    301 NNNWGFRPKRLNFKLFNIQVKEVTQNDGTTTIANNLTSTVQVFTDSEYQLPYVLGSAHQG
S2CM2    301 NNNWGFRPKRLNFKLFNIQVKEVTQNDGTTTIANNLTSTVQVFTDSEYQLPYVLGSAHQG
S3CM2    301 NNNWGFRPKRLNFKLFNIQVKEVTQNDGTTTIANNLTSTVQVFTDSVYQLPYVLGSAHQG
A1CM5    301 NNNWGFRPKRLNFKLFNIQVKEVTQNDGTTTIANNLTSTVQVFTDSEYQLPYVLSSAHQG
A3CM5    301 NNNWGFRPKRLNFKLFNIQVKEVTQNDGTTTIANNLPSTVQVFTDSEYQLPYVLGSAHQG
A1CM2    301 NNNWGLRPKRLNFKLFNIQVKEVTQNDGTTTIANNLTSTVQVFTDSEYQLPYVLGSAHQG
A2CM2    301 NNNWGFRPKRLNFKLFNIQVKEVTQNDGTTTIANNLTSTVQVFTDSEYQLPYVLGSAHQG
A3CM2    301 NNNWGFRPKRLNFKLFNIQVKEVTQNDGTTTIANNLTSTVQVFTDSEYQLPYVLGSAHQG 370        380        390        400        410        420
         ....|....|....|....|....|....|....|....|....|....|....|....|
AAV2 VP1 361 CLPPFPADVFMVPQYGYLTLNNGSQAVGRSSFYCLEYFPSQMLRTGNNFTFSYTFEDVPF
S1CM5    361 CLTPFPADVFMVPQYGYLTLNNGSQAVGRSSFYCLEYFPSQMLRTGNNFTFSYTFEDVPF
S2CM5    361 CLPPFPADAFMVPQYGYLTLNNGSQAVGRSSFYCLEYFPSQMLRTGNNFTFSYTFEDVPF
S2CM2    361 CLPPFPEDVFMVPQYGYLTLNNGSQAVGRSSFYCLEYFPSQMLRTGNNFTFSYTFEDVPF
S3CM2    361 CLPPFPADVFMVPQYGYLTLNNGSQAVGRSSFYCLEYFPSQMLRTGNNFTFSYTFEDVPF
A1CM5    361 CLPPFPADVFMVPQYGYLTLNNGSQAVGRSSFYCLEYFPSQMLRTGNNFTFSYTFEDVPF
A3CM5    361 CLPPFPADVFMVPQYGYLTLNNGSQAVGRSSFYCLEYFPSQMLRTGSNFTFSYTFEDVPF
A1CM2    361 CLPPFPADVFMVPQYGYLTLNNGSQAVGRTSFYCLEYFPSQMLRTGNNFTFSYTFEDVPF
A2CM2    361 CLPPFPADVFMVPQYGYLTLNNGSQAVGRSSFYCLEYFPSQMLRTGNNFTFSYTFEDVPF
A3CM2    361 CLPPFPADVFMVPQYGYLTLNNGSQAVGRSSFYCLEYFPSQMLRTGNNFTFSYTFEDVPF 430        440        450        460        470        480
         ....|....|....|....|....|....|....|....|....|....|....|....|
AAV2 VP1 421 HSSYAHSQSLDRLMNPLIDQYLYYLSRTNTPSGTTTQSRLQFSQAGASDIRDQSRNWLPG
S1CM5    421 HSSYAHSQSLDRLMNPLIDQYLYYLSRTNTPSGTTTQSRLQFSQAGASDIRDQSRNWLPG
S2CM5    421 HSSYAHSQSLDRLMNPLIDQYLYYLSRTNTPSGTTTQSRLQFSQAGASDIRDQSRNWLPG
S2CM2    421 HSSYAHSQGLDRLMNPLIDQYLYYLSRTNTPSGTTTQSRLQFSQAGASDIRDQSRNWLPG
S3CM2    421 HSSYAHSQSLDRLMNPLIDQYLYYLSRTNTPSGTTTQSRLQFSQAGASDIRDQSRNWLPG
A1CM5    421 HSSYAHSQSLDRLMNPLIDQYLYYLSRTNTPSGTTTQSRLQFSQAGASDIRDQSRNWLPG
A3CM5    421 HSSYAHSQSLDRLMNPLIDQYLYYLSRTNTPSGTTTQSRLQFSQAGASDIRDQSRNWLPG
A1CM2    421 HSSYAHSQSLDRLMNPLIDQYLYYLSRTNTPSGTTTQSRLQFSQAGASDIRDQSRNWLPG
A2CM2    421 HSSYAHSQSLDRLMNPLIDQYLYYLSRTNTPSGTTTQSRLQFSQAGASDIRDQSRNWLPG
A3CM2    421 HSSYAHSQSLDRLMNPLIDQYLYYLSRTNTPSGTTTQSGLQFSQAGASDIRDQSRNWLPG
```

FIG. 7C

```
             490       500       510       520       530       540
          ....|....|....|....|....|....|....|....|....|....|....|....|
AAV2 VP1  481 PCYRQQRVSKTSADNNNSEYSWTGATKYHLNGRDSLVNPGPAMASHKDDEEKFFPQSGVL
S1CM5     481 PCYRQQRVSKTSEDNNNSEYSWTGATKYHLNGRDSLVNPGPAMASHKDDEEKFFPQSGVL
S2CM5     481 PCYRQQRVSKTSADNNNSEYSWTGATKYHLNGRDSLVNPGPAMASHKDDEEKFFPQSGVL
S2CM2     481 PCYRQQRVSKTSEDNNNSEYSWTGATKYHLNGRDSLVNPGPAMASHKDDEEKFFPQSGVL
S3CM2     481 PCYRQQRVSKTSEDNNNSEYSWTGATKYHLNGRDSLVNPGPAMASHKDDEEKFFPQSGVL
A1CM5     481 PCYRQQRVSKTSADNNNSEYSWTGATKYHLNGRDSLVNPGPAMASHKDDEEKFFPQSGVL
A3CM5     481 PCYRQQRVSKTSEDNNNSEYSWTGATKYHLNGRDSLVNPGPAMASHKDDEEKFFPQSGVL
A1CM2     481 PCYRQQRVSKTSEDNNNSEYSWTGVTKYHLNGRDSLVNPGPAMASHKDDEEKFFPQSGVL
A2CM2     481 PCYRQQRVSKTSADNNNSEYSWTGATKYHLNGRDSLVNPGPAMASHKDDEEKFFPQSGVL
A3CM2     481 PCYRQQRVSKTSADNNNSEYSWTGATKYHLNGRDSLVNPGPTMASHKDDEEKFFPQSGVL 550       560       570       580       590       600
          ....|....|....|....|....|....|....|....|....|....|....|....|
AAV2 VP1  541 IFGKQGSEKTNVDIEKVMITDEEEIRTTNPVATEQYGSVSTNLQRGNRQAATADVNTQGV
S1CM5     541 IFGKQGSEKTNVDIEKVMITDEEEIRTTNPVATEQYGSVSTNLQRGNRQAATADVNTQGV
S2CM5     541 IFGKQGSEKTNVDIEKVMITDEEEIRTTNPVATEQYGSVSTNLQRGNRQAATEDVNTQGV
S2CM2     541 IFGKQGSEKTNVDIEKVMITDEEEIRTTNPVATEQYGSVPTNLQRGNRQAATADVNTQGV
S3CM2     541 IFGKQGSEKTDVDIEKVMITDEEEIRTTNPVATEQYGSVSTNLQRGNRQAATAEVNTQGV
A1CM5     541 IFGKQGSEKTNVDIEKVMITDEEEIRTTNPVATEQYGSVSTNLQRGNRQAATEDVNTQGV
A3CM5     541 ILGKQGSEKTNVDIEKVMITDEEEIRTTNPVATEQYGSVSTNLQRGNRQAATADVNTQGV
A1CM2     541 IFGKQGSEKTNVDIEKIMITDEEEIRTTNPVATEQYGSVSTNLQRGNRQAATADVNTQGV
A2CM2     541 IFGKQGSEKTNVDIEKVMITDEEEIRTTNPVATEQYGSVSTNLQRGNRQAATEDVNTQGV
A3CM2     541 IFGKQGSEKTNVDIEKVMITDEEEIRTTNPVATEQYGSVSTNLQRGNRQAATADVNTQGV 610       620       630       640       650       660
          ....|....|....|....|....|....|....|....|....|....|....|....|
AAV2 VP1  601 LPGMVWQDRDVYLQGPIWAKIPHTDGHFHPSPLMGGFGLKHPPPQILIKNTPVPANPSTT
S1CM5     601 LPGMVWQDRDVYLQGPIWAKIPHTDGHFHPSPLMGGFGLKHPPPQILIKNTPVPANPSTT
S2CM5     601 LPGMVWQDRDVYLQGPIWAKIPHTDGHFHPSPLMGGFGLKHPPPQILIKNTPVPANPSTT
S2CM2     601 LPGMVWQDRDVYLQGPIWAKIPHTDGHFHPSPLMGGFGLKHPLPQILIKNTPVPANPSTT
S3CM2     601 LPGMVWQDRDVYLQGPIWAKIPHTDGHFHPSPLMGGFGLKHPPPQILIKNTPVPANPSTT
A1CM5     601 LPGMVWQDRDVYLQGPIWAKIPHTDGHFHPSPLMGGFGLKHPPPQILIKNTPVPANPSTT
A3CM5     601 LPGMVWQDRDVYLQGPIWAKIPHTDGHFHPSPLMGGFGLKHPPPQILIKNTPVPANPSTT
A1CM2     601 LPGMVWQDRDVYLQGPIWAKIPHTDGHFHPSPLMGGFGLKHPPPQILIKNAPVPANPSTT
A2CM2     601 LPGMVWQDRDVYLQGPIWAKIPHTDGHFHPSPLMGGFGLKHPPPQILIKNTPVPANPSTT
A3CM2     601 LPGMVWQDRDVYLQGPIWAKIPHTDGHFHPSPLMGGFGLKHPPPQILIKNTPVPANPSTT 670       680       690       700       710       720
          ....|....|....|....|....|....|....|....|....|....|....|....|
AAV2 VP1  661 FSAAKFASFITQYSTGQVSVEIEWELQKENSKRWNPEIQYTSNYNKSVNVDFTVDTNGVY
S1CM5     661 FSAAKFASFITQYSTGQVSVEIEWELQKENSKRWNPEIQYTSNYNKSVNVDFTVDTNGVY
S2CM5     661 FSAAKFASFITQYSTGQVSVEIEWELQKENSKRWNPEIQYTSNYNKSVNVDFTVDTNGVY
S2CM2     661 FSAAKFASFITQYSTGQVSVEIEWVLQKENSKRWNPEIQYTSNYNKSVNVDFTVDTNGVY
S3CM2     661 FSAAKFASFITQYSTGQVSVEIEWELQKENSKRWNPEIQYTSNYNKSVNVDFTVDTNGVY
A1CM5     661 FSAAKFASFITQYSTGQVSVEIEWELQKENSKRWNPEIQYTSNYNKSVNVDFTVDTNGVY
A3CM5     661 FSAAKFASFITQYSTGQVSVEIEWKLQKENSKRWNPEIQYTSNYNKSVNVEFTVDTNGVY
A1CM2     661 FSAAKFASFITQYSTGQVSVEIEWELQKENSKRWNPEIQYTSNYNKSVNVDFTVDTNGVY
A2CM2     661 FSAAKFASFITQYSTGQVSVEIEWELQKENSKRWNPEIQYTSNYNKSVNVDFTVDTNGVY
A3CM2     661 FSVAKFASFITQYSTGQVSVGIEWELQKENSKRRNPEIQYTSNYNKSVNVDFTVDTNGVY
```

FIG. 7D

```
                    730
               ....|....|....|.
AAV2 VP1   721 SEPRPIGTRYLTRNL* (SEQ ID NO:5)
S1CM5      721 SEPRPIGTRYLTRNL* (SEQ ID NO:17)
S2CM5      721 SEPRPIGTRYLTSNL* (SEQ ID NO:19)
S2CM2      721 SEHRPIGTRYLTRNL* (SEQ ID NO:21)
S3CM2      721 SEPRPIGTRYLTRNL* (SEQ ID NO:23)
A1CM5      721 SEPRPIGTRYLTRNL* (SEQ ID NO:25)
A3CM5      721 SEPRPIGTRYLTRNL* (SEQ ID NO:27)
A1CM2      721 SEPRPIGTRYLTRNL* (SEQ ID NO:29)
A2CM2      721 SEPRPIGTRYLTRNL* (SEQ ID NO:31)
A3CM2      721 SEPRPIGTRYLTRNL* (SEQ ID NO:33)
```

FIG. 8A

```
                     10         20         30         40         50         60
                ....|....|....|....|....|....|....|....|....|....|....|....|
AAV2 VP1    1   atggctgccgatggttatcttccagattggctcgaggacactctctctgaaggaataaga
D14H1       1   ATGGCCGCCGATGGTTATCTTCCAGATTGGCTCGAGGACACTCTCTCTGAAGGAATAAGA
D14L3       1   ATGGCTGCCGATGGTTATCTTCCAGATTGGCTCGAGGACACTCTCTCTGAAGGAATAAGA
P1BH1       1   ATGGCTGCCGATGGTTATCTTCCAGATTGGCTCGAGGACACTCTCTCTGAAGGAATAAGA
P1BH2       1   ATGGCTGCCGATGGTTATCTTCCAGATTGGCTCGAGGACACTCTCTCTGAAGGAATAAGA 70         80         90        100        110        120
                ....|....|....|....|....|....|....|....|....|....|....|....|
AAV2 VP1   61   cagtggtggaagctcaaacctggcccaccaccaccaaagcccgcagagcggcataaggac
D14H1      61   CAGTGGTTGAAGCTCAAACCTGGCCCACCACCACCAAAGcCCGCAGAGCGGCATAAGGAC
D14L3      61   CAGTGGTTGAAGCTCAAACCTGGCCCACCACCACCAAAGCCCGCAGAGCGGCATAAGGAC
P1BH1      61   CAGTGGTGGAAGCTCAAACCTGGCCCACCACCACCAAAGCCCGCAGAGCGGCATAAGGAC
P1BH2      61   CAGTGGTGGAAGCTCAAACCTGGCCCACCACCACCAAAGCCCGCAGAGCGGCATAAGGAC 130        140        150        160        170        180
                ....|....|....|....|....|....|....|....|....|....|....|....|
AAV2 VP1  121   gacagcaggggtcttgtgcttcctgggtacaagtacctcggacccttcaacggactcgac
D14H1     121   GACAGCAGGGGTCTTGTGCTTCCTGGGTACAAGTACCTCGGACCCTTCAACGGACTCGAC
D14L3     121   GACAGCAGGGGTCTTGTGCTTCCTGGGTACAAGTACCTCGGACCCTTCAACGGACTCGAC
P1BH1     121   GACAGCAGGGGTCTTGTGCTTCCTGGGTACAAGTACCTCGGACCCTTCAACGGACTCGAC
P1BH2     121   GACAGCAGGGGTCTTGTGCTTCCTGGGTACAAGTACCTCGGACCCTTCAACGGACTCGAC 190        200        210        220        230        240
                ....|....|....|....|....|....|....|....|....|....|....|....|
AAV2 VP1  181   aagggagagccggtcaacgaggcagacgccgcggccctcgagcacgacaaagcctacgac
D14H1     181   AAGGGAGAGCCGGTCAACGAGGCAGACGCCGCGGCCCTCGAGCACGACAAAGCCTACGAC
D14L3     181   AAGGGAGAGCCGGTCAACGAGGCAGACGCCGCGGCCCTCGAGCACGACAAAGCCTACGAC
P1BH1     181   AAGGGAGAGCCGGTCAACGAGGCAGACGCCGCGGCCCTCGAGCACGACAAAGCCTACGAC
P1BH2     181   AAGGGAGAGCCGGTCAACGAGGCAGACGCCGCGGCCCTCGAGCACGACAAAGCCTACGAC 250        260        270        280        290        300
                ....|....|....|....|....|....|....|....|....|....|....|....|
AAV2 VP1  241   cggcagctcgacagcggagacaacccgtacctcaagtacaaccacgccgacgcggagttt
D14H1     241   CGGCAGCTCGACAGCGGAGACAACCCGTACCTCAAGTACAACCACGCCGACGCGGAGTTT
D14L3     241   CGGCAGCTCGACAGCGGAGACAACCCGTACCTCAAGTACAACCACGCCGACGCGGAGTTT
P1BH1     241   CGGCAGCTCGACAGCGGAGACAACCCGTACCTCAAGTACAACCACGCCGACGCGGAGTTT
P1BH2     241   CGGCAGCTCGACAGCGGAGACAACCCGTACCTCAAGTACAACCACGCCGACGCGGAGTTT 310        320        330        340        350        360
                ....|....|....|....|....|....|....|....|....|....|....|....|
AAV2 VP1  301   caggagcgccttaaagaagatacgtcttttgggggcaacctcggacgagcagtcttccag
D14H1     301   CAGGAGCGCCTTAAAGAAGATACGTCTTTTGGGGGCAACCTCGGACGAGCAGTCTTCCAG
D14L3     301   CAGGAGCGCCTTAAAGAAGATACGTCTTTTGGGGGCAACCTCGGACGAGCAGTCTTCCAG
P1BH1     301   CAGGAGCGCCTTAAAGAAGATACGTCTTTTGGGGGCAACCTCGGACGAGCAGTCTTCCAG
P1BH2     301   CAGGAGCGCCTTAAAGAAGATACGTCTTTTAGGGGCAACCTCGGACGAGCAGTCTTCCAG
```

FIG. 8B

```
                  370        380        390        400        410        420
              ....|....|....|....|....|....|....|....|....|....|....|....|
AAV2 VP1  361 gcgaaaaagagggttcttgaacctctgggcctggttgaggaacctgttaagacggctccg
D14H1     361 GCGAAAAAGAGGGTTCTTGAACCTCTGGGCCTGGTTGAGGAACCTGTTAAGACGGCTCCG
D14L3     361 GCGAAAAAGAGGGTTCTTGAACCTCTGGGCCTGGTTGAGGAACCTGTTAAGACGGCTCCG
P1BH1     361 GCGAAAAAGAGGGTTCTTGAACCTCTGGGCCTGGTTGAGGAACCTGTTAAGACGGCTCCG
P1BH2     361 GCGAAAAAGAGGGTTCTTGAACCTCTGGGCCTGGTTGAGGAACCTGTTAAGACGGCTCCG 430        440        450        460        470        480
              ....|....|....|....|....|....|....|....|....|....|....|....|
AAV2 VP1  421 ggaaaaaagaggccggtagagcactctcctgtggagccagactcctcctcgggaaccgga
D14H1     421 GGAAAAAAGAGGCCGGTAGAGCACTCTCCTGTGGAGCCAGACTCCTCCTCGGGAACCGGA
D14L3     421 GGAAAAAAGAGGCCGGTAGAGCACTCTCCTGTGGAGCCAGACTCCTCCTCGGGAACCGGA
P1BH1     421 GGAAAAAAGAGGCCGGTAGAGCACTCTCCTGTGGAGCCAGACTCCTCCTCGGGAACCGGA
P1BH2     421 GGAAAAAAGAGGCCGGTAGAGCACTCTCCTGTGGAGCCAGACTCCTCCTCGGGAACCGGA 490        500        510        520        530        540
              ....|....|....|....|....|....|....|....|....|....|....|....|
AAV2 VP1  481 aaggcgggccagcagcctgcaagaaaaagattgaattttggtcagactggagacgcagac
D14H1     481 AAGGCGGGCCAGCAGCCTGCAAGAAAAAGATTGAATTTTGGTCAGACTGGAGACGCAGAC
D14L3     481 AAGGCGGGCCAGCAGCCTGCAAGAAAAAGATTGAATTTTGGTCAGACTGGAGACGCAGAC
P1BH1     481 AAGGCGGGCCAGCAGCCTGCAAGAAAAAGATTGAATTTTGGTCAGACTGGAGACGCAGAC
P1BH2     481 AAGGCGGGCCAGCAGCCTGCAAGAAAAAGATTGAATTTTGGTCAGACTGGAGACGCAGAC 550        560        570        580        590        600
              ....|....|....|....|....|....|....|....|....|....|....|....|
AAV2 VP1  541 tcagtacctgacccccagcctctcggacagccaccagcagcccccctctggtctgggaact
D14H1     541 TCAGTACCTGACCCCCAGCCTCTCGGACAGCCACCAGCAGCCCCCTCTGGTCTGGGAACT
D14L3     541 TCAGTACCTGACCCCCAGCCTCTCGGACAGCCACCAGCAGCTCCCACTGGTCTGGGAACT
P1BH1     541 TCAGTACCTGACCCCCAGCCTCTCGGACAGCCACCAGCAGCCCCCTCTGGTCTGGGAACT
P1BH2     541 TCAGTACCTGACCCCCAGCCTCTCGGACAGCCACCAGCAGCCCCCTCTGGTCTGGGAACT 610        620        630        640        650        660
              ....|....|....|....|....|....|....|....|....|....|....|....|
AAV2 VP1  601 aatacgatggctacaggcagtggcgcaccaatggcagacaataacgagggcgccgacgga
D14H1     601 AATACGATGGCTACAGGCAGTGGCGCACCAATGGCAGACAATAACGAGGGCGCCGACGGA
D14L3     601 AATACGATGGCTACAGGCAGTGGCGCACCAATGGCAGACAATAACGAGGGCGCCGACGGA
P1BH1     601 AATACGATGGCTACAGGCAGTGGCGCACCAATGGCAGACAATAACGAGGGCGCCGACGGA
P1BH2     601 AATACGATGGCTACAGGCAGTGGCGCACCAATGGCAGACAATAACGAGGGCGCCGACGGA 670        680        690        700        710        720
              ....|....|....|....|....|....|....|....|....|....|....|....|
AAV2 VP1  661 gtgggtaattcctcgggaaattggcattgcgattccacatggatgggcgacagagtcatc
D14H1     661 GTGGGTAATTCCTCGGGAAATTGGCATTGCGGTTCCACATGGATGGGCGATAGAGTCATC
D14L3     661 GTGGGTAATTCCTCGGGAAATTGGCATTGCGGTTCCACATGGATGGGCGACAGAGTCATC
P1BH1     661 GTGGGTAATTCCTCGGGAAATTGGCATTGCGATTCCACATGGTGGGCGACAGAGTCATC
P1BH2     661 GTGGGTAATTCCTCGGGAAATTGGCATTGCGATTCCACATGGATGGGCGACAGAGTCATC
```

FIG. 8C

```
                  730        740        750        760        770        780
             ....|....|....|....|....|....|....|....|....|....|....|....|
AAV2 VP1 721 accaccagcacccgaacctgggccctgcccacctacaacaaccacctctacaaacaaatt
D14H1    721 ACCACCAGCACCCGAACCTGGGCCCTGCCCACCTACAACAACCACCTCTACAAACAAATT
D14L3    721 ACCACCAGCACCCGAACCTGGGCCCTGCCCACCTACAACAACCACCTCTACAAACAAATT
P1BH1    721 ACCACCAGCACCCGAACCTGGGCCCTGCCCACCTACAACAACCACCTCTACAAACAAATT
P1BH2    721 ACCACCAGCACCCGAACCTGGGCCCTGCCCACCTACAACAACCACCTCTACGAACAAATT 790        800        810        820        830        840
             ....|....|....|....|....|....|....|....|....|....|....|....|
AAV2 VP1 781 tccagccaatcaggagcctcgaacgacaatcactactttggctacagcacccccttggggg
D14H1    781 TTCAGCCAATCAGGAGCCTCGAACGACAATCACTACTTTGGCTACAGCACCCCTTGGGGG
D14L3    781 TTCAGCCAATCAGGAGCCTCGAACGACAATCACTACTTTGGCTACAGCACCCCTTGGGGG
P1BH1    781 TCCAGCCAATCAGGAGCCTCGAACGACAATCACTACTTTGGCTACAGCACCCCTTGGGGG
P1BH2    781 TCCAGCCAATCAGGAGCCTCGAACGACAATCACTACTTTGGCTACAGCACCCCCTTGGGGG 850        860        870        880        890        900
             ....|....|....|....|....|....|....|....|....|....|....|....|
AAV2 VP1 841 tatttTgacttcaacagattccactgccacttttcaccacgtgactggcaaagactcatc
D14H1    841 TACTTTGACTTCAACAGATTCCACTGCCACTTTTCACCACGTGACTGgCAAAGACTCATC
D14L3    841 TACTTTGACTTCAACAGATTCCACTGCCACTTTTCACCACGTGACTGgCAAAGACTCATC
P1BH1    841 TATTTTGACTTCAACAGATTCCACTGCCACTTTTCACCACGTGACTGGCAAAGACTCATC
P1BH2    841 TATTTTGACTTCAACAGATTCCACTGCCACTTTTCACCACGTGACTGGCAAAGACTCATC 910        920        930        940        950        960
             ....|....|....|....|....|....|....|....|....|....|....|....|
AAV2 VP1 901 aacaacaactggggattccgacccaagagactcaacttcaagctctttaacattcaagtc
D14H1    901 AACAACAACTGGGGATTCCGACCCAAGAGACTCAACTTCAAGCTCTTTAACATTCAAGTC
D14L3    901 AACAACAACTGGGGATTCCGACCCAAGAGACTCAACTTCAAGCTCTTTAACATTCAAGTC
P1BH1    901 AACAACAACTGGGGATTCCGACCCAAGAGACTCAACTTCAAGCTCTTTAACATTCAAGTC
P1BH2    901 AACAACAACTGGGGATTCCGACCCAAGAGACTCAACTTCAAGCCCTTTAACATTCAAGTC 970        980        990        1000       1010       1020
             ....|....|....|....|....|....|....|....|....|....|....|....|
AAV2 VP1 961 aaagaggtcacgcagaatgacggtacgacgacgattgccaataaccttaccagcacggtt
D14H1    961 AAAGAGTTCACGCAGAATGACGGTACGACGACGATTGCCAATAACCTTACCAGCACGGTT
D14L3    961 AAAGAGGTCACGCAGAATGACGGTACGACGACGATTGCCAATAACCTTACCAGCACGGTT
P1BH1    961 AAAGAGGTCACGCAGAATGACGGTACGACGACGATTGCCAATAACCTTACCAGCACGGTT
P1BH2    961 AAAGGGGTCACGCAGAATGACGGTACGACGACGATTGCCAATAACCTTACCAGCACGGTT 1030       1040       1050       1060       1070       1080
             ....|....|....|....|....|....|....|....|....|....|....|....|
AAV2 VP1 1021 caggtgtttactgactcggagtaccagctcccgtacgtcctcggctcggcgcatcaagga
D14H1    1021 CAGGTGTTTACTGACTCGGAGTACCCGCTCCCGTACGTCCTCGGCTCGGCGCATCAAGGA
D14L3    1021 CAGGTGTTTACTGACTCGGAGTACCCGCTCCCGTACGTCCTCGGCTCGGCGCATCAAGGA
P1BH1    1021 CAGGTGTTTACTGACTCGGAGTACCAGCTCCCGTACGTCCTCGGCTCGGCGCATCAAGGA
P1BH2    1021 CAGGTGTTTACTGACTCGGAGTACCAGCTCCCGTACGTCCTCGGCTCGGCGCATCAAGGA
```

FIG. 8D

```
              1090      1100      1110      1120      1130      1140
           ....|....|....|....|....|....|....|....|....|....|....|....|
AAV2 VP1 1081 tgcctcccgccgttcccagcagacgtcttcatggtgccacagtatggatacctcaccctg
D14H1    1081 TGCCTCCCGCCGTTCCCAGCAGACGTCTTCATGGTGCCACAGTATGGTTACCTCACCCTG
D14L3    1081 TGCCTCCCGCCGTTCCCAGCAGACGTCTTCATGGTGCCACAGTATGGTTACCTCACCCTG
P1BH1    1081 TGCCTCCCGCCGTTCCCAGCAGACGTCTTCATGGTGCCACAGTATGGATACCTCACCCTG
P1BH2    1081 TGCCTCCCGCCGTTCCCAGCAGACGTCTTCATGGTGCCACAGTATGGATACCTCACCCTG 1150      1160      1170      1180      1190      1200
           ....|....|....|....|....|....|....|....|....|....|....|....|
AAV2 VP1 1141 aacaacgggagtcaggcagtaggacgctcttcatttactgcctggagtactttccttct
D14H1    1141 AACAACGGGAGTCAGGCAGTAGGACGCTCTTCATTTTACTGCCTGGAGTACTTTCCTTCT
D14L3    1141 AACAACGGGAGTCAGGCAGTAGGACGCTCTTCATTTTACTGCCTGGAGTACTTTCCTTCT
P1BH1    1141 AACAACGGGAGTCAGGCAGTAGGACGCTCTTCATTTTACTGCCTGGAGTACTTTCCTTCT
P1BH2    1141 AACAACGGGAGTCAGGCAGTAGGACGCTCTTCATTTTACTGCCTGGAGTACTTTCCTTCT 1210      1220      1230      1240      1250      1260
           ....|....|....|....|....|....|....|....|....|....|....|....|
AAV2 VP1 1201 cagatgctgcgtaccggaaacaactttaccttcagctacacttttgaggacgttcctttc
D14H1    1201 CAGATGCTGCGTACCGAAAACGACTTTACCTTCAGCTACACTTTTGAGGACGTTCCTTTC
D14L3    1201 CAGATGCTGCGTACCGAAAACGACTTTACCTTCAGCTACACTTTTGAGGACGTTCCTTTC
P1BH1    1201 CGGATGCTGCGTACCGGAAACAACTTTACCTTCAGCTACACTTTTGAGGACGTTCCTTTC
P1BH2    1201 CAGATGCTGCGTACCGGAAACAACTTTACCTTCAGCTACACTTTTGAGGACGTTCCTTTC 1270      1280      1290      1300      1310      1320
           ....|....|....|....|....|....|....|....|....|....|....|....|
AAV2 VP1 1261 cacagcagctacgctcacagccagagtctggaccgtctcatgaatcctctcatcgaccag
D14H1    1261 CACAGCAGCTACGCTCACAGCCAGAGTCTGGACCGTCTCATGAATCCTCTCATTGACCAG
D14L3    1261 CACAGCAGCTACGCTCACAGCCaGAGTCTGGACCGTCTCATGAATCCTCTCATCGACCAG
P1BH1    1261 CACAGCAGCTACGCTCACAGCCAGAGTCTGGACCGTCTCATGAATCCTCACATCGACCAG
P1BH2    1261 CACAGCAGCTACGCTCACAGCCAGAGTCTGGACCGTCTCATGAATCCTCTCATCGACCAG 1330      1340      1350      1360      1370      1380
           ....|....|....|....|....|....|....|....|....|....|....|....|
AAV2 VP1 1321 tacctgtattacttgagcagaacaaacactccaagtggaaccaccacgcagtcaaggctt
D14H1    1321 TACCTGTATTACTTGAGCAGAACAAACACTCCAAGTGGAACCACCACGCAGTCAAGGCTT
D14L3    1321 TACCTGTATTACTTGAGCAGAACAAACACTCCAAGTGGAACCACCACGCAGTCAAGGCTT
P1BH1    1321 TACCTGTATTACTTGAGCAGAACAAACACTCCAAGTGGAACCACCACGCAGTCAAGGCTT
P1BH2    1321 TACCTGTATTACTTGAGCAGAACAAACACTCCAAGTGGAACTACCACGCAGTCAAGGCTT 1390      1400      1410      1420      1430      1440
           ....|....|....|....|....|....|....|....|....|....|....|....|
AAV2 VP1 1381 cagttttctcaggccggagcgagtgacattcgggaccagtctaggaactggcttcctgga
D14H1    1381 CAGTTTTCTCAGGCCGGAGCGAGTGACATTCGGGACCAGTCTAGGAACTGGCTTCCTGGA
D14L3    1381 CAGTTTTCTCAGGCCGGAGCGAGTGACATTCGGGACCAGTCTAGGAACTGGCTTCCTGGA
P1BH1    1381 CAGTTTTCTCAGGCCGGAGCGAGTGACATTCGGGACCAGTCTAGGAACTGGCTTCCTGGA
P1BH2    1381 CAGTTTTCTCAGGCCGGAGCGAGTGACATTCGGGACCAGTCTAGGAACTGGCTTCCTGGA
```

FIG. 8E

```
               1450       1460       1470       1480       1490       1500
            ....|....|....|....|....|....|....|....|....|....|....|....|
AAV2 VP1 1441 ccctgttaccgccagcagcgagtatcaaagacatctgcggataacaacaacagtgaatac
D14H1    1441 CCCTGTTACCGCCAGCAGCGAGTATCAAAGACATCTGCGGATAACAACAACAGTGAATAC
D14L3    1441 CCCTGTTACCGCCAGCAGCGAGTATCAAAGACATCTGCGGATAACAACAACAGTGAATAC
P1BH1    1441 CCCTGTTACCGCCAGCAGCGAGTATCAAAGACATCTGCGGATAACAACAACAGTGAATAC
P1BH2    1441 CCCTGTTACCGCCAGCAGCGAGTATCAAAGACATCTGCGGATAACAACAACAGTGAATAC 1510       1520       1530       1540       1550       1560
            ....|....|....|....|....|....|....|....|....|....|....|....|
AAV2 VP1 1501 tcgtggactggagctaccaagtaccacctcaatggcagagactctctggtgaatccgggc
D14H1    1501 TCGTGGACTGGAGCTACCAAGTACCACCTCAATGGCAGAGACTCTCTGGTGAATCCGGGC
D14L3    1501 TCGTGGACTGGAGCTACCAAGTACCACCTCAATGGCAGAGACTCTCTGGTGAATCCGGGC
P1BH1    1501 TCGTGGACTGGAGCTACCAAGTACCACCTCAATGGCAGAGACTCTCTGGTGAATCCGGGC
P1BH2    1501 TCGTGGACTGGAGCTACCAAGTACCACCTCAATGGCAGAGACTCTCTGGTGAATCCGGGC 1570       1580       1590       1600       1610       1620
            ....|....|....|....|....|....|....|....|....|....|....|....|
AAV2 VP1 1561 ccggccatggcaagccacaaggacgatgaagaaaagttttttcctcagagcggggttctc
D14H1    1561 CCGGCCATGGCAAGCCACAAGGACGATGAAGAAAAGTTTTTTCCTCAGAGCGGGGTTCTC
D14L3    1561 CCGGCCATGGCAAGCCACAAGGACGATGAAGAAAAGTTTTTTCCTCAGAGCGGGGTTCTC
P1BH1    1561 CCGGCCATGGCAAGCCACAAGGACGATGAAGAAAAGTTTTTTCCTCAGAGCGGGGTTCTC
P1BH2    1561 CCGGCCATGGCAAGCCACAAGGACGATGAAGAAAAGTTTTTTCCTCAGAGCGGGGTTCTC 1630       1640       1650       1660       1670       1680
            ....|....|....|....|....|....|....|....|....|....|....|....|
AAV2 VP1 1621 atctttgggaagcaaggctcagagaaaacaaatgtggacattgaaaaggtcatgattaca
D14H1    1621 ATCTTTGGGAAGCAAGGCTCAGAGAAAACAAATGTGGACATTGAAAAGGTCATGATTACA
D14L3    1621 ATCTTTGGGAAGCAAGGCTCAGAGAAAACAAATGTGGACATTGAAAAGGTCATGATTACA
P1BH1    1621 ATCTTTGGGAAGCAAGGCTCAGAGAAAACAAATGTGGACATTGAAAAGGTCATGATTACA
P1BH2    1621 ATCTTTGGGAAGCAAGGCTCAGAGAAAACAGATGTGGACATTGAAAAGGTCATGATTACA 1690       1700       1710       1720       1730       1740
            ....|....|....|....|....|....|....|....|....|....|....|....|
AAV2 VP1 1681 gacgaagaggaaatcaggacaaccaatcccgtggctacggagcagtatggttctgtatct
D14H1    1681 GACGAAGAGGAAATCAGGACAACCAATCCCGTGGCTACGGAGCAGTATGGTTCTGTATCT
D14L3    1681 GACGAAGAGGAAATCAGGACAACCGATCCCGTGGCTACGGAGCAGTATGGTTCAGTATCT
P1BH1    1681 GACGAAGAGGAAATCAGGACAACCAATCCCGTGGCTACGGAGCAGTATGGTTCTGTATCT
P1BH2    1681 GACGAAGAGGAAATCAGGACAACCAATCCCGTGGCTACGGAGCAGTATGGTTCTGTATCT 1750       1760       1770       1780       1790       1800
            ....|....|....|....|....|....|....|....|....|....|....|....|
AAV2 VP1 1741 accaacctccagagaggcaacagacaagcagctaccgcagatgtcaacacacaaggcgtt
D14H1    1741 ACCAACCTCCAGAGAGGCAACAGACAAGCGGCTACCGCAGATGTCAACACACAAGGCGTT
D14L3    1741 ACCAACCTCCAGAGAGGCAACAGACAAGCAGCTACCGCAGATGTCGACACACAAGGCGTT
P1BH1    1741 ACCACCCTCCAGAGAGGCAACAGACAAGCAGCTACCGCAGATGTCAACACACAAGGCGTT
P1BH2    1741 ACCAACCTCCAGAGAGGCAACAGACAAGCAGCTACCGCAGATGTCAACACACAAGGCGTT
```

FIG. 8F

```
                    1810       1820       1830       1840       1850       1860
                ....|....|....|....|....|....|....|....|....|....|....|....|
AAV2 VP1  1801  cttccaggcatggtctggcaggacagagatgtgtaccttcaggggcccatctgggcaaag
D14H1     1801  CTTCCAGGCATGGTCTGGCAAGACAGAGATGTGTACCTTCAGGGGCCCATCTGGGCAAAG
D14L3     1801  CTTCCAGGCATGGTCTGGCAGGACAGAGATGTGTACCTTCAGGGGCCCATCTGGGCAAAG
P1BH1     1801  CTTCCAGGCATGGTCTGGCAGGACAGAGATGTGTACCTTCAGGGGCCCATCTGGGCAAAG
P1BH2     1801  CTTCCAGGCATGATCTGGCAGGACAGAGATGTGTACCTTCAGGGGCCCATCTGGGCAAAG 1870       1880       1890       1900       1910       1920
                ....|....|....|....|....|....|....|....|....|....|....|....|
AAV2 VP1  1861  attccacacacggacggacattttcacccctctccctcatgggtggattcggacttaaa
D14H1     1861  ATTCCACACACGGACGGACATTTTCACCCCTCTCCCTCATGGGTGGATTCGGACTTAAA
D14L3     1861  ATTCCACACACGGACGGACATTTTCACCCCTCTCCCTCATGGGTGGATTCGGACTTAAA
P1BH1     1861  ATTCCACACACGGACGGACATTTTCACCCCTCTCCCTCATGGGTGGATTCGGACTTAAA
P1BH2     1861  ATTCCACACACGGACGGACATTTTCACCCCTCTCCCTCATGGGTGGATTCGGACTTAAA 1930       1940       1950       1960       1970       1980
                ....|....|....|....|....|....|....|....|....|....|....|....|
AAV2 VP1  1921  caccctcctccacagattctcatcaagaacaccccggtacctgcgaatccttcgaccacc
D14H1     1921  CACCCCCTCCACAGATTCTCATCAAGAACACCCCGGTACCTGCGAATCCTTCGACCACC
D14L3     1921  CACCCTCCTCCACAGATTCTCATCAAGAACACCCCGGTACCTGCGAATCCTTCGACCACC
P1BH1     1921  CACCCTCCTCCACAGATTCTCATCAAGAACACCCCGGTACCTGCGAATCCTTCGACCGCC
P1BH2     1921  CACCCTCCTCCACAGATTCTCATCAAGAACACCCCGGTACCTGCGAATCCTTCGACCACC 1990       2000       2010       2020       2030       2040
                ....|....|....|....|....|....|....|....|....|....|....|....|
AAV2 VP1  1981  ttcagtgcggcaaagtttgcttccttcatcacacagtactccacgggacaggtcagcgtg
D14H1     1981  TTCAGTGCGGCAAAGTTTGCTTCCTTCATCACACAGTACTCCACGGGACAGGTCAGCGTG
D14L3     1981  TTCAGTGCGGCAAAGTTTGCTTCCTTCATCACACAGTACTCCACGGGACAGGTCAGCGTG
P1BH1     1981  TTCAGTGCGGCAAAGTTTGCTTCCTTCATCACACAGTACTCCACGGGACAGGTCAGCGTG
P1BH2     1981  TTCAGTGCGGCAAAGTTTGCTTCCTTCATCACACAGTACTCCACGGGACAGGTCAGCGTG 2050       2060       2070       2080       2090       2100
                ....|....|....|....|....|....|....|....|....|....|....|....|
AAV2 VP1  2041  gagatcgagtgggagctgcagaaggaaaacagcaaacgctggaatcccgaaattcagtac
D14H1     2041  GAGATCGAGTGGGAGCTGCAGAAGGAAAACAGCAAACGCTGGAATCCCGAAATTCAGTAC
D14L3     2041  GAGATCGAGTGGGAGCTGCAGAAGGAAAACAGCAAACGCTGGAATCCCGAAATTCAGTAC
P1BH1     2041  GAGATCGAGTGGGAGCTGCAGAAGGAAAACAGCAAACGCTGGAATCCCGAAATTCAGTAC
P1BH2     2041  GAGATCGAGTGGGAGCTGCAGAAGGAAAACAGCAAACGCTGGAATCCCGAAATTCAGTAC 2110       2120       2130       2140       2150       2160
                ....|....|....|....|....|....|....|....|....|....|....|....|
AAV2 VP1  2101  acttccaactacaacaagtctgttaatgtggactttactgtggacactaatggcgtgtat
D14H1     2101  ACTTCCAACTACAACAAGTCTGTTAATGTGGACTTTACTGTGGACACTAATGGCGTGTAT
D14L3     2101  ACTTCCAACTACAACAAGTCTGTTAATGTGGACTTTACTGTGGACACTAATGGCGTGTAT
P1BH1     2101  ACTTCCAACTACAACAAGTCTGTTAATGTGGACTTTACTGTGGACACTAATGGCGTGTAT
P1BH2     2101  ACTTCCAACTACAACAAGTCTGTTAATGTGGACTTTACTGTGGACACTAATGGCGTGTAT
```

FIG. 8G

```
              2170      2180      2190      2200
         ....|....|....|....|....|....|....|....|....|...
AAV2 VP1 2161 tcagagcctcgccccattggcaccagatacctgactcgtaatctgtaa  (SEQ ID NO:4)
D14H1    2161 Tcagagcctcgccccattggcaccagatacctgactcgtaatctgtaa  (SEQ ID NO:34)
D14L3    2161 TcAGAGCctCGCCCCATTGGcaccagatacctgactcgtaatctgtaa  (SEQ ID NO:36)
P1BH1    2161 TCAGAGCctcgccccattggcaccagatacctgactcgtaatctgtaa  (SEQ ID NO:38)
P1BH2    2161 TCAGAGCctcgccccattggcaccagatacctgactcgtaatctgtaa  (SEQ ID NO:40)
```

FIG. 9A

```
               10         20         30         40         50         60
               ....|....|....|....|....|....|....|....|....|....|....|....|
AAV2 VP1    1  MAADGYLPDWLEDTLSEGIRQWWKLKPGPPPPKPAERHKDDSRGLVLPGYKYLGPFNGLD
D14H1       1  MAADGYLPDWLEDTLSEGIRQWLKLKPGPPPPKPAERHKDDSRGLVLPGYKYLGPFNGLD
D14L3       1  MAADGYLPDWLEDTLSEGIRQWLKLKPGPPPPKPAERHKDDSRGLVLPGYKYLGPFNGLD
P1BH1       1  MAADGYLPDWLEDTLSEGIRQWWKLKPGPPPPKPAERHKDDSRGLVLPGYKYLGPFNGLD
P1BH2       1  MAADGYLPDWLEDTLSEGIRQWWKLKPGPPPPKPAERHKDDSRGLVLPGYKYLGPFNGLD 70         80         90         100        110        120
               ....|....|....|....|....|....|....|....|....|....|....|....|
AAV2 VP1   61  KGEPVNEADAAALEHDKAYDRQLDSGDNPYLKYNHADAEFQERLKEDTSFGGNLGRAVFQ
D14H1      61  KGEPVNEADAAALEHDKAYDRQLDSGDNPYLKYNHADAEFQERLKEDTSFGGNLGRAVFQ
D14L3      61  KGEPVNEADAAALEHDKAYDRQLDSGDNPYLKYNHADAEFQERLKEDTSFGGNLGRAVFQ
P1BH1      61  KGEPVNEADAAALEHDKAYDRQLDSGDNPYLKYNHADAEFQERLKEDTSFGGNLGRAVFQ
P1BH2      61  KGEPVNEADAAALEHDKAYDRQLDSGDNPYLKYNHADAEFQERLKEDTSFRGNLGRAVFQ 130        140        150        160        170        180
               ....|....|....|....|....|....|....|....|....|....|....|....|
AAV2 VP1  121  AKKRVLEPLGLVEEPVKTAPGKKRPVEHSPVEPDSSSGTGKAGQQPARKRLNFGQTGDAD
D14H1     121  AKKRVLEPLGLVEEPVKTAPGKKRPVEHSPVEPDSSSGTGKAGQQPARKRLNFGQTGDAD
D14L3     121  AKKRVLEPLGLVEEPVKTAPGKKRPVEHSPVEPDSSSGTGKAGQQPARKRLNFGQTGDAD
P1BH1     121  AKKRVLEPLGLVEEPVKTAPGKKRPVEHSPVEPDSSSGTGKAGQQPARKRLNFGQTGDAD
P1BH2     121  AKKRVLEPLGLVEEPVKTAPGKKRPVEHSPVEPDSSSGTGKAGQQPARKRLNFGQTGDAD 190        200        210        220        230        240
               ....|....|....|....|....|....|....|....|....|....|....|....|
AAV2 VP1  181  SVPDPQPLGQPPAAPSGLGTNTMATGSGAPMADNNEGADGVGNSSGNWHCDSTWMGDRVI
D14H1     181  SVPDPQPLGQPPAAPSGLGTNTMATGSGAPMADNNEGADGVGNSSGNWHCGSTWMGDRVI
D14L3     181  SVPDPQPLGQPPAAPTGLGTNTMATGSGAPMADNNEGADGVGNSSGNWHCGSTWMGDRVI
P1BH1     181  SVPDPQPLGQPPAAPSGLGTNTMATGSGAPMADNNEGADGVGNSSGNWHCDSTWVGDRVI
P1BH2     181  SVPDPQPLGQPPAAPSGLGTNTMATGSGAPMADNNEGADGVGNSSGNWHCDSTWMGDRVI 250        260        270        280        290        300
               ....|....|....|....|....|....|....|....|....|....|....|....|
AAV2 VP1  241  TTSTRTWALPTYNNHLYKQISSQSGASNDNHYFGYSTPWGYFDFNRFHCHFSPRDWQRLI
D14H1     241  TTSTRTWALPTYNNHLYKQIFSQSGASNDNHYFGYSTPWGYFDFNRFHCHFSPRDWQRLI
D14L3     241  TTSTRTWALPTYNNHLYKQIFSQSGASNDNHYFGYSTPWGYFDFNRFHCHFSPRDWQRLI
P1BH1     241  TTSTRTWALPTYNNHLYKQISSQSGASNDNHYFGYSTPWGYFDFNRFHCHFSPRDWQRLI
P1BH2     241  TTSTRTWALPTYNNHLYEQISSQSGASNDNHYFGYSTPWGYFDFNRFHCHFSPRDWQRLI 310        320        330        340        350        360
               ....|....|....|....|....|....|....|....|....|....|....|....|
AAV2 VP1  301  NNNWGFRPKRLNFKLFNIQVKEVTQNDGTTTIANNLTSTVQVFTDSEYQLPYVLGSAHQG
D14H1     301  NNNWGFRPKRLNFKLFNIQVKEFTQNDGTTTIANNLTSTVQVFTDSEYPLPYVLGSAHQG
D14L3     301  NNNWGFRPKRLNFKLFNIQVKEVTQNDGTTTIANNLTSTVQVFTDSEYPLPYVLGSAHQG
P1BH1     301  NNNWGFRPKRLNFKLFNIQVKEVTQNDGTTTIANNLTSTVQVFTDSEYQLPYVLGSAHQG
P1BH2     301  NNNWGFRPKRLNFKPFNIQVKGVTQNDGTTTIANNLTSTVQVFTDSEYQLPYVLGSAHQG
```

FIG. 9B

```
             370        380        390        400        410        420
             ....|....|....|....|....|....|....|....|....|....|....|....|
AAV2 VP1 361 CLPPFPADVFMVPQYGYLTLNNGSQAVGRSSFYCLEYFPSQMLRTGN NFTFSYTFEDVPF
D14H1    361 CLPPFPADVFMVPQYGYLTLNNGSQAVGRSSFYCLEYFPSQMLRTEN DFTFSYTFEDVPF
D14L3    361 CLPPFPADVFMVPQYGYLTLNNGSQAVGRSSFYCLEYFPSQMLRTEN DFTFSYTFEDVPF
P1BH1    361 CLPPFPADVFMVPQYGYLTLNNGSQAVGRSSFYCLEYFPS RMLRTGNNFTFSYTFEDVPF
P1BH2    361 CLPPFPADVFMVPQYGYLTLNNGSQAVGRSSFYCLEYFPSQMLRTGN NFTFSYTFEDVPF 430        440        450        460        470        480
             ....|....|....|....|....|....|....|....|....|....|....|....|
AAV2 VP1 421 HSSYAHSQSLDRLMNPLIDQYLYYLSRTNTPSGTTTQSRLQFSQAGASDIRDQSRNWLPG
D14H1    421 HSSYAHSQSLDRLMNPLIDQYLYYLSRTNTPSGTTTQSRLQFSQAGASDIRDQSRNWLPG
D14L3    421 HSSYAHSQSLDRLMNPLIDQYLYYLSRTNTPSGTTTQSRLQFSQAGASDIRDQSRNWLPG
P1BH1    421 HSSYAHSQSLDRLMNP HIDQYLYYLSRTNTPSGTTTQSRLQFSQAGASDIRDQSRNWLPG
P1BH2    421 HSSYAHSQSLDRLMNPLIDQYLYYLSRTNTPSGTTTQSRLQFSQAGASDIRDQSRNWLPG 490        500        510        520        530        540
             ....|....|....|....|....|....|....|....|....|....|....|....|
AAV2 VP1 481 PCYRQQRVSKTSADNNNSEYSWTGATKYHLNGRDSLVNPGPAMASHKDDEEKFFPQSGVL
D14H1    481 PCYRQQRVSKTSADNNNSEYSWTGATKYHLNGRDSLVNPGPAMASHKDDEEKFFPQSGVL
D14L3    481 PCYRQQRVSKTSADNNNSEYSWTGATKYHLNGRDSLVNPGPAMASHKDDEEKFFPQSGVL
P1BH1    481 PCYRQQRVSKTSADNNNSEYSWTGATKYHLNGRDSLVNPGPAMASHKDDEEKFFPQSGVL
P1BH2    481 PCYRQQRVSKTSADNNNSEYSWTGATKYHLNGRDSLVNPGPAMASHKDDEEKFFPQSGVL 550        560        570        580        590        600
             ....|....|....|....|....|....|....|....|....|....|....|....|
AAV2 VP1 541 IFGKQGSEKTNVDIEKVMITDEEEIRTTNPVATEQYGSVSTNLQRGNRQAATADVNTQGV
D14H1    541 IFGKQGSEKTNVDIEKVMITDEEEIRTTNPVATEQYGSVSTNLQRGNRQAATADVNTQGV
D14L3    541 IFGKQGSEKTNVDIEKVMITDEEEIRTT DPVATEQYGSVSTNLQRGNRQAATADV DTQGV
P1BH1    541 IFGKQGSEKTNVDIEKVMITDEEEIRTTNPVATEQYGSVST TLQRGNRQAATADVNTQGV
P1BH2    541 IFGKQGSEKT DVDIEKVMITDEEEIRTTNPVATEQYGSVSTNLQRGNRQAATADVNTQGV 610        620        630        640        650        660
             ....|....|....|....|....|....|....|....|....|....|....|....|
AAV2 VP1 601 LPGMVWQDRDVYLQGPIWAKIPHTDGHFHPSPLMGGFGLKHPPPQILIKNTPVANPSTT
D14H1    601 LPGMVWQDRDVYLQGPIWAKIPHTDGHFHPSPLMGGFGLKHPPPQILIKNTPVANPSTT
D14L3    601 LPGMVWQDRDVYLQGPIWAKIPHTDGHFHPSPLMGGFGLKHPPPQILIKNTPVANPSTT
P1BH1    601 LPGMVWQDRDVYLQGPIWAKIPHTDGHFHPSPLMGGFGLKHPPPQILIKNTPVANPST A
P1BH2    601 LPGM IWQDRDVYLQGPIWAKIPHTDGHFHPSPLMGGFGLKHPPPQILIKNTPVANPSTT 670        680        690        700        710        720
             ....|....|....|....|....|....|....|....|....|....|....|....|
AAV2 VP1 661 FSAAKFASFITQYSTGQVSVEIEWELQKENSKRWNPEIQYTSNYNKSVNVDFTVDTNGVY
D14H1    661 FSAAKFASFITQYSTGQVSVEIEWELQKENSKRWNPEIQYTSNYNKSVNVDFTVDTNGVY
D14L3    661 FSAAKFASFITQYSTGQVSVEIEWELQKENSKRWNPEIQYTSNYNKSVNVDFTVDTNGVY
P1BH1    661 FSAAKFASFITQYSTGQVSVEIEWELQKENSKRWNPEIQYTSNYNKSVNVDFTVDTNGVY
P1BH2    661 FSAAKFASFITQYSTGQVSVEIEWELQKENSKRWNPEIQYTSNYNKSVNVDFTVDTNGVY
```

FIG. 9C

```
                    730
              ....|....|....|.
AAV2 VP1  721 SEPRPIGTRYLTRNL*  (SEQ ID NO:5)
D14H1     721 SEPRPIGTRYLTRNL*  (SEQ ID NO:35)
D14L3     721 SEPRPIGTRYLTRNL*  (SEQ ID NO:37)
P1BH1     721 SEPRPIGTRYLTRNL*  (SEQ ID NO:39)
P1BH2     721 SEPRPIGTRYLTRNL*  (SEQ ID NO:41)
```

```
             ....|....| ....|....| ....|....| ....|....| ....|....| ....|....|
                  5         15         25         35         45         55
AAV2.5T,  7  MAADGYLPDW LEDTLSEGIR QWWKLKPGPP PPKPAERHKD DSRGLVLPGY KYLGPFNGLD
CAP5,   743  MSFVDHPPDW LEEVG.EGLR EFLGLEAGPP KPKPNQQHQD QARGLVLPGY NYLGPGNGLD

....|....| ....|....| ....|....| ....|....| ....|....| ....|....|
                 65         75         85         95        105        115
AAV2.5T,  7  KGEPVNEADA AALEHDKAYD RQLDSGDNPY LKYNHADAEF QERLKEDTSF GGNLGRAVFQ
CAP5,   743  RGEPVNRADE VAREHDISYN EQLEAGDNPY LKYNHADAEF QEKLADDTSF GGNLGKAVFQ

....|....| ....|....| ....|....| ....|....| ....|....| ....|....|
                125        135        145        155        165        175
AAV2.5T,  7  AKKRVLEPFG LVEEGAKTAP TGKRIDDHFP KRKKARTEED SKPS...... ....TSSDAE
CAP5,   743  AKKRVLEPFG LVEEGAKTAP TGKRIDDHFP KRKKARTEED SKPS...... ....TSSDAE

....|....| ....|....| ....|....| ....|....| ....|....| ....|....|
                185        195        205        215        225        235
AAV2.5T,  7  AGPSGSQQLQ IPAQPASSLG ADTMSAGGGG PLGDNNQGAD GVGNASGDWH CDSTWMGDRV
CAP5,   743  AGPSGSQQLQ IPAQPASSLG ADTMSAGGGG PLGDNNQGAD GVGNASGDWH CDSTWMGDRV

....|....| ....|....| ....|....| ....|....| ....|....| ....|....|
                245        255        265        275        285        295
AAV2.5T,  7  VTKSTRTWVL PSYNNHQYRE IKSGSVDGSN ANAYFGYSTP WGYFDFNRFH SHWSPRDWQR
CAP5,   743  VTKSTRTWVL PSYNNHQYRE IKSGSVDGSN ANAYFGYSTP WGYFDFNRFH SHWSPRDWQR

....|....| ....|....| ....|....| ....|....| ....|....| ....|....|
                305        315        325        335        345        355
AAV2.5T,  7  LINNYWGFRP RSLRVKIFNI QVKEVTVQDS TTTIANNLTS TVQVFTDDDY QLPYVVGNGT
CAP5,   743  LINNYWGFRP RSLRVKIFNI QVKEVTVQDS TTTIANNLTS TVQVFTDDDY QLPYVVGNGT

....|....| ....|....| ....|....| ....|....| ....|....| ....|....|
                365        375        385        395        405        415
AAV2.5T,  7  EGCLPAFPPQ VFTLPQYGYA TLNRDNTENP TERSSFFCLE YFPSKMLRTG NNFEFTYNFE
CAP5,   743  EGCLPAFPPQ VFTLPQYGYA TLNRDNTENP TERSSFFCLE YFPSKMLRTG NNFEFTYNFE

....|....| ....|....| ....|....| ....|....| ....|....| ....|....|
                425        435        445        455        465        475
AAV2.5T,  7  EVPFHSSFAP SQNLFKLANP LVDQYLYRFV STNNTGG... ...VQFNKNL AGRYANTYKN
CAP5,   743  EVPFHSSFAP SQNLFKLANP LVDQYLYRFV STNNTGG... ...VQFNKNL AGRYANTYKN

....|....| ....|....| ....|....| ....|....| ....|....| ....|....|
                485        495        505        515        525        535
AAV2.5T,  7  WFPGPMGRTQ GWNLGSGVNR ASVSAFATTN RMELEGASYQ VPPQPNGMTN NLQGSNTYAL
CAP5,   743  WFPGPMGRTQ GWNLGSGVNR ASVSAFATTN RMELEGASYQ VPPQPNGMTN NLQGSNTYAL

....|....| ....|....| ....|....| ....|....| ....|....| ....|....|
                545        555        565        575        585        595
AAV2.5T,  7  ENTMIFNSQP ANPGTTATYL EGNMLITSES ETQPVNRVAY NVGGQMATNN QSSTTAPTTG
CAP5,   743  ENTMIFNSQP ANPGTTATYL EGNMLITSES ETQPVNRVAY NVGGQMATNN QSSTTAPATG

....|....| ....|....| ....|....| ....|....| ....|....| ....|....|
                605        615        625        635        645        655
AAV2.5T,  7  TYNLQEIVPG SVWMERDVYL QGPIWAKIPE TGAHFHPSPA MGGFGLKHPP PMMLIKNTPV
CAP5,   743  TYNLQEIVPG SVWMERDVYL QGPIWAKIPE TGAHFHPSPA MGGFGLKHPP PMMLIKNTPV
```

FIG. 10A

```
              ....|....| ....|....| ....|....| ....|....| ....|....| ....|....|
                  665        675        685        695        705        715
AAV2.5T, 7    PGN.ITSFSD VPVSSFITQY STGQVTVEME WELKKENSKR WNPEIQYTNN YNDPQFVDFA
CAP5, 743     PGN.ITSFSD VPVSSFITQY STGQVTVEME WELKKENSKR WNPEIQYTNN YNDPQFVDFA

....|....| ....|....| ...
                  725        735
AAV2.5T, 7    PDSTGEYRTT RPIGTRYLTR PL. (SEQ ID NO:42)
CAP5, 743     PDSTGEYRTT RPIGTRYLTR PL. (SEQ ID NO:43)
```

FIG. 10B

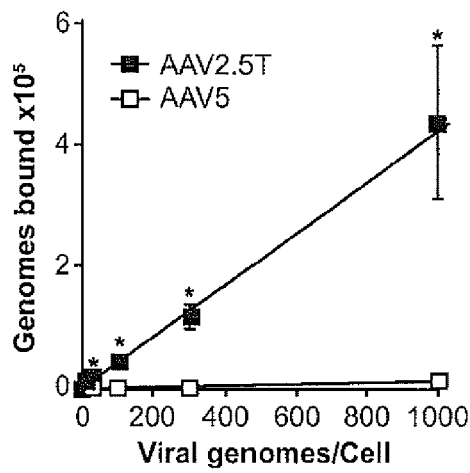
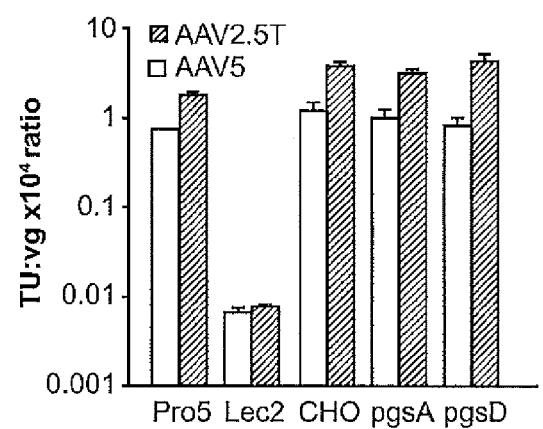
FIG. 12A
FIG. 12B
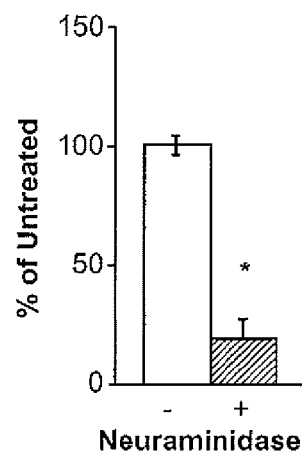
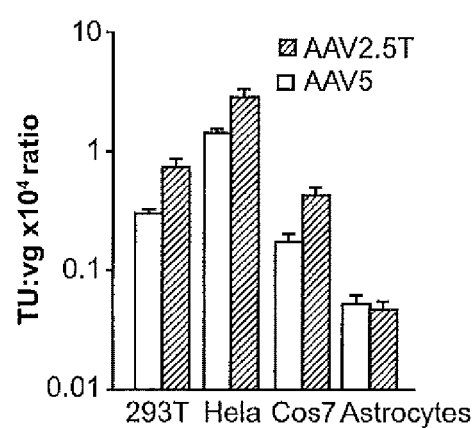
FIG. 12C
FIG. 12D

|          |       | 1                                                  50 |
|----------|-------|---------------------------------------------------------|
| hE 1.1   | (1)   | MAADGYLPDWLEDTLSEGIRQWWKLKPGPPPPKPAERHKDDSRGLVLPGY |
| hEr1.5   | (1)   | MAADGYLPDWLEDTLSEGIRQWWKLKPGPPPPKPAERHKDDSRGLVLPGY |
| hEr1.14  | (1)   | MAADGYLPDWLEDTLSEGIRQWWKLKPGPPPPKPAERHKDDSRGLVLPGY |
| hEr1.8   | (1)   | MAADGYLPDWLEDTLSEGIREWWALKPGAPKPKANQQKQDDGRGLVLPGY |
| hEr1.16  | (1)   | MAADGYLPDWLEDTLSEGIRQWWKLKPGPPPPKPAERHKDDSRGLVLPGY |
| hEr1.18  | (1)   | MAADGYLPDWLEDTLSEGIRQWWKLKPGPPPPKPAERHKDDSRGLVLPGY |
| hEr1.35  | (1)   | MAADGYLPDWLEDTLSEGIRQWWKLKPGPPPPKPAERHKDDSRGLVLPGY |
| hEr1.7   | (1)   | MASDGYLPDWLEDNLSEGIREWWDLKPGAPKPKANQQKQDDGRGLVLPGY |
| hEr1.36  | (1)   | MAADGYLPDWLEDTLSEGIRQWWKLKPGPPPPKPAERHKDDSRGLVLPGY |
| AAV2     | (1)   | MAADGYLPDWLEDTLSEGIRQWWKLKPGPPPPKPAERHKDDSRGLVLPGY |
|          |       | 51                                                100 |
| hE 1.1   | (51)  | KYLGPFNGLDKGEPVNEADAAALEHDKAYDRQLDSGDNPYLKYNHADAEF |
| hEr1.5   | (51)  | KYLGPFNGLDKGEPVNEADAAALEHDKAYDRQLDSGDNPYLKYNHADAEF |
| hEr1.14  | (51)  | KYLGPFNGLDKGEPVNAADAAALEHDKAYDRQLDSGDNPYLKYNHADAEF |
| hEr1.8   | (51)  | KYLGPFNGLDKGEPVNEADAAALEHDKAYDQQLQAGDNPYLRYNHADAEF |
| hEr1.16  | (51)  | KYLGPFNGLDKGEPVNEADAAALEHDKAYDRQLDSGDNPYLKYNHADAEF |
| hEr1.18  | (51)  | KYLGPFNGLDKGEPVNEADAAALEHDKAYDRQLDSGDNPYLKYNHADAEF |
| hEr1.35  | (51)  | KYLGPFNGLDKGEPVNEADAAALEHDKAYDRQLDSGDNPYLKYNHADAEF |
| hEr1.7   | (51)  | KYLGPFNGLDKGEPVNAADAAALEHDKAYDQQLKAGDNPYLRYNHADAEF |
| hEr1.36  | (51)  | KYLGPFNGLDKGEPVNEADAAALEHDKAYDRQLDSGDNPYLKYNHADAEF |
| AAV2     | (51)  | KYLGPFNGLDKGEPVNEADAAALEHDKAYDRQLDSGDNPYLKYNHADAEF |
|          |       | 101                                               150 |
| hE 1.1   | (101) | QERLKEDTSFGGNLGRAVFQAKKRVLEPLGLVEEPVKTAPGKKRPVEHSP |
| hEr1.5   | (101) | QERLKEDTSFGGNLGRAVFQAKKRVLEPLGLVEEPVKTAPGKKRPVEHSP |
| hEr1.14  | (101) | QERLKEDTSFGGNLGRAVFQAKKRVLEPLGLVEEPVKTAPGKKRPVEHSP |
| hEr1.8   | (101) | QERLQEDTSFGGNLGRAVFQAKKRVLEPLGLVEEPVKTAPGKKRPVEHSP |
| hEr1.16  | (101) | QERLKEDTSFGGNLGRAVFQAKKRVLEPLGLVEEPVKTAPGKKRPVEHSP |
| hEr1.18  | (101) | QERLKEDTSFGGNLGRAVFQAKKRVLEPLGLVEEPVKTAPGKKRPVEHSP |
| hEr1.35  | (101) | QERLKEDTSFGGNLGRAVFQAKKRVLEPLGLVEEPVKTAPGKKRPVEHSP |
| hEr1.7   | (101) | QERLQEDTSFGGNLGRAVFQAKKRVLEPFGLVEEGAKTAPGKKRPVEQSP |
| hEr1.36  | (101) | QERLKEDTSFGGNLGRAVFQAKKRVLEPLGLVEEPVKTAPGKKRPVEHSP |
| AAV2     | (101) | QERLKEDTSFGGNLGRAVFQAKKRVLEPLGLVEEPVKTAPGKKRPVEHSP |
|          |       | 151                                               200 |
| hE 1.1   | (151) | VEPDSSSGTGKAGQQPARKRLNFGQTGDADSVPDPQPLGEPPATPAAVGP |
| hEr1.5   | (151) | VEPDSSSGTGKAGQQPARKRLNFGQTGDADSVPDPQPLGQPPAAPSGLGT |
| hEr1.14  | (151) | VEPDSSSGTGKAGQQPARKRLNFGQTGDADSVPDPQPLGQPPAAPSGLGT |
| hEr1.8   | (151) | VEPDSSSGTGKSGQQPARKRLNFGQTGDADSVPDPQPLGQPPAAPSGLGT |
| hEr1.16  | (151) | VEPDSSSGTGKAGQQPARKRLNFGQTGDADSVPDPQPLGQPPAAPSGLGT |
| hEr1.18  | (151) | VEPDSSSGTGKAGQQPARKRLNFGQTGDADSVPDPQPLGQPPAAPSGLGT |
| hEr1.35  | (151) | VEPDSSSGTGKAGQQPARKRLNFGQTGDADSVPDPQPLGQPPAAPSGLGT |
| hEr1.7   | (151) | QEPDSSSGIGKTGQQPAKKRLNFGQTGDSESVPDPQPLGEPPATPAAVGP |
| hEr1.36  | (151) | VEPDSSSGTGKAGQQPARKRLNFGQTGDADSVPDPQPLGQPPAAPSGLGT |
| AAV2     | (151) | VEPDSSSGTGKAGQQPARKRLNFGQTGDADSVPDPQPLGQPPAAPSGLGT |

FIG. 14A

```
              201                                                250
hE 1.1  (201) TTMASGGGAPMADNNEGADGVGNASGNWHCDSTWLGDRVITTSTRTWALP
hEr1.5  (201) NTMATGSGAPMADNNEGADGVGNSSGNWHCDSTWMGDRVITTSTRTWALP
hEr1.14 (201) NTMATGSGAPMADNNEGADGVGNSSGNWHCDSTWMGDRVITTSTRTWALP
hEr1.8  (201) NTMATGSGAPMADNNEGADGVGNSSGNWHCDSTWMGDRVITTSTRTWALP
hEr1.16 (201) NTMATGSGAPMADNNEGADGVGNSSGNWHCDSTWMGDRVITTSTRTWALP
hEr1.18 (201) NTMATGSGAPMADNNEGADGVGNSSGNWHCDSTWMGDRVITTSTRTWALP
hEr1.35 (201) NTMATGSGAPMADNNEGADGVGNSSGNWHCDSTWMGDRVITTSTRTWALP
hEr1.7  (201) TTMASGGGAPMADNNEGADGVGNASGNWHCDSTWLGDRVITTSTRTWALP
hEr1.36 (201) NTMATGSGAPMADNNEGADGVGNSSGNWHCDSTWMGDRVITTSTRTWALP
   AAV2 (201) NTMATGSGAPMADNNEGADGVGNSSGNWHCDSTWMGDRVITTSTRTWALP
              251                                                300
hE 1.1  (251) TYNNHLYKQISSASTGASNDNHYFGYSTPWGYFDFNRFHCHFSPRDWQRL
hEr1.5  (251) TYNNHLYKQISS-QSGASNDNHYFGYSTPWGYFDFNRFHCHFSPRDWQRL
hEr1.14 (251) TYNNHLYKQISS-QSGASNDNHYFGYSTPWGYFDFNRFHCHFSPRDWQRL
hEr1.8  (251) TYNNHLYKQISS-QSGASNDNHYFGYSTPWGYFDFNRFHCHFSPRDWQRL
hEr1.16 (251) TYNNHLYKQISS-QSGASNDNHYFGYSTPWGYFDFNRFHCHFSPRDWQRL
hEr1.18 (251) TYNNHLYKQISS-QSGASNDNHYFGYSTPWGYFDFNRFHCHFSPRDWQRL
hEr1.35 (251) TYNNHLYKQISS-QSGASNDNHYFGYSTPWGYFDFNRFHCHFSPRDWQRL
hEr1.7  (251) TYNNHLYKQISSASTGASNDNHYFGYSTPWGYFDFNRFHCHFSPRDWQRL
hEr1.36 (251) TYNNHLYKQISS-QSGASNDNHYFGYSTPWGYFDFNRFHCHFSPRDWQRL
   AAV2 (251) TYNNHLYKQISS-QSGASNDNHYFGYSTPWGYFDFNRFHCHFSPRDWQRL
              301                                                350
hE 1.1  (301) INNNWGFRPKRLNFKLFNIQVKEVTQNDGTTTIANNLTSTVQVFTDSEYQ
hEr1.5  (300) INNNWGFRPKRLNFKLFNIQVKEVTQNDGTTTIANNLTSTVQVFTDSEYQ
hEr1.14 (300) INNNWGFRPKRLNFKLFNIQVKEVTQNDGTTTIANNLTSTVQVFTDSEYQ
hEr1.8  (300) INNNWGFRPKRLNFKLFNIQVKEVTQNDGTTTIANNLTSTVQVFTDSEYQ
hEr1.16 (300) INNNWGFRPKRLNFKLFNIQVKEVTQNDGTTTIANNLTSTVQVFTDSEYQ
hEr1.18 (300) INNNWGFRPKRLNFKLFNIQVKEVTQNDGTTTIANNLTSTVQVFTDSEYQ
hEr1.35 (300) INNNWGFRPKRLNFKLFNIQVKEVTQNDGTTTIANNLTSTVQVFTDSEYQ
hEr1.7  (301) INNNWGFRPKRLNFKLFNIQVKEVTTNDGTTTIANNLTSTVQVFTDSEYQ
hEr1.36 (300) INNNWGFRPKRLNFKLFNIQVKEVTQNDGTTTIANNLTSTVQVFTDSEYQ
   AAV2 (300) INNNWGFRPKRLNFKLFNIQVKEVTQNDGTTTIANNLTSTVQVFTDSEYQ
              351                                                400
hE 1.1  (351) LPYVLGSAHQGCLPPFPADVFMIPQYGYLTLNNGSQAVGRSSFYCLEYFP
hEr1.5  (350) LPYVLGSAHQGCLPPFPADVFMVPQYGYLTLNNGSQAVGRSSFYCLEYFP
hEr1.14 (350) LPYVLGSAHQGCLPPFPADVFMVPQYGYLTLNNGSQAVGRSSFYCLEYFP
hEr1.8  (350) LPYVLGSAHQGCLPPFPADVFMVPQYGYLTLNNGSQAVGRSSFYCLEYFP
hEr1.16 (350) LPYVLGSAHQGCLPPFPADVFMVPQYGYLTLNNGSQAVGRSSFYCLEYFP
hEr1.18 (350) LPYVLGSAHQGCLPPFPADVFMVPQYGYLTLNNGSQAVGRSSFYCLEYFP
hEr1.35 (350) LPYVLGSAHQGCLPPFPADVFMVPQYGYLTLNNGSQAVGRSSFYCLEYFP
hEr1.7  (351) LPYVLGSAHQGCLPPFPADVFMVPQYGYLTLNNGSQAVGRSSFYCLEYFP
hEr1.36 (350) LPYVLGSAHQGCLPPFPADVFMVPQYGYLTLNNGSQAVGRSSFYCLEYFP
   AAV2 (350) LPYVLGSAHQGCLPPFPADVFMVPQYGYLTLNNGSQAVGRSSFYCLEYFP
              401                                                450
hE 1.1  (401) SQMLRTGNNFTFSYTFEDVPFHSSYAHSQSLDRLMNPLIDQYLYYLNRTQ
hEr1.5  (400) SQMLRTGNNFTFSYTFEDVPFHSSYAHSQSLDRLMNPLIDQYLYYLSRTN
hEr1.14 (400) SQMLRTGNNFTFSYTFEDVPFHSSYAHSQSLDRLMNPLIDQYLYYLSRTN
hEr1.8  (400) SQMLRTGNNFTFSYTFEDVPFHSSYAHSQSLDRLMNPLIDQYLYYLSRTN
hEr1.16 (400) SQMLRTGNNFTFSYTFEDVPFHSSYAHSQSLDRLMNPLIDQYLYYLSRTN
hEr1.18 (400) SQMLRTGNNFTFSYTFEDVPFHSSYAHSQSLDRLMNPLIDQYLYYLSRTN
hEr1.35 (400) SQMLRTGNNFTFSYTFEDVPFHSSYAHSQSLDRLMNPLIDQYLYYLSRTN
hEr1.7  (401) SQMLRTGNNFTFSYTFEDVPFHSSYAHSQSLDRLMNPLIDQYLYYLSRTN
hEr1.36 (400) SQMLRTGNNFTFSYTFEDVPFHSSYAHSQSLDRLMNPLIDQYLYYLSRTN
   AAV2 (400) SQMLRTGNNFTFSYTFEDVPFHSSYAHSQSLDRLMNPLIDQYLYYLSRTN
```

FIG. 14B

```
                451                                                500
hE 1.1    (451) NQSGSAQDKALLFSRGSPAGMSVQPKNWLPGPCYRQQRVSKTKTDNNNSN
hEr1.5    (450) TPSGTTTQSGLQFSQAGASDIRDQSRNWLPGPCYRQQRVSKTSADNNNSE
hEr1.14   (450) TPSGTTTQSGLQFSQAGASDIRDQSRNWLPGPCYRQQRVSKTSADNNNSE
hEr1.8    (450) TPSGTTTQSGLQFSQAGASDIRDQSRNWLPGPCYRQQRVSKTSADNNNSE
hEr1.16   (450) TPSGTTTQSGLQFSQAGASDIRDQSRNWLPGPCYRQQRVSKTSADNNNSE
hEr1.18   (450) TPSGTTTQSGLQFSQAGASDIRDQSRNWLPGPCYRQQRVSKTSADNNNSE
hEr1.35   (450) TPSGTTTQSGLQFSQAGASDIRDQSRNWLPGPCYRQQRVSKTSADNNNSE
hEr1.7    (451) TPSGTTTQSGLQFSQAGASDIRDQSRNWLPGPCYRQQRVSKTSADNNNSE
hEr1.36   (450) TPSGTTTQSGLQFSQAGASDIRDQSRNWLPGPCYRQQRVSKTSADNNNSE
AAV2      (450) TPSGTTTQSRLQFSQAGASDIRDQSRNWLPGPCYRQQRVSKTSADNNNSE
                501                                                550
hE 1.1    (501) FTWTGASKYNLNGRESIINPGTAMASHKDDKDKFFPMSGVMIFGKESAGA
hEr1.5    (500) YSWTGATKYHLNGRDSLVNPGPAMASHKDDEEKFFPQSGVLIFGKQ--GS
hEr1.14   (500) YSWTGATKYHLNGRDSLVNPGPAMASHKDDEEKFFPQSGVLIFGKQ--GS
hEr1.8    (500) YSWTGATKYHLNGRDSLVNPGPAMASHKDDEEKFFPQSGVLIFGKQ--GS
hEr1.16   (500) YSWTGATMYHLNGRDSLVNPGPAMASHKDDEEKFFPQSGVLIFGKQ--GS
hEr1.18   (500) YSWTGATKYHLNGRDSLVNPGPAMASHKDDEEKFFPQSGVLIFGKQ--GS
hEr1.35   (500) YSWTGATKYHLNGRDSLVNPGPAMASHKDDEEKFFPQSGVLIFGKQ--GS
hEr1.7    (501) YSWTGATKYHLNGRDSLVNPGPAMASHKDDEEKFFPQSGVLIFGKQ--GS
hEr1.36   (500) YSWTGATKYHLNGRDSLVNPGPAMASHKDDEEKFFPQSGVLIFGKQ--GS
AAV2      (500) YSWTGATKYHLNGRDSLVNPGPAMASHKDDEEKFFPQSGVLIFGKQ--GS
                551                                                600
hE 1.1    (551) SNTALD--NVMITDEEEIKATNPVATERFGTVAVNFQSSS----------
hEr1.5    (548) EKTNVDIEKVMITDEEEIRTTNPVATEQYGSVSTNLQRGN----------
hEr1.14   (548) EKTNVDIEKVMITDEEEIRTTNPVATEQYGSVSTNLQRGN----------
hEr1.8    (548) EKTNVDIEKVMITDEEEIRTTNPVATEQYGSVSTNLQRGNLANHNNTTNA
hEr1.16   (548) EKTNVDIEKVMITDEEEIRTTNPVATEQYGSVSTNLQRGN----------
hEr1.18   (548) EKTNVDIEKVMITDEEEIRTTNPVATEQYGSVSTNLQRGN----------
hEr1.35   (548) EKTNVDIEKVMITDEEEIRTTNPVATEQYGSVSTNLQRGN----------
hEr1.7    (549) EKTNVDIEKVMITDEEEIRTTNPVATEQYGSVSTNLQRGN----------
hEr1.36   (548) EKTNVDIEKVMITDEEEIRTTNPVATEQYGSCIYQPPERQ----------
AAV2      (548) EKTNVDIEKVMITDEEEIRTTNPVATEQYGSVSTNLQRGN----------
                601                                                650
hE 1.1    (589) TDPATGDVHVMGALPGMVWQDRDVYLQGPIWAKIPHTDGHFHPSPLMGGF
hEr1.5    (588) RQAATADVNTQGVLPGMVWQDRDVYLQGPIWAKIPHTDGHFHPSPLMGGF
hEr1.14   (588) RQAATADVNTQGVLPGMVWQDRDVYLQGPIWAKIPHTDGHFHPSPLMGGF
hEr1.8    (598) RQAATADVNTQGVLPGMVWQDRDVYLQGPIWAKIPHTDGHFHPSPLMGGF
hEr1.16   (588) RQAATADVNTQGVLPGMVWQDRDVYLQGPIWAKIPHTDGHFHPSPLMGGF
hEr1.18   (588) RQAATADVNTQGVLPGMVWQDRDVYLQGPIWAKIPHTDGHFHPSPLMGGF
hEr1.35   (588) RQAATADVNTQGVLPGMVWQDRDVYLQGPIWAKIPHTDGHFHPSPLMGGF
hEr1.7    (589) RQAATADVNTQGVLPGMVWQDRDVYLQGPIWAKIPHTDGHFHPSPLMGGF
hEr1.36   (588) ----------QTSSYRRCQHTRRSSRHGLAGQRCVPSGAHLGKDSTHGRT
AAV2      (588) RQAATADVNTQGVLPGMVWQDRDVYLQGPIWAKIPHTDGHFHPSPLMGGF
                651                                                700
hE 1.1    (639) GLKHPPPQILIKNTPVPANPPAEFSATKFASFITQYSTGQVSVEIEWELQ
hEr1.5    (638) GLKHPPPQILIKNTPVPANPSTTFSAAKFASFITQYSTGQVSVEIEWELQ
hEr1.14   (638) GLKHPPPQILIKNTPVPANPSTTFSAAKFASFITQYSTGQVSVEIEWELQ
hEr1.8    (648) GLKHPPPQILIKNTPVPANPSTTFSAAKFASFITQYSTGQVSVEIEWELQ
hEr1.16   (638) GLKHPPPQILIKNTPVPANPSTTFSAAKFASFITQYSTGQVSVEIEWELQ
hEr1.18   (638) GLKHPPPQILIKNTPVPANPSTTFSEAKFASFITQYSTGQVSVEIEWELQ
hEr1.35   (638) GLKHPPPQILIKNTPVPANPSTTFSAAKFASFITQYSTGQVSVEIEWELQ
hEr1.7    (639) GLKHHPPQILIKNTPVPANPSTTFSAAKFASFITQYSTGQVSVEIEWELQ
hEr1.36   (628) FSPLSPHGWIRT-TPSSTDSHQEHPGTCESFDHLQCGKVCFLHHTVLHGT
AAV2      (638) GLKHPPPQILIKNTPVPANPSTTFSAAKFASFITQYSTGQVSVEIEWELQ
```

FIG. 14C

```
              701                                                 750
hE 1.1   (689) KENSKRWNPEVQYTSNYAKSANVDFTVDNNGLYTEPRPIGTRYLTRP---
hEr1.5   (688) KENSKRWNPEIQYTSNYNKSVNVDFTVDTNGVYSEPRPIGTRYLTRNLLL
hEr1.14  (688) KENSKRWNPEIQYTSNYNKSVNVDFTVDTNGVYSEPRPIGTRYLTRNLLL
hEr1.8   (698) KENSKRWNPEIQYTSNYNKSINVDFTVDTNGVYSEPRPIGTRYL------
hEr1.16  (688) KENSKRWNPEIQYTSNYNKSINVDFTVDTNGVYSEPRPIGTRYLTRN---
hEr1.18  (688) KENSKRWNPEIQYTSNYNKSVNVDFTVDTNGVYSEPRPIGTRYLTRN---
hEr1.35  (688) KENSKRWNPEIQYTSNYNKSVNVDFTVDTNGVYSEPRP------------
hEr1.7   (689) KENSKRWNPEIQYTSNYNKSVNVDFTVDTNGVYSEPRPIGTRYLTRNL-L
hEr1.36  (677) GQRGDRVRAAEGKQQTLESRNSVHFQLQQVC-------------------
AAV2     (688) KENSKRWNPEIQYTSNYNKSVNVDFTVDTNGVYSEPRPIGTRYLTRNL--

751
hE 1.1   (736) ---  (SEQ ID NO:44)
hEr1.5   (738) AA-  (SEQ ID NO:45)
hEr1.14  (738) AAA  (SEQ ID NO:46)
hEr1.8   (742) ---  (SEQ ID NO:47)
hEr1.16  (735) ---  (SEQ ID NO:48)
hEr1.18  (735) ---  (SEQ ID NO:49)
hEr1.35  (726) ---  (SEQ ID NO:50)
hEr1.7   (738) ---  (SEQ ID NO:51)
hEr1.36  (708) ---  (SEQ ID NO:52)
AAV2     (736) ---  (SEQ ID NO:5)
```

FIG. 14D

```
                    1                                                  50
hEr2.29    (1) MAADGYLPDWLEDTLSEGIRQWWKLKPGPPPPKPAERHKDDSRGLVLPGY
 hEr2.4    (1) MAADGYLPDWLEDTLSEGIRQWWKLKPGPPPPKPAERHKDDSRGLVLPGY
hEr2.16    (1) MASDGYLPDWLEDNLSEGIREWWDLKPGAPKPKANQQKQDDGRGLVLPGY
hEr2.30    (1) MASDGYLPDWLEDNLSEGIREWWDLKPGAPKPKANQQKQDDGRGLVLPGY
hEr2.31    (1) MASDGYLPDWLEDNLSEGIREWWDLKPGAPKPKANQQKQDDGRGLVLPGY
hEr2.36    (1) MAADGYLPDWLEDTLSEGIRQWWKLKPGPPPPKPAERHKDDSRGLVLPGC
   AAV2    (1) MAADGYLPDWLEDTLSEGIRQWWKLKPGPPPPKPAERHKDDSRGLVLPGY
                   51                                                 100
hEr2.29   (51) KYLGPFNGLDKGEPVNEADAAALEHDKAYDRQLDSGDNPYLKYNHADAEF
 hEr2.4   (51) KYLGPFNGLDKGEPVNEADAAALEHDKAYDRQLDSGDNPYLKYNHADAEF
hEr2.16   (51) KYLGPFNGLDKGEPVNAADAAALEHDKAYDQQLKAGDNPYLRYNHADAEF
hEr2.30   (51) KYLGPFNGLDKGEPVNAADAAALEHDKAYDQQLKAGDNPYLRYNHADAEF
hEr2.31   (51) KYLGPFNGLDKGEPVNAADAAALEHDKAYDQQLKAGDNPYLRYNHADAEF
hEr2.36   (51) KYLGPFNGLDKGEPVNEADAAALEHDKAYDRQLDSGDNPYLKYNHADAEF
   AAV2   (51) KYLGPFNGLDKGEPVNEADAAALEHDKAYDRQLDSGDNPYLKYNHADAEF
                  101                                                 150
hEr2.29  (101) QERLKEDTSFGGNLGRAVFQAKKRVLEPLGLVEEPVKTAPGKKRPVEHSP
 hEr2.4  (101) QERLKEDTSFGGNLGRAVFQAKKRVLEPLGLVEEPVKTAPGKKRPVEHSP
hEr2.16  (101) QERLQEDTSFGGNLGRAVFQAKKRVLEPFGLVEEGAKTAPGKKRPVEQSP
hEr2.30  (101) QERLQEDTSFGGNLGRAVFQAKKRVLEPFGLVEEGAKTAPGKKRPVEQSP
hEr2.31  (101) QERLQEDTSFGGNLGRAVFLAKKRVLEPFGLVEEGAKTAPGKKRPVEQSP
hEr2.36  (101) QERLKEDTSFGGNLGRAVFQAKKRVLEPLGLVEEPVKTAPGKKRPVEHSP
   AAV2  (101) QERLKEDTSFGGNLGRAVFQAKKRVLEPLGLVEEPVKTAPGKKRPVEHSP
                  151                                                 200
hEr2.29  (151) VEPDSSSGTGKAGQQPARKRLNFGQTGDADSVPDPQPLGQPPAAPSGLGT
 hEr2.4  (151) VEPDSSSGTGKAGQQPARKRLNFGQTGDADSVPDPQPLGQPPAAPSGLGT
hEr2.16  (151) QEPDSSSGIGKTGQQPAKKRLNFGQTGDSESVPDPQPLGEPPATPAAVGP
hEr2.30  (151) QEPDSSSGIGKTGQQPAKKRLNFGQTGDSESVPDPQPLGEPPATPAAVGP
hEr2.31  (151) QEPDSSSGIGKTGQQPAKKRLNFGQTGDSESVPDPQPLGEPPATPAAVGP
hEr2.36  (151) VEPDSSSGTGKAGQQPARKRLNFGQTGDADSVPDPQPLGQPPAAPSGLGT
   AAV2  (151) VEPDSSSGTGKAGQQPARKRLNFGQTGDADSVPDPQPLGQPPAAPSGLGT
                  201                                                 250
hEr2.29  (201) NTMATGSGAPMADNNEGADGVGNSSGNWHCDSTWMGDRVITTSTRTWALP
 hEr2.4  (201) NTMATGSGAPMADNNEGADGVGNSSGNWHCDSTWMGDRVITTSTRTWALS
hEr2.16  (201) TTMASGGGAPMADNNEGADGVGNASGNWHCDSTWLGDRVITTSTRTWALP
hEr2.30  (201) TTMASGGGAPMADNNEGADGVGNASGNWHCDSTWLGDRXITTSTRTWALP
hEr2.31  (201) TTMASGGGAPMADNNEGADGVGNASGNWHCDSTWLGDRVITTSTRTWALP
hEr2.36  (201) NTMATGSGAPMADNNEGADGVGNSSGNWHCDSTWMGDRVITTSTRTWALP
   AAV2  (201) NTMATGSGAPMADNNEGADGVGNSSGNWHCDSTWMGDRVITTSTRTWALP
                  251                                                 300
hEr2.29  (251) TYNNHLYKQISSQS-GASNDNHYFGYSTPWGYFDFNRFHCHFSPRDWQRL
 hEr2.4  (251) TYNNHLYKQISSQS-GASNDNHYFGYSTPWGYFDFNRFHCHFSPRDWQRL
hEr2.16  (251) TYNNHLYKQISSASTGASNDNHYFGYSTPWGYFDFNRFHCHFSPRDWQRL
hEr2.30  (251) TYNNHLYKQISSASTGASNDNHYFGYSTPWGYFDFNRFHCHFSPRDWQRL
hEr2.31  (251) TYNNHLYKQISSASTGASNDNHYFGYSTPWGYFDFNRFHCHFSPRDWQRL
hEr2.36  (251) TYNNHLYKQISSQS-GASNDNHYFGYSTPWGYFDFNRFHCHFSPRDWQRL
   AAV2  (251) TYNNHLYKQISSQS-GASNDNHYFGYSTPWGYFDFNRFHCHFSPRDWQRL
```

FIG. 16A

```
              301                                                350
hEr2.29 (300) INNNWGFRPKRLNFKLFNIQVKEVTQNDGTTTIANNLTSTVQVFTDSEYQ
 hEr2.4 (300) INNNWGFRPKRLNFKLFNIQVKEVTQNDGTTTIANNLTSTVQVFTDSEYQ
hEr2.16 (301) INNNWGFRPKRLNFKLFNIQVKEVTTNDGVTTIANNLTSTVQVFSDSEYQ
hEr2.30 (301) INNNWGFRPKRLNFKLFNIQVKEVTTNDGVTTIANNLTSTVQVFSDSEYQ
hEr2.31 (301) INNNWGFRPKRLNFKLFNIQVKEVTTNDGVTTIANNLTSTVQVFSDSEYQ
hEr2.36 (300) INNNWGFRPKRLNFKLFNIQVKEVTQNDGTTTIANNLTSTVQVFSDSEYQ
   AAV2 (300) INNNWGFRPKRLNFKLFNIQVKEVTQNDGTTTIANNLTSTVQVFTDSEYQ
              351                                                400
hEr2.29 (350) LPYVLGSAHQGCLPPFPADVFMVPQYGYLTLNNGSQAVGRSSFYCLEYFP
 hEr2.4 (350) LPYVLGSAHQGCLPPFPADVFMVPQYGYLTLNNGSQAVGRSSFYCLEYFP
hEr2.16 (351) LPYVLGSAHQGCLPPFPADVFMIPQYGYLTLNNGSQAVGRSSFYCLEYFP
hEr2.30 (351) LPYVLGSAHQGCLPPFPADVFMIPQYGYLTLNNGSQAVGRSSFYCLEYFP
hEr2.31 (351) LPYVLGSAHQGCLPPFPADVFMIPQYGYLTLNNGSQAVGRSSFYCLEYFP
hEr2.36 (350) LPYVLGSAHQGCLPPFPADVFMIPQYGYLTLNNGSQAVGRSSFYCLEYFP
   AAV2 (350) LPYVLGSAHQGCLPPFPADVFMVPQYGYLTLNNGSQAVGRSSFYCLEYFP
              401                                                450
hEr2.29 (400) SQMLRTGNNFTFSYTFEDVPFHSSYAHSQSLDRLMNPLIDQYLYYLSRTN
 hEr2.4 (400) SQMLRTGNNFTFSYTFEDVPFHSSYAHSQSLDRLMNPLIDQYLYYLSRTN
hEr2.16 (401) SQMLRTGNNFTFSYTFEDVPFHSSYAHSQSLDRLMNPLIDQYLYYLNRTQ
hEr2.30 (401) SQMLRTGNNFTFSYTFEDVPFHSSYAHSQSLDRLMNPLIDQYLYYLNRTQ
hEr2.31 (401) SQMLRTGNNFTFSYTFEDVPFHSSYAHSQSLDRLMNPLIDQYLYYLNRTQ
hEr2.36 (400) SQMLRTGNNFTFNYTFEDVPFHSSYAHSQSLDRLMNPLIDQYLYYLNRTQ
   AAV2 (400) SQMLRTGNNFTFSYTFEDVPFHSSYAHSQSLDRLMNPLIDQYLYYLSRTN
              451                                                500
hEr2.29 (450) TPSGTTTQSGLQFSQAGASDIRDQSRNWLPGPCYRQQRVSKTSADNNNSE
 hEr2.4 (450) TPSGTTTQSRLQFSQAGASDIRDQSRNWLPGPCYRQQRVSKTSADNNNSE
hEr2.16 (451) NQSGSAQNNDLLFSRGSPAGMSVQPKNWLPGPCYRQQRVSKTKTDNNNSN
hEr2.30 (451) NQSGSAQNNDLLFSRGSPAGMSVQPKNWLPGPCYRQQRVSKTKTDNNNSN
hEr2.31 (451) NQSGSAQNNDLLFSRGSPAGMSVQPKNWLPGPCYRQQRVSKTKTDNNNSN
hEr2.36 (450) NQSGSAQNNDLLFSRGSPAGMSVQPKNWLPGPCYRQQRVSKTKTDNNNSN
   AAV2 (450) TPSGTTTQSRLQFSQAGASDIRDQSRNWLPGPCYRQQRVSKTSADNNNSE
              501                                                550
hEr2.29 (500) YSWTGATKYHLNGRDSLVNPGPAMASHKDDEEKFFPQSGVLIFGKQGSEK
 hEr2.4 (500) YSWTGATKYHLNGRDSLVNPGPAMASHKDDEEKFFPQSGVLIFGKQGSEK
hEr2.16 (501) FTWTGASKYNLNGRESIINPGTAMASHKDDKDKFFPMSGVMIFGKESAGA
hEr2.30 (501) FTWTGASKYNLNGRESIINPGTAMASHKDDKDKFFPMSGVMIFGKESAGA
hEr2.31 (501) FTWTGASKYNLNGRESIINPGTAMASHKDDKDKFFPMSGVMIFGKESAGA
hEr2.36 (500) FTWTGASKYNLNGRESIINPGTAMASHKDDKDKFFPMSGVMIFGKESAGA
   AAV2 (500) YSWTGATKYHLNGRDSLVNPGPAMASHKDDEEKFFPQSGVLIFGKQGSEK
              551                                                600
hEr2.29 (550) TNVDIEKVMITDEEEIRTTNPVATEQYGSVSTNLQRGNRQAATADVNTQG
 hEr2.4 (550) TNVDIEKVMITDEEEIRTTNPVATEQYGSVSTNLQRGNRQAATADVNTQG
hEr2.16 (551) SNTALDNVMITDEEEIKATNPVATERFGTVAVNLQSSSTDPATGDVHVMG
hEr2.30 (551) SNTALDNVMITDEEEIKATNPVATERFGTVAVNLQSSSTDPATGDVHVMG
hEr2.31 (551) SNTALDNVMITDEEEIKATNPVATERFGTVAVNLQSSSTDPATGDVHVMG
hEr2.36 (550) SNTALDNVMITDEEEIKATNPVATERFGTVAVNLQSSSTDPATGDVHVMG
   AAV2 (550) TNVDIEKVMITDEEEIRTTNPVATEQYGSVSTNLQRGNRQAATADVNTQG
```

FIG. 16B

```
               601                                              650
hEr2.29  (600) VLPGMVWQDRDVYLQGPIWAKIPHTDGHFHPSPLMGGFGLKHPPPQILIK
 hEr2.4  (600) VLPGMVWQDRDVYLQGPIWAKIPHTDGHFHPSPLMGGFGLKHPPPQILIK
hEr2.16  (601) ALPGMVWQDRDVYLQGPIWAKIPHTDGHFHPSPLMGGFGLKNPPPQILIK
hEr2.30  (601) ALPGMVWQDRDVYLQGPIWAKIPHTDGHFHPSPLMGGFGLKNPPPQILIK
hEr2.31  (601) ALPGMVWQDRDVYLQGPIWAKIPHTDGHFHPSPLMGGFGLKNPPPQILIK
hEr2.36  (600) ALPGMVWQDRDVYLQGPIWAKIPHTDGHFHPSPLMGGFGLKNPPPQILIK
   AAV2  (600) VLPGMVWQDRDVYLQGPIWAKIPHTDGHFHPSPLMGGFGLKHPPPQILIK
               651                                              700
hEr2.29  (650) NTPVPANPSTTFSAAKFASFITQYSTGQVSVEIEWELQKENSKRWNPEIQ
 hEr2.4  (650) NTPVPANPSTTFSAAKFASFITQYSTGQVSVEIEWELQKENSKRWNPEIQ
hEr2.16  (651) NTPVPANPPAEFSATKFASFITQYSTGQVSVEIEWELQKENSKRWNPEVQ
hEr2.30  (651) NTPVPANPPAEFSATKFASFITQYSTGQVSVEIEWELQKENSKRWNPEVQ
hEr2.31  (651) NTPVPANPPAEFSATKFASFITQYSTGQVSVEIEWELQKENSKRWNPEVQ
hEr2.36  (650) NTPVPANPPAEFSATKFASFITQYSTGQVSVEIEWELQKENSKRWNPEVQ
   AAV2  (650) NTPVPANPSTTFSAAKFASFITQYSTGQVSVEIEWELQKENSKRWNPEIQ 701                         740
hEr2.29  (700) YTSNYNKSVNVDFTVDTNGVYSEPRPIGTRYLTRNLLLAA(SEQ ID NO:53)
 hEr2.4  (700) YTSNYNKSINVDFTVDTNGVYSEPRPIGTRYLTRN-----(SEQ ID NO:54)
hEr2.16  (701) YTSNYAKSANVDFTVDNNGLYTEPRPIGTR----------(SEQ ID NO:55)
hEr2.30  (701) YTSNYAKSANVDFTVDNNGLYTEPRPIGTRYLTRP-----(SEQ ID NO:56)
hEr2.31  (701) YTSNYAKSANVDFTVDNNGLYTEPRPIGTRYLT-------(SEQ ID NO:58)
hEr2.36  (700) YTSNYAKSANVDFTVDNNGLYTEPRPIGTRYLTRP-----(SEQ ID NO:58)
   AAV2  (700) YTSNYNKSVNVDFTVDTNGVYSEPRPIGTRYLTRNL----(SEQ ID NO:5)
```

FIG. 16C

```
                    1                                                50
     AAV2     (1)  MAADGYLPDWLEDTLSEGIRQWWKLKPGPPPPKPAERHKDDSRGLVLPGY
    hEr2.4    (1)  MAADGYLPDWLEDTLSEGIRQWWKLKPGPPPPKPAERHKDDSRGLVLPGY
    hEr1.23   (1)  MAADGYLPDWLEDTLSEGIRQWWKLKPGPPPPKPAERHKDDSRGLVLPGY
    hEr3.1    (1)  MAADGYLPDWLEDTLSEGIRQWWKLKPGPPPPKPAERHKDDSRGLVLPGY
                    51                                               100
     AAV2    (51)  KYLGPFNGLDKGEPVNEADAAALEHDKAYDRQLDSGDNPYLKYNHADAEF
    hEr2.4   (51)  KYLGPFNGLDKGEPVNEADAAALEHDKAYDRQLDSGDNPYLKYNHADAEF
    hEr1.23  (51)  KYLGPFNGLDKGEPVNEADAAALEHDKAYDRQLDSGDNPYLKYNHADAEF
    hEr3.1   (51)  KYLGPFNGLDKGEPVNEADAAALEHDKAYDRQLDGGDNPYLKYNHADAEF
                    101                                              150
     AAV2   (101)  QERLKEDTSFGGNLGRAVFQAKKRVLEPLGLVEEPVKTAPGKKRPVEHSP
    hEr2.4  (101)  QERLKEDTSFGGNLGRAVFQAKKRVLEPLGLVEEPVKTAPGKKRPVEHSP
    hEr1.23 (101)  QERLKEDTSFGGNLGRAVFQAKKRVLEPLGLVEEPVKTAPGKKRPVEHSP
    hEr3.1  (101)  QERLKEDTSFGGNLGRAVFQAKKRVLEPLGLVEEPVKTAPGKKRPVEHSP
                    151                                              200
     AAV2   (151)  VEPDSSSGTGKAGQQPARKRLNFGQTGDADSVPDPQPLGQPPAAPSGLGT
    hEr2.4  (151)  VEPDSSSGTGKAGQQPARKRLNFGQTGDADSVPDPQPLGQPPAAPSGLGT
    hEr1.23 (151)  VEPDSSSGTGKAGQQPARKRLNFGQTGDADSVPDPQPLGQPPAAPSGLGT
    hEr3.1  (151)  VEPDSSSGTGKAGQQPARKRLNFGQTGDADSVPDPQPLGQPPAAPSGLGT
                    201                                              250
     AAV2   (201)  NTMATGSGAPMADNNEGADGVGNSSGNWHCDSTWMGDRVITTSTRTWALP
    hEr2.4  (201)  NTMATGSGAPMADNNEGADGVGNSSGNWHCDSTWMGDRVITTSTRTWALS
    hEr1.23 (201)  NTMATGSGAPMADNNEGADGVGNSSGNWHCDSTWMGDRVITTSTRTWALP
    hEr3.1  (201)  NTMATGSGAPMADNNEGADGVGNSSGNWHCDSTWMGDRVITTSTRTWALP
                    251                                              300
     AAV2   (251)  TYNNHLYKQISSQSGASNDNHYFGYSTPWGYFDFNRFHCHFSPRDWQRLI
    hEr2.4  (251)  TYNNHLYKQISSQSGASNDNHYFGYSTPWGYFDFNRFHCHFSPRDWQRLI
    hEr1.23 (251)  TYNNHLYKQISSQSGASNDNHYFGYSTPWGYFDFNRFHCHFSPRDWQRLI
    hEr3.1  (251)  TYNNHLYKQISSQSGASNDNHYFGYSTPWGYFDFNRFHCHFSPRDWQRLI
                    301                                              350
     AAV2   (301)  NNNWGFRPKRLNFKLFNIQVKEVTQNDGTTTIANNLTSTVQVFTDSEYQL
    hEr2.4  (301)  NNNWGFRPKRLNFKLFNIQVKEVTQNDGTTTIANNLTSTVQVFTDSEYQL
    hEr1.23 (301)  NNNWGFRPKRLNFKLFNIQVKEVTQNDGTTTIANNLTSTVQVFTDSEYQL
    hEr3.1  (301)  NNNWGFRPKRLNFKLFNIQVKEVTQNDGTTTIANNLTSTVQVFTDSEYQL
                    351                                              400
     AAV2   (351)  PYVLGSAHQGCLPPFPADVFMVPQYGYLTLNNGSQAVGRSSFYCLEYFPS
    hEr2.4  (351)  PYVLGSAHQGCLPPFPADVFMVPQYGYLTLNNGSQAVGRSSFYCLEYFPS
    hEr1.23 (351)  PYVLGSAHQGCLPPFPADVFMVPQYGYLTLNNGSQAVGRSSFYCLEYFPS
    hEr3.1  (351)  PYVLGSAHQGCLPPFPADVFMVPQYGYLTLNNGSQAVGRSSFYCLEYFPS
                    401                                              450
     AAV2   (401)  QMLRTGNNFTFSYTFEDVPFHSSYAHSQSLDRLMNPLIDQYLYYLSRTNT
    hEr2.4  (401)  QMLRTGNNFTFSYTFEDVPFHSSYAHSQSLDRLMNPLIDQYLYYLSRTNT
    hEr1.23 (401)  QMLRTGNNFTFSYTFEDVPFHSSYAHSQSLDRLMNPLIDQYLYYLSRTNT
    hEr3.1  (401)  QMLRTGNNFTFSYTFEDVPFHSSYAHSQSLDRLMNPLIDQYLYYLSRTNT
                    451                                              500
     AAV2   (451)  PSGTTTQSRLQFSQAGASDIRDQSRNWLPGPCYRQQRVSKTSADNNNSEY
    hEr2.4  (451)  PSGTTTQSRLQFSQAGASDIRDQSRNWLPGPCYRQQRVSKTSADNNNSEY
    hEr1.23 (451)  PSGTTTQSGLQFSQAGASDIRDQSRNWLPGPCYRQQRVSKTSADNNNSEY
    hEr3.1  (451)  PSGTTTQSGLQFSQAGASDIRDQSRNWLPGPCYRQQRVSKTSADNNNSEY
                    501                                              550
     AAV2   (501)  SWTGATKYHLNGRDSLVNPGPAMASHKDDEEKFFPQSGVLIFGKQGSEKT
    hEr2.4  (501)  SWTGATKYHLNGRDSLVNPGPAMASHKDDEEKFFPQSGVLIFGKQGSEKT
    hEr1.23 (501)  SWTGATKYHLNGRDSLVNPGPAMASHKDDEEKFFPQSGVLIFGKQGSEKT
    hEr3.1  (501)  SWTGATKYHLNGRDSLVNPGPAMASHKDDEEKFFPQSGVLIFGKQGSEKT
```

FIG. 17A

```
AAV2    (551) NVDIEKVMITDEEEIRTTNPVATEQYGSVSTNLQRGNRQAATADVNTQGV
hEr2.4  (551) NVDIEKVMITDEEEIRTTNPVATEQYGSVSTNLQRGNRQAATADVNTQGV
hEr1.23 (551) NVDIEKVMITDEEEIRTTNPVATEQYGSVSTNLQRGNRQAATADVNTQGV
hEr3.1  (551) NVDIEKVMITDEEEIRTTNPVATEQYGSVSTNLQRGNRQAATADVNTQGV
              601                                              650
AAV2    (601) LPGMVWQDRDVYLQGPIWAKIPHTDGHFHPSPLMGGFGLKHPPPQILIKN
hEr2.4  (601) LPGMVWQDRDVYLQGPIWAKIPHTDGHFHPSPLMGGFGLKHPPPQILIKN
hEr1.23 (601) LPGMVWQDRDVYLQGPIWAKIPHTDGHFHPSPLMGGFGLKHPPPQILIKN
hEr3.1  (601) LPGMVWQDRDVYLQGPIWAKIPHTDGHFHPSPLMGGFGLKHPPPQILIKN
              651                                              700
AAV2    (651) TPVPANPSTTFSAAKFASFITQYSTGQVSVEIEWELQKENSKRWNPEIQY
hEr2.4  (651) TPVPANPSTTFSAAKFASFITQYSTGQVSVEIEWELQKENSKRWNPEIQY
hEr1.23 (651) TPVPANPSTTFSAAKFASFITQYSTGQVSVEIEWELQKENSKRWNPEIQY
hEr3.1  (651) TPVPANPSTTFSAAKFASFITQYSTGQVSVEIEWELQKENSKRWNPEIQY
              701                                743
AAV2    (701) TSNYNKSVNVDFTVDTNGVYSEPRPIGTRYLTRNL-------  (SEQ ID NO:5)
hEr2.4  (701) TSNYNKSINVDFTVDTNGVYSEPRPIGTRYLTRN--------  (SEQ ID NO:54)
hEr1.23 (701) TSNYNKSVNVDFTVDTNGVYSEPRPIGTRYLTRNL-LLAAAVI  (SEQ ID NO:53)
hEr3.1  (701) TSNYNKSVNVDFTVDTNGVYSEPRPIGTRYLTRNLLRP-----  (SEQ ID NO:59)
```

MUTANT ADENO-ASSOCIATED VIRUS VIRIONS AND METHODS OF USE THEREOF

CROSS-REFERENCE

This application is a continuation-in-part of U.S. patent application Ser. No. 10/880,297, filed Jun. 28, 2004, which claims the benefit of U.S. Provisional Patent Application No. 60/484,111 filed Jun. 30, 2003, which applications are incorporated herein by reference in their entirety.

FIELD OF THE INVENTION

The present invention is in the field of recombinant adeno-associated virus vectors.

BACKGROUND OF THE INVENTION

Adeno-associated virus (AAV) is a 4.7 kb, single stranded DNA virus that contains two open reading frames, rep and cap. The first gene encodes four proteins necessary for genome replication (Rep78, Rep68, Rep52, and Rep40), and the second expresses three structural proteins (VP1-3) that assemble to form the viral capsid. As its name implies, AAV is dependent upon the presence of a helper virus, such as an adenovirus or herpes virus, for active replication. In the absence of a helper it establishes a latent state in which its genome is maintained episomally or integrated into the host chromosome. To date, numerous AAV serotypes in humans have been identified.

In 1989 a recombinant AAV2 (rAAV) gene delivery vector system was first generated, and vectors based on AAV have subsequently been shown to offer numerous major advantages. First, vectors based on AAV are extremely safe, since wild-type AAV is nonpathogenic and has no etiologic association with any known diseases. In addition, AAV offers the capability for highly efficient gene delivery and sustained transgene expression in numerous tissues, including muscle, lung, and brain. Furthermore, AAV has enjoyed success in human clinical trials.

Despite this success, vector design problems remain. One major concern is the fact that much of the human population has already been exposed to various AAV serotypes, and as a result a significant fraction of any future patient population harbors neutralizing antibodies (NABs) that block gene delivery. Additional problems with rAAV vectors include limited tissue dispersion for serotypes that employ heparan sulfate as a receptor (AAV2 and 3), poor infection of non-permissive cell types such as stem cells, challenges with high efficiency targeting of gene delivery to selected cell populations, and a finite transgene carrying capacity.

There is a need in the art for improved AAV vectors that can infect cells that are non-permissive for AAV.

Literature

Halbert et al. (2000) *J Virol* 74, 1524-32; Blacklow et al. (1971) *Am J Epidemiol* 94, 359-66. (1971); Erles et al. (1999) *J Med Virol* 59, 406-11; Moskalenko et al. (2000) *J Virol* 74, 1761-6; Wobus et al. (2000) *J Virol* 74, 9281-93; Sun et al. (2003) *Gene Ther* 10, 964-76; Nguyen (2001) *Neuroreport* 12, 1961-4; Davidson et al. (2000) *Proc Natl Acad Sci USA* 97, 3428-32; Rabinowitz et al. (1999) *Virology* 265, 274-85; Opie et al. (2003) *J Virol* 77, 6995-7006; U.S. Pat. No. 6,596, 539; U.S. Pat. No. 6,733,757; U.S. Pat. No. 6,710,036; U.S. Pat. No. 6,703,237.

SUMMARY OF THE INVENTION

The present invention provides mutant adeno-associated virus (AAV) that exhibit altered capsid properties, e.g., reduced binding to neutralizing antibodies in serum and/or altered heparin binding and/or altered infectivity of particular cell types. The present invention further provides libraries of mutant AAV comprising one or more mutations in a capsid gene. The present invention further provides methods of generating the mutant AAV and mutant AAV libraries, and compositions comprising the mutant AAV. The present invention further provides recombinant AAV (rAAV) virions that comprise a mutant capsid protein. The present invention further provides nucleic acids comprising nucleotide sequences that encode mutant capsid proteins, and host cells comprising the nucleic acids. The present invention further provides methods of delivering a gene product to an individual, the methods generally involving administering an effective amount of a subject rAAV virion to an individual in need thereof.

BRIEF DESCRIPTION OF THE DRAWINGS

FIG. 2a depicts the fraction rescued (normalized with respect to zero stringency) at various stringencies (given as the ratio of neutralizing antibody titer (reciprocal dilution) divided by the actual dilution). FIG. 2b depicts the percent knockdown (reduction) in infection by rabbit antisera for wild type AAV, AAV library, and individual AAV escape mutants.

FIGS. 3A-C depict the nucleotide sequence of wild-type AAV cap (SEQ ID NO: 1) aligned with nucleotide sequences of cap of the neutralizing antibody escape mutants AbE2 (SEQ ID NO:2) and AbE L (SEQ ID NO:3). Boxes indicate changes in nucleotide sequence compared to wild-type.

FIGS. 4A-G depict an alignment of VP1-encoding nucleotide sequences of wild-type AAV-2 VP1 (SEQ ID NO:4), and exemplary neutralizing antibody evasion mutants.

FIGS. 5A-C depict an alignment of VP1-encoding amino acid sequences of wild-type AAV-2 VP1 (SEQ ID NO:5), and exemplary neutralizing antibody evasion mutants.

FIGS. 6A-J depict an alignment of VP1-encoding nucleotide sequences of wild-type AAV-2 VP1, and exemplary neutralizing antibody evasion mutants.

FIGS. 7A-D depict an alignment of VP1-encoding amino acid sequences of wild-type AAV-2 VP1, and exemplary neutralizing antibody evasion mutants.

FIGS. 8A-G depict an alignment of VP1-encoding nucleotide sequences of wild-type AAV-2 VP1, and exemplary heparin binding mutants.

FIGS. 9A-C depict an alignment of VP1-encoding amino acid sequences of wild-type AAV-2 VP1, and exemplary heparin binding mutants.

FIGS. 10A and 10B provide an alignment of VP1-encoding amino acid sequences of wild-type AAV-5 (SEQ ID NO:43) and AAV2.5T (SEQ ID NO:42), a capsid variant that confers increased infectivity of lung epithelial cells

FIGS. 16A-C provide an alignment of amino acid sequences of exemplary AAV capsid variants. hEr2.29 (SEQ ID NO:53); hEr2.4 (SEQ ID NO:54); hEr2.16 (SEQ ID NO:55); hEr2.30 (SEQ ID NO:56); hEr2.31 (SEQ ID NO:58); hEr2.36 (SEQ ID NO:57); and AAV2 (SEQ ID NO:5).

FIGS. 17A-B provide an alignment of amino acid sequences of exemplary AAV capsid variants hEr2.4, hEr1.23, and hEr3.1, compared to AAV2. AAV2 (SEQ ID NO:5); hEr2.4 (SEQ ID NO:54); hER1.23 (SEQ ID NO:53); and hEr3.1 (SEQ ID NO:59).

DEFINITIONS

Figure 1A:
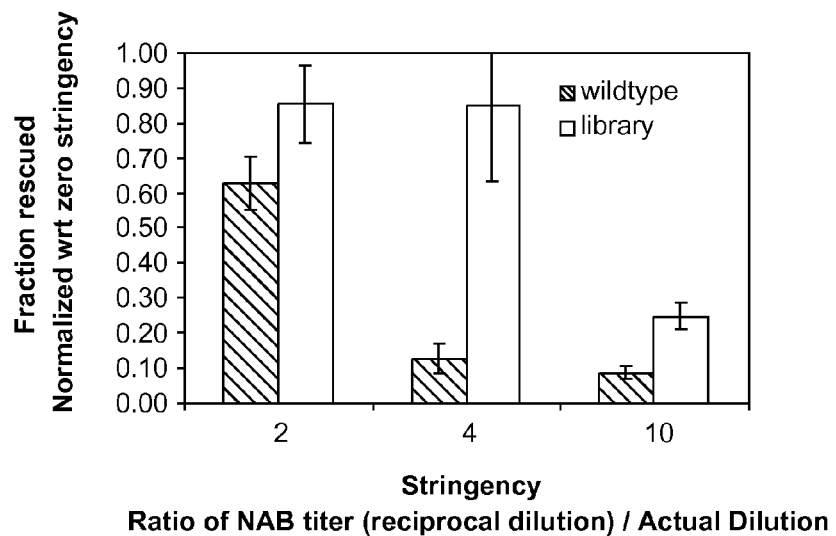
FIGS. 1a and 1b depict heparin binding characteristics of wild type AAV versus the viral library.

A "vector" as used herein refers to a macromolecule or association of macromolecules that comprises or associates with a polynucleotide and which can be used to mediate delivery of the polynucleotide to a cell. Illustrative vectors include, for example, plasmids, viral vectors, liposomes, and other gene delivery vehicles.

"AAV" is an abbreviation for adeno-associated virus, and may be used to refer to the virus itself or derivatives thereof. The term covers all subtypes and both naturally occurring and recombinant forms, except where required otherwise. The abbreviation "rAAV" refers to recombinant adeno-associated virus, also referred to as a recombinant AAV vector (or "rAAV vector"). The term "AAV" includes AAV type 1 (AAV-1), AAV type 2 (AAV-2), AAV type 3 (AAV-3), AAV type 4 (AAV-4), AAV type 5 (AAV-5), AAV type 6 (AAV-6), AAV type 7 (AAV-7), AAV type 8 (AAV-8), avian AAV, bovine AAV, canine AAV, equine AAV, primate AAV, non-primate AAV, and ovine AAV. "Primate AAV" refers to AAV that infect primates, "non-primate AAV" refers to AAV that infect non-primate mammals, "bovine AAV" refers to AAV that infect bovine mammals, etc.

An "rAAV vector" as used herein refers to an AAV vector comprising a polynucleotide sequence not of AAV origin (i.e., a polynucleotide heterologous to AAV), typically a sequence of interest for the genetic transformation of a cell. In general, the heterologous polynucleotide is flanked by at least one, and generally by two AAV inverted terminal repeat sequences (ITRs). The term rAAV vector encompasses both rAAV vector particles and rAAV vector plasmids.

An "AAV virus" or "AAV viral particle" or "rAAV vector particle" refers to a viral particle composed of at least one AAV capsid protein (typically by all of the capsid proteins of a wild-type AAV) and an encapsidated polynucleotide rAAV vector. If the particle comprises a heterologous polynucleotide (i.e. a polynucleotide other than a wild-type AAV genome such as a transgene to be delivered to a mammalian cell), it is typically referred to as an "rAAV vector particle" or simply an "rAAV vector". Thus, production of rAAV particle necessarily includes production of rAAV vector, as such a vector is contained within an rAAV particle.

"Packaging" refers to a series of intracellular events that result in the assembly and encapsidation of an AAV particle.

AAV "rep" and "cap" genes refer to polynucleotide sequences encoding replication and encapsidation proteins of adeno-associated virus. AAV rep and cap are referred to herein as AAV "packaging genes."

A "helper virus" for AAV refers to a virus that allows AAV (e.g. wild-type AAV) to be replicated and packaged by a mammalian cell. A variety of such helper viruses for AAV are known in the art, including adenoviruses, herpesviruses and poxviruses such as vaccinia. The adenoviruses encompass a number of different subgroups, although Adenovirus type 5 of subgroup C is most commonly used. Numerous adenoviruses of human, non-human mammalian and avian origin are known and available from depositories such as the ATCC. Viruses of the herpes family include, for example, herpes simplex viruses (HSV) and Epstein-Barr viruses (EBV), as well as cytomegaloviruses (CMV) and pseudorabies viruses (PRV); which are also available from depositories such as ATCC.

"Helper virus function(s)" refers to function(s) encoded in a helper virus genome which allow AAV replication and packaging (in conjunction with other requirements for replication and packaging described herein). As described herein, "helper virus function" may be provided in a number of ways, including by providing helper virus or providing, for example, polynucleotide sequences encoding the requisite function(s) to a producer cell in trans.

An "infectious" virus or viral particle is one that comprises a polynucleotide component which it is capable of delivering into a cell for which the viral species is trophic. The term does not necessarily imply any replication capacity of the virus. Assays for counting infectious viral particles are described elsewhere in this disclosure and in the art. Viral infectivity can be expressed as the P:I ratio, or the ratio of total viral particles to infective viral particles.

A "replication-competent" virus (e.g. a replication-competent AAV) refers to a phenotypically wild-type virus that is infectious, and is also capable of being replicated in an infected cell (i.e. in the presence of a helper virus or helper virus functions). In the case of AAV, replication competence generally requires the presence of functional AAV packaging genes. In general, rAAV vectors as described herein are replication-incompetent in mammalian cells (especially in human cells) by virtue of the lack of one or more AAV packaging genes. Typically, such rAAV vectors lack any AAV packaging gene sequences in order to minimize the possibility that replication competent AAV are generated by recombination between AAV packaging genes and an incoming rAAV vector. In many embodiments, rAAV vector preparations as described herein are those which contain few if any replication competent AAV (rcAAV, also referred to as RCA) (e.g., less than about 1 rcAAV per $10^2$ rAAV particles, less than about 1 rcAAV per $10^4$ rAAV particles, less than about 1 rcAAV per $10^8$ rAAV particles, less than about 1 rcAAV per $10^{12}$ rAAV particles, or no rcAAV).

The term "polynucleotide" refers to a polymeric form of nucleotides of any length, including deoxyribonucleotides or ribonucleotides, or analogs thereof. A polynucleotide may comprise modified nucleotides, such as methylated nucleotides and nucleotide analogs, and may be interrupted by non-nucleotide components. If present, modifications to the nucleotide structure may be imparted before or after assembly of the polymer. The term polynucleotide, as used herein, refers interchangeably to double- and single-stranded molecules. Unless otherwise specified or required, any embodiment of the invention described herein that is a polynucleotide encompasses both the double-stranded form and each of two complementary single-stranded forms known or predicted to make up the double-stranded form.

Nucleic acid hybridization reactions can be performed under conditions of different "stringency". Conditions that increase stringency of a hybridization reaction of widely known and published in the art. See, e.g., Sambrook et al. Molecular Cloning, A Laboratory Manual, 2nd Ed., Cold Spring Harbor Laboratory Press, Cold Spring Harbor, N.Y., 1989, herein incorporated by reference. For example, see page 7.52 of Sambrook et al. Examples of relevant conditions include (in order of increasing stringency): incubation temperatures of 25° C., 37° C., 50° C. and 68° C.; buffer concentrations of 10×SSC, 6×SSC, 1×SSC, 0.1×SSC (where 1×SSC is 0.15 M NaCl and 15 mM citrate buffer) and their equivalents using other buffer systems; formamide concentrations of 0%, 25%, 50%, and 75%; incubation times from 5 minutes to 24 hours; 1, 2, or more washing steps; wash incubation times of 1, 2, or 15 minutes; and wash solutions of 6×SSC, 1×SSC, 0.1×SSC, or deionized water. An example of stringent hybridization conditions is hybridization at 50° C. or higher and 0.1×SSC (15 mM sodium chloride/1.5 mM sodium citrate). Another example of stringent hybridization conditions is overnight incubation at 42° C. in a solution: 50% formamide, 1×SSC (150 mM NaCl, 15 mM sodium citrate), 50 mM sodium phosphate (pH 7.6), 5×Denhardt's solution, 10% dextran sulfate, and 20 μg/ml denatured, sheared salmon sperm DNA, followed by washing the filters in 0.1×SSC at about 65° C. As another example, stringent hybridization conditions comprise: prehybridization for 8 hours to overnight at 65° C. in a solution comprising 6× single strength citrate (SSC) (1×SSC is 0.15 M NaCl, 0.015 M Na citrate; pH 7.0), 5×Denhardt's solution, 0.05% sodium pyrophosphate and 100 μg/ml herring sperm DNA; hybridization for 18-20 hours at 65° C. in a solution containing 6×SSC, 1×Denhardt's solution, 100 μg/ml yeast tRNA and 0.05% sodium pyrophosphate; and washing of filters at 65° C. for 1 h in a solution containing 0.2×SSC and 0.1% SDS (sodium dodecyl sulfate).

Stringent hybridization conditions are hybridization conditions that are at least as stringent as the above representative conditions. Other stringent hybridization conditions are known in the art and may also be employed to identify nucleic acids of this particular embodiment of the invention.

"$T_m$" is the temperature in degrees Celsius at which 50% of a polynucleotide duplex made of complementary strands hydrogen bonded in anti-parallel direction by Watson-Crick base pairing dissociates into single strands under conditions of the experiment. $T_m$ may be predicted according to a standard formula, such as:

$$T_m = 81.5 + 16.6 \log [X^+] + 0.41 (\% \, G/C) - 0.61 (\% \, F) - 600/L$$

where [$X^+$] is the cation concentration (usually sodium ion, Na$^+$) in mol/L; (% G/C) is the number of G and C residues as a percentage of total residues in the duplex; (% F) is the percent formamide in solution (wt/vol); and L is the number of nucleotides in each strand of the duplex.

A polynucleotide or polypeptide has a certain percent "sequence identity" to another polynucleotide or polypeptide, meaning that, when aligned, that percentage of bases or amino acids are the same when comparing the two sequences. Sequence similarity can be determined in a number of different manners. To determine sequence identity, sequences can be aligned using the methods and computer programs, including BLAST, available over the world wide web at ncbi.nlm.nih.gov/BLAST/. Another alignment algorithm is FASTA, available in the Genetics Computing Group (GCG) package, from Madison, Wis., USA, a wholly owned subsidiary of Oxford Molecular Group, Inc. Other techniques for alignment are described in Methods in Enzymology, vol. 266: Computer Methods for Macromolecular Sequence Analysis (1996), ed. Doolittle, Academic Press, Inc., a division of Harcourt Brace & Co., San Diego, Calif., USA. Of particular interest are alignment programs that permit gaps in the sequence. The Smith-Waterman is one type of algorithm that permits gaps in sequence alignments. See Meth. Mol. Biol. 70: 173-187 (1997). Also, the GAP program using the Needleman and Wunsch alignment method can be utilized to align sequences. See J. Mol. Biol. 48: 443-453 (1970)

Of interest is the BestFit program using the local homology algorithm of Smith Waterman (Advances in Applied Mathematics 2: 482-489 (1981) to determine sequence identity. The gap generation penalty will generally range from 1 to 5, usually 2 to 4 and in many embodiments will be 3. The gap extension penalty will generally range from about 0.01 to 0.20 and in many instances will be 0.10. The program has default parameters determined by the sequences inputted to be compared. Preferably, the sequence identity is determined using the default parameters determined by the program. This program is available also from Genetics Computing Group (GCG) package, from Madison, Wis., USA.

Another program of interest is the FastDB algorithm. FastDB is described in Current Methods in Sequence Comparison and Analysis, Macromolecule Sequencing and Synthesis, Selected Methods and Applications, pp. 127-149, 1988, Alan R. Liss, Inc. Percent sequence identity is calculated by FastDB based upon the following parameters:

Mismatch Penalty: 1.00;
Gap Penalty: 1.00;
Gap Size Penalty: 0.33; and
Joining Penalty: 30.0.

A "gene" refers to a polynucleotide containing at least one open reading frame that is capable of encoding a particular protein after being transcribed and translated.

A "small interfering" or "short interfering RNA" or siRNA is a RNA duplex of nucleotides that is targeted to a gene interest (a "target gene"). An "RNA duplex" refers to the structure formed by the complementary pairing between two regions of a RNA molecule. siRNA is "targeted" to a gene in that the nucleotide sequence of the duplex portion of the siRNA is complementary to a nucleotide sequence of the targeted gene. In some embodiments, the length of the duplex of siRNAs is less than 30 nucleotides. In some embodiments, the duplex can be 29, 28, 27, 26, 25, 24, 23, 22, 21, 20, 19, 18, 17, 16, 15, 14, 13, 12, 11 or 10 nucleotides in length. In some embodiments, the length of the duplex is 19-25 nucleotides in length. The RNA duplex portion of the siRNA can be part of a hairpin structure. In addition to the duplex portion, the hairpin structure may contain a loop portion positioned between the two sequences that form the duplex. The loop can vary in length. In some embodiments the loop is 5, 6, 7, 8, 9, 10, 11, 12 or 13 nucleotides in length. The hairpin structure can also contain 3' or 5' overhang portions. In some embodiments, the overhang is a 3' or a 5' overhang 0, 1, 2, 3, 4 or 5 nucleotides in length.

"Recombinant," as applied to a polynucleotide means that the polynucleotide is the product of various combinations of cloning, restriction or ligation steps, and other procedures that result in a construct that is distinct from a polynucleotide found in nature. A recombinant virus is a viral particle comprising a recombinant polynucleotide. The terms respectively include replicates of the original polynucleotide construct and progeny of the original virus construct.

A "control element" or "control sequence" is a nucleotide sequence involved in an interaction of molecules that contributes to the functional regulation of a polynucleotide, including replication, duplication, transcription, splicing, translation, or degradation of the polynucleotide. The regulation may affect the frequency, speed, or specificity of the process, and may be enhancing or inhibitory in nature. Control elements known in the art include, for example, transcriptional regulatory sequences such as promoters and enhancers. A promoter is a DNA region capable under certain conditions of binding RNA polymerase and initiating transcription of a coding region usually located downstream (in the 3' direction) from the promoter.

"Operatively linked" or "operably linked" refers to a juxtaposition of genetic elements, wherein the elements are in a relationship permitting them to operate in the expected manner. For instance, a promoter is operatively linked to a coding region if the promoter helps initiate transcription of the coding sequence. There may be intervening residues between the promoter and coding region so long as this functional relationship is maintained.

An "expression vector" is a vector comprising a region which encodes a polypeptide of interest, and is used for effecting the expression of the protein in an intended target cell. An expression vector also comprises control elements operatively linked to the encoding region to facilitate expression of the protein in the target. The combination of control elements and a gene or genes to which they are operably linked for expression is sometimes referred to as an "expression cassette," a large number of which are known and available in the art or can be readily constructed from components that are available in the art.

"Heterologous" means derived from a genotypically distinct entity from that of the rest of the entity to which it is being compared. For example, a polynucleotide introduced by genetic engineering techniques into a plasmid or vector derived from a different species is a heterologous polynucleotide. A promoter removed from its native coding sequence and operatively linked to a coding sequence with which it is not naturally found linked is a heterologous promoter. Thus, for example, an rAAV that includes a heterologous nucleic acid encoding a heterologous gene product is an rAAV that includes a nucleic acid not normally included in a naturally-occurring, wild-type AAV, and the encoded heterologous gene product is a gene product not normally encoded by a naturally-occurring, wild-type AAV.

The terms "genetic alteration" and "genetic modification" (and grammatical variants thereof), are used interchangeably herein to refer to a process wherein a genetic element (e.g., a polynucleotide) is introduced into a cell other than by mitosis or meiosis. The element may be heterologous to the cell, or it may be an additional copy or improved version of an element already present in the cell. Genetic alteration may be effected, for example, by transfecting a cell with a recombinant plasmid or other polynucleotide through any process known in the art, such as electroporation, calcium phosphate precipitation, or contacting with a polynucleotide-liposome complex. Genetic alteration may also be effected, for example, by transduction or infection with a DNA or RNA virus or viral vector. Generally, the genetic element is introduced into a chromosome or mini-chromosome in the cell; but any alteration that changes the phenotype and/or genotype of the cell and its progeny is included in this term.

A cell is said to be "stably" altered, transduced, genetically modified, or transformed with a genetic sequence if the sequence is available to perform its function during extended culture of the cell in vitro. Generally, such a cell is "heritably" altered (genetically modified) in that a genetic alteration is introduced which is also inheritable by progeny of the altered cell.

The terms "polypeptide," "peptide," and "protein" are used interchangeably herein to refer to polymers of amino acids of any length. The terms also encompass an amino acid polymer that has been modified; for example, disulfide bond formation, glycosylation, lipidation, phosphorylation, or conjugation with a labeling component. Polypeptides such as "CFTR," "p53," "EPO" and the like, when discussed in the context of delivering a gene product to a mammalian subject, and compositions therefor, refer to the respective intact polypeptide, or any fragment or genetically engineered derivative thereof, that retains the desired biochemical function of the intact protein. Similarly, references to CFTR, p53, EPO genes, and other such genes for use in delivery of a gene product to a mammalian subject (which may be referred to as "transgenes" to be delivered to a recipient cell), include polynucleotides encoding the intact polypeptide or any fragment or genetically engineered derivative possessing the desired biochemical function.

An "isolated" plasmid, nucleic acid, vector, virus, host cell, or other substance refers to a preparation of the substance devoid of at least some of the other components that may also be present where the substance or a similar substance naturally occurs or is initially prepared from. Thus, for example, an isolated substance may be prepared by using a purification technique to enrich it from a source mixture. Enrichment can be measured on an absolute basis, such as weight per volume of solution, or it can be measured in relation to a second, potentially interfering substance present in the source mixture. Increasing enrichments of the embodiments of this invention are increasingly more isolated. An isolated plasmid, nucleic acid, vector, virus, host cell, or other substance is in some embodiments purified, e.g., from about 80% to about 90% pure, at least about 90% pure, at least about 95% pure, at least about 98% pure, or at least about 99%, or more, pure.

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse affect attributable to the disease. "Treatment," as used herein, covers any treatment of a disease in a mammal, particularly in a human, and includes: (a) preventing the disease from occurring in a subject which may be predisposed to the disease or at risk of acquiring the disease but has not yet been diagnosed as having it; (b) inhibiting the disease, i.e., arresting its development; and (c) relieving the disease, i.e., causing regression of the disease.

The terms "individual," "host," "subject," and "patient" are used interchangeably herein, and refer to a mammal, including, but not limited to, human and non-human primates, including simians and humans; mammalian sport animals (e.g., horses); mammalian farm animals (e.g., sheep, goats, etc.); mammalian pets (dogs, cats, etc.); and rodents (e.g., mice, rats, etc.).

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "an rAAV vector" includes a plurality of such vectors and reference to "the mutant AAV capsid protein" includes reference to one or more mutant AAV capsid proteins and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION OF THE INVENTION

The present invention provides mutant adeno-associated virus (AAV) that exhibit altered capsid properties, e.g., reduced binding to neutralizing antibodies in serum and/or altered heparin binding and/or altered infectivity of particular cell types. The present invention further provides libraries of mutant AAV comprising one or more mutations in a capsid gene. The present invention further provides methods of generating the mutant AAV, mutant AAV libraries, and compositions comprising the mutant AAV or mutant AAV libraries. The present invention further provides recombinant AAV (rAAV) virions that comprise a mutant capsid protein. The present invention further provides nucleic acids comprising nucleotide sequences that encode mutant capsid proteins, and host cells comprising the nucleic acids. The present invention further provides methods of delivering a gene product to an individual, the methods generally involving administering an effective amount of a subject rAAV virion to an individual in need thereof. In many embodiments, a subject mutant AAV virion, a subject nucleic acid, etc., is isolated.

A subject mutant AAV virion or a subject rAAV virion exhibits one or more of the following properties: 1) increased heparan sulfate binding affinity relative to wild-type AAV; 2) decreased heparan sulfate binding affinity relative to wild-type AAV; 3) increased infectivity of a cell that is resistant to infection with AAV, or that is less permissive to infection with AAV than a prototypical permissive cell; 4) increased evasion of neutralizing antibodies; and 5) increased ability to cross an endothelial cell layer.

A subject nucleic acid encoding a mutant AAV capsid protein is useful for generating recombinant AAV virions that exhibit altered properties such as increased heparan sulfate binding, decreased heparan sulfate binding, increased infectivity of a cell that is resistant to infection with AAV or that is less permissive to infection with AAV, increased evasion of neutralizing antibodies, increased ability to cross an endothelial cell layer, and the like. A subject rAAV virion is useful for delivering a gene product to an individual.

Cell membrane-associated heparan sulfate proteoglycan is a primary cell surface receptor for AAV, e.g., AAV-2. Increased heparan sulfate binding (e.g., increased heparin affinity) is advantageous where, e.g., the rAAV particle is being delivered in a localized manner, e.g., where diffusion of the rAAV particle away from the site of delivery is not desired. Many cell types produce heparan sulfate, which remains on the surface of the cell or in the immediate environment of the cell. Thus, an rAAV virion with increased heparan sulfate binding affinity would remain relatively close to the site of administration. For example, localized delivery of a subject rAAV virion is advantageous for delivery of a gene product to a tumor that is localized to a particular anatomical site (but not, e.g., to surrounding non-cancerous tissue), for delivery of a gene product to a diseased cardiac vessel (but not to the surrounding healthy heart tissue), etc.

In many embodiments of the present invention, AAV-2, and mutants of AAV-2, are exemplified. However, the exemplification of AAV-2 herein is in no way meant to be limiting. Those skilled in the art can readily adapt the methods as discussed herein to generate capsid mutants of other AAV, including, e.g., AAV-3, AAV-4, AAV-5, etc. Thus, e.g., where an AAV binds to the $\beta_5$ subunit of integrin $\alpha_v\beta_5$, the present invention contemplates mutant AAV that exhibit increased or decreased binding to the $\beta_5$ subunit of integrin $\alpha_v\beta_5$, compared to the corresponding wild-type AAV. As another example, where an AAV (e.g., AAV-4) binds to O-linked sialic acid, the present invention contemplates mutant AAV that exhibit increased or decreased binding to O-linked sialic acid. As another example, where an AAV (e.g., AAV-5) binds to N-linked sialic acid or to a platelet-derived growth factor receptor (PDGFR), the present invention contemplates mutant AAV that exhibit increased or decreased binding to N-linked sialic acid or PDGFR. See, e.g., Kaludov et al. ((2001) *J. Virol.* 75:6884); Pasquale et al. ((2003) *Nat. Med.* 9:1306); and Walters et al. ((2001) *J. Biol. Chem.* 276:20610) for descriptions of AAV receptors.

Increased heparin affinity is also advantageous in that it confers increased infectivity of cell types that are typically refractory to infection with AAV, e.g., non-permissive cell types and "less-permissive" cell types (e.g., cells that are less permissive than a prototypical permissive cell). Such cell types include those with relatively low amounts of heparan sulfate on their surface. Increased heparan sulfate binding affinity allows an increased level of binding to cells that have relatively low levels of surface heparan sulfate, and therefore leads to increased infectivity of these cells. An example of cells that are refractory to infection with AAV is a stem cell. Thus, a subject rAAV virion is advantageous because it can infect stem cells and can deliver gene products to stem cells. Other examples of cells that are non-permissive or less permissive to infection with AAV include lung epithelial cells and hepatocytes.

Decreased heparan sulfate binding (e.g., decreased heparin affinity) is advantageous for therapeutic strategies in which more widespread, or systemic delivery of a subject rAAV virion is desired. Such rAAV virions diffuse away from the site of administration, and thus infect a greater number of cells than rAAV virions with wild-type capsid protein(s).

Decreased binding to neutralizing antibodies is advantageous. Neutralizing antibodies bind to wild-type capsid proteins. Binding of neutralizing antibodies to wild-type capsid proteins may have several effects, including limiting the residence time of an rAAV virions that comprises wild-type capsid proteins in the viral particle, preventing the virus from binding to the cell surface, aggregating the virus, induction of structural alterations in the capsid, and prevention of viral disassembly and uncoating (a step necessary to release the DNA). An rAAV particle that has decreased binding to neutralizing antibodies thus has increased capacity to infect cells, and increased residence time in the body of an individual administered with the rAAV virion. Thus, the effective duration of delivery of gene product is increased.

Increased ability to cross an endothelial cell layer allows the rAAV virion to gain access to tissues and cells that are separated from the site of administration by an endothelial cell layer. For example, the blood-brain barrier, the tumor vasculature, and the cardiovascular system all present endothelial cell layers that form a barrier to access of a particular anatomical site. A subject rAAV virion thus may exhibit one or more of the following properties: 1) increased ability to cross the blood-brain barrier; 2) increased ability to cross the tumor vasculature and infect tumor cells; and 3) increased ability to cross the endothelial layer within the heart.

Mutant Adeno-Associated Virus Virions

The present invention provides mutant adeno-associated virus comprising mutant capsid proteins that exhibit altered capsid properties. By virtue of comprising one or more mutant capsid proteins, a subject mutant AAV exhibits one or more of the following properties: 1) increased heparin binding affinity relative to wild-type AAV; 2) decreased heparin binding affinity relative to wild-type AAV; 3) increased infectivity of a cell that is resistant to infection with AAV; 4) increased evasion of neutralizing antibodies; and 5) increased ability to cross an endothelial cell layer. The properties of a subject mutant AAV are compared to a corresponding parental, AAV, e.g., a wild-type AAV. In some embodiments, the corresponding parental AAV is a chimeric AAV, e.g., an AAV with a chimeric capsid protein comprising a first stretch of contiguous amino acids from a first AAV serotype and a second stretch of contiguous amino acids from a second AAV serotype. In some embodiments, the corresponding parental AAV is wild-type AAV. Thus, e.g., where the parental, wild-type AAV is AAV-2, and the subject mutant AAV is a mutant of wild-type AAV-2, the properties of the subject mutant are compared to that same property of wild-type AAV-2.

Mutants with Increased Heparin Affinity

In some embodiments, a capsid protein encoded by a subject mutant AAV exhibits increased binding affinity to heparan sulfate relative to wild-type AAV. In these embodiments, a capsid protein encoded by a subject mutant AAV exhibits at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 2-fold, at least 2.5-fold, at least about 5-fold, at least about 10-fold, at least about 15-fold, at least about 50 fold, at least about 75-fold, or at least about 100-fold or more, higher affinity for heparan sulfate than wild-type AAV capsid. Because heparin is a molecule that is structurally similar to heparan sulfate, heparin is frequently used to determine experimentally whether a capsid protein has altered binding to heparan sulfate. Thus, the terms "heparin binding affinity," and "heparan sulfate binding affinity," and similar terms, are used interchangeably herein.

For example, whereas the binding affinity of AAV-2 to heparin has a K(d) value of approximately 2.0 nM, a subject mutant AAV has a binding affinity to heparin that is at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 2-fold, at least 2.5-fold, at least about 5-fold, at least about 10-fold, at least about 15-fold, at least about 50 fold, at least about 75-fold, or at least about 100-fold or more, higher than the affinity of wild-type AAV-2 to heparin.

Typically, wild-type AAV elutes from a heparin affinity chromatography medium with a NaCl concentration in a range of from about 450 mM to about 550 mM. In some embodiments, a subject mutant AAV elutes from a heparin affinity chromatography medium with a NaCl concentration of greater than about 550 mM, e.g., from about 575 mM NaCl to about 600 mM NaCl, from about 600 mM NaCl to about 625 mM NaCl, from about 625 mM NaCl to about 650 mM NaCl, from about 650 mM NaCl to about 675 mM NaCl, from about 675 mM NaCl to about 700 mM NaCl, from about 700 mM NaCl to about 725 mM NaCl, from about 725 mM NaCl to about 750 mM NaCl, from about 750 mM NaCl to about 775 mM NaCl, or from about 775 mM NaCl to about 800 mM NaCl, or higher.

Mutants with Decreased Heparin Affinity

In other embodiments, a subject mutant AAV exhibits a lower affinity for heparan sulfate than wild-type AAV. In these embodiments, a subject mutant AAV, when packaged in a viral particle, has at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, or at least about 85% lower affinity for heparin than wild-type AAV (e.g., wild-type AAV-2). In some embodiments, a subject mutant AAV, when packaged into a viral particle, elutes from a heparin affinity chromatography medium with concentration of NaCl in the range of from about 440 mM NaCl to about 400 mM NaCl, from about 400 mM NaCl to about 375 mM NaCl, from about 375 mM NaCl to about 350 mM NaCl, from about 350 mM NaCl to about 325 mM NaCl, from about 325 mM NaCl to about 300 mM NaCl, from about 300 mM NaCl to about 275 mM NaCl, from about 275 mM NaCl to about 250 mM NaCl, from about 250 mM NaCl to about 225 mM NaCl, from about 225 mM NaCl to about 200 mM NaCl or lower.

Heparin binding affinity can be determined using any known assay. For example, affinity of variant capsids for heparan sulfate can be measured by binding viral particles to immobilized heparin. See, e.g., Qui et al. (2000) *Virology* 269:137-147.

Neutralizing Antibody-Evading Mutants

In some embodiments, a subject mutant AAV exhibits increased resistance to neutralizing antibodies compared to wild-type AAV ("wt AAV") or AAV comprising a wild-type capsid protein. In these embodiments, a subject mutant AAV has from about 10-fold to about 10,000-fold greater resistance to neutralizing antibodies than wt AAV, e.g., a subject mutant AAV has from about 10-fold to about 25-fold, from about 25-fold to about 50-fold, from about 50-fold to about 75-fold, from about 75-fold to about 100-fold, from about 100-fold to about 150-fold, from about 150-fold to about 200-fold, from about 200-fold to about 250-fold, from about 250-fold to about 300-fold, at least about 350-fold, at least about 400-fold, from about 400-fold to about 450-fold, from about 450-fold to about 500-fold, from about 500-fold to about 550-fold, from about 550-fold to about 600-fold, from about 600-fold to about 700-fold, from about 700-fold to about 800-fold, from about 800-fold to about 900-fold, from about 900-fold to about 1000-fold, from about 1,000-fold to about 2,000-fold, from about 2,000-fold to about 3,000-fold, from about 3,000-fold to about 4,000-fold, from about 4,000-fold to about 5,000-fold, from about 5,000-fold to about 6,000-fold, from about 6,000-fold to about 7,000-fold, from about 7,000-fold to about 8,000-fold, from about 8,000-fold to about 9,000-fold, or from about 9,000-fold to about 10,000-fold greater resistance to neutralizing antibodies than a wild-type AAV or an AAV comprising a wild-type capsid protein.

In some embodiments, a subject mutant AAV exhibits decreased binding to a neutralizing antibody that binds a wild-type AAV capsid protein. For example, a subject mutant AAV exhibits from about 10-fold to about 10,000-fold reduced binding to a neutralizing antibody that binds a wild-type AAV capsid protein. For example, a subject mutant AAV exhibits from about 10-fold to about 25-fold, from about 25-fold to about 50-fold, from about 50-fold to about 75-fold, from about 75-fold to about 100-fold, from about 100-fold to about 150-fold, from about 150-fold to about 200-fold, from about 200-fold to about 250-fold, from about 250-fold to about 300-fold, at least about 350-fold, at least about 400-fold, from about 400-fold to about 450-fold, from about 450-fold to about 500-fold, from about 500-fold to about 550-fold, from about 550-fold to about 600-fold, from about 600-fold to about 700-fold, from about 700-fold to about 800-fold, from about 800-fold to about 900-fold, from about 900-fold to about 1000-fold, from about 1,000-fold to about 2,000-fold, from about 2,000-fold to about 3,000-fold, from about 3,000-fold to about 4,000-fold, from about 4,000-fold to about 5,000-fold, from about 5,000-fold to about 6,000-fold, from about 6,000-fold to about 7,000-fold, from about 7,000-fold to about 8,000-fold, from about 8,000-fold to about 9,000-fold, or from about 9,000-fold to about 10,000-fold reduced binding (e.g., reduced affinity) to a neutralizing antibody that binds a wild-type capsid AAV protein, compared to the binding affinity of the antibody to wild-type AAV capsid protein.

In some embodiments, an anti-AAV neutralizing antibody binds to a subject neutralizing antibody escape mutant AAV with an affinity of less than about $10^{-7}$ M, less than about $5 \times 10^{-6}$ M, less than about $10^{-6}$ M, less than about $5 \times 10^{-5}$ M, less than about $10^{-5}$ M, less than about $10^{-4}$ M, or lower.

In some embodiments, a subject mutant AAV exhibits increased in vivo residence time compared to a wild-type AAV. For example, a subject mutant AAV exhibits a residence time that is at least about 10%, at least about 25%, at least about 50%, at least about 100%, at least about 3-fold, at least about 5-fold, at least about 10-fold, at least about 25-fold, at least about 50-fold, at least about 100-fold, or more, longer than the residence time of a wild-type AAV.

Whether a given mutant AAV exhibits reduced binding to a neutralizing antibody and/or increased resistance to neutralizing antibody can be determined using any known assay, including the assay described in Example 1. For example, mutant AAV is contacted with a permissive cell type, e.g., 293 cells, in the presence of neutralizing antibody. A control sample contains the cells, mutant AAV, and no neutralizing antibody. After a suitable time, the cells are contacted with adenovirus, and AAV particles are detected. The level of AAV particles is compared to the amount of AAV particles that are generated in the absence of neutralizing antibody.

Mutants with Increased Infectivity of a Non-Permissive Cell

In some embodiments, a subject mutant AAV virion that exhibits increased infectivity of cells that are non-permissive to infection with AAV, and cells that are less permissive to infection with AAV. A subject mutant AAV virion comprises a variant AAV capsid protein, where the variant AAV capsid protein comprises at least one amino acid substitution relative to a corresponding parental AAV capsid protein, and where the variant capsid protein confers increased infectivity of a non-permissive cell compared to the infectivity of the non-permissive cell by an AAV virion comprising the corresponding parental AAV capsid protein. Thus, a subject mutant AAV virion exhibits increased infectivity of a nonpermissive cell compared to a corresponding parental AAV virion comprising a corresponding parental AAV capsid protein.

Cells that are non-permissive to infection with AAV, and cells that are less permissive to infection with AAV, are collectively referred to herein as "non-permissive cells." When a population of permissive cells is contacted in vitro or in vivo with AAV at a multiplicity of infection (moi) of 5, from about 70% to about 100% of the cell population becomes infected with the AAV. When a population of non-permissive cells is contacted in vitro or in vivo with AAV at an moi of 5, less than about 70% of the population becomes infected with AAV, e.g., no greater than from about 60% to about 69%, from about 50% to about 60%, from about 40% to about 50%, from about 30% to about 40%, from about 20% to about 30%, from about 10% to about 20%, or from about 1% to about 10%, of the population becomes infected with AAV, and in some cell types, essentially none of the cells becomes infected with AAV.

Whether a cell is permissive or non-permissive to infection with AAV can be readily determined by contacting in vitro or in vivo a population of a particular cell type with an rAAV construct that comprises a nucleotide sequence encoding a protein that provides a detectable signal (e.g., a fluorescent protein such as a green fluorescent protein), at an moi of 5. The proportion of cells that become positive for the detectable protein is an indication of the percentage of cells that became infected with the rAAV. Where from about 0% to about 69% of the cells become infected with the rAAV, the cells are said to be non-permissive to infection with AAV. Where from about 70% to about 100% of the cells become infected with the rAAV, the cells are said to be permissive to infection with AAV. Infectivity can be expressed relative to infectivity of 293 cells. In some embodiments, a non-permissive cell exhibits reduced infectivity with AAV compared to 293 cells, e.g., a non-permissive cell exhibits less than about 70% of the infectivity of 293 cells to AAV, e.g., a non-permissive cells exhibits less than about 70%, less than about 60%, less than about 50%, less than about 40%, less than about 30%, less than about 20%, less than about 10%, or less, of the infectivity of 293 cells to AAV.

In some embodiments, a subject mutant AAV exhibits increased ability to infect a cell that is relatively refractory to AAV infection (e.g., a non-permissive cell). In these embodiments, a subject mutant AAV exhibits at least about 10%, at least about 20%, at least about 30%, at least about 40%, at least about 50%, at least about 60%, at least about 70%, at least about 80%, at least about 90%, at least about 2-fold, at least about 4-fold, at least about 5-fold, at least about 10-fold, at least about 25-fold, or more, greater infectivity of a non-permissive cell than a wild-type AAV.

Examples of cells that are relatively refractory to AAV infection include stem cells. Further examples of non-permissive cell types include, but are not limited to, lung epithelial cells, and hepatocytes.

The term "stem cell" is used herein to refer to a mammalian cell that has the ability both to self-renew, and to generate differentiated progeny (see, e.g., Morrison et al. (1997) Cell 88:287-298). Generally, stem cells also have one or more of the following properties: an ability to undergo asynchronous, or symmetric replication, that is where the two daughter cells after division can have different phenotypes; extensive self-renewal capacity; capacity for existence in a mitotically quiescent form; and clonal regeneration of all the tissue in which they exist, for example the ability of hematopoietic stem cells to reconstitute all hematopoietic lineages. "Progenitor cells" differ from stem cells in that they typically do not have the extensive self-renewal capacity, and often can only regenerate a subset of the lineages in the tissue from which they derive, for example only lymphoid, or erythroid lineages in a hematopoietic setting.

Stem cells may be characterized by both the presence of markers associated with specific epitopes identified by antibodies and the absence of certain markers as identified by the lack of binding of specific antibodies. Stem cells may also be identified by functional assays both in vitro and in vivo, particularly assays relating to the ability of stem cells to give rise to multiple differentiated progeny.

Stem cells of interest include hematopoietic stem cells and progenitor cells derived therefrom (U.S. Pat. No. 5,061,620); neural crest stem cells (see Morrison et al. (1999) Cell 96:737-749); adult neural stem cells and neural progenitor cells; embryonic stem cells; mesenchymal stem cells; mesodermal stem cells; etc. Other hematopoietic "progenitor" cells of interest include cells dedicated to lymphoid lineages, e.g. immature T cell and B cell populations.

Structural Features

A subject mutant AAV virion comprises a mutation in at least one capsid protein (e.g., at least one of VP1, VP2, and VP3). Thus, at least one of VP1, VP2, and VP3 has at least one amino acid substitution compared to a corresponding parental AAV capsid protein, e.g., a wild-type AAV capsid protein. In some embodiments, at least one of VP1, VP2, and VP3 has from one to about 50 amino acid substitutions compared to wild-type AAV VP1, VP2, and VP3, e.g., from about one to about 5, from about 5 to about 10, from about 10 to about 15, from about 15 to about 20, from about 20 to about 25, from about 25 to about 30, from about 30 to about 40, from about 40 to about 45, or from about 45 to about 50, amino acid substitutions compared to wild-type AAV VP1, VP2, and VP3. Alternatively, a subject mutant AAV virion comprises one or more amino acid deletions and/or insertions in at least one capsid protein relative to a corresponding parental AAV capsid protein, e.g., a wild-type capsid protein. In some embodiments, a subject mutant AAV virion comprises one or more amino acid substitutions and/or deletions and/or insertions in a capsid protein relative to a corresponding parental AAV capsid protein, e.g., a wild-type capsid protein. In some embodiments, a subject mutant AAV virion comprises one or more amino acid substitutions compared to a corresponding parental AAV capsid protein, and can further comprise from one to about 10 amino acid deletions compared to a corresponding parental AAV capsid protein. In some embodiments, a subject mutant AAV virion comprises one or more amino acid substitutions compared to a corresponding parental AAV capsid protein, and does not comprise any amino acid insertions, e.g., does not comprise any insertions of amino acids that provide an epitope not present in a corresponding parental AAV capsid protein (e.g., a wild-type AAV capsid protein).

The corresponding, parental AAV capsid protein can be a wild-type capsid protein (e.g., a wild-type AAV2 capsid protein, a wild-type AAV5 capsid protein, etc.). The corresponding, parental AAV capsid protein can be a chimeric AAV capsid protein, e.g., an AAV capsid protein comprising a first contiguous stretch of amino acids of a first AAV serotype, and a second contiguous stretch of amino acids of a second AAV serotype. As one non-limiting example, a parental AAV capsid protein can comprise a contiguous stretch of from about 10 amino acids to about 120 amino acids of the amino-terminal 120 amino acids of AAV2; and a contiguous stretch of from about 400 amino acids to about 550 contiguous amino acids of the carboxyl-terminal 550 amino acid of AAV5.

In some embodiments, a subject mutant AAV virion exhibits reduced binding to neutralizing antibody compared to wild-type AAV, and comprises a VP1 that has an amino acid sequence that has at least about 85%, at least about 90%, at least about 95%, at least about 98%, or at least about 99%, or greater, amino acid sequence identity to an amino acid sequence as set forth in one of SEQ ID NOs:7, 9, 11, 13, 15, 17, 19, 21, 23, 25, 27, 29, 31, and 33, or as set forth in FIGS. 5A-C or FIGS. 7A-D. In some embodiments, a subject mutant AAV virion exhibits reduced binding to neutralizing antibody compared to wild-type AAV, and comprises a VP1 that has an amino acid sequence that has from 1-5, from 5-10, or from 10-20 amino acid differences from an amino acid sequence as set forth in one of SEQ ID NOs:7, 9, 11, 13, 15, 17, 19, 21, 23, 25, 27, 29, 31, and 33 or as set forth in FIGS. 5A-C or FIGS. 7A-D. In some embodiments, a subject mutant AAV virion exhibits reduced binding to neutralizing antibody compared to wild-type AAV, and comprises a VP1 that has an amino acid sequence as set forth in one of SEQ ID NOs:7, 9, 11, 13, 15, 17, 19, 21, 23, 25, 27, 29, 31, and 33 or as set forth in FIGS. 5A-C or FIGS. 7A-D.

In some embodiments, a subject mutant AAV virion exhibits increased heparan sulfate affinity compared to wild-type AAV, and comprises a VP1 that has an amino acid sequence that has at least about 85%, at least about 90%, at least about 95%, at least about 98%, or at least about 99%, or greater, amino acid sequence identity to an amino acid sequence as set forth in SEQ ID NO:35 or SEQ ID NO:37, or as set forth in FIGS. 9A-C (D14H1 or D14L3). In some embodiments, a subject mutant AAV virion exhibits increased heparan sulfate affinity compared to wild-type AAV, and comprises a VP1 that has an amino acid sequence that has from 1-5, from 5-10, or from 10-20 amino acid differences from an amino acid sequence as set forth in SEQ ID NO:35 or SEQ ID NO:37, or as set forth in FIGS. 9A-C (D14H1 or D14L3). In some embodiments, a subject mutant AAV virion exhibits increased heparan sulfate affinity compared to wild-type AAV, and comprises a VP1 that has an amino acid sequence as set forth in SEQ ID NO:35 or SEQ ID NO:37, or as set forth in FIGS. 9A-C (D14H1 or D14L3).

In some embodiments, a subject mutant AAV virion exhibits reduced heparan sulfate affinity compared to wild-type AAV, and comprises a VP1 that has an amino acid sequence that has at least about 85%, at least about 90%, at least about 95%, at least about 98%, or at least about 99%, or greater, amino acid sequence identity to an amino acid sequence as set forth in SEQ ID NO:39 or SEQ ID NO:41, or as set forth in FIGS. 9A-C (P1BH1 or P1BH2). In some embodiments, a subject mutant AAV virion exhibits reduced heparan sulfate affinity compared to wild-type AAV, and comprises a VP1 that has an amino acid sequence that has from 1-5, from 5-10, or from 10-20 amino acid differences from an amino acid sequence as set forth in SEQ ID NO:39 or SEQ ID NO:41, or as set forth in FIGS. 9A-C (P1BH1 or P1BH2). In some embodiments, a subject mutant AAV virion exhibits decreased heparan sulfate affinity compared to wild-type AAV, and comprises a VP1 that has an amino acid sequence as set forth in SEQ ID NO:39 or SEQ ID NO:41, or as set forth in FIGS. 9A-C (P1BH1 or P1BH2).

In some embodiments, a subject mutant AAV virion exhibits increased infectivity of a non-permissive lung epithelial cell compared to a corresponding parental AAV (e.g., a wild-type AAV; or a chimeric AAV), and comprises a VP1 that has an amino acid sequence that has at least about 85%, at least about 90%, at least about 95%, at least about 98%, or at least about 99%, or greater, amino acid sequence identity to the amino acid sequence as set forth in SEQ ID NO:42, or as set forth in FIGS. 10A-B (AAV2.5T), where the VP1 of the mutant AAV virion comprises an amino acid sequence that has from 1-5, from 5-10, from 10-20, from 20 to 25, or from 25-45 amino acid differences from the amino acid sequence as set forth in SEQ ID NO:43 (AAV5). In some embodiments, a subject mutant AAV virion exhibits increased infectivity of a non-permissive lung epithelial cell compared to a corresponding parental AAV (e.g., a wild-type AAV; or a chimeric AAV), and comprises a VP1 that comprises an A581T substitution compared to the amino acid sequence of an AAV5 capsid protein set forth in SEQ ID NO:43.

In some embodiments, a subject mutant AAV virion exhibits increased infectivity of a non-permissive stem cell compared to a corresponding parental AAV (e.g., a wild-type AAV), and comprises a VP1 that comprises an amino acid sequence that has at least about 85%, at least about 90%, at least about 95%, at least about 98%, or at least about 99%, or greater, amino acid sequence identity to the amino acid sequence as set forth in any one of SEQ ID NOs:44-58, where the VP1 of the mutant AAV virion comprises from 1 to 5, from 5 to 10, or from 10 to 15 amino acid substitutions compared to the amino acid sequence of AAV2 as set forth in SEQ ID NO:5. In some embodiments, a subject mutant AAV virion exhibits increased infectivity of a non-permissive stem cell compared to wild-type AAV2, and comprises an R459G substitution compared to the amino acid sequence of AAV2 as set forth in SEQ ID NO:5. In some embodiments, a subject mutant AAV virion exhibits increased infectivity of a non-permissive stem cell compared to wild-type AAV2, and comprises a V708I substitution and a P250S substitution compared to the amino acid sequence of AAV2 as set forth in SEQ ID NO:5.

In some embodiments, a subject mutant AAV virion exhibits increased infectivity of a non-permissive stem cell compared to a corresponding parental AAV (e.g., a wild-type AAV), and comprises a VP1 that comprises an amino acid sequence that has at least about 85%, at least about 90%, at least about 95%, at least about 98%, or at least about 99%, or greater, amino acid sequence identity to the amino acid sequence as set forth in SEQ ID NO: 59, where the VP1 of the mutant AAV virion comprises from 1 to 5, from 5 to 10, or from 10 to 15 amino acid substitutions compared to the amino acid sequence of AAV2 as set forth in SEQ ID NO:5. In some embodiments, a subject mutant AAV virion exhibits increased infectivity of a non-permissive stem cell compared to wild-type AAV2, and comprises an S85G substitution and an R459G substitution compared to the amino acid sequence of AAV2 as set forth in SEQ ID NO:5.

In some embodiments, a subject mutant AAV virion comprises wild-type Rep78, Rep68, Rep52, and Rep40 proteins. In other embodiments, a subject mutant AAV comprises, in addition to one or more mutant capsid proteins, one or more mutations in one or more of Rep78, Rep68, Rep52, and Rep40 proteins.

Nucleic Acids and Host Cells

The present invention provides nucleic acids comprising nucleotide sequences encoding a mutant AAV capsid protein, as well as host cells comprising a subject nucleic acid. The nucleic acids and host cells are useful for generating rAAV virions, as described below. A subject nucleic acid encodes one or more of VP1, VP2, and VP3 comprising one or more amino acid substitutions. A subject nucleic acid comprises a nucleotide sequence encoding at least one of VP1, VP2, and VP3, wherein the encoded capsid protein comprises from one to about 15 amino acid substitutions compared to a wild-type AAV capsid protein, e.g., from about one to about 5, from about 5 to about 10, from about 10 to about 15, from about 15 to about 20, or from about 20 to about 25 amino acid substitutions compared to a corresponding parental AAV capsid protein (e.g., compared to a wild-type AAV capsid protein). The encoded capsid protein may, alternatively or in addition, comprise one or more amino acid deletions and/or insertions relative to a wild-type AAV capsid protein. In some embodiments, a the encoded mutant capsid protein comprises one or more amino acid substitutions and/or deletions and/or insertions relative to a corresponding parental AAV capsid protein, e.g., a wild-type capsid protein. In some embodiments, the encoded mutant capsid protein comprises one or more amino acid substitutions compared to a corresponding parental AAV capsid protein, e.g., a wild-type capsid protein, and can further comprise from one to about 10 amino acid deletions corresponding parental AAV capsid protein, e.g., a wild-type capsid protein. In some embodiments, the encoded mutant capsid protein comprises one or more amino acid substitutions compared to a corresponding parental AAV capsid protein, e.g., a wild-type capsid protein, and does not comprise any amino acid insertions, e.g., does not comprise any insertions of amino acids that provide an epitope not present in the corresponding AAV capsid protein (e.g., wild-type AAV capsid protein).

In some embodiments, a subject nucleic acid comprises a nucleotide sequence that comprises from about 1 to about 30 nucleotide differences (e.g., from about 1 to about 5, from about 5 to about 10, from about 10 to about 20, or from about 20 to about 30 nucleotide differences) from a nucleotide sequence as set forth in any one of SEQ ID NOs:2, 3, 6, 8, 10, 12, 14, 16, 18, 20, 22, 24, 26, 28, 30, 32, 34, 36, 38, and 40, or any one of the nucleotide sequences set forth in FIGS. 4A-G, FIGS. 6A-J, or FIGS. 8A-G. In some embodiments, a subject nucleic acid comprises a nucleotide sequence that hybridizes under stringent hybridization conditions to a nucleic acid having a nucleotide sequence as set forth in any one of SEQ ID NOs:2, 3, 6, 8, 10, 12, 14, 16, 18, 20, 22, 24, 26, 28, 30, 32, 34, 36, 38, and 40, or any one of the nucleotide sequences set forth in FIGS. 4A-G, FIGS. 6A-J, or FIGS. 8A-G. In some embodiments, a subject nucleic acid comprises a nucleotide sequence that is at least about 80%, at least about 85%, at least about 90%, at least about 95%, at least about 98%, at least about 99%, or more, identical to a nucleotide sequence as set forth in any one of SEQ ID NOs:2, 3, 6, 8, 10, 12, 14, 16, 18, 20, 22, 24, 26, 28, 30, 32, 34, 36, 38, and 40, or any one of the nucleotide sequences set forth in FIGS. 4A-G, FIGS. 6A-J, or FIGS. 8A-G. In some embodiments, a subject nucleic acid comprises a nucleic acid having a nucleotide sequence as set forth in any one of SEQ ID NOs:2, 3, 6, 8, 10, 12, 14, 16, 18, 20, 22, 24, 26, 28, 30, 32, 34, 36, 38, and 40, or any one of the nucleotide sequences set forth in FIGS. 4A-G, FIGS. 6A-J, or FIGS. 8A-G.

In some embodiments, a subject nucleic acid comprises a nucleotide sequence that encodes a variant AAV capsid protein that comprises an amino acid sequence that has at least about 85%, at least about 90%, at least about 95%, at least about 98%, or at least about 99%, or greater, amino acid sequence identity to the amino acid sequence as set forth in SEQ ID NO:42, or as set forth in FIGS. 10A-B (AAV2.5T), where the VP1 of the mutant AAV virion comprises an amino acid sequence that has from 1-5, from 5-10, from 10-20, from 20 to 25, or from 25-45 amino acid differences from the amino acid sequence as set forth in SEQ ID NO:43 (AAV5). In some embodiments, a subject nucleic acid comprises a nucleotide sequence that encodes a variant AAV capsid protein that comprises an A581T substitution compared to the amino acid sequence of an AAV5 capsid protein set forth in SEQ ID NO:43.

In some embodiments, a subject nucleic acid comprises a nucleotide sequence that encodes a variant AAV capsid protein that comprises an amino acid sequence that has at least about 85%, at least about 90%, at least about 95%, at least about 98%, or at least about 99%, or greater, amino acid sequence identity to the amino acid sequence as set forth in any one of SEQ ID NOs:44-58, where the VP1 of the mutant AAV virion comprises from 1 to 5, from 5 to 10, or from 10 to 15 amino acid substitutions compared to the amino acid sequence of AAV2 as set forth in SEQ ID NO:5. In some embodiments, a subject nucleic acid comprises a nucleotide sequence that encodes a variant AAV capsid protein that comprises an R459G substitution compared to the amino acid sequence of AAV2 as set forth in SEQ ID NO:5. In some embodiments, a subject nucleic acid comprises a nucleotide sequence that encodes a variant AAV capsid protein that comprises a V708I substitution and a P250S substitution compared to the amino acid sequence of AAV2 as set forth in SEQ ID NO:5.

In some embodiments, a subject nucleic acid comprises a nucleotide sequence that encodes a variant AAV capsid protein that comprises an amino acid sequence that has at least about 85%, at least about 90%, at least about 95%, at least about 98%, or at least about 99%, or greater, amino acid sequence identity to the amino acid sequence as set forth in SEQ ID NO:59, where the VP1 of the mutant AAV virion comprises from 1 to 5, from 5 to 10, or from 10 to 15 amino acid substitutions compared to the amino acid sequence of AAV2 as set forth in SEQ ID NO:5. In some embodiments, a subject nucleic acid comprises a nucleotide sequence that encodes a variant AAV capsid protein that comprises an S85G substitution and an R459G substitution compared to the amino acid sequence of AAV2 as set forth in SEQ ID NO:5.

In some embodiments, a subject nucleic acid comprises, in addition to a nucleotide sequence that encodes a variant AAV capsid protein (as described above), a gene-targeting cassette that provides for increased frequency of homologous recombination of the subject nucleic acid with a target nucleotide sequence in the genome of a host cell (e.g., a cell in an individual).

The present invention further provides host cells, e.g., isolated (genetically modified) host cells, comprising a subject nucleic acid. A subject host cell is typically an isolated cell, e.g., a cell in in vitro culture. A subject host cell is useful for producing a subject rAAV virion, as described below. Where a subject host cell is used to produce a subject rAAV virion, it is referred to as a "packaging cell." In some embodiments, a subject host cell is stably genetically modified with a subject nucleic acid. In other embodiments, a subject host cell is transiently genetically modified with a subject nucleic acid.

A subject nucleic acid is introduced stably or transiently into a host cell, using established techniques, including, but not limited to, electroporation, calcium phosphate precipitation, liposome-mediated transfection, and the like. For stable transformation, a subject nucleic acid will generally further include a selectable marker, e.g., any of several well-known selectable markers such as neomycin resistance, and the like.

A subject host cell is generated by introducing a subject nucleic acid into any of a variety of cells, e.g., mammalian cells, including, e.g., murine cells, and primate cells (e.g., human cells). Suitable mammalian cells include, but are not limited to, primary cells and cell lines, where suitable cell lines include, but are not limited to, 293 cells, COS cells, HeLa cells, Vero cells, 3T3 mouse fibroblasts, C3H10T1/2 fibroblasts, CHO cells, and the like.

In some embodiments, a subject host cell includes, in addition to a nucleic acid comprising a nucleotide sequence encoding a mutant capsid protein, a nucleic acid that comprises a nucleotide sequence encoding one or more AAV rep proteins. In other embodiments, a subject host cell further comprises an rAAV vector, as described below. As described in more detail below, an rAAV virion is generated using a subject host cell.

rAAV Virions

A mutant capsid protein may be incorporated into an AAV that comprises a heterologous nucleic acid that provides for production of a heterologous gene product (e.g., a heterologous nucleic acid or a heterologous protein). A subject recombinant AAV virion ("rAAV virion") comprises a mutant capsid protein, and includes a heterologous nucleic acid that encodes a heterologous gene product. Thus, the present invention provides rAAV virions that comprise a mutant capsid protein, as described above; and a heterologous nucleic acid. A subject rAAV virion is useful for introducing a gene product into an individual.

A subject rAAV virion comprises a mutant capsid protein, as described above. By virtue of comprising a mutant capsid protein, a subject rAAV virion exhibits one or more of the following properties: 1) increased heparin binding affinity relative to wild-type AAV; 2) decreased heparin binding affinity relative to wild-type AAV; 3) increased infectivity of a cell that is non-permissive to infection with AAV; 4) increased evasion of neutralizing antibodies; and 5) increased ability to cross an endothelial cell layer.

In some embodiments, a subject rAAV virion exhibits increased binding affinity to heparin relative to a wild-type AAV virion. In these embodiments, a capsid protein encoded by a subject rAAV virion exhibits at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 2-fold, at least 2.5-fold, at least about 5-fold, at least about 10-fold, at least about 15-fold, at least about 50 fold, at least about 75-fold, or at least about 100-fold or more, higher affinity for heparin than wild-type AAV capsid. Typically, wild-type AAV elutes from a heparin affinity chromatography medium with a NaCl concentration in a range of from about 450 mM to about 550 mM. In some embodiments, a subject rAAV virion elutes from a heparin affinity chromatography medium with a NaCl concentration of greater than about 550 mM, e.g., from about 575 mM NaCl to about 600 mM NaCl, from about 600 mM NaCl to about 625 mM NaCl, from about 625 mM NaCl to about 650 mM NaCl, from about 650 mM NaCl to about 675 mM NaCl, from about 675 mM NaCl to about 700 mM NaCl, from about 700 mM NaCl to about 725 mM NaCl, from about 725 mM NaCl to about 750 mM NaCl, from about 750 mM NaCl to about 775 mM NaCl, or from about 775 mM NaCl to about 800 mM NaCl, or higher.

In other embodiments, a subject rAAV virion exhibits a lower affinity for heparin than wild-type AAV. In these embodiments, a subject rAAV virion has at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, or at least about 85% lower affinity for heparin than wild-type AAV. In some embodiments, a subject rAAV virion elutes from a heparin affinity chromatography medium with concentration of NaCl in the range of from about 440 mM NaCl to about 400 mM NaCl, from about 400 mM NaCl to about 375 mM NaCl, from about 375 mM NaCl to about 350 mM NaCl, from about 350 mM NaCl to about 325 mM NaCl, from about 325 mM NaCl to about 300 mM NaCl, from about 300 mM NaCl to about 275 mM NaCl, from about 275 mM NaCl to about 250 mM NaCl, from about 250 mM NaCl to about 225 mM NaCl, from about 225 mM NaCl to about 200 mM NaCl or lower.

Heparin binding affinity can be determined using any known assay. For example, affinity of variant capsids for heparan sulfate can be measured by binding viral particles to immobilized heparin. See, e.g., Qui et al. (2000) *Virology* 269:137-147.

In some embodiments, a subject rAAV virion exhibits increased resistance to neutralizing antibodies compared to wild-type AAV or AAV comprising a wild-typo capsid protein. In these embodiments, a subject rAAV virion has from about 10-fold to about 10,000-fold greater resistance to neutralizing antibodies than wt AAV, e.g., a subject rAAV virion has from about 10-fold to about 25-fold, from about 25-fold to about 50-fold, from about 50-fold to about 75-fold, from about 75-fold to about 100-fold, from about 100-fold to about 150-fold, from about 150-fold to about 200-fold, from about 200-fold to about 250-fold, from about 250-fold to about 300-fold, at least about 350-fold, at least about 400-fold, from about 400-fold to about 450-fold, from about 450-fold to about 500-fold, from about 500-fold to about 550-fold, from about 550-fold to about 600-fold, from about 600-fold to about 700-fold, from about 700-fold to about 800-fold, from about 800-fold to about 900-fold, from about 900-fold to about 1000-fold, from about 1,000-fold to about 2,000-fold, from about 2,000-fold to about 3,000-fold, from about 3,000-fold to about 4,000-fold, from about 4,000-fold to about 5,000-fold, from about 5,000-fold to about 6,000-fold, from about 6,000-fold to about 7,000-fold, from about 7,000-fold to about 8,000-fold, from about 8,000-fold to about 9,000-fold, or from about 9,000-fold to about 10,000-fold greater resistance to neutralizing antibodies than a wild-type AAV or an AAV comprising a wild-type capsid protein.

In some embodiments, a subject rAAV virion exhibits decreased binding to a neutralizing antibody that binds a wild-type AAV capsid protein. For example, a subject mutant rAAV virion exhibits from about 10-fold to about 10,000-fold reduced binding to a neutralizing antibody that binds a wild-type AAV capsid protein. For example, a subject mutant rAAV virion exhibits from about 10-fold to about 25-fold, from about 25-fold to about 50-fold, from about 50-fold to about 75-fold, from about 75-fold to about 100-fold, from about 100-fold to about 150-fold, from about 150-fold to about 200-fold, from about 200-fold to about 250-fold, from about 250-fold to about 300-fold, at least about 350-fold, at least about 400-fold, from about 400-fold to about 450-fold, from about 450-fold to about 500-fold, from about 500-fold to about 550-fold, from about 550-fold to about 600-fold, from about 600-fold to about 700-fold, from about 700-fold to about 800-fold, from about 800-fold to about 900-fold, from about 900-fold to about 1000-fold, from about 1,000-fold to about 2,000-fold, from about 2,000-fold to about 3,000-fold, from about 3,000-fold to about 4,000-fold, from about 4,000-fold to about 5,000-fold, from about 5,000-fold to about 6,000-fold, from about 6,000 fold to about 7,000-fold, from about 7,000-fold to about 8,000-fold, from about 8,000-fold to about 9,000-fold, or from about 9,000-fold to about 10,000-fold reduced binding to a neutralizing antibody that binds a wild-type capsid AAV protein, compared to the binding affinity of the antibody to wild-type AAV capsid protein.

In some embodiments, an anti-AAV neutralizing antibody binds to a subject rAAV virion with an affinity of less than about $10^{-7}$ M, less than about $5\times10^{-6}$ M, less than about $10^{-6}$ M, less than about $5\times10^{-5}$ M, less than about $10^{-5}$ M, less than about $10^{-4}$ M, or lower.

A subject rAAV virion that exhibits reduced binding to neutralizing antibodies has increased residence time in the body, compared to the residence time of an AAV virion comprising wild-type capsid proteins. Thus, e.g., a subject rAAV virion has at least about 25%, at least about 50%, at least about 75%, at least about 2-fold, at least about 2,5-fold, at least about 3-fold, at least about 4-fold, at least about 5-fold at least about 10-fold, at least about 15-fold, at least about 20-fold, at least about 50-fold, or more, increased residence time in vivo compared to the residence time of an AAV virion comprising wild-type capsid proteins.

Whether a given mutant rAAV virion exhibits reduced binding to a neutralizing antibody and/or increased resistance to neutralizing antibody can be determined using any known assay, including the assay described in the Example. For example, mutant rAAV virion is contacted with a permissive cell type, e.g., 293 cells, in the presence of neutralizing antibody. A control sample contains the cells, mutant rAAV virion, and no neutralizing antibody. After a suitable time, the cells are contacted with adenovirus, and rAAV particles are detected. The level of rAAV particles is compared to the amount of rAAV particles that are generated in the absence of neutralizing antibody.

In some embodiments, a subject rAAV virion exhibits increased ability to infect a cell that is relatively refractory to AAV infection (e.g., a non-permissive cell). In these embodiments, a subject mutant AAV exhibits at least about 10%, at least about 20%, at least about 30%, at least about 40%, at least about 50%, at least about 60%, at least about 70%, at least about 80%, at least about 90%, at least about 2-fold, at least about 4-fold, at least about 10-fold, at least about 20-fold, or at least about 50-fold, or more, greater infectivity of a non-permissive cell than a wild-type AAV or an rAAV virion comprising wild-type capsid protein.

Examples of cells that are relatively refractory to AAV infection include, but are not limited to stem cells, hepatocytes, and lung epithelial cells.

The term "stem cell" is used herein to refer to a mammalian cell that has the ability both to self-renew, and to generate differentiated progeny (see, e.g., Morrison et al. (1997) Cell 88:287-298). Generally, stem cells also have one or more of the following properties: an ability to undergo asynchronous, or symmetric replication, that is where the two daughter cells after division can have different phenotypes; extensive self-renewal capacity; capacity for existence in a mitotically quiescent form; and clonal regeneration of all the tissue in which they exist, for example the ability of hematopoietic stem cells to reconstitute all hematopoietic lineages. "Progenitor cells" differ from stem cells in that they typically do not have the extensive self-renewal capacity, and often can only regenerate a subset of the lineages in the tissue from which they derive, for example only lymphoid, or erythroid lineages in a hematopoietic setting.

Stem cells may be characterized by both the presence of markers associated with specific epitopes identified by antibodies and the absence of certain markers as identified by the lack of binding of specific antibodies. Stem cells may also be identified by functional assays both in vitro and in vivo, particularly assays relating to the ability of stem cells to give rise to multiple differentiated progeny.

Stem cells of interest include hematopoietic stem cells and progenitor cells derived therefrom (U.S. Pat. No. 5,061,620); neural crest stem cells (see Morrison et al. (1999) Cell 96:737-749); adult neural stem cells and neural progenitor cells; embryonic stem cells; mesenchymal stem cells; mesodermal stem cells; etc. Other hematopoietic "progenitor" cells of interest include cells dedicated to lymphoid lineages, e.g. immature T cell and B cell populations.

In some embodiments, a subject rAAV virion exhibits increased ability to cross an endothelial cell layer. For example, in these embodiments, a subject rAAV virion exhibits at least about 10%, at least about 20%, at least about 30%, at least about 40%, at least about 50%, at least about 60%, at least about 70%, at least about 80%, at least about 90%, at least about 2-fold, at least about 5-fold, at least about 10-fold, at least about 25-fold, or at least about 50-fold increase in ability to cross an endothelial cell layer.

Whether a given rAAV virion exhibits an increased ability to cross an endothelial cell layer can be determined experimentally using well-known systems.

A subject rAAV virion comprises a mutation in at least one capsid protein (e.g., at least one of VP1, VP2, and VP3). Thus, at least one of VP1, VP2, and VP3 has at least one amino acid substitution compared to wild-type AAV capsid protein. In some embodiments, at least one of VP1, VP2, and VP3 has from one to about 25 amino acid substitutions compared to wild-type AAV VP1, VP2, and VP3, e.g., from about one to about 5, from about 5 to about 10, from about 10 to about 15, from about 15 to about 20, or from about 20 to about 25 amino acid substitutions compared to wild-type AAV VP1, VP2, and VP3. Alternatively, a subject rAAV virion comprises one or more amino acid deletions and/or insertions in at least one capsid protein relative to wild-type capsid protein. In some embodiments, a subject rAAV virion comprises one or more amino acid substitutions and/or deletions and/or insertions in a capsid protein relative to a wild-type capsid protein.

In some embodiments, a subject rAAV virion exhibits reduced binding to neutralizing antibody compared to wild-type AAV, and comprises a VP1 that has an amino acid sequence that has at least about 85%, at least about 90%, at least about 95%, at least about 98%, or at least about 99%, or greater, amino acid sequence identity to an amino acid sequence as set forth in one of SEQ ID NOs:7, 9, 11, 13, 15, 17, 19, 21, 23, 25, 27, 29, 31, and 33, or as set forth in FIGS. 5A-C or FIGS. 7A-D. In some embodiments, a subject rAAV virion exhibits reduced binding to neutralizing antibody compared to wild-type AAV, and comprises a VP1 that has an amino acid sequence that has from 1-5, from 5-10, or from 10-20 amino acid differences from an amino acid sequence as set forth in one of SEQ ID NOs: 7, 9, 11, 13, 15, 17, 19, 21, 23, 25, 27, 29, 31, and 33, or as set forth in FIGS. 5A-C or FIGS. 7A-D. In some embodiments, a subject rAAV virion exhibits reduced binding to neutralizing antibody compared to wild-type AAV, and comprises a VP1 that has an amino acid sequence as set forth in one of SEQ ID NOs: 7, 9, 11, 13, 15, 17, 19, 21, 23, 25, 27, 29, 31, and 33, or as set forth in FIGS. 5A-C or FIGS. 7A-D.

In some embodiments, a subject rAAV virion exhibits increased heparan sulfate affinity compared to wild-type AAV, and comprises a VP1 that has an amino acid sequence that has at least about 85%, at least about 90%, at least about 95%, at least about 98%, or at least about 99%, or greater, amino acid sequence identity to an amino acid sequence as set forth in SEQ ID NO:35 or SEQ ID NO:37, or as set forth in FIGS. 9A-C (D14H1 or D14L3). In some embodiments, a subject rAAV virion exhibits increased heparan sulfate affinity compared to wild-type AAV, and comprises a VP1 that has an amino acid sequence that has from 1-5, from 5-10, or from 10-20 amino acid differences from an amino acid sequence as set forth in SEQ ID NO:35 or SEQ ID NO:37, or as set forth in FIGS. 9A-C (D14H1 or D14L3). In some embodiments, a subject rAAV virion exhibits increased heparan sulfate affinity compared to wild-type AAV, and comprises a VP1 that has an amino acid sequence as set forth in SEQ ID NO:35 or SEQ ID NO:37, or as set forth in FIGS. 9A-C (D14H1 or D14L3).

In some embodiments, a subject rAAV virion exhibits reduced heparan sulfate affinity compared to wild-type AAV, and comprises a VP1 that has an amino acid sequence that has at least about 85%, at least about 90%, at least about 95%, at least about 98%, or at least about 99%, or greater, amino acid sequence identity to an amino acid sequence as set forth in SEQ ID NO:39 or SEQ ID NO:41, or as set forth in FIGS. 9A-C (P1BH1 or P1BH2). In some embodiments, a subject rAAV virion exhibits reduced heparan sulfate affinity compared to wild-type AAV, and comprises a VP1 that has an amino acid sequence that has from 1-5, from 5-10, or from 10-20 amino acid differences from an amino acid sequence as set forth in SEQ ID NO:39 or SEQ ID NO:41, or as set forth in FIGS. 9A-C (P1BH1 or P1BH2). In some embodiments, a subject rAAV virion exhibits decreased heparan sulfate affinity compared to wild-type AAV, and comprises a VP1 that has an amino acid sequence as set forth in SEQ ID NO:39 or SEQ ID NO:41, or as set forth in FIGS. 9A-C (P1BH1 or P1BH2).

In some embodiments, a subject rAAV virion exhibits increased infectivity of a non-permissive cell (e.g., a lung epithelial cell) compared to the infectivity of the non-permissive cell by a corresponding parental AAV virion (e.g., wild-type AAV), and comprises a variant AAV capsid protein that comprises an amino acid sequence that has at least about 85%, at least about 90%, at least about 95%, at least about 98%, or at least about 99%, or greater, amino acid sequence identity to the amino acid sequence as set forth in SEQ ID NO:42, or as set forth in FIGS. 10A-B (AAV2.5T), where the VP1 of the rAAV virion comprises an amino acid sequence that has from 1-5, from 5-10, from 10-20, from 20 to 25, or from 25-45 amino acid differences from the amino acid sequence as set forth in SEQ ID NO:43 (AAV5). In some embodiments, a subject rAAV virion exhibits increased infectivity of a non-permissive cell (e.g., a lung epithelial cell) compared to the infectivity of the non-permissive cell by a corresponding parental AAV virion (e.g., wild-type AAV), and comprises a variant AAV capsid protein that comprises an A581T substitution compared to the amino acid sequence of an AAV5 capsid protein set forth in SEQ ID NO:43.

In some embodiments, a subject rAAV virion exhibits increased infectivity of a non-permissive cell (e.g., a stem cell) compared to the infectivity of the non-permissive cell by a corresponding parental AAV virion (e.g., wild-type AAV), and comprises a variant AAV capsid protein that comprises an amino acid sequence that has at least about 85%, at least about 90%, at least about 95%, at least about 98%, or at least about 99%, or greater, amino acid sequence identity to the amino acid sequence as set forth in any one of SEQ ID NOs:44-58, where the VP1 of the rAAV virion comprises from 1 to 5, from 5 to 10, or from 10 to 15 amino acid substitutions compared to the amino acid sequence of AAV2 as set forth in SEQ ID NO:5. In some embodiments, a subject rAAV virion exhibits increased infectivity of a non-permissive cell (e.g., a stem cell) compared to the infectivity of the non-permissive cell by a corresponding parental AAV virion (e.g., wild-type AAV), and comprises a variant AAV capsid protein that comprises an R459G substitution compared to the amino acid sequence of AAV2 as set forth in SEQ ID NO:5. In some embodiments, a subject rAAV virion exhibits increased infectivity of a non-permissive cell (e.g., a stem cell) compared to the infectivity of the non-permissive cell by a corresponding parental AAV virion (e.g., wild-type AAV), and comprises a variant AAV capsid protein that comprises a V708I substitution and a P250S substitution compared to the amino acid sequence of AAV2 as set forth in SEQ ID NO:5.

In some embodiments, a subject mutant AAV virion exhibits increased infectivity of a non-permissive stem cell compared to a corresponding parental AAV (e.g., a wild-type AAV), and comprises a VP1 that comprises an amino acid sequence that has at least about 85%, at least about 90%, at least about 95%, at least about 98%, or at least about 99%, or greater, amino acid sequence identity to the amino acid sequence as set forth in SEQ ID NO: 59, where the VP1 of the mutant AAV virion comprises from 1 to 5, from 5 to 10, or from 10 to 15 amino acid substitutions compared to the amino acid sequence of AAV2 as set forth in SEQ ID NO:5. In some embodiments, a subject mutant AAV virion exhibits increased infectivity of a non-permissive stem cell compared to wild-type AAV2, and comprises an S85G substitution and an R459G substitution compared to the amino acid sequence of AAV2 as set forth in SEQ ID NO:5.

Generation of Subject rAAV Virions

By way of introduction, it is typical to employ a host or "producer" cell for rAAV vector replication and packaging. Such a producer cell (usually a mammalian host cell) generally comprises or is modified to comprise several different types of components for rAAV production. The first component is a recombinant adeno-associated viral (rAAV) vector genome (or "rAAV pro-vector") that can be replicated and packaged into vector particles by the host packaging cell. The rAAV pro-vector will normally comprise a heterologous polynucleotide (or "transgene"), with which it is desired to genetically alter another cell in the context of gene therapy (since the packaging of such a transgene into rAAV vector particles can be effectively used to deliver the transgene to a variety of mammalian cells). The transgene is generally flanked by two AAV inverted terminal repeats (ITRs) which comprise sequences that are recognized during excision, replication and packaging of the AAV vector, as well as during integration of the vector into a host cell genome.

A second component is a helper virus that can provide helper functions for AAV replication. Although adenovirus is commonly employed, other helper viruses can also be used as is known in the art. Alternatively, the requisite helper virus functions can be isolated genetically from a helper virus and the encoding genes can be used to provide helper virus functions in trans. The AAV vector elements and the helper virus (or helper virus functions) can be introduced into the host cell either simultaneously or sequentially in any order.

The final components for AAV production to be provided in the producer cell are "AAV packaging genes" such as AAV rep and cap genes that provide replication and encapsidation proteins, respectively. Several different versions of AAV packaging genes can be provided (including rep-cap cassettes and separate rep and/or cap cassettes in which the rep and/or cap genes can be left under the control of the native promoters or operably linked to heterologous promoters. Such AAV packaging genes can be introduced either transiently or stably into the host packaging cell, as is known in the art and described in more detail below.

1. rAAV Vector

A subject rAAV virion, including the heterologous DNA of interest (where "heterologous DNA of interest" is also referred to herein as "heterologous nucleic acid"), can be produced using standard methodology, known to those of skill in the art. The methods generally involve the steps of (1) introducing a subject rAAV vector into a host cell; (2) introducing an AAV helper construct into the host cell, where the helper construct includes AAV coding regions capable of being expressed in the host cell to complement AAV helper functions missing from the AAV vector; (3) introducing one or more helper viruses and/or accessory function vectors into the host cell, wherein the helper virus and/or accessory function vectors provide accessory functions capable of supporting efficient recombinant AAV ("rAAV") virion production in the host cell; and (4) culturing the host cell to produce rAAV virions. The AAV expression vector, AAV helper construct and the helper virus or accessory function vector(s) can be introduced into the host cell, either simultaneously or serially, using standard transfection techniques.

AAV expression vectors are constructed using known techniques to at least provide as operatively linked components in the direction of transcription, control elements including a transcriptional initiation region, the DNA of interest and a transcriptional termination region. The control elements are selected to be functional in a mammalian muscle cell. The resulting construct which contains the operatively linked components is bounded (5' and 3') with functional AAV ITR sequences.

The nucleotide sequences of AAV ITR regions are known. See, e.g., Kotin, R. M. (1994) Human Gene Therapy 5:793-801; Berns, K. I. "Parvoviridae and their Replication" in Fundamental Virology, 2nd Edition, (B. N. Fields and D. M. Knipe, eds.) for the AAV-2 sequence. AAV ITRs used in the vectors of the invention need not have a wild-type nucleotide sequence, and may be altered, e.g., by the insertion, deletion or substitution of nucleotides. Additionally, AAV ITRs may be derived from any of several AAV serotypes, including without limitation, AAV-1, AAV-2, AAV-3, AAV-4, AAV-5, AAV-7, etc. Furthermore, 5' and 3' ITRs which flank a selected nucleotide sequence in an AAV expression vector need not necessarily be identical or derived from the same AAV serotype or isolate, so long as they function as intended, i.e., to allow for excision and rescue of the sequence of interest from a host cell genome or vector, and to allow integration of the DNA molecule into the recipient cell genome when AAV Rep gene products are present in the cell. ITRs allow replication of the vector sequence in the presence of an appropriate mixture of Rep proteins. ITRs also allow for the incorporation of the vector sequence into the capsid to generate an AAV particle.

A suitable heterologous DNA molecule (also referred to herein as a "heterologous nucleic acid") for use in a subject rAAV vector will generally be less than about 5 kilobases (kb) in size and will include, for example, a gene (a nucleotide sequence) that encodes a protein that is defective or missing from a recipient subject; a gene that encodes a protein having a desired biological or therapeutic effect (e.g., an antibacterial, antiviral or antitumor function); a nucleotide sequence that encodes an RNA that inhibits or reduces production of a deleterious or otherwise undesired protein; a nucleotide sequence that encodes an antigenic protein; or a nucleotide sequence that encodes an RNA that inhibits or reduces production of a protein.

Suitable heterologous nucleic acids include, but are not limited to, those encoding proteins used for the treatment of endocrine, metabolic, hematologic, cardiovascular, neurologic, musculoskeletal, urologic, pulmonary and immune disorders, including such disorders as inflammatory diseases, autoimmune, chronic and infectious diseases, such as acquired immunodeficiency syndrome (AIDS), cancer, hypercholestemia, insulin disorders such as diabetes, growth disorders, various blood disorders including various anemias, thalassemias and hemophilia; genetic defects such as cystic fibrosis, Gaucher's Disease, Hurler's Disease, adenosine deaminase (ADA) deficiency, emphysema, or the like.

Suitable heterologous nucleic acids include, but are not limited to, those encoding any of a variety of proteins, including, but not limited to: an interferon (e.g., IFN-γ, IFN-α, IFN-β, IFN-ω; IFN-τ); an insulin (e.g., Novolin®, Humulin®, Humalog®, Lantus®, Ultralente, etc.); an erythropoietin ("EPO"; e.g., Procrit®, Eprex®, or Epogen® (epoetin-α); Aranesp® (darbepoietin-α); NeoRecormon®, Epogin® (epoetin-β); and the like); an antibody (e.g., a monoclonal antibody) (e.g., Rituxan® (rituximab); Remicade® (infliximab); Herceptin® (trastuzumab); Humira™ (adalimumab); Xolair® (omalizumab); Bexxar® (tositumomab); Raptiva™ (efalizumab); Erbitux™ (cetuximab); and the like), including an antigen-binding fragment of a monoclonal antibody; a blood factor (e.g., Activase® (alteplase) tissue plasminogen activator; NovoSeven® (recombinant human factor VIIa); Factor VIIa; Factor VIII (e.g., Kogenate®); Factor IX; β-globin; hemoglobin; and the like); a colony stimulating factor (e.g., Neupogen® (filgrastim; G-CSF); Neulasta® (pegfilgrastim); granulocyte colony stimulating factor (G-CSF), granulocyte-monocyte colony stimulating factor, macrophage colony stimulating factor, megakaryocyte colony stimulating factor; and the like); a growth hormone (e.g., a somatotropin, e.g., Genotropin®, Nutropin®, Norditropin®, Saizen®, Serostim®, Humatrope®, etc.; a human growth hormone; and the like); an interleukin (e.g., IL-1; IL-2, including, e.g., Proleukin®; IL-3, IL-4, IL-5, IL-6, IL-7, IL-8, IL-9; etc.); a growth factor (e.g., Regranex® (beclapermin; PDGF); Fiblast® (trafermin; bFGF); Stemgen® (ancestim; stem cell factor); keratinocyte growth factor; an acidic fibroblast growth factor, a stem cell factor, a basic fibroblast growth factor, a hepatocyte growth factor; and the like); a soluble receptor (e.g., a TNF-α-binding soluble receptor such as Enbrel® (etanercept); a soluble VEGF receptor; a soluble interleukin receptor; a soluble γ/δ T cell receptor; and the like); an enzyme (e.g., α-glucosidase; Cerazyme® (imiglucarase; β-glucocerebrosidase, Ceredase® (alglucerase); an enzyme activator (e.g., tissue plasminogen activator); a chemokine (e.g., IP-10; Mig; Groα/IL-8, RANTES; MIP-1α; MIP-1β; MCP-1; PF-4; and the like); an angiogenic agent (e.g., vascular endothelial growth factor (VEGF); an anti-angiogenic agent (e.g., a soluble VEGF receptor); a protein vaccine; a neuroactive peptide such as bradykinin, cholecystokinin, gastin, secretin, oxytocin, gonadotropin-releasing hormone, beta-endorphin, enkephalin, substance P, somatostatin, prolactin, galanin, growth hormone-releasing hormone, bombesin, dynorphin, neurotensin, motilin, thyrotropin, neuropeptide Y, luteinizing hormone, calcitonin, insulin, glucagon, vasopressin, angiotensin II, thyrotropin-releasing hormone, vasoactive intestinal peptide, a sleep peptide, etc.; other proteins such as a thrombolytic agent, an atrial natriuretic peptide, bone morphogenic protein, thrombopoietin, relaxin, glial fibrillary acidic protein, follicle stimulating hormone, a human alpha-1 antitrypsin, a leukemia inhibitory factor, a transforming growth factor, an insulin-like growth factor, a luteinizing hormone, a macrophage activating factor, tumor necrosis factor, a neutrophil chemotactic factor, a nerve growth factor a tissue inhibitor of metalloproteinases; a vasoactive intestinal peptide, angiogenin, angiotropin, fibrin; hirudin; a leukemia inhibitory factor; an IL-1 receptor antagonist (e.g., Kineret® (anakinra)); an ion channel, e.g., cystic fibrosis transmembrane conductance regulator (CFTR); dystrophin; utrophin, a tumor suppressor; lysosomal enzyme acid α-glucosidase (GAA); and the like. Suitable nucleic acids also include those that encode a functional fragment of any of the aforementioned proteins; and nucleic acids that encode functional variants of any of the aforementioned proteins.

Suitable heterologous nucleic acids also include those that encode antigenic proteins. A subject rAAV that comprises a heterologous nucleic acid that encodes an antigenic protein is suitable for stimulating an immune response to the antigenic protein in a mammalian host. The antigenic protein is derived from an autoantigen, an allergen, a tumor-associated antigen, a pathogenic virus, a pathogenic bacterium, a pathogenic protozoan, a pathogenic helminth, or any other pathogenic organism that infects a mammalian host. As used herein, the term "a nucleic acid encoding an antigenic protein derived from" includes nucleic acids encoding wild-type antigenic proteins, e.g., a nucleic acid isolated from a pathogenic virus that encodes a viral protein; synthetic nucleic acids generated in the laboratory that encode antigenic proteins that are identical in amino acid sequence to a naturally-occurring antigenic protein; synthetic nucleic acids generated in the laboratory that encode antigenic proteins that differ in amino acid sequence (e.g., by from one amino acid to about 15 amino acids) from a naturally-occurring antigenic protein, but that nonetheless induce an immune response to the corresponding naturally-occurring antigenic protein; synthetic nucleic acids generated in the laboratory that encode fragments of antigenic proteins (e.g., fragments of from about 5 amino acids to about 50 amino acids, which fragments comprises one or more antigenic epitopes), which fragments induce an immune response to the corresponding naturally-occurring antigenic protein; etc.

Similarly, an antigenic protein "derived from" an autoantigen, an allergen, a tumor-associated antigen, a pathogenic virus, a pathogenic bacterium, a pathogenic protozoan, a pathogenic helminth, or any other pathogenic organism that infects a mammalian host, includes proteins that are identical in amino acid sequence to a naturally-occurring antigenic protein, and proteins that differ in amino acid sequence (e.g., by from one amino acid to about 15 amino acids) from a naturally-occurring antigenic protein, but that nonetheless induce an immune response to the corresponding naturally-occurring antigenic protein; and fragments of antigenic proteins (e.g., fragments of from about 5 amino acids to about 50 amino acids, which fragments comprises one or more antigenic epitopes), which fragments induce an immune response to the corresponding naturally-occurring antigenic protein.

In some embodiments, an immune response to an antigenic protein encoded by a subject rAAV will stimulate a protective immune response to a pathogenic organism that displays the antigenic protein or antigenic epitope (or a protein or an epitope that is cross-reactive with the rAAV-encoded antigenic protein or antigenic epitopes) in the mammalian host. In some embodiments, a cytotoxic T lymphocyte (CTL) response to the rAAV-encoded antigenic protein will be induced in the mammalian host. In other embodiments, a humoral response to the rAAV-encoded antigenic protein will be induced in the mammalian host, such that antibodies specific to the antigenic protein are generated. In many embodiments, a TH1 immune response to the rAAV-encoded antigenic protein will be induced in the mammalian host. Suitable antigenic proteins include tumor-associated antigens, viral antigens, bacterial antigens, and protozoal antigens; and antigenic fragments thereof. In some embodiments, the antigenic protein is derived from an intracellular pathogen. In other embodiments, the antigenic protein is a self-antigen. In yet other embodiments, the antigenic protein is an allergen.

Tumor-specific antigens include, but are not limited to, any of the various MAGEs (Melanoma-Associated Antigen E), including MAGE 1 (e.g., GenBank Accession No. M77481), MAGE 2 (e.g., GenBank Accession No. U03735), MAGE 3, MAGE 4, etc.; any of the various tyrosinases; mutant ras; mutant p53 (e.g., GenBank Accession No. X54156 and AA494311); and p97 melanoma antigen (e.g., GenBank Accession No. M12154). Other tumor-specific antigens include the Ras peptide and p53 peptide associated with advanced cancers, the HPV 16/18 and E6/E7 antigens associated with cervical cancers, MUCI1-KLH antigen associated with breast carcinoma (e.g., GenBank Accession No. J03651), CEA (carcinoembryonic antigen) associated with colorectal cancer (e.g., GenBank Accession No. X98311), gp100 (e.g., GenBank Accession No. S73003) or MART1 antigens associated with melanoma, and the PSA antigen associated with prostate cancer (e.g., GenBank Accession No. X14810). The p53 gene sequence is known (See e.g., Harris et al. (1986) Mol. Cell, Biol., 6:4650-4656) and is deposited with GenBank under Accession No. M14694. Thus, the present invention can be used as immunotherapeutics for cancers including, but not limited to, cervical, breast, colorectal, prostate, lung cancers, and for melanomas.

Viral antigens are derived from known causative agents responsible for diseases including, but not limited to, measles, mumps, rubella, poliomyelitis, hepatitis A, B (e.g., GenBank Accession No. E02707), and C (e.g., GenBank Accession No. E06890), as well as other hepatitis viruses, influenza, adenovirus (e.g., types 4 and 7), rabies (e.g., GenBank Accession No. M34678), yellow fever, Japanese encephalitis (e.g., GenBank Accession No. E07883), dengue (e.g., GenBank Accession No. M24444), hantavirus, and human immunodeficiency virus (e.g., GenBank Accession No. U18552).

Suitable bacterial and parasitic antigens include those derived from known causative agents responsible for diseases including, but not limited to, diphtheria, pertussis (e.g., GenBank Accession No. M35274), tetanus (e.g., GenBank Accession No. M64353), tuberculosis, bacterial and fungal pneumonias (e.g., *Haemophilus influenzae*, *Pneumocystis carinii*, etc.), cholera, typhoid, plague, shigellosis, salmonellosis (e.g., GenBank Accession No. L03833), Legionnaire's Disease, Lyme disease (e.g., GenBank Accession No. U59487), malaria (e.g., GenBank Accession No. X53832), hookworm, onchocerciasis (e.g., GenBank Accession No. M27807), schistosomiasis (e.g., GenBank Accession No. L08198), trypanosomiasis, leshmaniasis, giardiasis (e.g., GenBank Accession No. M33641), amoebiasis, filariasis (e.g., GenBank Accession No. J03266), borreliosis, and trichinosis.

In some embodiments, e.g., in the context of stem cells, suitable heterologous nucleic acids include, but are not limited to, those encoding any of a variety of proteins, including, but not limited to: a growth factor, a morphogen, a cytokine, a receptor, a protein involved in intracellular signal transduction, a protein that provides a detectable signal, and a transcription factor.

In some embodiments, e.g., in the context of stem cells, a suitable heterologous nucleic acid includes a heterologous nucleic acid comprising a nucleotide sequence encoding a protein including, but not limited to, a growth factor (e.g., epidermal growth factor, fibroblast growth factor, vascular endothelial growth factor, neurotrophin, a TGFβ family member, a Delta family member, a Jagged family member); a morphogen (e.g., a Wnt or Hedgehog protein); a cytokine (e.g., an interleukin, a tumor necrosis family member, etc.); a receptor (e.g., a growth factor receptor, a cytokine receptor, a neurotransmitter receptor, a neutrotrophin receptor, an ion channel, a Notch family member, a Patched family member, a TGFβ receptor family member, a steroid hormone receptor, etc.); a protein involved in intracellular signal transduction (e.g., MAPK, MEKK, PI3-kinase, Akt, PKC, PKA, PKG, a member of the Jak family, a member of the Src family, etc.); a transcription factor (e.g., a member of the GATA, Gli, Sp, Hes, Hey, NF-κB, LIM, Olig, Mash, Math, TCF, Elk, Forkhead, histone acetyltransferase, histone methyltransferase, or histone deacetylase families); and the like.

In some embodiments, e.g., in the context of lung epithelial cells, suitable heterologous nucleic acids include, but are not limited to, those encoding any of a variety of proteins, including, but not limited to: a cystic fibrosis transmembrane conductance regulator, an immunogen (e.g., an antigen, as described elsewhere herein), and an antiviral protein. Non-limiting examples of suitable immunogens include a protein from influenza, a *Bacillus anthracis* polypeptide, a cancer-associated antigen, and other antigens as described elsewhere herein. In the context of lung epithelial cells, a suitable heterologous nucleic acid comprises a nucleotide sequence encoding an antiviral protein (e.g., interferon-beta, interferon-gamma, interleukin-2, etc.).

Suitable heterologous nucleic acids that encode heterologous gene products include non-translated RNAs, such as an antisense RNA, a ribozyme, an RNAi, an shRNA, and an siRNA. Interfering RNA (RNAi) fragments, particularly double-stranded (ds) RNAi, can be used to inhibit gene expression. One approach well known in the art for inhibiting gene expression is short interfering RNA (siRNA) mediated gene silencing, where the level of expression product of a target gene is reduced by specific double stranded siRNA nucleotide sequences that are complementary to at least a 19-25 nucleotide long segment (e.g., a 20-21 nucleotide sequence) of the target gene transcript, including the 5' untranslated (UT) region, the ORF, or the 3' UT region. In some embodiments, short interfering RNAs are about 19-25 nt in length. See, e.g., PCT applications WO0/44895, WO99/32619, WO01/75164, WO01/92513, WO01/29058, WO01/89304, WO02/16620, and WO02/29858; and U.S. Patent Publication No. 20040023390 for descriptions of siRNA technology. The siRNA can be encoded by a nucleic acid sequence, and the nucleic acid sequence can also include a promoter. The nucleic acid sequence can also include a polyadenylation signal. In some embodiments, the polyadenylation signal is a synthetic minimal polyadelylation signal.

Target genes include any gene encoding a target gene product (RNA or protein) that is deleterious (e.g., pathological); a target gene product that is malfunctioning; a target gene product. Target gene products include, but are not limited to, huntingtin; hepatitis C virus; human immunodeficiency virus; amyloid precursor protein; tau; a protein that includes a polyglutamine repeat; a herpes virus (e.g., varicella zoster); any pathological virus; and the like.

As such a subject rAAV that includes a heterologous nucleic acid encoding an siRNA is useful for treating a variety of disorders and conditions, including, but not limited to, neurodegenerative diseases, e.g., a trinucleotide-repeat disease, such as a disease associated with polyglutamine repeats, e.g., Huntington's disease, spinocerebellar ataxia, spinal and bulbar muscular atrophy (SBMA), dentatorubropallidoluysian atrophy (DRPLA), etc.; an acquired pathology (e.g., a disease or syndrome manifested by an abnormal physiological, biochemical, cellular, structural, or molecular biological state) such as a viral infection, e.g., hepatitis that occurs or may occur as a result of an HCV infection, acquired immunodeficiency syndrome, which occurs as a result of an HIV infection; and the like.

In many embodiments, a heterologous nucleic acid encoding an siRNA is operably linked to a promoter. Suitable promoters are known those skilled in the art and include the promoter of any protein-encoding gene, e.g., an endogenously regulated gene or a constitutively expressed gene. For example, the promoters of genes regulated by cellular physiological events, e.g., heat shock, oxygen levels and/or carbon monoxide levels, e.g., in hypoxia, may be operably linked to an siRNA-encoding nucleic acid.

The selected heterologous nucleotide sequence, such as EPO-encoding or nucleic acid of interest, is operably linked to control elements that direct the transcription or expression thereof in the nucleotide sequence in vivo. Such control elements can comprise control sequences normally associated with the selected gene (e.g., endogenous cellular control elements). Alternatively, heterologous control sequences can be employed. Useful heterologous control sequences generally include those derived from sequences encoding mammalian or viral genes. Examples include, but are not limited to, the SV40 early promoter, mouse mammary tumor virus long terminal repeat (LTR) promoter; adenovirus major late promoter (Ad MLP); a herpes simplex virus (HSV) promoter, an endogenous cellular promoter that is heterologous to the gene of interest, a cytomegalovirus (CMV) promoter such as the CMV immediate early promoter region (CMVIE), a rous sarcoma virus (RSV) promoter, synthetic promoters, hybrid promoters, and the like. In addition, sequences derived from nonviral genes, such as the murine metallothionein gene, will also find use herein. Such promoter sequences are commercially available from, e.g., Stratagene (San Diego, Calif.).

In some embodiments, cell type-specific or tissue-specific promoter will be operably linked to the heterologous nucleic acid encoding the heterologous gene product, such that the gene product is produced selectively or preferentially in a particular cell type(s) or tissue(s). In some embodiments, an inducible promoter will be operably linked to the heterologous nucleic acid.

For example, muscle-specific and inducible promoters, enhancers and the like, are useful for delivery of a gene product to a muscle cell. Such control elements include, but are not limited to, those derived from the actin and myosin gene families, such as from the myoD gene family; the myocyte-specific enhancer binding factor MEF-2; control elements derived from the human skeletal actin gene and the cardiac actin gene; muscle creatine kinase sequence elements and the murine creatine kinase enhancer (mCK) element; control elements derived from the skeletal fast-twitch troponin C gene, the slow-twitch cardiac troponin C gene and the slow-twitch troponin I gene; hypoxia-inducible nuclear factors; steroid-inducible elements and promoters, such as the glucocorticoid response element (GRE); the fusion consensus element for RU486 induction; and elements that provide for tetracycline regulated gene expression.

The AAV expression vector which harbors the DNA molecule of interest (the heterologous DNA) bounded by AAV ITRs, can be constructed by directly inserting the selected sequence(s) into an AAV genome which has had the major AAV open reading frames ("ORFs") excised therefrom. Other portions of the AAV genome can also be deleted, so long as a sufficient portion of the ITRs remain to allow for replication and packaging functions. Such constructs can be designed using techniques well known in the art. See, e.g., U.S. Pat. Nos. 5,173,414 and 5,139,941; International Publication Nos. WO 92/01070 (published Jan. 23, 1992) and WO 93/03769 (published Mar. 4, 1993); Lebkowski et al. (1988) Molec. Cell, Biol. 8:3988-3996; Vincent et al. (1990) Vaccines 90 (Cold Spring Harbor Laboratory Press); Carter, B. J. (1992) Current Opinion in Biotechnology 3:533-539; Muzyczka, N. (1992) Current Topics in Microbiol. and Immunol. 158:97-129; Kotin, R. M. (1994) Human Gene Therapy 5:793-801; Shelling and Smith (1994) Gene Therapy 1:165-169; and Zhou et al. (1994) J. Exp. Med. 179:1867-1875.

Alternatively, AAV ITRs can be excised from the viral genome or from an AAV vector containing the same and fused 5' and 3' of a selected nucleic acid construct that is present in another vector using standard ligation techniques, such as those described in Sambrook et al., supra. For example, ligations can be accomplished in 20 mM Tris-Cl pH 7.5, 10 mM $MgCl_2$, 10 mM DTT, 33 µg/ml BSA, 10 mM-50 mM NaCl, and either 40 µM ATP, 0.01-0.02 (Weiss) units T4 DNA ligase at 0° C. to 16° C. (for "sticky end" ligation) or 1 mM ATP, 0.3-0.6 (Weiss) units T4 DNA ligase at 14° C. (for "blunt end" ligation). Intermolecular "sticky end" ligations are usually performed at 30-100 µg/ml total DNA concentrations (5-100 nM total end concentration). AAV vectors which contain ITRs have been described in, e.g., U.S. Pat. No. 5,139,941. In particular, several AAV vectors are described therein which are available from the American Type Culture Collection ("ATCC") under Accession Numbers 53222, 53223, 53224, 53225 and 53226.

Additionally, chimeric genes can be produced synthetically to include AAV ITR sequences arranged 5' and 3' of one or more selected nucleic acid sequences. Preferred codons for expression of the chimeric gene sequence in mammalian muscle cells can be used. The complete chimeric sequence is assembled from overlapping oligonucleotides prepared by standard methods. See, e.g., Edge, Nature (1981) 292:756; Nambair et al. Science (1984) 223:1299; Jay et al. J. Biol. Chem. (1984) 259:6311.

In order to produce rAAV virions, an AAV expression vector is introduced into a suitable host cell using known techniques, such as by transfection. A number of transfection techniques are generally known in the art. See, e.g., Graham et al. (1973) Virology, 52:456, Sambrook et al. (1989) Molecular Cloning, A Laboratory Manual, Cold Spring Harbor Laboratories, New York, Davis et al. (1986) Basic Methods in Molecular Biology, Elsevier, and Chu et al. (1981) Gene 13:197. Particularly suitable transfection methods include calcium phosphate co-precipitation (Graham et al. (1973) Virol. 52:456-467), direct micro-injection into cultured cells (Capecchi, M. R. (1980) Cell 22:479-488), electroporation (Shigekawa et al. (1988) BioTechniques 6:742-751), liposome mediated gene transfer (Mannino et al. (1988) BioTechniques 6:682-690), lipid-mediated transduction (Felgner et al. (1987) Proc. Natl. Acad. Sci. USA 84:7413-7417), and nucleic acid delivery using high-velocity microprojectiles (Klein et al. (1987) Nature 327:70-73).

For the purposes of the invention, suitable host cells for producing rAAV virions include microorganisms, yeast cells, insect cells, and mammalian cells, that can be, or have been, used as recipients of a heterologous DNA molecule. The term includes the progeny of the original cell which has been transfected. Thus, a "host cell" as used herein generally refers to a cell which has been transfected with an exogenous DNA sequence. Cells from the stable human cell line, 293 (readily available through, e.g., the American Type Culture Collection under Accession Number ATCC CRL1573) are used in many embodiments. Particularly, the human cell line 293 is a human embryonic kidney cell line that has been transformed with adenovirus type-5 DNA fragments (Graham et al. (1977) J. Gen. Virol. 36:59), and expresses the adenoviral E1a and E1b genes (Aiello et al. (1979) Virology 94:460). The 293 cell line is readily transfected, and provides a particularly convenient platform in which to produce rAAV virions.

2. AAV Helper Functions

Host cells containing the above-described AAV expression vectors must be rendered capable of providing AAV helper functions in order to replicate and encapsidate the nucleotide sequences flanked by the AAV ITRs to produce rAAV virions. AAV helper functions are generally AAV-derived coding sequences which can be expressed to provide AAV gene products that, in turn, function in trans for productive AAV replication. AAV helper functions are used herein to complement necessary AAV functions that are missing from the AAV expression vectors. Thus, AAV helper functions include one, or both of the major AAV ORFs, namely the rep and cap coding regions, or functional homologues thereof. In the context of the instant invention, the cap functions include one or more mutant capsid proteins, wherein at least one capsid protein comprises at least one mutation, as described above.

By "AAV rep coding region" is meant the art-recognized region of the AAV genome which encodes the replication proteins Rep 78, Rep 68, Rep 52 and Rep 40. These Rep expression products have been shown to possess many functions, including recognition, binding and nicking of the AAV origin of DNA replication, DNA helicase activity and modulation of transcription from AAV (or other heterologous) promoters. The Rep expression products are collectively required for replicating the AAV genome. For a description of the AAV rep coding region, see, e.g., Muzyczka, N. (1992) Current Topics in Microbiol. and Immunol. 158:97-129; and Kotin, R. M. (1994) Human Gene Therapy 5:793-801. Suitable homologues of the AAV rep coding region include the human herpesvirus 6 (HHV-6) rep gene which is also known to mediate AAV-2 DNA replication (Thomson et al. (1994) Virology 204:304-311).

AAV cap proteins include VP1, VP2, and VP3, wherein at least one of VP1, VP2, and VP3 comprises at least one mutation, as described above.

AAV helper functions are introduced into the host cell by transfecting the host cell with an AAV helper construct either prior to, or concurrently with, the transfection of the AAV expression vector. AAV helper constructs are thus used to provide at least transient expression of AAV rep and/or cap genes to complement missing AAV functions that are necessary for productive AAV infection. AAV helper constructs lack AAV ITRs and can neither replicate nor package themselves. These constructs can be in the form of a plasmid, phage, transposon, cosmid, virus, or virion. A number of AAV helper constructs have been described, such as the commonly used plasmids pAAV/Ad and pIM29+45 which encode both Rep and Cap expression products. See, e.g., Samulski et al. (1989) J. Virol. 63:3822-3828; and McCarty et al. (1991) J. Virol. 65:2936-2945. A number of other vectors have been described which encode Rep and/or Cap expression products. See, e.g., U.S. Pat. No. 5,139,941.

Both AAV expression vectors and AAV helper constructs can be constructed to contain one or more optional selectable markers. Suitable markers include genes which confer antibiotic resistance or sensitivity to, impart color to, or change the antigenic characteristics of those cells which have been transfected with a nucleic acid construct containing the selectable marker when the cells are grown in an appropriate selective medium. Several selectable marker genes that are useful in the practice of the invention include the hygromycin B resistance gene (encoding Aminoglycoside phosphotranferase (APH)) that allows selection in mammalian cells by conferring resistance to hygromycin; the neomycin phosphotranferase gene (encoding neomycin phosphotransferase) that allows selection in mammalian cells by conferring resistance to G418; and the like. Other suitable markers are known to those of skill in the art.

3. AAV Accessory Functions

The host cell (or packaging cell) must also be rendered capable of providing non AAV derived functions, or "accessory functions," in order to produce rAAV virions. Accessory functions are non AAV derived viral and/or cellular functions upon which AAV is dependent for its replication. Thus, accessory functions include at least those non AAV proteins and RNAs that are required in AAV replication, including those involved in activation of AAV gene transcription, stage specific AAV mRNA splicing, AAV DNA replication, synthesis of Cap expression products and AAV capsid assembly. Viral-based accessory functions can be derived from any of the known helper viruses.

Particularly, accessory functions can be introduced into and then expressed in host cells using methods known to those of skill in the art. Commonly, accessory functions are provided by infection of the host cells with an unrelated helper virus. A number of suitable helper viruses are known, including adenoviruses; herpesviruses such as herpes simplex virus types 1 and 2; and vaccinia viruses. Nonviral accessory functions will also find use herein, such as those provided by cell synchronization using any of various known agents. See, e.g., Buller et al. (1981) J. Virol. 40:241-247; McPherson et al. (1985) Virology 147:217-222; Schlehofer et al. (1986) Virology 152:110-117.

Alternatively, accessory functions can be provided using an accessory function vector. Accessory function vectors include nucleotide sequences that provide one or more accessory functions. An accessory function vector is capable of being introduced into a suitable host cell in order to support efficient AAV virion production in the host cell. Accessory function vectors can be in the form of a plasmid, phage, transposon, cosmid, or another virus. Accessory vectors can also be in the form of one or more linearized DNA or RNA fragments which, when associated with the appropriate control elements and enzymes, can be transcribed or expressed in a host cell to provide accessory functions.

Nucleic acid sequences providing the accessory functions can be obtained from natural sources, such as from the genome of an adenovirus particle, or constructed using recombinant or synthetic methods known in the art. In this regard, adenovirus-derived accessory functions have been widely studied, and a number of adenovirus genes involved in accessory functions have been identified and partially characterized. See, e.g., Carter, B. J. (1990) "Adeno-Associated Virus Helper Functions," in CRC Handbook of Parvoviruses, vol. I (P. Tijssen, ed.), and Muzyczka, N. (1992) Curr. Topics. Microbiol. and Immun. 158:97-129. Specifically, early adenoviral gene regions E1a, E2a, E4, VAI RNA and, possibly, E1b are thought to participate in the accessory process, Janik et al. (1981) Proc. Natl. Acad. Sci. USA 78:1925-1929. Herpesvirus-derived accessory functions have been described. See, e.g., Young et al. (1979) Prog. Med. Virol. 25:113. Vaccinia virus-derived accessory functions have also been described. See, e.g., Carter, B. J. (1990), supra., Schlehofer et al. (1986) Virology 152:110-117.

As a consequence of the infection of the host cell with a helper virus, or transfection of the host cell with an accessory function vector, accessory functions are expressed which transactivate the AAV helper construct to produce AAV Rep and/or Cap proteins. The Rep expression products excise the recombinant DNA (including the DNA of interest, e.g., the heterologous nucleic acid) from the AAV expression vector. The Rep proteins also serve to duplicate the AAV genome. The expressed Cap proteins assemble into capsids, and the recombinant AAV genome is packaged into the capsids. Thus, productive AAV replication ensues, and the DNA is packaged into rAAV virions.

Following recombinant AAV replication, rAAV virions can be purified from the host cell using a variety of conventional purification methods, such as CsCl gradients. Further, if infection is employed to express the accessory functions, residual helper virus can be inactivated, using known methods. For example, adenovirus can be inactivated by heating to temperatures of approximately 60° C. for, e.g., 20 minutes or more. This treatment effectively inactivates only the helper virus since AAV is extremely heat stable while the helper adenovirus is heat labile.

The resulting rAAV virions are then ready for use for DNA delivery, such as in gene therapy applications, or for the delivery of a gene product to a mammalian host.

Delivery of a Gene Product

The present invention further provides methods of delivering a gene product to an individual in need thereof. The methods generally involve introducing a subject rAAV virion into an individual.

Generally, rAAV virions are introduced into a cell using either in vivo or in vitro transduction techniques. If transduced in vitro, the desired recipient cell will be removed from the subject, transduced with rAAV virions and reintroduced into the subject. Alternatively, syngeneic or xenogeneic cells can be used where those cells will not generate an inappropriate immune response in the subject.

Suitable methods for the delivery and introduction of transduced cells into a subject have been described. For example, cells can be transduced in vitro by combining recombinant AAV virions with cells e.g., in appropriate media, and screening for those cells harboring the DNA of interest using conventional techniques such as Southern blots and/or PCR, or by using selectable markers. Transduced cells can then be formulated into pharmaceutical compositions, described more fully below, and the composition introduced into the subject by various techniques, such as by intramuscular, intravenous, subcutaneous and intraperitoneal injection.

For in vivo delivery, the rAAV virions will be formulated into pharmaceutical compositions and will generally be administered parenterally (e.g., administered via an intramuscular, subcutaneous, intratumoral, transdermal, intrathecal, etc., route of administration).

Pharmaceutical compositions will comprise sufficient genetic material to produce a therapeutically effective amount of the gene product of interest, i.e., an amount sufficient to reduce or ameliorate symptoms of the disease state in question or an amount sufficient to confer the desired benefit. The pharmaceutical compositions will also contain a pharmaceutically acceptable excipient. Such excipients include any pharmaceutical agent that does not itself induce the production of antibodies harmful to the individual receiving the composition, and which may be administered without undue toxicity. Pharmaceutically acceptable excipients include, but are not limited to, liquids such as water, saline, glycerol and ethanol. Pharmaceutically acceptable salts can be included therein, for example, mineral acid salts such as hydrochlorides, hydrobromides, phosphates, sulfates, and the like; and the salts of organic acids such as acetates, propionates, malonates, benzoates, and the like. Additionally, auxiliary substances, such as wetting or emulsifying agents, pH buffering substances, and the like, may be present in such vehicles. A wide variety of pharmaceutically acceptable excipients are known in the art and need not be discussed in detail herein. Pharmaceutically acceptable excipients have been amply described in a variety of publications, including, for example, A. Gennaro (2000) "Remington: The Science and Practice of Pharmacy," 20th edition, Lippincott, Williams, & Wilkins; Pharmaceutical Dosage Forms and Drug Delivery Systems (1999) H. C. Ansel et al., eds., $7^{th}$ ed., Lippincott, Williams, & Wilkins; and Handbook of Pharmaceutical Excipients (2000) A. H. Kibbe et al., eds., $3^{rd}$ ed. Amer. Pharmaceutical Assoc.

Appropriate doses will depend on the mammal being treated (e.g., human or nonhuman primate or other mammal), age and general condition of the subject to be treated, the severity of the condition being treated, the particular therapeutic protein in question, its mode of administration, among other factors. An appropriate effective amount can be readily determined by one of skill in the art.

Thus, a "therapeutically effective amount" will fall in a relatively broad range that can be determined through clinical trials. For example, for in vivo injection, i.e., injection directly to skeletal or cardiac muscle, a therapeutically effective dose will be on the order of from about $10^6$ to about $10^{15}$ of the rAAV virions, e.g., from about $10^8$ to $10^{12}$ rAAV virions. For in vitro transduction, an effective amount of rAAV virions to be delivered to cells will be on the order of from about $10^8$ to about $10^{13}$ of the rAAV virions. Other effective dosages can be readily established by one of ordinary skill in the art through routine trials establishing dose response curves.

Dosage treatment may be a single dose schedule or a multiple dose schedule. Moreover, the subject may be administered as many doses as appropriate. One of skill in the art can readily determine an appropriate number of doses.

In some embodiments, the present invention provides methods of delivering a gene product to a stem cell. In these embodiments, a subject rAAV virion is introduced into a stem cell, either in vitro or in vivo. Stem cells of interest include hematopoietic stem cells and progenitor cells derived therefrom (U.S. Pat. No. 5,061,620); neural crest stem cells (see Morrison et al. (1999) Cell 96:737-749); adult neural stem cells or neural progenitor cells; embryonic stem cells; mesenchymal stem cells; mesodermal stem cells; etc. Other hematopoietic "progenitor" cells of interest include cells dedicated to lymphoid lineages, e.g. immature T cell and B cell populations.

Purified populations of stem or progenitor cells may be used. For example, human hematopoietic stem cells may be positively selected using antibodies specific for CD34, thy-1; or negatively selected using lineage specific markers which may include glycophorin A, CD3, CD24, CD16, CD14, CD38, CD45RA, CD36, CD2, CD19, CD56, CD66a, and CD66b; T cell specific markers, tumor specific markers, etc, Markers useful for the separation of mesodermal stem cells include FcγRII, FcγRIII, Thy-1, CD44, VLA-4α, LFA-1β, HSA, ICAM-1, CD45, Aa4.1, Sca-1, etc. Neural crest stem cells may be positively selected with antibodies specific for low-affinity nerve growth factor receptor (LNGFR), and negatively selected for the markers sulfatide, glial fibrillary acidic protein (GFAP), myelin protein P$_o$, peripherin and neurofilament. Human mesenchymal stem cells may be positively separated using the markers SH2, SH3 and SH4.

The cells of interest are typically mammalian, where the term refers to any animal classified as a mammal, including humans, domestic and farm animals, and zoo, laboratory, sports, or pet animals, such as dogs, horses, cats, cows, mice, rats, rabbits, etc. In some embodiments, the stem cell is a human stem cell.

The cells which are employed may be fresh, frozen, or have been subject to prior culture. They may be fetal, neonate, adult. Hematopoietic cells may be obtained from fetal liver, bone marrow, blood, particularly G-CSF or GM-CSF mobilized peripheral blood, or any other conventional source. The manner in which the stem cells are separated from other cells of the hematopoietic or other lineage is not critical to this invention. As described above, a substantially homogeneous population of stem or progenitor cells may be obtained by selective isolation of cells free of markers associated with differentiated cells, while displaying epitopic characteristics associated with the stem cells.

Any of a variety of proteins can be delivered to an individual using a subject method. Suitable proteins include, but are not limited to, an interferon (e.g., IFN-γ, IFN-α, IFN-β, IFN-ω; IFN-τ); an insulin (e.g., Novolin®, Humulin®, Humalog®, Lantus®, Ultralente, etc.); an erythropoietin ("EPO"; e.g., Procrit®, Eprex®, or Epogen® (epoetin-α); Aranesp® (darbepoietin-α); NeoRecormon®, Epogin® (epoetin-β) and the like); an antibody (e.g., a monoclonal antibody) (e.g., Rituxan® (rituximab); Remicade® (infliximab); Herceptin® (trastuzumab); Humira™ (adalimumab); Xolair® (omalizumab); Bexxar® (tositumomab); Raptiva™ (efalizumab); Erbitux™ (cetuximab); and the like), including an antigen-binding fragment of a monoclonal antibody; a blood factor (e.g., Activase® (alteplase) tissue plasminogen activator; NovoSeven® (recombinant human factor VIIa); Factor VIIa; Factor VIII (e.g., Kogenate®); Factor IX; β-globin; hemoglobin; and the like); a colony stimulating factor (e.g., Neupogen® (filgrastim; G-CSF); Neulasta® (pegfilgrastim); granulocyte colony stimulating factor (G-CSF), granulocyte-monocyte colony stimulating factor, macrophage colony stimulating factor, megakaryocyte colony stimulating factor; and the like); a growth hormone (e.g., a somatotropin, e.g., Genotropin®, Nutropin®, Norditropin®, Saizen®, Serostim®, Humatrope®, etc.; a human growth hormone; and the like); an interleukin (e.g., IL-1; IL-2, including, e.g., Proleukin®; IL-3, IL-4, IL-5, IL-6, IL-7, IL-8, IL-9; etc.); a growth factor (e.g., Regranex® (beclapermin; PDGF); Fiblast® (trafermin; bFGF); Stemgen® (ancestim; stem cell factor); keratinocyte growth factor; an acidic fibroblast growth factor, a stem cell factor, a basic fibroblast growth factor, a hepatocyte growth factor; and the like); a soluble receptor (e.g., a TNF-α-binding soluble receptor such as Enbrel® (etanercept); a soluble VEGF receptor; a soluble interleukin receptor; a soluble γ/δ T cell receptor; and the like); an enzyme (e.g., α-glucosidase; Cerazyme® (imiglucarase; β-glucocerebrosidase, Ceredase® (alglucerase); an enzyme activator (e.g., tissue plasminogen activator); a chemokine (e.g., IP-10; Mig; Groα/IL-8, RANTES; MIP-1α; MIP-1β; MCP-1; PF-4; and the like); an angiogenic agent (e.g., vascular endothelial growth factor (VEGF)); an anti-angiogenic agent (e.g., a soluble VEGF receptor); a protein vaccine; a neuroactive peptide such as bradykinin, cholecystokinin, gastin, secretin, oxytocin, gonadotropin-releasing hormone, beta-endorphin, enkephalin, substance P, somatostatin, prolactin, galanin, growth hormone-releasing hormone, bombesin, dynorphin, neurotensin, motilin, thyrotropin, neuropeptide Y, luteinizing hormone, calcitonin, insulin, glucagon, vasopressin, angiotensin II, thyrotropin-releasing hormone, vasoactive intestinal peptide, a sleep peptide, etc.; other proteins such as a thrombolytic agent, an atrial natriuretic peptide, bone morphogenic protein, thrombopoietin, relaxin, glial fibrillary acidic protein, follicle stimulating hormone, a human alpha-1 antitrypsin, a leukemia inhibitory factor, a transforming growth factor, an insulin-like growth factor, a luteinizing hormone, a macrophage activating factor, tumor necrosis factor, a neutrophil chemotactic factor, a nerve growth factor a tissue inhibitor of metalloproteinases; a vasoactive intestinal peptide, angiogenin, angiotropin, fibrin; hirudin; a leukemia inhibitory factor; an IL-1 receptor antagonist (e.g., Kineret® (anakinra)); an ion channel, e.g., cystic fibrosis transmembrane conductance regulator (CFTR); dystrophin; utrophin, a tumor suppressor; lysosomal enzyme acid α-glucosidase (GAA); and the like. Proteins that can be delivered using a subject method also include a functional fragment of any of the aforementioned proteins; and functional variants of any of the aforementioned proteins.

In some embodiments, a therapeutically effective amount of a protein is produced in the mammalian host. Whether a therapeutically effective amount of a particular protein is produced in the mammalian host using a subject method is readily determined using assays appropriate to the particular protein. For example, where the protein is EPO, hematocrit is measured.

Where the rAAV encodes an antigenic protein, suitable antigenic proteins that can be delivered to an individual using a subject method include, but are not limited to, tumor-associated antigens, autoantigens ("self" antigens), viral antigens, bacterial antigens, protozoal antigens, and allergens; and antigenic fragments thereof. In some embodiments, a cytotoxic T lymphocyte (CTL) response to the rAAV-encoded antigenic protein will be induced in the mammalian host. In other embodiments, a humoral response to the rAAV-encoded antigenic protein will be induced in the mammalian host, such that antibodies specific to the antigenic protein are generated. In many embodiments, a TH1 immune response to the rAAV-encoded antigenic protein will be induced in the mammalian host. Whether an immune response to the antigenic protein has been generated is readily determined using well-established methods. For example, an enzyme-linked immunosorbent assay can be used to determine whether antibody to an antigenic protein has been generated. Methods of detecting antigen-specific CTL are well known in the art. For example, a detectably labeled target cell expressing the antigenic protein on its surface is used to assay for the presence of antigen-specific CTL in a blood sample.

In some embodiments, e.g., in the context of stem cells, suitable proteins, include, but are not limited to: a growth factor, a morphogen, a cytokine, a receptor, a protein involved in intracellular signal transduction, a protein that provides a detectable signal, and a transcription factor. For example, in some embodiments, e.g., in the context of stem cells, suitable proteins include, but are not limited to, a growth factor (e.g., epidermal growth factor, fibroblast growth factor, vascular endothelial growth factor, neurotrophin, a TGFβ family member, a Delta family member, a Jagged family member); a morphogen (e.g., a Wnt or Hedgehog protein); a cytokine (e.g., an interleukin, a tumor necrosis family member, etc.); a receptor (e.g., a growth factor receptor, a cytokine receptor, a neurotransmitter receptor, a neutrotrophin receptor, an ion channel, a Notch family member, a Patched family member, a TGFβ receptor family member, a steroid hormone receptor, etc.); a protein involved in intracellular signal transduction (e.g., MAPK, MEKK, PI3-kinase, Akt, PKC, PKA, PKG, a member of the Jak family, a member of the Src family, etc.); a transcription factor (e.g., a member of the GATA, Gli, Sp, Hes, Hey, NF-κB, LIM, Olig, Mash, Math, TCF, Elk, Forkhead, histone acetyltransferase, histone methyltransferase, or histone deacetylase families); and the like.

In some embodiments, e.g., in the context of lung epithelial cells, suitable proteins include, but are not limited to: a cystic fibrosis transmembrane conductance regulator, an immunogen (e.g., an antigen, as described elsewhere herein), and an antiviral protein. Non-limiting examples of suitable immunogens include a protein from influenza, a *Bacillus anthracis* polypeptide, a cancer-associated antigen, and other antigens as described elsewhere herein. In the context of lung epithelial cells, a suitable heterologous nucleic acid comprises a nucleotide sequence encoding an antiviral protein (e.g., interferon-beta, interferon-gamma, interleukin-2, etc.).

Nucleic acids that can be delivered to an individual using a subject method include non-translated RNAs, such as an antisense RNA, a ribozyme, an RNAi, an shRNA, and an siRNA. In some embodiments, a therapeutically effective amount of the non-translated RNA is produced in the mammalian host. Whether a therapeutically effective amount of a non-translated RNA has been delivered to a mammalian host using a subject method is readily determined using any appropriate assay. For example, where the gene product is an siRNA that inhibits HIV, viral load can be measured.

Methods of Generating Mutant AAV Virions

The present invention provides a method of generating a mutant AAV virion comprising one or more mutations in one or more of VP1, VP2, and VP3. The method generally involves generating a mutant AAV library; and selecting the library for capsid mutants with altered capsid properties. The present invention further provides mutant AAV libraries, and compositions comprising the mutant AAV libraries.

In some embodiments, a given selection step is repeated two, three, four, or more times to enrich a subject AAV library for altered capsid properties. In some embodiments, following selection of an AAV library, individual clones are isolated and sequenced.

Generation of Mutant AAV Library

A mutant AAV library is generated that comprises one or more mutations in an AAV cap gene. Mutations in the AAV cap gene are generated using any known method. Suitable methods for mutagenesis of an AAV cap gene include, but are not limited to, a polymerase chain reaction (PCR)-based method, oligonucleotide-directed mutagenesis, and the like. Methods for generating mutations are well described in the art. See, e.g., Zhao et al. (1998) *Nat. Biotechnol.* 16:234-235; U.S. Pat. No. 6,579,678; U.S. Pat. No. 6,573,098; and U.S. Pat. No. 6,582,914.

In some embodiments, a mutant AAV library comprising mutations in the cap gene will be generated using a staggered extension process. The staggered extension process involves amplification of the cap gene using a PCR-based method. The template cap gene is primed using specific PCR primers, followed by repeated cycles of denaturation and very short annealing/polymerase-catalyzed extension. In each cycle, the growing fragments anneal to different templates based on sequence complementarity and extend further. The cycles of denaturation, annealing, and extension are repeated until full-length sequences form. The resulting full-length sequences include at least one mutation in the cap gene compared to a wild-type AAV cap gene.

The PCR products comprising AAV cap sequences that include one or more mutations are inserted into a plasmid containing a wild-type AAV genome. The result is a library of AAV cap mutants. Thus, the present invention provides a mutant AAV cap gene library comprising from about 10 to about $10^{10}$ members, and comprising mutations in the AAV cap gene. A given member of the library has from about one to about 50 mutations in the AAV cap gene. A subject library comprises from 10 to about $10^9$ distinct members, each having a different mutation(s) in the AAV cap gene.

Once a cap mutant library is generated, viral particles are produced that can then be selected on the basis of altered capsid properties. Library plasmid DNA is transfected into a suitable host cell (e.g., 293 cells), followed by introduction into the cell of helper virus. Viral particles produced by the transfected host cells ("AAV library particles) are collected.

Library Selection

Once a library is generated, it is selected for a particular capsid property. Viral particles are generated as discussed above, and subjected to one or more selection steps. Capsid properties that are selected for include, but are not limited to: 1) increased heparin binding affinity relative to wild-type AAV; 2) decreased heparin binding affinity relative to wild-type AAV; 3) increased infectivity of a cell that is resistant to infection with AAV; 4) increased evasion of neutralizing antibodies; and 5) increased ability to cross an endothelial cell layer.

1. Selection for Altered Heparin Binding

In some embodiments, a subject library is selected for altered heparin binding, including increased heparin binding and decreased heparin binding relative to wild-type AAV virion heparin binding. AAV library particles are contacted with a heparin affinity matrix. For example, AAV library particles are loaded onto a heparin affinity column under conditions that permit binding of the AAV library particles to the heparin. Exemplary conditions include equilibration of the column with 0.15 M NaCl and 50 mM Tris at pH 7.5. After allowing the AAV library particle to bind to the heparin affinity matrix, the AAV library particle/heparin affinity matrix complex is washed with volumes of buffer containing progressively increasing concentrations of NaCl, and at each NaCl concentration, eluted AAV library particles are collected. For example, after binding the AAV library particle/heparin affinity matrix complex is washed with a volume of 50 mM Tris buffer, pH 7.5, containing 200 mM NaCl, and eluted AAV library particles are collected. The elution step is repeated with a 50 mM Tris buffer, pH 7.5, containing about 250 mM NaCl, about 300 mM NaCl, about 350 mM, about 400 mM NaCl, about 450 mM NaCl, about 500 mM NaCl, about 550 mM NaCl, about 600 mM NaCl, about 650 mM NaCl, about 700 mM NaCl, or about 750 mM NaCl.

AAV library particles that elute at NaCl concentrations lower than about 450 mM NaCl exhibit decreased heparin binding properties relative to wild-type AAV. AAV library particles that elute at NaCl concentrations higher than about 550 mM NaCl exhibit increased heparin binding properties relative to wild-type AAV.

In some embodiments, eluted AAV library particles are amplified by co-infection of permissive cells with a helper virus, and are re-fractionated on heparin affinity matrix. This step can be repeated a number of times to enrich for AAV library particles with altered heparin binding properties.

2. Selection for Reduced Binding to Neutralizing Antibodies

In some embodiments, a subject AAV library is selected for reducing binding to neutralizing antibodies that bind to an neutralize wild-type AAV virions, compared to the binding of such antibodies to wild-type AAV virions and neutralization of wild-type AAV virions. AAV library particles are contacted with neutralizing antibodies and the ability of the AAV library particles to infect a permissive host cell is tested. Typically, AAV library particles are contacted with various concentrations of neutralizing antibodies. The higher the concentration of neutralizing antibodies that is required to reduce infectivity of the AAV library particles, the more resistant the AAV particles are to neutralization.

3. Selection for Increased Infectivity of Non-Permissive Cells

In some embodiments, a subject AAV library is selected for increased infectivity of non-permissive cells. AAV library particles are contacted with a non-permissive cell (e.g., a population of non-permissive cells). After a suitable amount of time to allow for infection of the cells with AAV library particles, helper virus is added, and AAV library particles that successfully infected the non-permissive cell(s) are harvested. In some embodiments, the cycle of infection, addition of helper virus, and harvesting of AAV particles is repeated one, two, three, or more times.

In the present methods, one or more selection steps may follow generation of AAV library particles. For example, in some embodiments, the method comprises selecting for increased heparin binding, followed by selecting for decreased binding to neutralizing antibodies. In other embodiments, the method comprises selecting for decreased binding to neutralizing antibodies, followed by selecting for increased heparin binding. In other embodiments, the method comprises selecting for decreased heparin binding, followed by selecting for decreased binding to neutralizing antibodies. In other embodiments, the method comprises selecting for decreased binding to neutralizing antibodies, followed by selecting for decreased heparin binding. In other embodiments, the method comprises selecting for decreased binding to neutralizing antibodies, followed by selecting for increased infectivity of a stem cell.

Thus, the present invention provides an adeno-associated virus (AAV) library, that includes a plurality of nucleic acids, each of which nucleic acids include a nucleotide sequence that encodes a mutant AAV capsid protein. The encoded mutant AAV capsid protein includes at least one amino acid substitution relative to a wild-type AAV capsid protein. The present invention provides a library of mutant adeno-associated virus (AAV) particles, including a plurality of AAV particles each of which includes an AAV capsid protein that includes at least one amino acid substitution relative to a wild-type AAV capsid protein. Nucleic acids encoding mutant AAV capsid proteins are described above, as are the properties of the encoded mutant AAV capsid proteins.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s, second(s); min, minute(s); hr, hour(s); and the like.

Example 1

Generation and Characterization of AAV Capsid Variants

Methods
Library Generation and Vector Packaging

An AAV2 cap ORF genetic library was generated using the staggered extension process described by Zhao at al. ((1998) *Nat. Biotechnol.* 16:258-261), and the resulting cap product was inserted into a plasmid containing the wild type AAV2 genome. The result was transformed into *E. coli* for large scale plasmid production and purification. AAV was then produced and purified by CsCl centrifugation essentially as previously described (Kaspar et al. (2002) *Proc. Natl. Acad. Sci. USA* 99:2320-2325; and Lai et al. (2003) *Nat. Neurosci.* 6:21-27). Briefly, the library plasmid DNA was transfected into 293 human embryonic kidney cells (ATCC) using the calcium phosphate method, followed by addition of serotype 5 adenovirus (Ad5) at a multiplicity of infection (MOI) of 3. Virus was purified using CsCl density centrifugation. For all experiments, the AAV genomic titer was determined by extracting vector DNA as previously described (Kaspar et al. supra; and Lai et al., supra) followed by quantification using real time PCR with SYBR-Green dye (Molecular Probes) and a Biorad iCycler.

Heparin Column Chromatography

Approximately $10^{12}$ AAV library particles were loaded onto a 1 mL HiTrap heparin column (Amersham) previously equilibrated with 0.15 M NaCl and 50 mM Tris at pH 7.5. Washes were performed using 0.75 ml volumes of the same buffer with increasing increments of 50 mM NaCl up to 750 mM, followed by a 1 M wash. As a control, rAAV-GFP was also subjected to heparin affinity chromatography. To isolate individual viral clones from library fractions that eluted at different salt concentrations, viral DNA was extracted from the fractions, amplified by PCR, and inserted into a rAAV packaging plasmid based on pAd8. rAAV-GFP was then packaged in order to analyze the ability of these mutant capsids to package rAAV vector. Capsid variants were sequenced at the U.C. Berkeley DNA sequencing facility. Finally, the affinity of the variant capsids for heparin was quantified by using the method of Qiu et al. ((2000) *Virol.* 269:137-147), except that virus bound to the immobilized heparin was quantified by real time PCR.

Antisera Generation and Antibody Neutralization Screen

Polyclonal sera containing neutralizing antibodies (NABs) against AAV2 were generated in two New Zealand White rabbits in accordance with the U.C. Berkeley Animal Care and Use Committee and NIH standards for laboratory animal care. Briefly, $5 \times 10^{10}$ CsCl-purified rAAV2 particles were mixed with 0.5 mL TitreMax adjuvant (CytRx) and injected into the anterior hindlimb muscle. Two boosts were performed at 3-week intervals using the same AAV dosage, followed by antiserum collection.

Both wild type and a mutant AAV library were incubated with varying amounts of serum (0-6.25 μl) in 75 μl of phosphate-buffered saline (PBS) (pH 7.4) for 30 minutes at room temperature, followed by addition to $2.5 \times 10^5$ 293 cells in a 6-well format. After 48 hours, AAV was rescued from infected cells by addition of Ad5, and cells were harvested 24 hours later.

Individual viral clones from the library fraction that successfully infected cells even in the presence of NAB were inserted into the rAAV packaging plasmid, and rAAV-GFP was produced as above. rAAV with mutant capsids were then incubated in 5 μl polyclonal sera as above, followed by addition to 1×10⁵ 293 cells. At 72 hours post-infection, the fraction of green cells was quantified by flow cytometry at the U.C. Berkeley Cancer Center (Beckman-Coulter EPICS).

Results

Library Generation

The staggered extension process (Zhao et al., supra), a polymerase chain reaction (PCR)-based method that generates diverse genetic libraries in a manner similar to that of DNA shuffling, was used to generate a library of cap mutants with point mutations randomly distributed throughout VP1-3. This product was inserted into a plasmid containing the complete wild type AAV genome to yield a viral library with approximately 10⁶ independent clones, as determined by quantifying the number of colonies following bacterial transformation. To assess its degree of sequence diversity, the plasmid library was sequenced. The plasmid was then packaged into virus by transient transfection into 293 cells followed by Ad5 infection to yield a viral particle library. This large AAV library is selected for viral variants with any variety of new properties or functions, and the capsid structure conferring these new functions are readily recovered by DNA sequence analysis of the AAV genome encapsidated in the particles.

Heparin Binding Mutants

As an initial gauge of how the library's sequence diversity translated into capsid functional diversity, CsCl-purified library particles were subjected to heparin affinity chromatography with steps of increasing NaCl concentration. As previously reported (Zolotukhin et al. (1999) *Gene Ther.* 6:973-985) wild type AAV elutes from heparin between 450 and 550 mM NaCl (FIG. 1). In stark contrast, the AAV mutant library elutes at a wide range of salt concentrations, from the 150 mM load to the final 750 mM fraction. This result demonstrates that the library encompasses significant sequence and functional diversity. Since its affinity for heparan sulfate limits the spread of rAAV2 vectors upon injection in vivo, lower affinity mutants may be desirable as gene delivery vectors when wide dissemination through a large tissue or region is needed. In contrast, a higher affinity mutant may be advantageous for regionally pinpointed, high level gene expression.

Figure 1B:
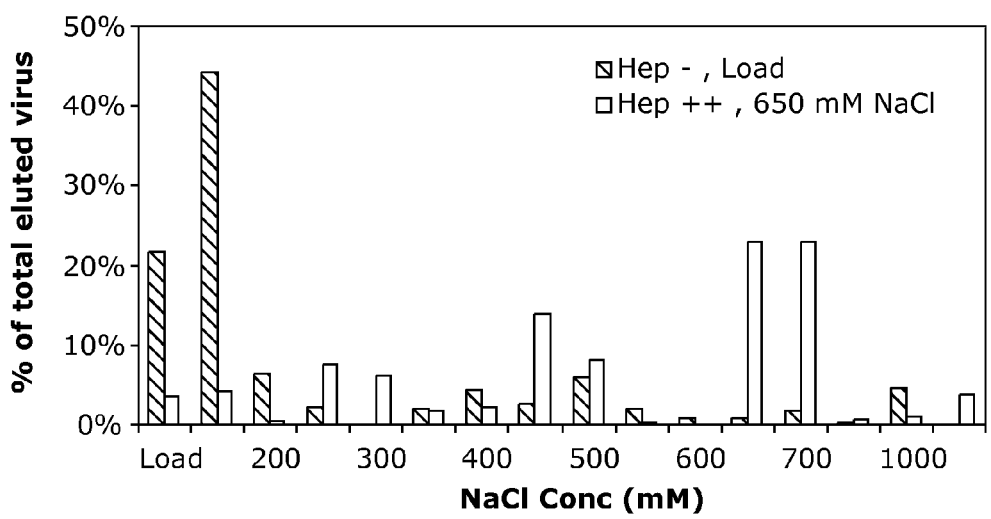
Figure 2A:
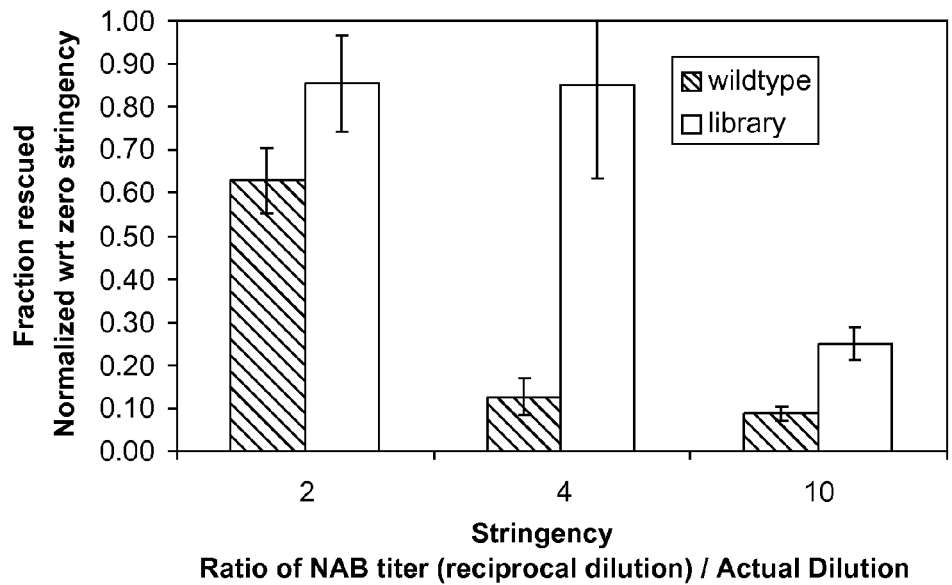
FIGS. 2a and 2b depict generation of antibody neutralization escape mutants.
Figure 2B:
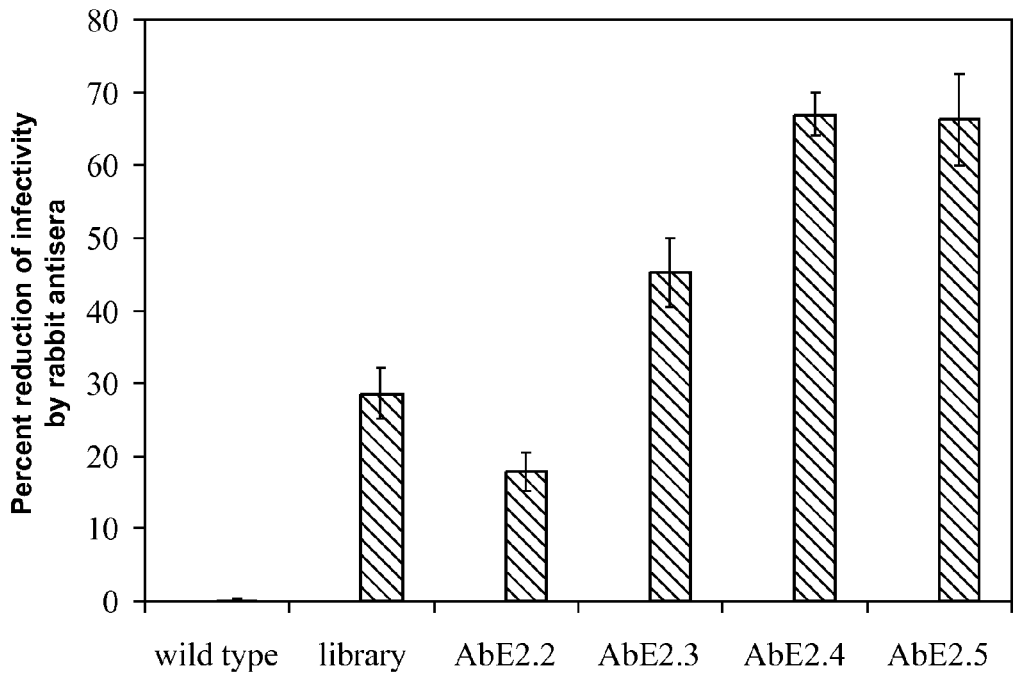

FIGS. 1a and 1b. Heparin binding characteristics of wild type AAV vs. the viral library. a) The heparin affinity column chromatogram of elution of wild type AAV (hatched bars) and the mutant library (open bars) is shown. Virus gradually elutes from the column as the NaCl concentration is increased. b) Chromatograms of pools from the mutant library selected for lower (hatched bars) and higher (open bars) heparin affinities.

To isolate mutants with both low and high heparin affinity, the 150 mM and 700 mM NaCl fractions from the initial library were separately amplified by co-infection of 293 cells with Ad5, and refractionated on the heparin column. After three rounds of enrichment, the majority of the two resulting viral pools eluted from the column at 150 mM and 750 mM (FIG. 1b). Importantly, since each round of enrichment involved 293 cell infection, these pools are still composed of highly infectious virus. Next, individual capsid clones were isolated from each of these salt fractions and sequenced.

The fact that these mutants eluted from the heparin column at different salt concentrations indicates that they had different affinities for heparin. To accurately measure these affinities, however, the method of Qiu et al supra can be used. By performing Scatchard binding analysis of virus to heparin immobilized to microtiter plates, the difference in the affinity of the mutants for heparin, compared to the affinity of wild-type AAV for heparin, is determined.

Neutralizing Antiserum Escape Mutants

The isolation of functionally diverse heparin binding mutants from our AAV mutant library demonstrates the utility of this approach for creating vectors with novel properties. This approach was applied to a much more significant problem: vector elimination by neutralizing antibodies. Rabbit anti-AAV2 neutralizing antiserum was generated, and a 1:1500 serum dilution was sufficient to inhibit rAAV-GFP gene delivery to 293 cells by 50%, comparable to NAB titers in human serum.

FIGS. 2*a* and 2*b*. Generation of antibody neutralization escape mutants. a) Virus was incubated with antiserum before addition to 293 cells. The level of virus that successfully evaded antibody neutralization as compared to control infection in the absence of antiserum was measured by addition of Ad5 and titering of rescued AAV by quantitative real time PCR on AAV genomes. b) The data on individual variants is presented.

Antibody escape mutants were isolated from the viral library. During successive rounds of selection, the library was subjected to increasing stringencies, where stringency is defined as the ratio of the dilution necessary to reduce rAAV2 with wild type capsid by 50% (a 1500-fold for the rabbit antiserum) to the dilution actually used. Therefore, the more antiserum added to the virus, the higher the stringency. After three rounds of selection, followed by co-infection of 293 cells with Ad5 for amplification, the resulting viral pool was less susceptible to antibody neutralization as compared to wild type virus. Next, five individual capsid clones from this pool were analyzed by using them to package rAAV-GFP. The results demonstrated that the resulting recombinant vector is between 100 and 1000-fold more resistant to neutralizing antibodies. This is a therapeutically relevant result.

Neutralizing antibody inhibition of rAAV gene delivery can be observed as follows. rAAV2 with wild type capsid is added to 293 cells and visualized after 24 hours. Virus is visualized in green (Alexa 488), microtubules in red (Alexa 546), and the nucleus in blue (TO-PRO-3). After preincubation in neutralizing antiserum, the intracellular transport of rAAV2 with wild type capsid is expected to be significantly inhibited.

In FIGS. 3A-C, the cap nucleotide sequences of two neutralizing antibody escape mutants is shown, compared to wild-type cap sequence.

Example 2

Characterization of Further AAV Capsid Variants

AAV Mutants—including antibody evaders, mutants with reduced heparin binding, and mutants with increased heparin binding—were generated as follows.

Library Generation:

A combination of error prone PCR and the staggered extension process (StEP) was used to generate a library of mutant DNA fragments encoding the capsid protein. This library was then inserted into a plasmid in order to package it into virus, by transfection of these plasmids plus an adenoviral helper plasmid into 293 cells. The library was then purified by cesium chloride density centrifugation.

Selection:

The library was then passed through screening steps. For example, for the antibody evasion mutant, a sample of the library was mixed together with polyclonal anti-AAV antiserum, then added to 293 cells. Addition of adenovirus amplifies the variants that are able to successfully evade the antiserum.

After amplification of the 'successful' variants (e.g., variants that infected the 293 cells in the presence of anti-AAV antibody) in 293 cells, the variants were purified, mixed again with antiserum, and allowed to infect 293 cells, and finally reamplified with adenovirus to further enrich for variants. After several rounds of enrichment, the viral DNA was purified, cloned, and sequenced to determine which mutations resulted in successful variants.

Generating Vector:

At this point, only the viral capsid DNA had been used to package replication competent virus, i.e. viruses with a genome that contained rep and the mutant cap genes and were therefore capable of replicating in the presence of adenovirus. However, to use the variants in a gene therapy setting, it was important to use the mutant cap gene to package recombinant particles containing a therapeutic gene. To demonstrate that the mutant cap genes described herein are capable of packaging recombinant virus, the cap gene was moved into a packaging/helper plasmid. Addition of this helper along with an adenoviral helper plasmid and a vector plasmid containing a promoter driving the expression of a reporter gene (GFP) to cells results in the generation of recombinant particles.

Antibody Evasion Mutants

Two sources of antiserum were used to generate antibody evasion mutants. One is rabbit serum that was generated by injecting rabbits with wild type AAV particles (Anti-AAV Rabbit Serum produced from New Zealand White rabbits). The second is human serum pooled from a number of individuals (Sigma Product #H-1388; Lot #122K0424; Origin: 40 North American donors).

Heparin Binding Mutants

To generate heparin binding mutants, CsCl-purified library viral particles were subjected to heparin affinity chromatography with steps of increasing NaCl concentration, as described in Example 1. Mutants with reduced heparin binding were eluted with the same NaCl concentration used to load the viral particles (e.g., 0.15 M NaCl). Mutants with reduced heparin binding were eluted at between 650-700 mM NaCl.

Characterization

Tables 1-4, below, provide the location of the amino acid differences in VP1 from wild-type AAV VP1 for the various mutants. All amino acid differences are relative to the VP1 amino acid sequence shown in FIGS. 5A-C (SEQ ID NO:5). VP1-encoding nucleotide sequence of the various mutants are provided in FIGS. 4A-G, FIGS. 6A-J, and FIGS. 8A-G. In FIGS. 4A-G, FIGS. 6A-J, and FIGS. 8A-G, nucleotide differences from wild-type AAV-2 VP1 are shown in bold. VP1 amino acid sequences of the various mutants are provided in FIGS. 5A-C, FIGS. 7A-D, and FIGS. 9A-C. In FIGS. 5A-C, FIGS. 7A-D, and FIGS. 9A-C, conservative amino acid changes are indicated with a box; and non-conservative amino acid changes are indicated in bold.

Table 1 provides the clone number and amino acid changes for various AAV neutralizing antibody escape mutants.

TABLE 1

Mutations in 5 rabbit antisera evader clones

| Clone | Mutation | Region |
|---|---|---|
| rAbE1 | T713R | 2-fold dimple* |
|  | T716A | 2-fold dimple* |
| rAbE2 | V418L | Antigenic peptide 53* |
|  | T713R | 2-fold dimple* |
|  | T716A | 2-fold dimple* |
| rAbE3 | T716A | 2-fold dimple* |
| rAbE4 | D180N | A69 linear epitope† |
|  | T716A | 2-fold dimple* |
| rAbE5 | A493G | C37-B conformational epitope† |
|  | T716A | 2-fold dimple* |

*Moskalenko et al. (2000) *J. Virol.* 74: 1761-1766
†Wobus et al. (2000) *J. Virol.* 74: 9281-9293
‡Xie et al. (2002) *Proc. Natl. Acad. Sci. USA* 99: 10405-10410

Table 2 provides the clone number and amino acid changes for various AAV neutralizing antibody escape mutants.

TABLE 2

Mutations in 9 human antisera evader clones

| Clone | Mutation | Region |
|---|---|---|
| S1CM5 | K169R | Peptide 22-23* & Bordering A69 linear epitope† |
|  | S181P | A69 linear epitope† |
|  | A333V | 5-fold cylinder* |
|  | P363T | Between 5-fold cylinder and A20 conformational epitope |
|  | A493E | C37-B conformational epitope† |
| S2CM5 | I19V | "Lip" insertion (Peptide 4-5)* |
|  | V369A | A20 conformational epitope† |
|  | A593E | Accessible surface region in Loop 4 on β-GH13‡ |
| S2CM2 | G189E | 6 aa proximity to A69 linear epitope† |
|  | N215I | Near N-terminus VP3 |
|  | A367E | Between 5-fold cylinder and A20 conformational epitope, 2 aa proximity to A20 |
|  | S429G | α-GH1‡ |
|  | A493E | C37-B conformational epitope† |
|  | S580P | End of b-GH12, 1 aa proximity to accessible surface region loop 4, β-GH13‡ |
|  | P643L | Proline residue between β-GH16 and β-H in β barrel core‡ |
|  | E685V |  |
| S3CM2 | R20S | "Lip" insertion (Peptide 4-5)* |
|  | N57S |  |
|  | E347V | 5-fold cylinder* |
|  | A493E | C37-B conformational epitope† |
|  | N551D |  |
|  | D594E | Accessible surface region in Loop 4 on β-GH13‡ |

TABLE 2-continued

Mutations in 9 human antisera evader clones

| Clone | Mutation | Region |
|---|---|---|
| A1CM5 | K26R | "Lip" insertion (Peptide 4-5)* |
|  | N215D |  |
|  | G355S | 5-fold cylinder* |
|  | A593E | Accessible surface region in Loop 4 on β-GH13‡ |
| A3CM5 | G49E |  |
|  | S196P |  |
|  | T337P | 5-fold cylinder* |
| A1CM2 | K24E | "Lip" insertion (Peptide 4-5)* |
|  | L91P |  |
|  | K137T |  |
|  | Q186L | 3 aa proximity A69 linear epitope* |
|  | T251A | Minor Peptide 33, Canyon Epitope* |
|  | H290L |  |
|  | F306L | End of 5-fold cylinder* |
|  | S390T |  |
|  | A493E | C37-B conformational epitope† |
|  | A505V | 1 aa proximity to C37-B conformational epitope† |
|  | V557I |  |
|  | T651A |  |
| A2CM2 | V46A |  |
|  | S196P | Between A20 and C37 minor Conformational Epitope† |
|  | A593E | Accessible surface region in Loop 4 on β-GH13‡ |
| A3CM2 | P31L |  |
|  | F100S |  |
|  | I260T | Minor Peptide 33, Canyon Epitope* |
|  | R459G | 3-fold spike in Loop 3 (peptide 58)* |
|  | A522T |  |
|  | A663V |  |
|  | E681G |  |
|  | W694R |  |

Table 3 provides the clone number and amino acid changes for various AAV mutants with increased heparin binding.

TABLE 3

Mutations of Clones with Increased Heparin Affinity

| Clone | Mutation |
|---|---|
| D14H1 | W23L |
|  | D231G |
|  | S261F |
|  | V323F |
|  | Q349P |
|  | G406E |
|  | N408D |
| D14L3 | W23L |
|  | S196T |
|  | D231G |
|  | S261F |
|  | Q349P |
|  | G406E |
|  | N408D |
|  | N569D |
|  | N596D |

Table 4 provides the clone number and amino acid changes for various AAV mutants with reduced heparin binding.

TABLE 4

Mutations of Clones with Reduced Heparin Affinity

| Clone | Mutation |
|---|---|
| P1BH1 | M235V |
|  | Q401R |
|  | L437H |
|  | N582D |
|  | T660A |
| P1BH2 | G111R |
|  | K258E |
|  | L315P |
|  | E322G |
|  | N551D |
|  | V605I |

Example 3

Infectious Virus Exhibiting Infectivity of Lung Epithelial Cells

To develop better treatments for cystic fibrosis (CF) and other airway disorders, AAV was evolved to be more infectious for human lung tissue, e.g., for lung epithelial cells.

Methods

Selection of AVV Library Using Well-Differentiated Human Airway Epithelia

Figure 11A:
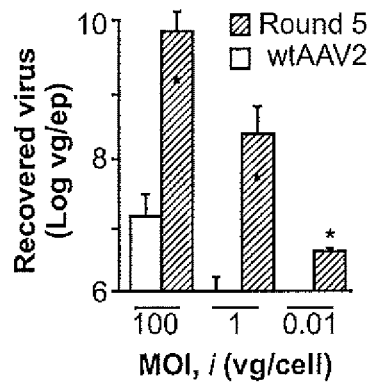
FIGS. 11A-E depict the infectivity and the transduction of AVV vectors for pulmonary gene deliv (SEQ ID NO:49); hEr1.35 (SEQ ID NO:50); hEr1.7 (SEQ ID NO:51); hEr1.36 (SEQ ID NO:52); and AAV2 (SEQ ID NO:5).

Two divergent serotypes that utilize distinct receptors, AAV2 and AAV5 were combined, by subjecting the cap genes encoding the viral capsomeres to DNA shuffling and error-prone PCR, to yield a highly diverse library of ~$10^6$ independent chimeric viral sequences. Species-specific differences in various cell types, particularly airway epithelia, have been shown to impact viral infection; therefore, to evolve the virus towards clinical gene therapy, a well-differentiated organotypic human airway model was employed. Specifically, extensive selections were performed on human airway epithelial cultures (15 donors) by apical application of the AAV viral library, followed by amplification via basolateral application of helper wild-type adenovirus. AAV library was applied apically for decreasing times and multiplicity of infection (MOI) over 5 rounds (FIG. 11a). Additional diversification (A) was performed after round 3.

Apical transduction by the novel AAV chimera, several corresponding variants, and serotypes 2, 5, and 9, harboring luciferase was monitored over a twenty-eight day time course. Quantitative expression was determined after d-luciferin addition to each culture by IVIS imaging (Xenogen). Characterization of Cystic Fibrosis Transmembrane Conductance Regulator (CFTR) Expressed by AAV Variants.

To investigate whether AAV2.5T could efficiently express CFTR and correct the chloride transport defect, cystic fibrosis airway epithelia were transduced with AAV2.5T encoding CFTR at a MOI of 50,000. Thirty days post-transduction, epithelia were analyzed in Ussing chambers as previously described (Ostedgaard, L. Sl. et al. (2005) *Proc Natl Acad Sci USA* 102:2952-7).

Results

Efficient Variants for Pulmonary Gene Delivery

With every round of selection, increasing amounts of viral progeny were recovered relative to wild-type AAV2. AAV-luciferase expression peaked at day 21 post-transduction. By round 5, recovery of the evolved progeny was ~550-fold higher than AAV2 (FIG. 11a). Sequencing of eight random clones from the progeny revealed a single AAV variant, AAV2.5T (SEQ ID NO:42), which includes several amino acid differences from AAV2, including a point mutation at amino acid 581 (A581T). Alignment of this variant with wild-type AAV2 capsid is shown in FIG. 10A-B.

Figure 11B:
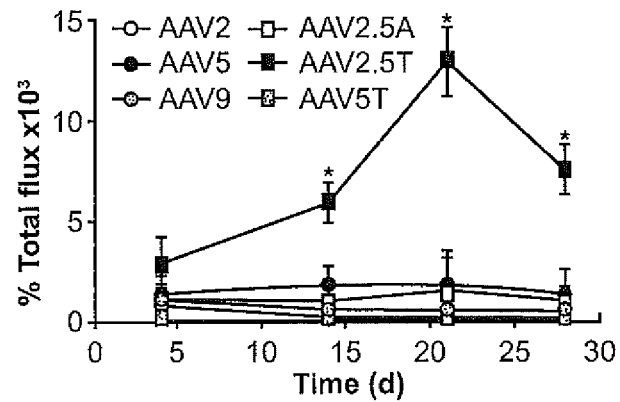
Figure 11C:
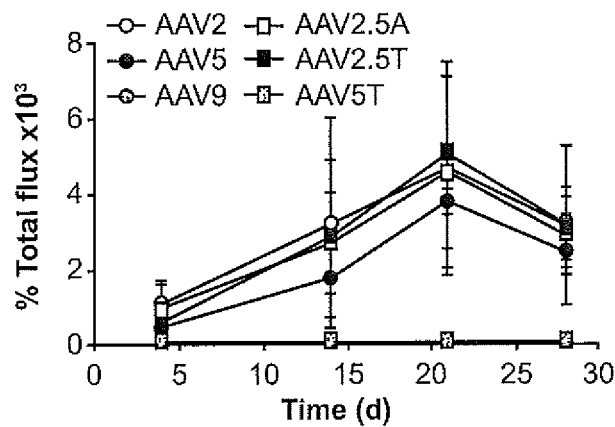

Strikingly, twenty-one days post-transduction, AAV2.5T-Luc outperformed AAV2-Luc (100-fold), AAV5-Luc (10-fold), and AAV9-Luc (20-fold) (FIG. 11b). No difference in basolateral transduction was observed (FIG. 11c), indicating that the advantage of AAV2.5T was specific for the apical surface.

FIGS. 11A-E depict the infectivity and the transduction of AVV vectors for pulmonary gene delivery in well-differentiated human airway epithelia. A) AAV library was applied apically for decreasing times and multiplicity of infection (MOI) over 5 rounds. AAV-luciferase expression after apical B) or basolateral C) transduction was monitored over 28 days and peaked at day 21 post-transduction. E) Cystic fibrosis (CF) epithelia lack cAMP-regulated chloride transport. F) AAV2.5T-CFTR (MOI 50,000) corrected cAMP-regulated chloride current.

Binding and Transduction of Variant AAV

Recombinant AAV2.5T bound to the apical surface significantly better than AAV5 (100-fold, FIG. 12a), and in contrast to AAV5, binding of AAV2.5T did not saturate at doses ranging from 10 to 1000 genome copies/cell (vg/cell). This suggested that the number of viral receptors and possibly binding affinity were increased. AAV2.5T mirrors parental AAV5 sensitivity for sialic acid and does not efficiently transduce sialic acid deficient Lec2 cells whereas transduction is not altered on heparan sulfate mutants pgsA or pgsD.

Furthermore, AAV2.5T binding to the apical surface of human airway epithelia is significantly reduced by pretreatment with neuraminidase (p<0.001) (FIG. 12c). In contrast to airway epithelia, similar transduction was observed between AAV2.5T and AAV5 in several cell lines and primary human astrocytes (FIG. 12d). Hence, transduction studies on other cell types indicate the advantage of AAV2.5T is cell-type specific and that AAV2.5T requires sialic acid for efficient transduction.

Interestingly, when the mutation (AAV5-A581T) and chimera (AAV2.5) were studied independently, neither was better than AAV5 at binding or transduction (FIG. 12). The A581T mutation occurs in a region critical to AAV5 sialic acid binding. Therefore, a mutation in this region may potentially influence the binding affinity for sialic acid, the type of linkages recognized, and/or species specificity. Similar effects have been observed for single mutations in other parvoviruses and influenza. However, the AAV5-A581T virus produced low genomic titers and failed to bind or transduce airway epithelia (FIG. 11b). Likewise, AAV2.5 offered no advantage over AAV5 in airway epithelia, even though aa1-128 from AAV2 may potentially alter intracellular trafficking. In total, our data suggest that the recombination event rescues a structurally deleterious yet functionally advantageous mutation (A581T).

FIGS. 12 A-D depict binding and cell specificity of an exemplary mutant infectious for lung tissue. A) AAV2.5T binding does not saturate at doses between 300 and 1,000 viral genomes per cell (vg/cell). AAV2.5T mirrors parental AAV5 sensitivity for sialic acid and does not efficiently transduce sialic acid deficient Lec2 cells whereas B) transduction is not altered on heparan sulfate mutants pgsA or pgsD. C) AAV2.5T binding to the apical surface of human airway epithelia is significantly reduced by pretreatment with neuraminidase (p<0.001). D) In contrast to airway epithelia, similar transduction was observed between AAV2.5T and AAV5 in several cell lines and primary human astrocytes.

Characterization of CFTR Expressed by AAV Variants

Figure 11D:
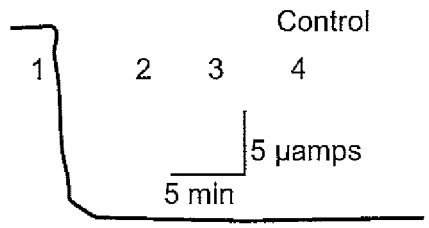
Figure 11E:
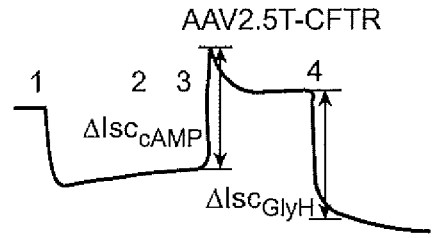

CF epithelia did not transport chloride via CFTR, as shown by the lack of change in current after treatment with IBMX/Forskolin ($\Delta Isc_{cAMP}$ 0±0 $\mu A.cm^{-2}$) or with the CFTR blocker GlyH-101 ($\Delta Isc_{GlyH}$ 0±0 $\mu A.cm^{-2}$) (FIG. 11d). CFTR was undetectable by immunocytochemistry. In stark contrast, AAV2.5T-CFTR restored CFTR chloride current ($\Delta Isc_{cAMP}$ 12±4 $\mu A.cm^{-2}$, $\Delta Isc_{GlyH}$ 18±9 $\mu A.cm^{-2}$) (FIG. 11e), and readily-detectable CFTR protein was properly localized at the apical membrane of the epithelial cells. In addition, immunostaining of normal airway epithelia failed to detect CFTR, suggesting that even lower MOIs may be sufficient for chloride transport correction.

Example 4

AAV Capsid Variants Conferring Increased Infectivity of Human Embryonic Stem Cells AAV virions with variant capsid proteins were generated as described above. Variants that exhibit increased infectivity of human ES cells, compared to the infectivity of wild-type AAV for human ES cells, were selected. The viral library was added to human embryonic stem cell line hSF6, followed by the addition of wild type adenovirus type 5 to induce replication of AAV variants that successfully infected the cells. The cells were then lysed to harvest the virus, and the AAV sequences were recovered by PCR and reinserted into an AAV genome plasmid. The selected AAV library was then repackaged. After three such selection steps, i.e. infection and amplification, the viral capsid encoding sequence was subjected to additional genetic diversification by error prone PCR.

Figure 13:
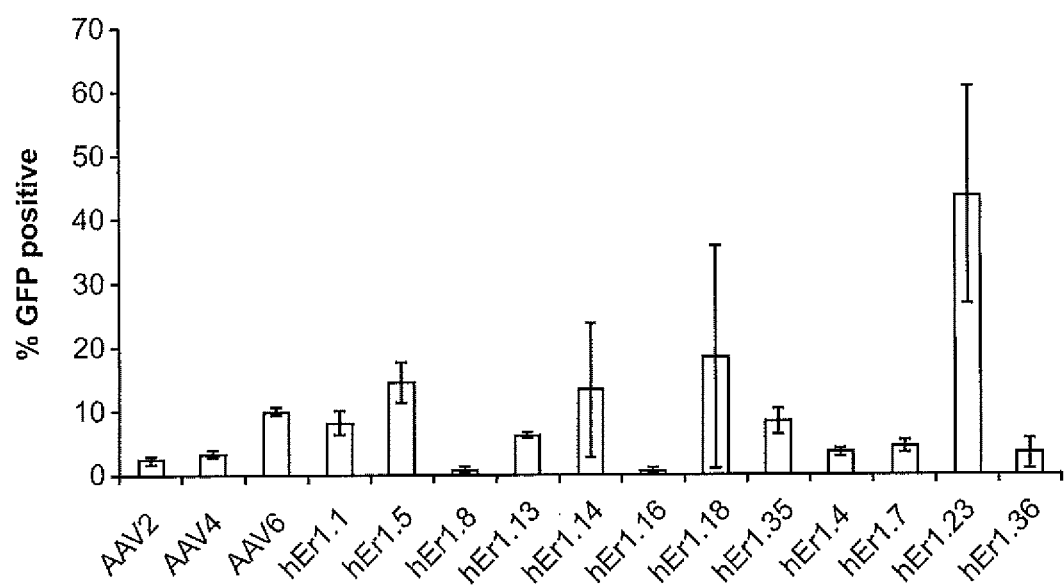
Figure 15:
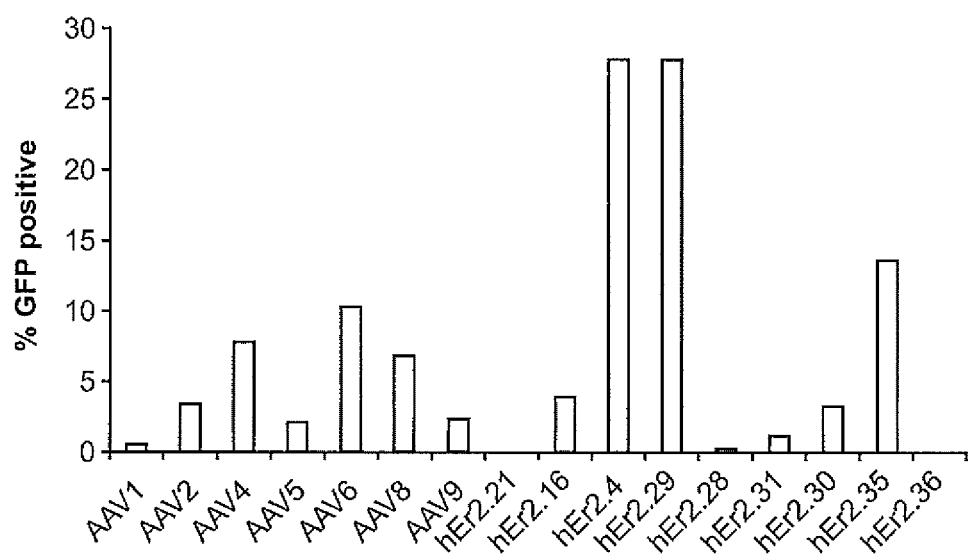
FIG. 15 depicts infectivity of human embryonic stem cells of wild-type AAV and AAV comprising variant capsid protein.

Amino acid sequences of capsid proteins of variants produced after a first and a second round of evolution were determined, where each round of evolution was composed of genetic diversification and three selection steps. Infectivity of human ES (hES) cells of the first-round variants is shown in FIG. 13. Amino acid sequences of capsid proteins of first-round variants are shown in FIGS. 14A-D. Infectivity (expressed as % GFP positive cells) of hES cells of the second-round variants is shown in FIG. 15. Amino acid sequences of capsid proteins of first-round variants are shown in FIGS. 16A-C.

As shown in FIG. 13, a number of AAV variants exhibited infectivity of hES cells that is greater than the infectivity of wild-type AAV (e.g., AAV2, AAV4, AAV6) for these cells. In addition, as shown in FIG. 15, the variants designated hEr2.4 and hEr2.29 exhibited greater infectivity of hES cells (expressed as % GFP positive cells), compared to AAV2. It is noted that the variant designated hEr2.29 and the variant designated hEr1.23 have the same capsid amino acid sequence.

Figure 18:
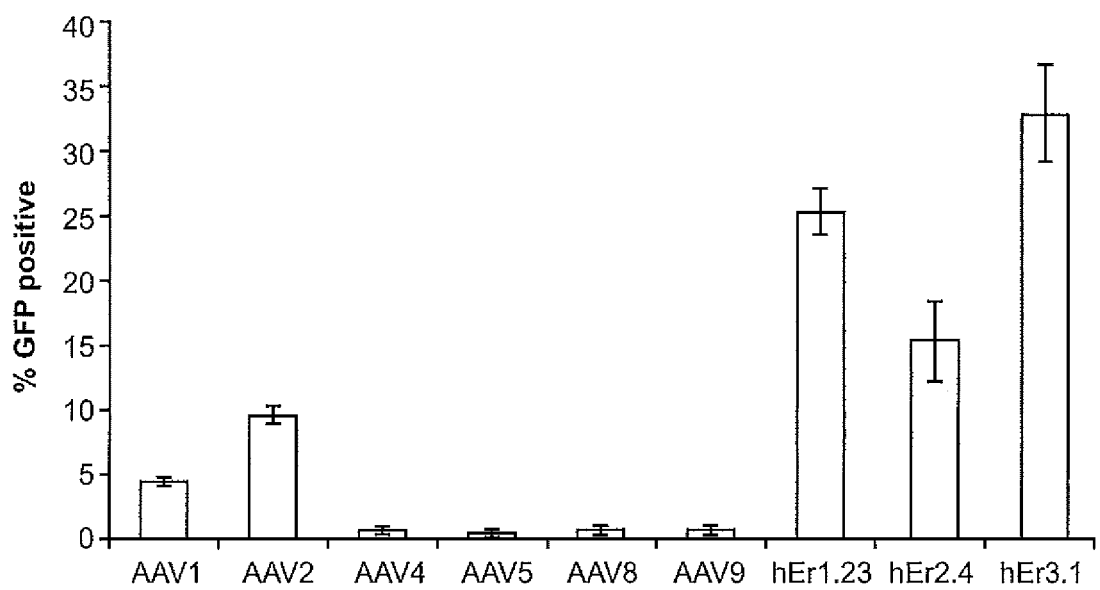
FIG. 18 depicts infectivity of human embryonic stem cells of wild-type AAV and AAV comprising variant capsid protein.

FIGS. 17A and 17B provide an amino acid sequence alignment of the amino acid sequences of hEr2.4, hEr1.23, and hEr3.1 capsids, compared with that of AAV2 capsid. FIG. 18 shows infectivity of hES cells (represented as % GFP-positive) for hEr1.23, hEr2.4, and hEr3.1, compared with that of wild-type AAV1, AAV2, AAV4, AAV5, AAV8, and AAV9. The data are summarized in Table 5, below.

TABLE 5

|  | Avg | Std | 1 | 2 | 3 |
|---|---|---|---|---|---|
| AAV1 | 4.48333 | 0.37072 | 4.84 | 4.1 | 4.51 |
| AAV2 | 9.576667 | 0.697878 | 10.08 | 8.78 | 9.87 |
| AAV4 | 0.64 | 0.105357 | 0.53 | 0.74 | 0.62 |
| AAV5 | 0.353333 | 0.160728 | 0.42 | 0.47 | 0.17 |
| AAV5 | 0/683333 | 0.155349 | 0.51 | 0.81 | 0.73 |
| AAV9 | 0.763333 | 0.126623 | 0.74 | 0.9 | 0.65 |
| hEr1.23 | 25.29667 | 1.815746 | 23.99 | 27.37 | 24.53 |
| hEr2.4 | 15.20333 | 3.082764 | 16.68 | 11.66 | 17.27 |
| hEr3.1 | 32.86 | 3.74992 | 30.71 | 30.68 | 37.19 |

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A recombinant adeno-associated virus (rAAV) virion comprising:
   a) a variant AAV capsid protein, wherein the variant capsid protein comprises an amino acid sequence having at least about 95% amino acid sequence identity to the entire length of the amino acid sequence set forth in SEQ ID NO:5, wherein the variant capsid protein confers increased infectivity of a stem cell compared to the infectivity of the stem cell by an AAV virion comprising a wild-type AAV capsid protein, and wherein the variant capsid protein comprises an R459G amino acid substitution; and
   b) a heterologous nucleic acid comprising a nucleotide sequence encoding a gene product.

2. The rAAV virion of claim 1, wherein the rAAV virion exhibits at least 5-fold increased infectivity of a stem cell compared to the infectivity of the stem cell by an AAV virion comprising the wild-type AAV capsid protein.

3. The rAAV virion of claim 1, wherein the rAAV virion exhibits at least 10-fold increased infectivity of a stem cell compared to the infectivity of the stem cell by an AAV virion comprising the wild-type AAV capsid protein.

4. The rAAV virion of claim 1, wherein the rAAV virion exhibits at least 25-fold increased infectivity of a stem cell compared to the infectivity of the stem cell by an AAV virion comprising the wild-type AAV capsid protein.

5. The rAAV virion of claim 1, wherein the rAAV virion exhibits at least 50-fold increased infectivity of a stem cell compared to the infectivity of the stem cell by an AAV virion comprising the wild-type AAV capsid protein.

6. The rAAV virion of claim 1, wherein the variant capsid protein comprises from one to 15 amino acid sequence substitutions compared to the amino acid sequence of an AAV2 capsid protein set forth in SEQ ID NO:5.

7. The rAAV virion of claim 1, wherein gene product is an interfering RNA.

8. The rAAV virion of claim 1, wherein the gene product is a polypeptide.

9. A method of delivering a gene product to a stem cell in an individual, the method comprising administering to the individual a recombinant adeno-associated virus (rAAV) virion according to claim 1.

10. The method of claim 9, wherein the gene product is a protein.

11. The method of claim 9, wherein the gene product is a short interfering RNA.

12. The method of claim 10, wherein the protein is a growth factor, a morphogen, a cytokine, a receptor, a protein involved in intracellular signal transduction, or a transcription factor.

13. The rAAV virion of claim 1, wherein the variant capsid protein comprises an amino acid sequence having at least about 98% amino acid sequence identity to the amino acid sequence set forth in SEQ ID NO:5.

14. The rAAV virion of claim 1, wherein the variant capsid protein comprises an amino acid sequence having at least about 99% amino acid sequence identity to the amino acid sequence set forth in SEQ ID NO:5.

15. A recombinant adeno-associated virus (rAAV) virion comprising:
   a) a variant AAV capsid protein, wherein the variant capsid protein comprises:
      (i) an amino acid sequence having at least about 95% amino acid sequence identity to the entire length of the amino acid sequence set forth in SEQ ID NO:54, wherein the variant capsid protein comprises V708I and P250S amino acid substitutions relative to SEQ ID NO:5; or
      (ii) an amino acid sequence having at least about 95% amino acid sequence identity to the entire length of the amino acid sequence set forth in SEQ ID NO:59, wherein the variant capsid protein comprises S85G and R459G amino acid substitutions relative to SEQ ID NO:5;
   wherein the variant capsid protein confers increased infectivity of a stem cell compared to the infectivity of the stem cell by an AAV virion comprising a wild-type AAV capsid protein; and
   b) a heterologous nucleic acid comprising a nucleotide sequence encoding a gene product.

16. The rAAV virion of claim 15, wherein the rAAV virion exhibits at least 5-fold increased infectivity of a stem cell compared to the infectivity of the stem cell by an AAV virion comprising the wild-type AAV capsid protein.

17. The rAAV virion of claim 15, wherein the rAAV virion exhibits at least 10-fold increased infectivity of a stem cell compared to the infectivity of the stem cell by an AAV virion comprising the wild-type AAV capsid protein.

18. The rAAV virion of claim 15, wherein the rAAV virion exhibits at least 25-fold increased infectivity of a stem cell compared to the infectivity of the stem cell by an AAV virion comprising the wild-type AAV capsid protein.

19. The rAAV virion of claim 15, wherein the rAAV virion exhibits at least 50-fold increased infectivity of a stem cell compared to the infectivity of the stem cell by an AAV virion comprising the wild-type AAV capsid protein.

20. The rAAV virion of claim 15, wherein the variant capsid protein comprises from 5 to 10 or from 10 to 15 amino acid sequence substitutions compared to the amino acid sequence of an AAV2 capsid protein set forth in SEQ ID NO:5.

21. The rAAV virion of claim 15, wherein gene product is an interfering RNA.

22. The rAAV virion of claim 15, wherein the gene product is a polypeptide.

23. The rAAV virion of claim 15, wherein:
the variant capsid protein of (i) comprises an amino acid sequence having at least about 98% amino acid sequence identity to the amino acid sequence set forth in SEQ ID NO:54; or
the variant capsid protein of (ii) comprises an amino acid sequence having at least about 98% amino acid sequence identity to the amino acid sequence set forth in SEQ ID NO:59.

24. The rAAV virion of claim 15, wherein:
the variant capsid protein of (i) comprises an amino acid sequence having at least about 99% amino acid sequence identity to the amino acid sequence set forth in SEQ ID NO:54; or
the variant capsid protein of (ii) comprises an amino acid sequence having at least about 99% amino acid sequence identity to the amino acid sequence set forth in SEQ ID NO:59.

25. A method of delivering a gene product to a stem cell in an individual, the method comprising administering to the individual a recombinant adeno-associated virus (rAAV) virion according to claim 15.

26. The method of claim 25, wherein the gene product is a protein.

27. The method of claim 25, wherein the gene product is a short interfering RNA.

28. The method of claim 25, wherein the protein is a growth factor, a morphogen, a cytokine, a receptor, a protein involved in intracellular signal transduction, or a transcription factor.

* * * * *

SEQUENCE LISTING

<160> NUMBER OF SEQ ID NOS: 59

<210> SEQ ID NO 1
<211> LENGTH: 2225
<212> TYPE: DNA
<213> ORGANISM: adeno-associated virus

<400> SEQUENCE: 1

```
atggctgccg atggttatct tccagattgg ctcgaggaca ctctctctga aggaataaga      60
cagtggtgga agctcaaacc tggcccacca ccaccaaagc ccgcagagcg gcataaggac     120
gacagcaggg gtcttgtgct tcctgggtac aagtacctcg gacccttcaa cggactcgac     180
aagggagagc cggtcaacga ggcagacgcc gcggccctcg agcacgacaa agcctacgac     240
cggcagctcg acagcggaga caacccgtac ctcaagtaca accacgccga cgcggagttt     300
caggagcgcc ttaaagaaga tacgtctttt ggggggcaacc tcggacgagc agtcttccag     360
gcgaaaaaga gggttcttga accctctggc ctggttgagg aacctgttaa gacggctccg     420
ggaaaaaaga ggccggtaga gcactctcct gtggagccag actcctcctc gggaaccgga     480
aaggcgggcc agcagcctgc aagaaaaaga ttgaattttg gtcagactgg agacgcagac     540
tcagtacctg accccagcc tctcggacag ccaccagcag ccccctctgg tctgggaact     600
aatacgatgg ctacaggcag tggcgcacca atggcagaca taacgagggg cgccgacgga     660
gtgggtaatt cctcgggaaa ttggcattgc gattccacat ggatgggcga cagagtcatc     720
accaccagca cccgaacctg gcctgcc acctacaaca accacctcta caacaaatt     780 tccagccaat caggagcctc gaacgacaat cactactttg gctacagcac cccttggggg     840
tattttgact tcaacagatt ccactgccac gttgactggca aagactcatc     900 aacaacaact ggggattccg acccaagaga ctcaacttca gctctttaa cattcaagtc     960 aaagaggtca cgcagaatga cggtacgacg acgattgcca ataaccttac cagcacggtt    1020
caggtgttta ctgactcgga gtaccagctc ccgtacgtcc tcggctcgcc gcatcaagga    1080
tgcctcccgc gttcccagc agacgtcttc atggtgccac agtatggata cctcaccctg    1140
aacaacggga gtcaggcagt aggacgctct tcatttact gcctggagta ctttccttct    1200
```

-continued

```
cagatgctgc gtaccggaaa caactttacc ttcagctaca cttttgagga cgttcctttc   1260
cacagcagct acgctcacag ccagagtctg gaccgtctca tgaatcctct catcgaccag   1320
tacctgtatt acttgagcag aacaaacact ccaagtggaa ccaccacgca gtcaaggctt   1380
cagttttctc aggccggagc gagtgacatt cgggaccagt ctaggaactg gcttcctgga   1440
ccctgttacc gccagcagcg agtatcaaag acatctgcgg ataacaacaa cagtgaatac   1500
tcgtggactg gagctaccaa gtaccacctc aatggcagag actctctggt gaatccgggc   1560
ccggccatgg caagccacaa ggacgatgaa gaaaagtttt tccctcagag cggggttctc   1620
atctttggga agcaaggctc agagaaaaca aatgtggaca ttgaaaaggt catgattaca   1680
gacgaagagg aaatcaggac aaccaatccc gtggctacgg agcagtatgg ttctgtatct   1740
accaacctcc agagaggcaa cagacaagca gctaccgcag atgtcaacac acaaggcgtt   1800
cttccaggca tggtctggca ggacagagat gtgtaccttc aggggcccat ctgggcaaag   1860
attccacaca cggacggaca ttttcacccc tctcccctca tgggtggatt cggacttaaa   1920
caccctcctc cacagattct catcaagaac accccggtac ctgcgaatcc ttcgaccacc   1980
ttcagtgcgg caaagtttgc ttccttcatc acacagtact ccacgggaca ggtcagcgtg   2040
gagatcgagt gggagctgca aaaggaaaac agcaaacgct ggaatcccga aattcagtac   2100
acttccaact acaacaagtc tgttaatgtg gactttactg tggacactaa tggcgtgtat   2160
tcagagcctc gccccattgg caccagatac ctgactcgta atctgtaatt gcttgcggcc   2220
gcccc                                                              2225
```

<210> SEQ ID NO 2
<211> LENGTH: 2187
<212> TYPE: DNA
<213> ORGANISM: adeno-associated virus-2
<220> FEATURE:
<221> NAME/KEY: misc_feature
<222> LOCATION: (2169)...(2169)
<223> OTHER INFORMATION: n = A, G, C or T
<220> FEATURE:
<221> NAME/KEY: misc_feature
<222> LOCATION: (2170)...(2170)
<223> OTHER INFORMATION: n = A, G, C or T
<220> FEATURE:
<221> NAME/KEY: misc_feature
<222> LOCATION: (2171)...(2171)
<223> OTHER INFORMATION: n = A, G, C or T
<220> FEATURE:
<221> NAME/KEY: misc_feature
<222> LOCATION: 2169, 2170, 2171
<223> OTHER INFORMATION: n = A,T,C or G

<400> SEQUENCE: 2

```
atggctgccg atggttatct tccagattgg ctcgaggaca ctctctctga aggaataaga    60
cagtggtgga agctcaaacc tggcccacca ccaccaaagc ccgcagagcg gcataaggac   120
gacagcaggg gtcttgtgct tcctgggtac aagtacctcg gacccttcaa cggactcgac   180
aagggagagc cggtcaacga ggcagacgcc gcggccctcg agcacgacaa agcctacgac   240
cggcagctcg acagcggaga caacccgtac ctcaagtaca accacgccga cgcggagttt   300
caggagcgcc ttaaagaaga tacgtctttt gggggcaacc tcggacgagc agtcttccag   360
gcgaaaaaga gggttcttga acctctgggc ctggttgagg aacctgttaa gacggctccg   420
ggaaaaaaga ggccggtaga gcactctcct gtggagccag actcctcctc gggaaccgga   480
aaggcgggcc agcagcctgc aagaaaaaga ttgaattttg gtcagactgg agacgcagac   540
tcagtacctg acccccagcc tctcggacag ccaccagcag cccctctctg gctgggaact   600
```

```
aatacgatgg ctacaggcag tggcgcgcca atggcagaca ataacgaggg cgccgacgga      660
gtgggtaatt cctcgggaaa ttggcattgc gattccacat ggatgggcga cagagtcatc      720
accaccagca cccgaacctg ggccctgccc acctacaaca accacctcta caaacaaatt      780
tccagccaat caggagcctc gaacgacaat cactactttg ctacagcac ccttggggg       840 tattttgact tcaacagatt ccactgccac ttttcaccac gtgactggca aagactcatc      900
aacaacaact ggggattccg acccaagaga ctcaacttca agctctttaa cattcaagtc      960
aaagaggtca cgcagaatga cggtacgacg acgattgcca ataaccttac cagcacggtt     1020
caggtgttta ctgactcgga gtaccagctc ccgtacgtcc tcggctcggc gcatcaagga     1080
tgcctcccgc cgttcccagc agacgtcttc atggtgccac agtatggata cctcaccctg     1140
aacaacggga gtcaggcagt aggacgctct tcatttact gcctggagta ctttccttct      1200
cagatgctgc gtaccggaaa caactttacc ttcagctaca cttttgagga ccttccttc     1260 cacagcagct acgctcacag ccagagtctg gaccgtctca tgaatcctct catcgaccag     1320
tacctgtatt acttgagcag aacaaacact ccaagtggaa ccaccacgca gtcaaggctt     1380
cagttttctc aggctggagc gagtgacatt cgggaccagt ctaggaactg gcttcctgga     1440
ccctgttacc gccagcagag agtatcaaag acatctgcgg ataacaacaa cagtgaatac     1500
tcgtggactg gagctaccaa gtaccacctc aatggcagag actctctggt gaatccgggc     1560
ccggccatgg caagccacaa ggacgatgaa gaaaagtttt tccctcagag cggggttctc     1620
atctttggga agcaaggctc agagaaaaca aatgtggaca ttgaaaaggt catgattaca     1680
gacgaagagg aaatcaggac aaccaatccc gtggctacgg agcagtatgg ttctgtatct     1740
accaacctcc agagaggcaa cagacaagca gctaccgcag atgtcaacac acaaggcgtt     1800
cttccaggca tggtctggca ggacagagat gtgtaccttc aggggcccat ctgggcaaag     1860
attccacaca cggacggaca ttttcacccc tctccctca tgggtggatt cggacttaaa     1920
caccctcctc cacagattct catcaagaac accccggtac ctgcgaatcc ttcgaccacc     1980
ttcagtgcgg caaagtttgc ttccttcatc acacagtact ccacgggaca ggtcagcgtg     2040
gagatcgagt gggagctgca gaaggaaaac agcaaacgct ggaatccga aattcagtac     2100 acttccaact acaacaagtc tgttaatgtg gactttagga tggacgctaa tggcgtgtat     2160
tcagagccnn nccccattgg caccagt                                         2187

<210> SEQ ID NO 3
<211> LENGTH: 2187
<212> TYPE: DNA
<213> ORGANISM: adeno-associated virus-2
<220> FEATURE:
<221> NAME/KEY: misc_feature
<222> LOCATION: (2139)...(2139)
<223> OTHER INFORMATION: n = A, G, C, or T
<220> FEATURE:
<221> NAME/KEY: misc_feature
<222> LOCATION: (2169)...(2169)
<223> OTHER INFORMATION: n = A, G, C, or T
<220> FEATURE:
<221> NAME/KEY: misc_feature
<222> LOCATION: (2170)...(2170)
<223> OTHER INFORMATION: n = A, G, C, or T
<220> FEATURE:
<221> NAME/KEY: misc_feature
<222> LOCATION: 2139, 2169, 2170
<223> OTHER INFORMATION: n = A,T,C or G

<400> SEQUENCE: 3
```

-continued

| | |
|---|---|
| atggctgccg atggttatct tccagattgg ctcgaggaca ctctctctga aggaataaga | 60 |
| cagtggtgga agctcaaacc tggcccacca ccaccaaagc ccgcagagcg gcataaggac | 120 |
| gacagcaggg gtcttgtgct tcctgggtac aagtacctcg gacccttcaa cggactcgac | 180 |
| aagggagagc cggtcaacga ggcagacgcc gcggccctcg agcacgacaa agcctacgac | 240 |
| cggcagctcg acagcggaga caacccgtac ctcaagtaca accacgccga cgcggagttt | 300 |
| caggagcgcc ttaaagaaga tacgtctttt gggggcaacc tcggacgagc agtcttccag | 360 |
| gcgaaaaaga gggttcttga acctctgggc ctggttgagg aacctgttaa gacggctccg | 420 |
| ggaaaaaaga ggccggtaga gcactctcct gtggagccag actcctcctc gggaaccgga | 480 |
| aaggcgggcc agcagcctgc aagaaaaaga ttgaattttg gtcagactgg agacgcagac | 540 |
| tcagtacctg acccccagcc tctcggacag ccaccagcag cccctctgg tctgggaact | 600 |
| aatacgatgg ctacaggcag tggcgcgcca atggcagaca taacgagggg cgccgacgga | 660 |
| gtgggtaatt cctcgggaaa ttggcattgc gattccacat ggatgggcga cagagtcatc | 720 |
| accaccagca cccgaacctg ggcccttgcc acctacaaca accacctcta caaacaaatt | 780 |
| tccagccaat caggagcctc gaacgacaat cactactttg ctacagcac cccttggggg | 840 |
| tattttgact tcaacagatt ccactgccac ttttcaccac gtgactggca agactcatc | 900 |
| aacaacaact ggggattccg acccaagaga ctcaacttca gctctttaa cattcaagtc | 960 |
| aaagaggtca cgcagaatga cggtacgacg acgattgcca ataaccttac cagcacggtt | 1020 |
| caggtgttta ctgactcgga gtaccagctc ccgtacgtcc tcggctcggc gcatcaagga | 1080 |
| tgcctcccgc cgttcccagc agacgtcttc atggtgccac agtatggata cctcaccctg | 1140 |
| aacaacggga gtcaggcagt aggacgctct tcattttact gcctggagta ctttccttct | 1200 |
| cagatgctgc gtaccggaaa caactttacc ttcagctaca cttttgagga cgttcctttc | 1260 |
| cacagcagct acgctcacag ccagagtctg gaccgtctca tgaatcctct catcgaccag | 1320 |
| tacctgtatt acttgagcag aacaaacact ccaagtggaa ccaccacgca gtcaaggctt | 1380 |
| cagttttctc aggctggagc gagtgacatt cgggaccagt ctaggaactg gcttcctgga | 1440 |
| ccctgttacc gccagcagag agtatcaaag acatctgcgg ataacaacaa cagtgaatac | 1500 |
| tcgtggactg gagctaccaa gtaccacctc aatggcagag actctctggt gaatccgggc | 1560 |
| ccggccatgg caagccacaa ggacgatgaa gaaaagtttt tccctcagag cggggttctc | 1620 |
| atctttggga agcaaggctc agagaaaaca aatgtggaca ttgaaaaggt catgattaca | 1680 |
| gacgaagagg aaatcaggac aaccaatccc gtggctacgg agcagtatgg ttctgtatct | 1740 |
| accaacctcc agagaggcaa cagacaagca gctaccgcag atgtcaacac acaaggcgtt | 1800 |
| cttccaggca tggtctggca ggacagagat gtgtaccttc agggccccat ctgggcaaag | 1860 |
| attccacaca cggacggaca ttttcacccc tctccctca tgggtggatt cggacttaaa | 1920 |
| caccctcctc acagattct catcaagaac accccggtac ctgcgaatcc ttcgaccacc | 1980 |
| ttcagtgcgg caaagtttgc ttccttcatc acacagtact ccacgggaca ggtcagcgtg | 2040 |
| gagatcgagt gggagctgca gaaggaaaac agcaaacgct ggaatcccga aattcagtac | 2100 |
| acttccaact acaacaagtc tgttaatgtg gactttacng tggacgctaa tggcgtgtat | 2160 |
| tcagagccnn gccccattgg caccagt | 2187 |

<210> SEQ ID NO 4
<211> LENGTH: 2201
<212> TYPE: DNA
<213> ORGANISM: adeno-associated virus-2

<400> SEQUENCE: 4

```
atggctgccg atggttatct tccagattgg ctcgaggaca ctctctctga aggaataaga      60
cagtggtgga agctcaaacc tggcccacca ccaccaaagc ccgcagagcg cataaggac      120
gacagcaggg gtcttgtgct tcctgggtac aagtacctcg dacccttcaa cggactcgac     180
aagggagagc cggtcaacga ggcagacgcc gcggccctcg agcacgacaa agcctacgac     240
cggcagctcg acagcggaga caacccgtac ctcaagtaca accacgccga cgcggagttt     300
caggagcgcc ttaaagaaga tacgtctttt gggggcaacc tcggacgagc agtcttccag     360
gcgaaaaaga gggttcttga acctctgggc ctggttgagg aacctgttaa dacggctccg     420
ggaaaaaaga ggccggtaga gcactctcct gtggagccag actcctcctc gggaaccgga     480
aaggcgggcc agcagcctgc aagaaaaaga ttgaattttg gtcagactgg agacgcagac     540
tcagtacctg accccagcc tctcggacag ccaccagcag ccccctctgg tctgggaact      600
aatacgatgg ctacaggcag tggcgcacca atggcagaca taacgagggg cgccgacgga     660
gtgggtaatt cctcgggaaa ttggcattgc gattccacat ggatgggcga cagagtcatc     720
accaccagca cccgaacctg ggccctgccc acctacaaca accacctcta caaacaaatt     780
tccagccaat caggagcctc gaacgacaat cactactttg gctacagcac cccttggggg     840
tattttgact tcaacagatt ccactgccac ttttcaccac gtgactggca aagactcatc     900
aacaacaact ggggattccg acccaagaga ctcaacttca gctctttaa cattcaagtc      960
aaagaggtca cgcagaatga cggtacgacg acgattgcca ataaccttac cagcacggtt    1020
caggtgttta ctgactcgga gtaccagctc ccgtacgtcc tcggctcggc gcatcaagga    1080
tgcctcccgc cgttcccagc agacgtcttc atggtgccac agtatggata cctcacctg     1140
aacaacggga gtcaggcagt aggacgctct tcattttact gcctggagta ctttcctct     1200
cagatgctgc gtaccggaaa caactttacc ttcagctaca cttttgagga cgttcctttc    1260
cacagcagct acgctcacag ccagagtctg gaccgtctca tgaatcctct catcgaccag    1320
tacctgtatt acttgagcag aacaaacact ccaagtggaa ccaccacgca gtcaaggctt    1380
cagtttctc aggccggagc gagtgacatt cgggaccagt ctaggaactg gcttcctgga     1440
ccctgttacc gccagcagcg agtatcaaag acatctgcgg ataacaacaa cagtgaatac    1500
tcgtggactg gagctaccaa gtaccacctc aatggcagag actctctggt gaatccgggc    1560
ccggccatgg caagccacaa ggacgatgaa gaaagttttt ttcctcagag cggggttctc    1620
atctttggga agcaaggctc agagaaaaca aatgtggaca ttgaaaggt catgattaca     1680
gacgaagagg aaatcaggac aaccaatccc gtggctacgg agcagtatgg ttctgtatct    1740
accaacctcc agagaggcaa cagacaagca gctaccgcag atgtcaacac acaaggcgtt    1800
cttccaggca tggtctggca ggacagagat gtgtaccttc aggggcccat ctgggcaaag    1860
attccacaca cggacggaca ttttcacccc tctcccctca tgggtggatt cggacttaaa    1920
caccctcctc cacagattct catcaagaac accccggtac ctgcgaatcc ttcgaccacc    1980
ttcagtgcgg caaagtttgc ttccttcatc acacagtact ccacgggaca ggtcagcgtg    2040
gagatcgagt gggagctgca gaaggaaaac agcaaacgct ggaatcccga aattcagtac    2100
acttccaact acaacaagtc tgttaatgtg gactttactg tggacactaa tggcgtgtat    2160
tcagagcctc gccccattgg caccagatac ctgactcgta a                        2201
```

<210> SEQ ID NO 5

```
<211> LENGTH: 733
<212> TYPE: PRT
<213> ORGANISM: adeno-associated virus-2

<400> SEQUENCE: 5

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
    130                 135                 140

Pro Val Glu His Ser Pro Val Glu Pro Asp Ser Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
    290                 295                 300

Gly Phe Arg Pro Lys Arg Leu Asn Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
        355                 360                 365

Val Phe Met Val Pro Gln Tyr Gly Tyr Leu Thr Leu Asn Asn Gly Ser
    370                 375                 380

Gln Ala Val Gly Arg Ser Ser Phe Tyr Cys Leu Glu Tyr Phe Pro Ser
```

```
385                 390                 395                 400
Gln Met Leu Arg Thr Gly Asn Asn Phe Thr Phe Ser Tyr Thr Phe Glu
                405                 410                 415
Asp Val Pro Phe His Ser Ser Tyr Ala His Ser Gln Ser Leu Asp Arg
                420                 425                 430
Leu Met Asn Pro Leu Ile Asp Gln Tyr Leu Tyr Tyr Leu Ser Arg Thr
                435                 440                 445
Asn Thr Pro Ser Gly Thr Thr Thr Gln Ser Arg Leu Gln Phe Ser Gln
450                 455                 460
Ala Gly Ala Ser Asp Ile Arg Asp Gln Ser Arg Asn Trp Leu Pro Gly
465                 470                 475                 480
Pro Cys Tyr Arg Gln Gln Arg Val Ser Lys Thr Ser Ala Asp Asn Asn
                485                 490                 495
Asn Ser Glu Tyr Ser Trp Thr Gly Ala Thr Lys Tyr His Leu Asn Gly
                500                 505                 510
Arg Asp Ser Leu Val Asn Pro Gly Pro Ala Met Ala Ser His Lys Asp
                515                 520                 525
Asp Glu Glu Lys Phe Phe Pro Gln Ser Gly Val Leu Ile Phe Gly Lys
                530                 535                 540
Gln Gly Ser Glu Lys Thr Asn Val Asp Ile Glu Lys Val Met Ile Thr
545                 550                 555                 560
Asp Glu Glu Glu Ile Arg Thr Thr Asn Pro Val Ala Thr Glu Gln Tyr
                565                 570                 575
Gly Ser Val Ser Thr Asn Leu Gln Arg Gly Asn Arg Gln Ala Ala Thr
                580                 585                 590
Ala Asp Val Asn Thr Gln Gly Val Leu Pro Gly Met Val Trp Gln Asp
                595                 600                 605
Arg Asp Val Tyr Leu Gln Gly Pro Ile Trp Ala Lys Ile Pro His Thr
                610                 615                 620
Asp Gly His Phe His Pro Ser Pro Leu Met Gly Gly Phe Gly Leu Lys
625                 630                 635                 640
His Pro Pro Pro Gln Ile Leu Ile Lys Asn Thr Pro Val Pro Ala Asn
                645                 650                 655
Pro Ser Thr Thr Phe Ser Ala Ala Lys Phe Ala Ser Phe Ile Thr Gln
                660                 665                 670
Tyr Ser Thr Gly Gln Val Ser Val Glu Ile Glu Trp Glu Leu Gln Lys
                675                 680                 685
Glu Asn Ser Lys Arg Trp Asn Pro Glu Ile Gln Tyr Thr Ser Asn Tyr
                690                 695                 700
Asn Lys Ser Val Asn Val Asp Phe Thr Val Asp Thr Asn Gly Val Tyr
705                 710                 715                 720
Ser Glu Pro Arg Pro Ile Gly Thr Arg Tyr Leu Thr Arg
                725                 730

<210> SEQ ID NO 6
<211> LENGTH: 2201
<212> TYPE: DNA
<213> ORGANISM: adeno-associated virus-2

<400> SEQUENCE: 6
atggctgccg atggttatct tccagattgg ctcgaggaca ctctctctga aggaataaga      60
cagtggtgga agctcaaacc tggcccacca ccaccaaagc ccgcagagcg gcataaggac     120
gacagcaggg gtcttgtgct tcctgggtac aagtacctcg gacccttcaa cggactcgac     180
```

```
aagggagagc cggtcaacga ggcagacgcc gcggccctcg agcacgacaa agcctacgac      240
cggcagctcg acagcggaga caacccgtac ctcaagtaca accacgccga cgcggagttt      300
caggagcgcc ttaaagaaga tacgtctttt gggggcaacc tcggacgagc agtcttccag      360
gcgaaaaaga gggttcttga acctctgggc ctggttgagg aacctgttaa dacggctccg      420
ggaaaaaaga ggccggtaga gcactctcct gtggagccag actcctcctc gggaaccgga      480
aaggcgggcc agcagcctgc aagaaaaaga ttgaattttg gtcagactgg agacgcagac      540
tcagtacctg acccccagcc tctcggacag ccaccagcag cccctctgg tctgggaact       600 aatacgatgg ctacaggcag tggcgcgcca atggcagaca taacgagggg cgccgacgga      660
gtgggtaatt cctcgggaaa ttggcattgc gattccacat ggatgggcga cagagtcatc      720
accaccagca cccgaacctg ggccctgccc acctacaaca accacctcta caaacaaatt      780
tccagccaat caggagcctc gaacgacaat cactactttg gctacagcac cccttggggg      840
tattttgact caacagatt ccactgccac ttttcaccac gtgactggca aagactcatc       900
aacaacaact ggggattccg acccaagaga ctcaacttca gctctttaa cattcaagtc       960 aaagaggtca cgcagaatga cggtacgacg acgattgcca ataaccttac cagcacggtt     1020
caggtgttta ctgactcgga gtaccagctc ccgtacgtcc tcggctcggc gcatcaagga     1080
tgcctcccgc cgttcccagc agacgtcttc atggtgccac agtatggata cctcaccctg     1140
aacaacggga gtcaggcagt aggacgctct tcatttact gcctggagta ctttccttct      1200
cagatgctgc gtaccggaaa caactttacc ttcagctaca cttttgagga cgttcctttc     1260
cacagcagct acgctcacag ccagagtctg gaccgtctca tgaatcctct catcgaccag     1320
tacctgtatt acttgagcag aacaaacact ccaagtggaa ccaccacgca gtcaaggctt     1380
cagttttctc aggctggagc gagtgacatt cgggaccagt ctaggaactg gcttcctgga     1440
ccctgttacc gccagcagag agtatcaaag acatctgcgg ataacaacaa cagtgaatac     1500
tcgtggactg gagctaccaa gtaccacctc aatggcagag actctctggt gaatccgggc     1560
ccggccatgg caagccacaa ggacgatgaa gaaaagtttt tccctcagag cggggttctc     1620
atctttggga agcaaggctc agagaaaaca aatgtggaca ttgaaaaggt catgattaca     1680
gacgaagagg aaatcaggac aaccaatccc gtggctacgg agcagtatgg ttctgtatct     1740
accaacctcc agagaggcaa cagacaagca gctaccgcag atgtcaacac acaaggcgtt     1800
cttccaggca tggtctggca ggacagagat gtgtaccttc aggggcccat ctgggcaaag     1860
attccacaca cggacggaca ttttcacccc tctcccctca tgggtggatt cggacttaaa     1920
caccctcctc cacagattct catcaagaac accccggtac ctgcgaatcc ttcgaccacc     1980
ttcagtgcgg caaagtttgc ttccttcatc acacagtact ccacgggaca ggtcagcgtg     2040
gagatcgagt gggagctgca gaaggaaaac agcaaacgct ggaatcccga aattcagtac     2100
acttccaact acaacaagtc tgttaatgtg gactttaggg tggacgctaa tggcgtgtat     2160
tcagagcctc gccccattgg caccagatac ctgactcgta a                        2201
```

<210> SEQ ID NO 7
<211> LENGTH: 735
<212> TYPE: PRT
<213> ORGANISM: adeno-associated virus-2

<400> SEQUENCE: 7

Met Ala Ala Asp Gly Tyr Leu Pro Asp Trp Leu Glu Asp Thr Leu Ser
1               5                   10                  15

```
Glu Gly Ile Arg Gln Trp Trp Lys Leu Lys Pro Gly Pro Pro Pro
         20                  25                  30
Lys Pro Ala Glu Arg His Lys Asp Asp Ser Arg Gly Leu Val Leu Pro
         35                  40                  45
Gly Tyr Lys Tyr Leu Gly Pro Phe Asn Gly Leu Asp Lys Gly Glu Pro
         50                  55                  60
Val Asn Glu Ala Asp Ala Ala Ala Leu Glu His Asp Lys Ala Tyr Asp
65                  70                  75                  80
Arg Gln Leu Asp Ser Gly Asp Asn Pro Tyr Leu Lys Tyr Asn His Ala
                 85                  90                  95
Asp Ala Glu Phe Gln Glu Arg Leu Lys Glu Asp Thr Ser Phe Gly Gly
             100                 105                 110
Asn Leu Gly Arg Ala Val Phe Gln Ala Lys Lys Arg Val Leu Glu Pro
         115                 120                 125
Leu Gly Leu Val Glu Glu Pro Val Lys Thr Ala Pro Gly Lys Lys Arg
         130                 135                 140
Pro Val Glu His Ser Pro Val Glu Pro Asp Ser Ser Gly Thr Gly
145                 150                 155                 160
Lys Ala Gly Gln Gln Pro Ala Arg Lys Arg Leu Asn Phe Gly Gln Thr
                 165                 170                 175
Gly Asp Ala Asp Ser Val Pro Asp Pro Gln Pro Leu Gly Gln Pro Pro
             180                 185                 190
Ala Ala Pro Ser Gly Leu Gly Thr Asn Thr Met Ala Thr Gly Ser Gly
         195                 200                 205
Ala Pro Met Ala Asp Asn Asn Glu Gly Ala Asp Gly Val Gly Asn Ser
         210                 215                 220
Ser Gly Asn Trp His Cys Asp Ser Thr Trp Met Gly Asp Arg Val Ile
225                 230                 235                 240
Thr Thr Ser Thr Arg Thr Trp Ala Leu Pro Thr Tyr Asn Asn His Leu
                 245                 250                 255
Tyr Lys Gln Ile Ser Ser Gln Ser Gly Ala Ser Asn Asp Asn His Tyr
             260                 265                 270
Phe Gly Tyr Ser Thr Pro Trp Gly Tyr Phe Asp Phe Asn Arg Phe His
         275                 280                 285
Cys His Phe Ser Pro Arg Asp Trp Gln Arg Leu Ile Asn Asn Asn Trp
         290                 295                 300
Gly Phe Arg Pro Lys Arg Leu Asn Phe Lys Leu Phe Asn Ile Gln Val
305                 310                 315                 320
Lys Glu Val Thr Gln Asn Asp Gly Thr Thr Thr Ile Ala Asn Asn Leu
                 325                 330                 335
Thr Ser Thr Val Gln Val Phe Thr Asp Ser Glu Tyr Gln Leu Pro Tyr
             340                 345                 350
Val Leu Gly Ser Ala His Gln Gly Cys Leu Pro Pro Phe Pro Ala Asp
         355                 360                 365
Val Phe Met Val Pro Gln Tyr Gly Tyr Leu Thr Leu Asn Asn Gly Ser
         370                 375                 380
Gln Ala Val Gly Arg Ser Ser Phe Tyr Cys Leu Glu Tyr Phe Pro Ser
385                 390                 395                 400
Gln Met Leu Arg Thr Gly Asn Asn Phe Thr Phe Ser Tyr Thr Phe Glu
                 405                 410                 415
Asp Val Pro Phe His Ser Ser Tyr Ala His Ser Gln Ser Leu Asp Arg
             420                 425                 430
Leu Met Asn Pro Leu Ile Asp Gln Tyr Leu Tyr Tyr Leu Ser Arg Thr
```

```
                435                 440                 445
Asn Thr Pro Ser Gly Thr Thr Thr Gln Ser Arg Leu Gln Phe Ser Gln
    450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
                485                 490                 495

Asn Ser Glu Tyr Ser Trp Thr Gly Ala Thr Lys Tyr His Leu Asn Gly
            500                 505                 510

Arg Asp Ser Leu Val Asn Pro Gly Pro Ala Met Ala Ser His Lys Asp
        515                 520                 525

Asp Glu Glu Lys Phe Phe Pro Gln Ser Gly Val Leu Ile Phe Gly Lys
    530                 535                 540

Gln Gly Ser Glu Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
                565                 570                 575

Gly Ser Val Ser Thr Asn Leu Gln Arg Gly Asn Arg Gln Ala Ala Thr
            580                 585                 590

Ala Asp Val Asn Thr Gln Gly Val Leu Pro Gly Met Val Trp Gln Asp
        595                 600                 605

Arg Asp Val Tyr Leu Gln Gly Pro Ile Trp Ala Lys Ile Pro His Thr
    610                 615                 620

Asp Gly His Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asn
                645                 650                 655

Pro Ser Thr Thr Phe Ser Ala Ala Lys Phe Ala Ser Phe Ile Thr Gln
            660                 665                 670

Tyr Ser Thr Gly Gln Val Ser Val Glu Ile Glu Trp Glu Leu Gln Lys
        675                 680                 685

Glu Asn Ser Lys Arg Trp Asn Pro Glu Ile Gln Tyr Thr Ser Asn Tyr
    690                 695                 700

Asn Lys Ser Val Asn Val Asp Phe Arg Val Asp Ala Asn Gly Val Tyr
705                 710                 715                 720

Ser Glu Pro Arg Pro Ile Gly Thr Arg Tyr Leu Thr Arg Asn Leu
                725                 730                 735

<210> SEQ ID NO 8
<211> LENGTH: 2201
<212> TYPE: DNA
<213> ORGANISM: adeno-associated virus-2

<400> SEQUENCE: 8
atggctgccg atggttatct tccagattgg ctcgaggaca ctctctctga aggaataaga     60
cagtggtgga agctcaaacc tggcccacca ccaccaaagc ccgcagagcg gcataaggac    120
gacagcaggg gtcttgtgct tcctgggtac aagtacctcg gacccttcaa cggactcgac    180
aagggagagc cggtcaacga ggcagacgcc gcggccctcg agcacgacaa agcctacgac    240
cggcagctcg acagcggaga caacccgtac ctcaagtaca accacgccga cgcggagttt    300
caggagcgcc ttaaagaaga tacgtctttt gggggcaacc tcggacgagc agtcttccag    360
gcgaaaaaga gggttcttga acctctgggc ctggttgagg aacctgttaa gacggctccg    420
ggaaaaaaga ggccggtaga gcactctcct gtggagccag actcctcctc gggaaccgga    480
```

-continued

```
aaggcgggcc agcagcctgc aagaaaaaga ttgaattttg gtcagactgg agacgcagac      540
tcagtacctg acccccagcc tctcggacag ccaccagcag cccctctgg tctgggaact       600 aatacgatgg ctacaggcag tggcgcgcca atggcagaca taacgaggg cgccgacgga       660 gtgggtaatt cctcgggaaa ttggcattgc gattccacat ggatgggcga cagagtcatc     720
accaccagca cccgaacctg ggccctgccc acctacaaca accacctcta caaacaaatt     780
tccagccaat caggagcctc gaacgacaat cactactttg ctacagcac ccttggggg       840 tattttgact tcaacagatt ccactgccac ttttcaccac gtgactggca aagactcatc    900
aacaacaact ggggattccg acccaagaga ctcaacttca agctctttaa cattcaagtc    960
aaagaggtca cgcagaatga cggtacgacg acgattgcca ataaccttac cagcacggtt   1020
caggtgttta ctgactcgga gtaccagctc ccgtacgtcc tcggctcggc gcatcaagga   1080
tgcctcccgc cgttcccagc agacgtcttc atggtgccac agtatggata cctcaccctg   1140
aacaacggga gtcaggcagt aggacgctct tcatttttact gcctggagta ctttccttct   1200
cagatgctgc gtaccggaaa caactttacc ttcagctaca cttttgagga ccttcctttc   1260
cacagcagct acgctcacag ccagagtctg gaccgtctca tgaatcctct catcgaccag   1320
tacctgtatt acttgagcag aacaaacact ccaagtggaa ccaccacgca gtcaaggctt   1380
cagttttctc aggctggagc gagtgacatt cgggaccagt ctaggaactg gcttcctgga   1440
ccctgttacc gccagcagag agtatcaaag acatctgcgg ataacaacaa cagtgaatac   1500
tcgtggactg gagctaccaa gtaccacctc aatggcagag actctctggt gaatccgggc   1560
ccggccatgg caagccacaa ggacgatgaa gaaaagtttt tccctcagag cggggttctc   1620
atctttggga agcaaggctc agagaaaaca aatgtggaca ttgaaaaggt catgattaca   1680
gacgaagagg aaatcaggac aaccaatccc gtggctacgg agcagtatgg ttctgtatct   1740
accaacctcc agagaggcaa cagacaagca gctaccgcag atgtcaacac acaaggcgtt   1800
cttccaggca tggtctggca ggacagagat gtgtaccttc aggggcccat ctgggcaaag   1860
attccacaca cggacggaca ttttcacccc tctcccctca tgggtggatt cggacttaaa   1920
caccctcctc cacagattct catcaagaac accccggtac tgcgaatcc ttcgaccacc   1980 ttcagtgcgg caaagtttgc ttccttcatc acacagtact ccacgggaca ggtcagcgtg   2040
gagatcgagt gggagctgca aaaggaaaac agcaaacgct ggaatcccga aattcagtac   2100
acttccaact acaacaagtc tgttaatgtg gactttagga tggacgctaa tgccgtgtat   2160
tcagagcctc gccccattgg caccagatac ctgactcgta a                        2201
```

<210> SEQ ID NO 9
<211> LENGTH: 735
<212> TYPE: PRT
<213> ORGANISM: adeno-associated virus-2

<400> SEQUENCE: 9

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

```
Val Asn Glu Ala Asp Ala Ala Leu Glu His Asp Lys Ala Tyr Asp
 65                  70                  75                  80

Arg Gln Leu Asp Ser Gly Asp Asn Pro Tyr Leu Lys Tyr Asn His Ala
                 85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
130                 135                 140

Pro Val Glu His Ser Pro Val Glu Pro Asp Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
        195                 200                 205

Ala Pro Met Ala Asp Asn Asn Glu Gly Ala Asp Gly Val Gly Asn Ser
210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
290                 295                 300

Gly Phe Arg Pro Lys Arg Leu Asn Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
        355                 360                 365

Val Phe Met Val Pro Gln Tyr Gly Tyr Leu Thr Leu Asn Asn Gly Ser
370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
                405                 410                 415

Asp Leu Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Ser Arg Thr
        435                 440                 445

Asn Thr Pro Ser Gly Thr Thr Thr Gln Ser Arg Leu Gln Phe Ser Gln
450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
```

-continued

```
                485                 490                 495
Asn Ser Glu Tyr Ser Trp Thr Gly Ala Thr Lys Tyr His Leu Asn Gly
            500                 505                 510

Arg Asp Ser Leu Val Asn Pro Gly Pro Ala Met Ala Ser His Lys Asp
            515                 520                 525

Asp Glu Glu Lys Phe Phe Pro Gln Ser Gly Val Leu Ile Phe Gly Lys
        530                 535                 540

Gln Gly Ser Glu Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
                565                 570                 575

Gly Ser Val Ser Thr Asn Leu Gln Arg Gly Asn Arg Gln Ala Ala Thr
            580                 585                 590

Ala Asp Val Asn Thr Gln Gly Val Leu Pro Gly Met Val Trp Gln Asp
        595                 600                 605

Arg Asp Val Tyr Leu Gln Gly Pro Ile Trp Ala Lys Ile Pro His Thr
    610                 615                 620

Asp Gly His Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asn
                645                 650                 655

Pro Ser Thr Thr Phe Ser Ala Ala Lys Phe Ala Ser Phe Ile Thr Gln
            660                 665                 670

Tyr Ser Thr Gly Gln Val Ser Val Glu Ile Glu Trp Glu Leu Gln Lys
        675                 680                 685

Glu Asn Ser Lys Arg Trp Asn Pro Glu Ile Gln Tyr Thr Ser Asn Tyr
    690                 695                 700

Asn Lys Ser Val Asn Val Asp Phe Arg Val Asp Ala Asn Gly Val Tyr
705                 710                 715                 720

Ser Glu Pro Arg Pro Ile Gly Thr Arg Tyr Leu Thr Arg Asn Leu
                725                 730                 735

<210> SEQ ID NO 10
<211> LENGTH: 2200
<212> TYPE: DNA
<213> ORGANISM: adeno-associated virus-2

<400> SEQUENCE: 10
atggctgccg atggttatct tccagattgg ctcgaggaca ctctctctga aggaataaga    60
cagtggtgga agctcaaacc tggcccacca ccaccaaagc ccgcagagcg cataaggac   120 gacagcaggg gtcttgtgct tcctgggtac aagtacctcg gacccttcaa cggactcgac   180
aagggagagc cggtcaacga ggcagacgcc gcggccctcg agcacgacaa agcctacgac   240
cggcagctcg acagcggaga caacccgtac ctcaagtaca accacgccga cgcggagttt   300
caggagcgcc ttaaagaaga tacgtctttt gggggcaacc tcggacgagc agtcttccag   360
gcgaaaaaga gggttcttga acctctgggc ctggttgagg aacctgttaa gacggctccg   420
ggaaaaaaga ggccggtaga gcactctcct gtggagccag actcctcctc gggaaccgga   480
aaggcgggcc agcagcctgc aagaaaaaga ttgaattttg gtcagactgg agacgcagac   540
tcagtacctg acccccagcc tctcggacag ccaccagcag ccccctctgg tctgggaact   600
aatacgatgg ctacaggcag tggcgcgcca atgcagacaa taacgagggg cgccgacgga   660
gtgggtaatt cctcgggaaa ttggcattgc gattccacat ggatgggcga cagagtcatc   720
```

-continued

```
accaccagca cccgaacctg ggccctgccc acctacaaca accacctcta caaacaaatt      780
tccagccaat caggagcctc gaacgacaat cactactttg ctacagcac ccctgggg        840
tattttgact tcaacagatt ccactgccac ttttcaccac gtgactggca aagactcatc      900
aacaacaact ggggattccg acccaagaga ctcaacttca agctctttaa cattcaagtc      960
aaagaggtca cgcagaatga cggtacgacg acgattgcca ataaccttac cagcacggtt     1020
caggtgttta ctgactcgga gtaccagctc ccgtacgtcc tcggctcggc gcatcaagga     1080
tgcctcccgc cgttcccagc agacgtcttc atggtgccac agtatggata cctcaccctg     1140
aacaacggga gtcaggcagt aggacgctct tcatttttact gcctggagta ctttcctcct     1200
cagatgctgc gtaccggaaa caactttacc ttcagctaca cttttgagga cgttcctttc     1260
cacagcagct acgctcacag ccagagtctg gaccgtctca tgaatcctct catcgaccag     1320
tacctgtatt acttgagcag aacaaacact ccaagtggaa ccaccacgca gtcaaggctt     1380
cagttttctc aggctggagc gagtgacatt cgggaccagt ctaggaactg gcttcctgga     1440
ccctgttacc gccagcagag agtatcaaag acatctgcgg ataacaacaa cagtgaatac     1500
tcgtggactg gagctaccaa gtaccacctc aatggcagag actctctggt gaatccgggc     1560
ccggccatgg caagccacaa ggacgatgaa gaaaagtttt tccctcagag cggggttctc     1620
atctttggga agcaaggctc agagaaaaca aatgtggaca ttgaaaaggt catgattaca     1680
gacgaagagg aaatcaggac aaccaatccc gtggctacgg agcagtatgg ttctgtatct     1740
accaacctcc agagaggcaa cagacaagca gctaccgcag atgtcaacac acaaggcgtt     1800
cttccaggca tggtctggca ggacagagat gtgtaccttc aggggcccat ctgggcaaag     1860
attccacaca cggacggaca ttttcacccc tctcccctca tgggtggatt cggacttaaa     1920
cacccctcc cacagattct catcaagaac ccccggtac ctgcgaatcc ttcgaccacc      1980
ttcagtgcgg caaagtttgc ttccttcatc acacagtact ccacgggaca ggtcagcgtg     2040
gagatcgagt gggagctgca gaaggaaaac agcaaacgct ggaatcccga aattcagtac     2100
acttccaact acaacaagtc tgttaatgtg gactttaggt ggacgctaat ggcgtgtatt     2160
cagagcctcg ccccattggc accagatacc tgactcgtaa                           2200
```

<210> SEQ ID NO 11
<211> LENGTH: 735
<212> TYPE: PRT
<213> ORGANISM: adeno-associated virus-2

<400> SEQUENCE: 11

```
Met Ala Ala Asp Gly Tyr Leu Pro Asp Trp Leu Glu Asp Thr Leu Ser
 1               5                  10                  15

Glu Gly Ile Arg Gln Trp Trp Lys Leu Lys Pro Gly Pro Pro Pro
             20                  25                  30

Lys Pro Ala Glu Arg His Lys Asp Asp Ser Arg Gly Leu Val Leu Pro
         35                  40                  45

Gly Tyr Lys Tyr Leu Gly Pro Phe Asn Gly Leu Asp Lys Gly Glu Pro
     50                  55                  60

Val Asn Glu Ala Asp Ala Ala Ala Leu Glu His Asp Lys Ala Tyr Asp
 65                  70                  75                  80

Arg Gln Leu Asp Ser Gly Asp Asn Pro Tyr Leu Lys Tyr Asn His Ala
                 85                  90                  95

Asp Ala Glu Phe Gln Glu Arg Leu Lys Glu Asp Thr Ser Phe Gly Gly
            100                 105                 110
```

```
Asn Leu Gly Arg Ala Val Phe Gln Ala Lys Lys Arg Val Leu Glu Pro
            115                 120                 125

Leu Gly Leu Val Glu Glu Pro Val Lys Thr Ala Pro Gly Lys Lys Arg
130                 135                 140

Pro Val Glu His Ser Pro Val Glu Pro Asp Ser Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
        195                 200                 205

Ala Pro Met Ala Asp Asn Asn Glu Gly Ala Asp Gly Val Gly Asn Ser
210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
290                 295                 300

Gly Phe Arg Pro Lys Arg Leu Asn Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
        355                 360                 365

Val Phe Met Val Pro Gln Tyr Gly Tyr Leu Thr Leu Asn Asn Gly Ser
370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
                405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Ser Arg Thr
        435                 440                 445

Asn Thr Pro Ser Gly Thr Thr Thr Gln Ser Arg Leu Gln Phe Ser Gln
450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
                485                 490                 495

Asn Ser Glu Tyr Ser Trp Thr Gly Ala Thr Lys Tyr His Leu Asn Gly
            500                 505                 510

Arg Asp Ser Leu Val Asn Pro Gly Pro Ala Met Ala Ser His Lys Asp
        515                 520                 525

Asp Glu Glu Lys Phe Phe Pro Gln Ser Gly Val Leu Ile Phe Gly Lys
```

```
                530                 535                 540
Gln Gly Ser Glu Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
                565                 570                 575

Gly Ser Val Ser Thr Asn Leu Gln Arg Gly Asn Arg Gln Ala Ala Thr
                580                 585                 590

Ala Asp Val Asn Thr Gln Gly Val Leu Pro Gly Met Val Trp Gln Asp
                595                 600                 605

Arg Asp Val Tyr Leu Gln Gly Pro Ile Trp Ala Lys Ile Pro His Thr
                610                 615                 620

Asp Gly His Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asn
                645                 650                 655

Pro Ser Thr Thr Phe Ser Ala Ala Lys Phe Ala Ser Phe Ile Thr Gln
                660                 665                 670

Tyr Ser Thr Gly Gln Val Ser Val Glu Ile Glu Trp Glu Leu Gln Lys
                675                 680                 685

Glu Asn Ser Lys Arg Trp Asn Pro Glu Ile Gln Tyr Thr Ser Asn Tyr
690                 695                 700

Asn Lys Ser Val Asn Val Asp Phe Thr Val Asp Ala Asn Gly Val Tyr
705                 710                 715                 720

Ser Glu Pro Arg Pro Ile Gly Thr Arg Tyr Leu Thr Arg Asn Leu
                725                 730                 735

<210> SEQ ID NO 12
<211> LENGTH: 2201
<212> TYPE: DNA
<213> ORGANISM: adeno-associated virus-2

<400> SEQUENCE: 12
atggctgccg atggttatct tccagattgg ctcgaggaca ctctctctga aggaataaga     60
cagtggtgga agctcaaacc tggcccacca ccaccaaagc ccgcagagcg cataaggac    120
gacagcaggg gtcttgtgct tcctgggtac aagtacctcg gacccttcaa cggactcgac    180
aagggagagc cggtcaacga ggcagacgcc gcggccctcg agcacgacaa agcctacgac    240
cggcagctcg acagcggaga caacccgtac ctcaagtaca accacgccga cgcggagttt    300
caggagcgcc ttaaagaaga tacgtctttt gggggcaacc tcggacgagc agtcttccag    360
gcgaaaaaga gggttcttga acctctgggc ctggttgagg aacctgttaa gacggctccg    420
ggaaaaaaga ggccggtaga gcactctcct gtggagccag actcctcctc gggaaccgga    480
aaggcgggcc agcagcctgc aagaaaaaga ttgaattttg gtcagactgg agacgcaaac    540
tcagtacctg acccccagcc tctcggacag ccaccagcag cccctctgg tctgggaact    600
aatacgatgg ctacaggcag tggcgcgcca atggcagaca taacgagggg cgccgacgga    660
gtgggtaatt cctcgggaaa ttggcattgc gattccacat ggatgggcga cagagtcatc    720
accaccagca cccgaacctg ggcctgcc acctacaaca ccacctcta caacaaatt    780
tccagccaat caggagcctc gaacgacaat cactactttg gctacagcac cccttggggg    840
tattttgact tcaacagatt ccactgccac ttttcaccac gtgactggca agactcatc    900
aacaacaact ggggattccg acccaagaga ctcaacttca gctctttaa cattcaagtc    960
aaagaggtca cgcagaatga cggtacgacg acgattgcca ataaccttac cagcacggtt   1020
```

```
caggtgttta ctgactcgga gtaccagctc ccgtacgtcc tcggctcggc gcatcaagga    1080
tgcctcccgc cgttcccagc agacgtcttc atggtgccac agtatggata cctcaccctg    1140
aacaacggga gtcaggcagt aggacgctct tcattttact gcctggagta ctttccttct    1200
cagatgctgc gtaccggaaa caactttacc ttcagctaca cttttgagga cgttcctttc    1260
cacagcagct acgctcacag ccagagtctg accgtctca tgaatcctct catcgaccag    1320
tacctgtatt acttgagcag aacaaacact ccaagtggaa ccaccacgca gtcaaggctt    1380
cagttttctc aggctggagc gagtgacatt cgggaccagt ctaggaactg cttcctgga    1440 ccctgttacc gccagcagag agtatcaaag acatctgcgg ataacaacaa cagtgaatac    1500
tcgtggactg gagctaccaa gtaccacctc aatggcagag actctctggt gaatccgggc    1560
ccggccatgg caagccacaa ggacgatgaa gaaaagtttt tcctcagag cggggttctc    1620 atctttggga agcaaggctc agagaaaaca atgtggaca ttgaaaaggt catgattaca    1680
gacgaagagg aaatcaggac aaccaatccc gtggctacgg agcagtatgg ttctgtatct    1740
accaacctcc agagaggcaa cagacaagca gctaccgcag atgtcaacac acaaggcgtt    1800
cttccaggca tggtctggca ggacagagat gtgtaccttc aggggcccat ctgggcaaag    1860
attccacaca cggacggaca ttttcacccc tctcccctca tgggtggatt cggacttaaa    1920
caccctcctc acagattct catcaagaac accccggtac ctgcgaatcc ttcgaccacc    1980
ttcagtgcgg caaagtttgc ttccttcatc acacagtact ccacgggaca ggtcagcgtg    2040
gagatcgagt gggagctgca gaaggaaaac agcaaacgct ggaatcccga aattcagtac    2100
acttccaact acaacaagtc tgttaatgtg gactttactg tggacgctaa tggcgtgtat    2160
tcagagcctc gccccattgg caccagatac ctgactcgta a                        2201
```

<210> SEQ ID NO 13
<211> LENGTH: 735
<212> TYPE: PRT
<213> ORGANISM: adeno-associated virus-2

<400> SEQUENCE: 13

```
Met Ala Ala Asp Gly Tyr Leu Pro Asp Trp Leu Glu Asp Thr Leu Ser
 1               5                  10                  15

Glu Gly Ile Arg Gln Trp Trp Lys Leu Lys Pro Gly Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
    130                 135                 140

Pro Val Glu His Ser Pro Val Glu Pro Asp Ser Ser Gly Thr Gly
145                 150                 155                 160
```

```
Lys Ala Gly Gln Gln Pro Ala Arg Lys Arg Leu Asn Phe Gly Gln Thr
                165                 170                 175
Gly Asp Ala Asn Ser Val Pro Asp Pro Gln Pro Leu Gly Gln Pro Pro
            180                 185                 190
Ala Ala Pro Ser Gly Leu Gly Thr Asn Thr Met Ala Thr Gly Ser Gly
        195                 200                 205
Ala Pro Met Ala Asp Asn Asn Glu Gly Ala Asp Gly Val Gly Asn Ser
    210                 215                 220
Ser Gly Asn Trp His Cys Asp Ser Thr Trp Met Gly Asp Arg Val Ile
225                 230                 235                 240
Thr Thr Ser Thr Arg Thr Trp Ala Leu Pro Thr Tyr Asn Asn His Leu
                245                 250                 255
Tyr Lys Gln Ile Ser Ser Gln Ser Gly Ala Ser Asn Asp Asn His Tyr
            260                 265                 270
Phe Gly Tyr Ser Thr Pro Trp Gly Tyr Phe Asp Phe Asn Arg Phe His
        275                 280                 285
Cys His Phe Ser Pro Arg Asp Trp Gln Arg Leu Ile Asn Asn Asn Trp
    290                 295                 300
Gly Phe Arg Pro Lys Arg Leu Asn Phe Lys Leu Phe Asn Ile Gln Val
305                 310                 315                 320
Lys Glu Val Thr Gln Asn Asp Gly Thr Thr Thr Ile Ala Asn Asn Leu
                325                 330                 335
Thr Ser Thr Val Gln Val Phe Thr Asp Ser Glu Tyr Gln Leu Pro Tyr
            340                 345                 350
Val Leu Gly Ser Ala His Gln Gly Cys Leu Pro Pro Phe Pro Ala Asp
        355                 360                 365
Val Phe Met Val Pro Gln Tyr Gly Tyr Leu Thr Leu Asn Asn Gly Ser
    370                 375                 380
Gln Ala Val Gly Arg Ser Ser Phe Tyr Cys Leu Glu Tyr Phe Pro Ser
385                 390                 395                 400
Gln Met Leu Arg Thr Gly Asn Asn Phe Thr Phe Ser Tyr Thr Phe Glu
                405                 410                 415
Asp Val Pro Phe His Ser Ser Tyr Ala His Ser Gln Ser Leu Asp Arg
            420                 425                 430
Leu Met Asn Pro Leu Ile Asp Gln Tyr Leu Tyr Tyr Leu Ser Arg Thr
        435                 440                 445
Asn Thr Pro Ser Gly Thr Thr Thr Gln Ser Arg Leu Gln Phe Ser Gln
    450                 455                 460
Ala Gly Ala Ser Asp Ile Arg Asp Gln Ser Arg Asn Trp Leu Pro Gly
465                 470                 475                 480
Pro Cys Tyr Arg Gln Gln Arg Val Ser Lys Thr Ser Ala Asp Asn Asn
                485                 490                 495
Asn Ser Glu Tyr Ser Trp Thr Gly Ala Thr Lys Tyr His Leu Asn Gly
            500                 505                 510
Arg Asp Ser Leu Val Asn Pro Gly Pro Ala Met Ala Ser His Lys Asp
        515                 520                 525
Asp Glu Glu Lys Phe Phe Pro Gln Ser Gly Val Leu Ile Phe Gly Lys
    530                 535                 540
Gln Gly Ser Glu Lys Thr Asn Val Asp Ile Glu Lys Val Met Ile Thr
545                 550                 555                 560
Asp Glu Glu Glu Ile Arg Thr Thr Asn Pro Val Ala Thr Glu Gln Tyr
                565                 570                 575
Gly Ser Val Ser Thr Asn Leu Gln Arg Gly Asn Arg Gln Ala Ala Thr
```

|   |   |   |   |   | 580 |   |   |   | 585 |   |   |   | 590 |   |   |
|---|---|---|---|---|---|---|---|---|---|---|---|---|---|---|---|
| Ala | Asp | Val | Asn | Thr | Gln | Gly | Val | Leu | Pro | Gly | Met | Val | Trp | Gln | Asp |
|   |   |   | 595 |   |   |   | 600 |   |   |   | 605 |   |   |   |   |
| Arg | Asp | Val | Tyr | Leu | Gln | Gly | Pro | Ile | Trp | Ala | Lys | Ile | Pro | His | Thr |
|   |   | 610 |   |   |   | 615 |   |   |   | 620 |   |   |   |   |   |
| Asp | Gly | His | Phe | His | Pro | Ser | Pro | Leu | Met | Gly | Gly | Phe | Gly | Leu | Lys |
| 625 |   |   |   | 630 |   |   |   | 635 |   |   |   |   |   |   | 640 |
| His | Pro | Pro | Pro | Gln | Ile | Leu | Ile | Lys | Asn | Thr | Pro | Val | Pro | Ala | Asn |
|   |   |   | 645 |   |   |   | 650 |   |   |   | 655 |   |   |   |   |
| Pro | Ser | Thr | Thr | Phe | Ser | Ala | Ala | Lys | Phe | Ala | Ser | Phe | Ile | Thr | Gln |
|   |   | 660 |   |   |   | 665 |   |   |   | 670 |   |   |   |   |   |
| Tyr | Ser | Thr | Gly | Gln | Val | Ser | Val | Glu | Ile | Glu | Trp | Glu | Leu | Gln | Lys |
|   | 675 |   |   |   | 680 |   |   |   | 685 |   |   |   |   |   |   |
| Glu | Asn | Ser | Lys | Arg | Trp | Asn | Pro | Glu | Ile | Gln | Tyr | Thr | Ser | Asn | Tyr |
|   | 690 |   |   |   | 695 |   |   |   | 700 |   |   |   |   |   |   |
| Asn | Lys | Ser | Val | Asn | Val | Asp | Phe | Thr | Val | Asp | Ala | Asn | Gly | Val | Tyr |
| 705 |   |   |   | 710 |   |   |   | 715 |   |   |   |   |   |   | 720 |
| Ser | Glu | Pro | Arg | Pro | Ile | Gly | Thr | Arg | Tyr | Leu | Thr | Arg | Asn | Leu |   |
|   |   |   | 725 |   |   |   | 730 |   |   |   | 735 |   |   |   |   |

<210> SEQ ID NO 14
<211> LENGTH: 2201
<212> TYPE: DNA
<213> ORGANISM: adeno-associated virus-2

<400> SEQUENCE: 14

```
atggctgccg atggttatct tccagattgg ctcgaggaca ctctctctga aggaataaga      60
cagtggtgga agctcaaacc tggcccacca ccaccaaagc ccgcagagcg gcataaggac     120
gacagcaggg gtcttgtgct tcctgggtac aagtaccctc gacccttcaa cggactcgac     180
aagggagagc cggtcaacga ggcagacgcc gcggccctcg agcacgacaa agcctacgac     240
cggcagctcg acagcggaga caacccgtac ctcaagtaca accacgccga cgcggagttt     300
caggagcgcc ttaaagaaga tacgtctttt gggggcaacc tcggacgagc agtcttccag     360
gcgaaaaaga gggttcttga acctctgggc ctggttgagg aacctgttaa gacggctccg     420
ggaaaaaaga ggccggtaga gcactctcct gtggagccag actcctcctc gggaaccgga     480
aaggcgggcc agcagcctgc aagaaaaaga ttgaattttg gtcagactgg agacgcagac     540
tcagtacctg accccagcc tctcggacag ccaccagcag cccctctgg tctgggaact     600
aatacgatgg ctacaggcag tggcgcgcca atggcagaca taacgaggg cgccgacgga     660
gtgggtaatt cctcgggaaa ttggcattgc gattccacat ggatgggcga cagagtcatc     720
accaccagca cccgaacctg gcccctgccc acctacaaca accacctcta caaacaaatt     780
tccagccaat caggagcctc gaacgacaat cactactttg gctacagcac cccttggggg     840
tattttgact tcaacagatt ccactgccac ttttcaccac gtgactggca agactcatc     900
aacaacaact gggggattcc gacccaagag ctcaacttca gctctttaa cattcaagtc     960
aaagaggtca cgcagaatga cggtacgacg acgattgcca ataaccttac cagcacggtt    1020
caggtgttta ctgactcgga gtaccagctc ccgtacgtcc tcggctcggc gcatcaagga    1080
tgcctcccgc cgttcccagc agacgtcttc atggtgccac agtatggata cctcacccctg    1140
aacaacggga gtcaggcagt aggacgctct tcatttttact gcctggagta ctttccttct    1200
cagatgctgc gtaccggaaa caacttttacc ttcagctaca cttttgagga cgttcctttc    1260
```

```
cacagcagct acgctcacag ccagagtctg gaccgtctca tgaatcctct catcgaccag    1320
tacctgtatt acttgagcag aacaaacact ccaagtggaa ccaccacgca gtcaaggctt    1380
cagttttctc aggctggagc gagtgacatt cgggaccagt ctaggaactg gcttcctgga    1440
ccctgttacc gccagcagag agtatcaaag acatctgggg ataacaacaa cagtgaatac    1500
tcgtggactg gagctaccaa gtaccacctc aatggcagag actctctggt gaatccgggc    1560
ccggccatgg caagccacaa ggacgatgaa gaaaagtttt tccctcagag cggggttctc    1620
atctttggga agcaaggctc agagaaaaca aatgtggaca ttgaaaaggt catgattaca    1680
gacgaagagg aaatcaggac aaccaatccc gtggctacgg agcagtatgg ttctgtatct    1740
accaacctcc agagaggcaa cagacaagca gctaccgcag atgtcaacac acaaggcgtt    1800
cttccaggca tggtctggca ggacagagat gtgtaccttc aggggcccat ctgggcaaag    1860
attccacaca cggacggaca ttttcacccc tctcccctca tgggtggatt cggacttaaa    1920
caccctcctc cacagattct catcaagaac accccggtac ctgcgaatcc ttcgaccacc    1980
ttcagtgcgg caaagtttgc ttccttcatc acacagtact ccacgggaca ggtcagcgtg    2040
gagatcgagt gggagctgca gaaggaaaac agcaaacgct ggaatcccga aattcagtac    2100
acttccaact acaacaagtc tgttaatgtg gactttactg tggacgctaa tggcgtgtat    2160
tcagagcctc gccccattgg caccagatac ctgactcgta a                        2201
```

<210> SEQ ID NO 15
<211> LENGTH: 735
<212> TYPE: PRT
<213> ORGANISM: adeno-associated virus-2

<400> SEQUENCE: 15

```
Met Ala Ala Asp Gly Tyr Leu Pro Asp Trp Leu Glu Asp Thr Leu Ser
  1               5                  10                  15

Glu Gly Ile Arg Gln Trp Trp Lys Leu Lys Pro Gly Pro Pro Pro Pro
             20                  25                  30

Lys Pro Ala Glu Arg His Lys Asp Asp Ser Arg Gly Leu Val Leu Pro
         35                  40                  45

Gly Tyr Lys Tyr Leu Gly Pro Phe Asn Gly Leu Asp Lys Gly Glu Pro
     50                  55                  60

Val Asn Glu Ala Asp Ala Ala Ala Leu Glu His Asp Lys Ala Tyr Asp
 65                  70                  75                  80

Arg Gln Leu Asp Ser Gly Asp Asn Pro Tyr Leu Lys Tyr Asn His Ala
                 85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
    130                 135                 140

Pro Val Glu His Ser Pro Val Glu Pro Asp Ser Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
        195                 200                 205
```

-continued

```
Ala Pro Met Ala Asp Asn Asn Glu Gly Ala Asp Gly Val Gly Asn Ser
    210                 215                 220
Ser Gly Asn Trp His Cys Asp Ser Thr Trp Met Gly Asp Arg Val Ile
225                 230                 235                 240
Thr Thr Ser Thr Arg Thr Trp Ala Leu Pro Thr Tyr Asn Asn His Leu
                245                 250                 255
Tyr Lys Gln Ile Ser Gln Ser Gly Ala Ser Asn Asp Asn His Tyr
            260                 265                 270
Phe Gly Tyr Ser Thr Pro Trp Gly Tyr Phe Asp Phe Asn Arg Phe His
            275                 280                 285
Cys His Phe Ser Pro Arg Asp Trp Gln Arg Leu Ile Asn Asn Asn Trp
290                 295                 300
Gly Phe Arg Pro Lys Arg Leu Asn Phe Lys Leu Phe Asn Ile Gln Val
305                 310                 315                 320
Lys Glu Val Thr Gln Asn Asp Gly Thr Thr Thr Ile Ala Asn Asn Leu
                325                 330                 335
Thr Ser Thr Val Gln Val Phe Thr Asp Ser Glu Tyr Gln Leu Pro Tyr
                340                 345                 350
Val Leu Gly Ser Ala His Gln Gly Cys Leu Pro Pro Phe Pro Ala Asp
            355                 360                 365
Val Phe Met Val Pro Gln Tyr Gly Tyr Leu Thr Leu Asn Asn Gly Ser
370                 375                 380
Gln Ala Val Gly Arg Ser Ser Phe Tyr Cys Leu Glu Tyr Phe Pro Ser
385                 390                 395                 400
Gln Met Leu Arg Thr Gly Asn Asn Phe Thr Phe Ser Tyr Thr Phe Glu
                405                 410                 415
Asp Val Pro Phe His Ser Ser Tyr Ala His Ser Gln Ser Leu Asp Arg
            420                 425                 430
Leu Met Asn Pro Leu Ile Asp Gln Tyr Leu Tyr Tyr Leu Ser Arg Thr
        435                 440                 445
Asn Thr Pro Ser Gly Thr Thr Thr Gln Ser Arg Leu Gln Phe Ser Gln
    450                 455                 460
Ala Gly Ala Ser Asp Ile Arg Asp Gln Ser Arg Asn Trp Leu Pro Gly
465                 470                 475                 480
Pro Cys Tyr Arg Gln Gln Arg Val Ser Lys Thr Ser Gly Asp Asn Asn
                485                 490                 495
Asn Ser Glu Tyr Ser Trp Thr Gly Ala Thr Lys Tyr His Leu Asn Gly
            500                 505                 510
Arg Asp Ser Leu Val Asn Pro Gly Pro Ala Met Ala Ser His Lys Asp
        515                 520                 525
Asp Glu Glu Lys Phe Phe Pro Gln Ser Gly Val Leu Ile Phe Gly Lys
    530                 535                 540
Gln Gly Ser Glu Lys Thr Asn Val Asp Ile Glu Lys Val Met Ile Thr
545                 550                 555                 560
Asp Glu Glu Glu Ile Arg Thr Thr Asn Pro Val Ala Thr Glu Gln Tyr
                565                 570                 575
Gly Ser Val Ser Thr Asn Leu Gln Arg Gly Asn Arg Gln Ala Ala Thr
            580                 585                 590
Ala Asp Val Asn Thr Gln Gly Val Leu Pro Gly Met Val Trp Gln Asp
        595                 600                 605
Arg Asp Val Tyr Leu Gln Gly Pro Ile Trp Ala Lys Ile Pro His Thr
    610                 615                 620
Asp Gly His Phe His Pro Ser Pro Leu Met Gly Gly Phe Gly Leu Lys
```

```
                625               630              635              640
             His Pro Pro Gln Ile Leu Ile Lys Asn Thr Pro Val Pro Ala Asn
                             645               650              655
             Pro Ser Thr Thr Phe Ser Ala Ala Lys Phe Ala Ser Phe Ile Thr Gln
                             660               665              670
             Tyr Ser Thr Gly Gln Val Ser Val Glu Ile Glu Trp Glu Leu Gln Lys
                             675               680              685
             Glu Asn Ser Lys Arg Trp Asn Pro Glu Ile Gln Tyr Thr Ser Asn Tyr
                             690               695              700
             Asn Lys Ser Val Asn Val Asp Phe Thr Val Asp Ala Asn Gly Val Tyr
                             705               710              715              720
             Ser Glu Pro Arg Pro Ile Gly Thr Arg Tyr Leu Thr Arg Asn Leu
                             725               730              735

<210> SEQ ID NO 16
<211> LENGTH: 2207
<212> TYPE: DNA
<213> ORGANISM: adeno-associated virus-2

<400> SEQUENCE: 16
atggctgccg atggttatct tccagattgg ctcgaggaca ctctctctga aggaataaga    60
cagtgtggaa gctcaaacct ggcccaccac caccaaagcc cgcagagcgg cataaggacg   120
acagcagggg tcttgtgctt cctgggtaca agtacctcgg acccttcaac ggactcgaca   180
agggagagcc ggtcaacgag gcagacgccg cggccctcga gcacgacaaa gcctacgacc   240
ggcagctcga cagcggagac aacccgtacc tcaagtacaa ccacgccgac gcggagtttc   300
aggagcgcct taaagaagat acgtcttttg ggggcaacct cggacgagca gtcttccagg   360
cgaaaaagag ggttcttgaa cctctgggcc tggttgagga acctgttaag acggctccgg   420
gaaaaaagag gccggtagag cactctcctg tggagccaga ctcctcctcg ggaaccggaa   480
aggcaggcca gcagcctgca agaagaagat tgaattttgg tcagactgga gacgcagacc   540
cagtacctga ccccagcct tcggacagc accagcagc ccctctggt ctgggaacta   600 atacgatggc tacgggcagt ggcgcaccaa tggcagacaa taacgagggc gccgacggag   660
tgggtaattc ctcgggaaat tggcattgcg attccacatg gatgggcgac agagtcatca   720
ccaccagcac ccgaacctgg gccctgccca cctacaacaa ccacctctac aaacaaattt   780
ccagccaatc aggagcctcg aacgacaatc actactttgg ctacagcacc ccttgggggt   840
attttgactt caacagattc cactgccact ttttcaccacg tgactggcaa agactcatca   900
acaacaactg gggattccga cccaagagac tcaacttcaa gctctttaac attcaagtca   960
aagaggtcac gcagaatgac ggtacgacga cgattgtcaa taaccttacc agcacggttc  1020
aggtgtttac tgactcggag taccagctcc cgtacgtcct cggctcggcg catcaaggat  1080
gcctcacgcc gttcccagca gacgtcttca tggtgccaca gtatggatac ctcaccctga  1140
acaacgggag tcaggcagta ggacgctctt cattttactg cctggagtac tttccttctc  1200
agatgctgcg taccggaaac aactttacct tcagctacac ttttgaggac gttccttttc  1260
acagcagcta cgctcacagc cagagtctgg accgtctcat gaatcctctc atcgaccagt  1320
acctgtatta cttgagcaga acaaacactc aagtggaaac caccacgcag tcaaggcttc  1380
agttttctca ggccggagcg agtgacattg ggaccagtc taggaactgg cttcctggac  1440
cctgttaccg ccagcagcga gtatcaaaga catctgagga taacaacaac agtgaatact  1500
cgtggactgg agctaccaag taccaccctca atggcagaga ctctctggtg aatccgggcc  1560
```

-continued

```
cggccatggc aagccacaag gacgatgaag aaaagttttt tcctcagagc ggggttctca   1620
tctttgggaa gcaaggctca gagaaaacaa atgtggacat tgaaaaggtc atgattacag   1680
acgaagagga aatcaggaca accaatcccg tggctacgga gcagtatggt tctgtatcta   1740
ccaacctcca gaggggcaac aggcaagcag ctaccgcaga tgtcaacaca caaggcgttc   1800
ttccaggcat ggtctggcag gacagagatg tgtaccttca ggggcccatc tgggcaaaga   1860
ttccacacac ggacggacat tttcacccct ctcccctcat gggtggattc ggacttaaac   1920
accctcctcc acagattctc atcaagaaca ccccggtacc tgcgaatcct tcgaccacct   1980
tcagtgcggc aaagtttgct tccttcatca cacagtactc cacgggacag gtcagcgtgg   2040
agatcgagtg ggagctgcag aaggaaaaca gcaaacgctg gaatcccgaa attcagtaca   2100
cttccaacta caacaagtct gttaatgtgg actttactgt ggacactaat ggcgtgtatt   2160
cagagcctcg ccccattggc accagatacc tgactcgtaa tctgtaa               2207
```

<210> SEQ ID NO 17
<211> LENGTH: 735
<212> TYPE: PRT
<213> ORGANISM: adeno-associated virus-2

<400> SEQUENCE: 17

```
Met Ala Ala Asp Gly Tyr Leu Pro Asp Trp Leu Glu Asp Thr Leu Ser
  1               5                  10                  15

Glu Gly Ile Arg Gln Trp Trp Lys Leu Lys Pro Gly Pro Pro Pro Pro
             20                  25                  30

Lys Pro Ala Glu Arg His Lys Asp Asp Ser Arg Gly Leu Val Leu Pro
         35                  40                  45

Gly Tyr Lys Tyr Leu Gly Pro Phe Asn Gly Leu Asp Lys Gly Glu Pro
     50                  55                  60

Val Asn Glu Ala Asp Ala Ala Leu Glu His Asp Lys Ala Tyr Asp
 65                  70                  75                  80

Arg Gln Leu Asp Ser Gly Asp Asn Pro Tyr Leu Lys Tyr Asn His Ala
                 85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
    130                 135                 140

Pro Val Glu His Ser Pro Val Glu Pro Asp Ser Ser Ser Gly Thr Gly
145                 150                 155                 160

Lys Ala Gly Gln Gln Pro Ala Arg Arg Arg Leu Asn Phe Gly Gln Thr
                165                 170                 175

Gly Asp Ala Asp Pro Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255
```

-continued

```
Tyr Lys Gln Ile Ser Ser Gln Ser Gly Ala Ser Asn Asp Asn His Tyr
            260                 265                 270
Phe Gly Tyr Ser Thr Pro Trp Gly Tyr Phe Asp Phe Asn Arg Phe His
        275                 280                 285
Cys His Phe Ser Pro Arg Asp Trp Gln Arg Leu Ile Asn Asn Asn Trp
    290                 295                 300
Gly Phe Arg Pro Lys Arg Leu Asn Phe Lys Leu Phe Asn Ile Gln Val
305                 310                 315                 320
Lys Glu Val Thr Gln Asn Asp Gly Thr Thr Thr Ile Val Asn Asn Leu
                325                 330                 335
Thr Ser Thr Val Gln Val Phe Thr Asp Ser Glu Tyr Gln Leu Pro Tyr
            340                 345                 350
Val Leu Gly Ser Ala His Gln Gly Cys Leu Thr Pro Phe Pro Ala Asp
        355                 360                 365
Val Phe Met Val Pro Gln Tyr Gly Tyr Leu Thr Leu Asn Asn Gly Ser
    370                 375                 380
Gln Ala Val Gly Arg Ser Ser Phe Tyr Cys Leu Glu Tyr Phe Pro Ser
385                 390                 395                 400
Gln Met Leu Arg Thr Gly Asn Asn Phe Thr Phe Ser Tyr Thr Phe Glu
                405                 410                 415
Asp Val Pro Phe His Ser Ser Tyr Ala His Ser Gln Ser Leu Asp Arg
            420                 425                 430
Leu Met Asn Pro Leu Ile Asp Gln Tyr Leu Tyr Tyr Leu Ser Arg Thr
        435                 440                 445
Asn Thr Pro Ser Gly Thr Thr Thr Gln Ser Arg Leu Gln Phe Ser Gln
    450                 455                 460
Ala Gly Ala Ser Asp Ile Arg Asp Gln Ser Arg Asn Trp Leu Pro Gly
465                 470                 475                 480
Pro Cys Tyr Arg Gln Gln Arg Val Ser Lys Thr Ser Glu Asp Asn Asn
                485                 490                 495
Asn Ser Glu Tyr Ser Trp Thr Gly Ala Thr Lys Tyr His Leu Asn Gly
            500                 505                 510
Arg Asp Ser Leu Val Asn Pro Gly Pro Ala Met Ala Ser His Lys Asp
        515                 520                 525
Asp Glu Glu Lys Phe Phe Pro Gln Ser Gly Val Leu Ile Phe Gly Lys
    530                 535                 540
Gln Gly Ser Glu Lys Thr Asn Val Asp Ile Glu Lys Val Met Ile Thr
545                 550                 555                 560
Asp Glu Glu Glu Ile Arg Thr Thr Asn Pro Val Ala Thr Glu Gln Tyr
                565                 570                 575
Gly Ser Val Ser Thr Asn Leu Gln Arg Gly Asn Arg Gln Ala Ala Thr
            580                 585                 590
Ala Asp Val Asn Thr Gln Gly Val Leu Pro Gly Met Val Trp Gln Asp
        595                 600                 605
Arg Asp Val Tyr Leu Gln Gly Pro Ile Trp Ala Lys Ile Pro His Thr
    610                 615                 620
Asp Gly His Phe His Pro Ser Pro Leu Met Gly Gly Phe Gly Leu Lys
625                 630                 635                 640
His Pro Pro Pro Gln Ile Leu Ile Lys Asn Thr Pro Val Pro Ala Asn
                645                 650                 655
Pro Ser Thr Thr Phe Ser Ala Ala Lys Phe Ala Ser Phe Ile Thr Gln
            660                 665                 670
Tyr Ser Thr Gly Gln Val Ser Val Glu Ile Glu Trp Glu Leu Gln Lys
```

```
                675                 680                 685
Glu Asn Ser Lys Arg Trp Asn Pro Glu Ile Gln Tyr Thr Ser Asn Tyr
            690                 695                 700

Asn Lys Ser Val Asn Val Asp Phe Thr Val Asp Thr Asn Gly Val Tyr
705                 710                 715                 720

Ser Glu Pro Arg Pro Ile Gly Thr Arg Tyr Leu Thr Arg Asn Leu
                725                 730                 735

<210> SEQ ID NO 18
<211> LENGTH: 2208
<212> TYPE: DNA
<213> ORGANISM: adeno-associated virus-2

<400> SEQUENCE: 18
atggctgccg atggttatct tccagattgg ctcgaggaca ctctctctga aggagtaaga       60
cagtggtgga agctcaaacc tggcccacca ccaccaaagc ccgcagagcg cataaggac      120 gacagcaggg gtcttgtgct cctgggtac aagtacctcg acccttcaa cggactcgac       180 aagggagagc cggtcaacga ggcagacgcc gcggccctcg agcacgacaa agcctacgac     240
cggcagctcg acagcggaga caacccgtac ctcaagtaca accacgccga cgcggagttt     300
caggagcgcc ttaaagaaga tacgtctttt gggggcaacc tcggacgagc agtcttccag     360
gcgaaaaaga gggttcttga acctctgggc ctggttgagg aacctgttaa acgggctccg     420
ggaaaaaaga ggccggtaga gcactctcct gtggagccag actcctcctc gggaaccgga     480
aaggcgggcc agcagcctgc aagaaaaaga ttgaattttg gtcagactgg agacgcagac     540
tcagtacctg acccccagcc tctcggacag ccaccagcag ccccctctgg tctgggaact     600
aatacgatgg ctacaggcag tggcgcacca atggcagaca ataacgaggg cgccgacgga     660
gtgggtaatt cctcgggaaa ttggcattgc gattccacat ggatgggcga cagagtcatc     720
accaccagca cccgaacctg gcccctgccc acctacaaca accacctcta caaacaaatt     780
tccagccaat caggagcctc gaacgacaat cactactttg gctacagcac ccttggggg     840 tattttgact tcaacagatt ccactgccac ttttcaccac gtgactggca agactcatc      900 aacaacaact ggggattccg acccaagaga ctcaacttca agctctttaa cattcaagtc     960
aaagaggtca cgcagaatga cggtacgacg acgattgcca ataacctta cagcacggtt    1020 caggtgttta ctgactcgga gtaccagctc ccgtacgttc tcggctcggc gcatcaagga    1080
tgcctcccgc cgttcccagc agacgccttc atggtgccac agtatggata cctcaccctg    1140
aacaacggga gtcaggcagt aggacgctct tcatttac gcctggagta ctttccttct    1200
cagatgctgc gtaccggaaa caactttacc ttcagctaca cttttgagga cgttcctttc    1260
cacagcagct acgctcacag ccagagtctg gaccgtctca tgaatcctct catcgaccag    1320
tacctgtatt acttgagcag aacaaacact ccaagtggaa ccaccacgca gtcaaggctt    1380
cagttttctc aggccggagc gagtgacatt cgggaccagt ctaggaactg gcttcctgga    1440
ccctgttacc gccagcagcg agtatcaaag acatctgcgg ataacaacaa cagtgaatac    1500
tcgtggactg gagctaccaa gtaccacctc aatggcagag actctctggt gaatccgggc    1560
ccggccatgg caagccacaa ggacgatgaa gaaaagtttt tccctcagag cggggttctc    1620
atctttggga agcaaggctc agagaaaaca aatgtggaca ttgaaaaggt catgattaca    1680
gacgaagagg aaatcaggac aaccaatccc gtggctacgg agcagtatgg ttctgtatct    1740
accaacctcc agagaggcaa cagacaagca gctaccgaag atgtcaacac tcaaggcgtt    1800
```

-continued

```
cttccaggca tggtctggca ggacagagat gtgtaccttc aggggcccat ctgggcaaag    1860
attccacaca cggacggaca ttttcacccc tctcccctca tgggtggatt cggacttaaa    1920
caccctcctc cacagattct catcaagaac accccggtac ctgcgaatcc ttcgaccacc    1980
ttcagtgcgg caaagtttgc ttccttcatc acacagtact ccacgggaca ggtcagcgtg    2040
gagatcgagt gggagctaca aaggaaaac agcaaacgct ggaatcccga aattcagtac     2100
acttccaact acaacaagtc tgttaatgtg gactttactg tggacactaa tggcgtgtat    2160
tcagagcctc gccccattgg caccagatac ctgactagta atctgtaa                 2208
```

<210> SEQ ID NO 19
<211> LENGTH: 735
<212> TYPE: PRT
<213> ORGANISM: adeno-associated virus-2

<400> SEQUENCE: 19

```
Met Ala Ala Asp Gly Tyr Leu Pro Asp Trp Leu Glu Asp Thr Leu Ser
 1               5                  10                  15

Glu Gly Val Arg Gln Trp Trp Lys Leu Lys Pro Gly Pro Pro Pro Pro
             20                  25                  30

Lys Pro Ala Glu Arg His Lys Asp Asp Ser Arg Gly Leu Val Leu Pro
         35                  40                  45

Gly Tyr Lys Tyr Leu Gly Pro Phe Asn Gly Leu Asp Lys Gly Glu Pro
     50                  55                  60

Val Asn Glu Ala Asp Ala Ala Leu Glu His Asp Lys Ala Tyr Asp
 65                  70                  75                  80

Arg Gln Leu Asp Ser Gly Asp Asn Pro Tyr Leu Lys Tyr Asn His Ala
                 85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
    130                 135                 140

Pro Val Glu His Ser Pro Val Glu Pro Asp Ser Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
    290                 295                 300
```

```
Gly Phe Arg Pro Lys Arg Leu Asn Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
                340                 345                 350

Val Leu Gly Ser Ala His Gln Gly Cys Leu Pro Pro Phe Pro Ala Asp
                355                 360                 365

Ala Phe Met Val Pro Gln Tyr Gly Tyr Leu Thr Leu Asn Asn Gly Ser
        370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
                405                 410                 415

Asp Val Pro Phe His Ser Ser Tyr Ala His Ser Gln Ser Leu Asp Arg
                420                 425                 430

Leu Met Asn Pro Leu Ile Asp Gln Tyr Leu Tyr Tyr Leu Ser Arg Thr
                435                 440                 445

Asn Thr Pro Ser Gly Thr Thr Thr Gln Ser Arg Leu Gln Phe Ser Gln
                450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
                485                 490                 495

Asn Ser Glu Tyr Ser Trp Thr Gly Ala Thr Lys Tyr His Leu Asn Gly
                500                 505                 510

Arg Asp Ser Leu Val Asn Pro Gly Pro Ala Met Ala Ser His Lys Asp
                515                 520                 525

Asp Glu Glu Lys Phe Phe Pro Gln Ser Gly Val Leu Ile Phe Gly Lys
                530                 535                 540

Gln Gly Ser Glu Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
                565                 570                 575

Gly Ser Val Ser Thr Asn Leu Gln Arg Gly Asn Arg Gln Ala Ala Thr
                580                 585                 590

Glu Asp Val Asn Thr Gln Gly Val Leu Pro Gly Met Val Trp Gln Asp
                595                 600                 605

Arg Asp Val Tyr Leu Gln Gly Pro Ile Trp Ala Lys Ile Pro His Thr
610                 615                 620

Asp Gly His Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asn
                645                 650                 655

Pro Ser Thr Thr Phe Ser Ala Ala Lys Phe Ala Ser Phe Ile Thr Gln
                660                 665                 670

Tyr Ser Thr Gly Gln Val Ser Val Glu Ile Glu Trp Glu Leu Gln Lys
                675                 680                 685

Glu Asn Ser Lys Arg Trp Asn Pro Glu Ile Gln Tyr Thr Ser Asn Tyr
                690                 695                 700

Asn Lys Ser Val Asn Val Asp Phe Thr Val Asp Thr Asn Gly Val Tyr
705                 710                 715                 720

Ser Glu Pro Arg Pro Ile Gly Thr Arg Tyr Leu Thr Arg Asn Leu
```

<210> SEQ ID NO 20
<211> LENGTH: 2208
<212> TYPE: DNA
<213> ORGANISM: adeno-associated virus-2

<400> SEQUENCE: 20

| | | | | | |
|---|---|---|---|---|---|
| atggctgccg | atggttatct | tccagattgg | ctcgaggaca | ctctctctga | aggaataaga | 60 |
| cagtggtgga | agctcaaacc | tggcccacca | ccaccaaagc | ccgcagagcg | gcataaggac | 120 |
| gacagcaggg | gtcttgtgct | tcctgggtac | aagtacctcg | acccttcaa | cggactcgac | 180 |
| aagggagagc | cggtcaacga | ggcagacgcc | gcggccctcg | agcacgacaa | agcctacgac | 240 |
| cggcagctcg | acagcggaga | caacccgtac | ctcaagtaca | accacgccga | cgcggagttt | 300 |
| caggagcgcc | ttaaagaaga | tacgtctttt | gggggcaacc | tcggacgagc | agtcttccag | 360 |
| gcgaaaaaga | gggttcttga | acctctgggc | ctggttgagg | aacctgttaa | gacggctccg | 420 |
| ggaaaaaaga | ggccggtaga | gcactctcct | gtggagccag | actcctcctc | gggaaccgga | 480 |
| aaggcgggcc | agcagcctgc | aagaaaaaga | ttgaattttg | gtcagactgg | agacgcagac | 540 |
| tcagtacctg | accccagcc | tctcgaacag | ccaccagcag | ccccctctgg | tctgggaact | 600 |
| aatacgatgg | ctacaggcag | tggcgcacca | atggcagaca | atatcgaggg | cgccgacgga | 660 |
| gtgggtaatt | cctcgggaaa | ttggcattgc | gattccacat | ggatgggcga | cagagtcatc | 720 |
| accaccagca | cccgaacctg | ggcctgccc | acctacaaca | accacctcta | caaacaaatt | 780 |
| tccagccaat | caggagcctc | gaacgacaat | cactactttg | ctacagcac | cccttggggg | 840 |
| tattttgact | tcaacagatt | ccactgccac | ttttcaccac | gtgactggca | agactcatc | 900 |
| aacaacaact | ggggattccg | acccaagaga | ctcaacttca | agctctttaa | cattcaagtc | 960 |
| aaagaggtca | cgcagaatga | cggtacgacg | acgattgcca | ataaccttac | cagcacggtt | 1020 |
| caggtgttta | ctgactcgga | gtaccagctc | ccgtacgtcc | tcggctcggc | gcatcaagga | 1080 |
| tgcctcccgc | cgttcccaga | gacgtcttc | atggtgccac | agtatggata | cctcaccctg | 1140 |
| aacaacggga | gtcaggcagt | aggacgctct | tcatttttact | gcctggagta | cttcccctct | 1200 |
| cagatgctgc | gtaccggaaa | caactttacc | ttcagctaca | cttttgagga | cgttcctttc | 1260 |
| cacagcagct | acgctcacag | ccagggtctg | gaccgtctca | tgaatcctct | catcgaccag | 1320 |
| tacctgtatt | acttgagcag | aacaaacact | ccaagtggaa | ccaccacgca | gtcaaggctt | 1380 |
| cagttttctc | aggccggagc | gagtgacatt | cgggaccagt | ctaggaactg | gcttcctgga | 1440 |
| ccctgttacc | gccagcagcg | agtatcaaag | acatctgagg | ataacaacaa | cagtgaatac | 1500 |
| tcgtggactg | gagctaccaa | gtaccacctc | aatggcagag | actctctggt | gaatccgggc | 1560 |
| ccggccatgg | caagccacaa | ggacgatgaa | gaaaagtttt | tccctcagag | cggggttctc | 1620 |
| atctttggga | agcaaggctc | agagaaaaca | aatgtggaca | ttgaaaaggt | catgattaca | 1680 |
| gacgaagagg | aaatcaggac | aaccaatccc | gtggctacgg | agcagtatgg | ttctgtacct | 1740 |
| accaacctcc | agagaggcaa | cagacaagca | gctaccgcag | atgtcaacac | acaaggcgtt | 1800 |
| cttccaggca | tggtctggca | ggacagagat | gtgtaccttc | aggggcccat | ctgggcaaag | 1860 |
| attccacaca | cggacggaca | ttttcacccc | tctcccctca | tgggtggatt | cggacttaaa | 1920 |
| cacccttcttc | acagattct | catcaagaac | accccggtac | ctgcgaatcc | ttcgaccacc | 1980 |
| ttcagtgcgg | caaagtttgc | ttccttcatc | acacagtact | ccacgggaca | ggtcagcgtg | 2040 |
| gagatcgagt | gggtgctgca | gaaggaaaac | agcaaacgct | ggaatcccga | aattcagtac | 2100 |

```
acttccaact acaacaagtc tgttaatgtg gactttactg tggacactaa tggcgtgtat    2160
tcagagcatc gccccattgg caccagatac ctgactcgta atctgtaa                 2208

<210> SEQ ID NO 21
<211> LENGTH: 735
<212> TYPE: PRT
<213> ORGANISM: adeno-associated virus-2

<400> SEQUENCE: 21

Met Ala Ala Asp Gly Tyr Leu Pro Asp Trp Leu Glu Asp Thr Leu Ser
 1               5                  10                  15

Glu Gly Ile Arg Gln Trp Trp Lys Leu Lys Pro Gly Pro Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
    130                 135                 140

Pro Val Glu His Ser Pro Val Glu Pro Asp Ser Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Glu Gln Pro Pro
            180                 185                 190

Ala Ala Pro Ser Gly Leu Gly Thr Asn Thr Met Ala Thr Gly Ser Gly
        195                 200                 205

Ala Pro Met Ala Asp Asn Ile Glu Gly Ala Asp Gly Val Gly Asn Ser
    210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
    290                 295                 300

Gly Phe Arg Pro Lys Arg Leu Asn Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Asp Ser Glu Tyr Gln Leu Pro Tyr
            340                 345                 350
```

```
Val Leu Gly Ser Ala His Gln Gly Cys Leu Pro Phe Pro Glu Asp
            355                 360                 365

Val Phe Met Val Pro Gln Tyr Gly Tyr Leu Thr Leu Asn Asn Gly Ser
    370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
                405                 410                 415

Asp Val Pro Phe His Ser Ser Tyr Ala His Ser Gln Gly Leu Asp Arg
                420                 425                 430

Leu Met Asn Pro Leu Ile Asp Gln Tyr Leu Tyr Tyr Leu Ser Arg Thr
            435                 440                 445

Asn Thr Pro Ser Gly Thr Thr Thr Gln Ser Arg Leu Gln Phe Ser Gln
        450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Glu Asp Asn Asn
                485                 490                 495

Asn Ser Glu Tyr Ser Trp Thr Gly Ala Thr Lys Tyr His Leu Asn Gly
            500                 505                 510

Arg Asp Ser Leu Val Asn Pro Gly Pro Ala Met Ala Ser His Lys Asp
        515                 520                 525

Asp Glu Glu Lys Phe Phe Pro Gln Ser Gly Val Leu Ile Phe Gly Lys
        530                 535                 540

Gln Gly Ser Glu Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
                565                 570                 575

Gly Ser Val Pro Thr Asn Leu Gln Arg Gly Asn Arg Gln Ala Ala Thr
            580                 585                 590

Ala Asp Val Asn Thr Gln Gly Val Leu Pro Gly Met Val Trp Gln Asp
        595                 600                 605

Arg Asp Val Tyr Leu Gln Gly Pro Ile Trp Ala Lys Ile Pro His Thr
    610                 615                 620

Asp Gly His Phe His Pro Ser Pro Leu Met Gly Gly Phe Gly Leu Lys
625                 630                 635                 640

His Pro Leu Pro Gln Ile Leu Ile Lys Asn Thr Pro Val Pro Ala Asn
                645                 650                 655

Pro Ser Thr Thr Phe Ser Ala Ala Lys Phe Ala Ser Phe Ile Thr Gln
            660                 665                 670

Tyr Ser Thr Gly Gln Val Ser Val Glu Ile Glu Trp Val Leu Gln Lys
        675                 680                 685

Glu Asn Ser Lys Arg Trp Asn Pro Glu Ile Gln Tyr Thr Ser Asn Tyr
        690                 695                 700

Asn Lys Ser Val Asn Val Asp Phe Thr Val Asp Thr Asn Gly Val Tyr
705                 710                 715                 720

Ser Glu Pro Arg Pro Ile Gly Thr Arg Tyr Leu Thr Arg Asn Leu
                725                 730                 735

<210> SEQ ID NO 22
<211> LENGTH: 2208
<212> TYPE: DNA
<213> ORGANISM: adeno-associated virus-2

<400> SEQUENCE: 22
```

```
atggctgccg atggttatct tccagattgg ctcgaggaca ctctctctga aggaataagc    60
cagtggtgga agctcaaacc tggcccacca ccaccaaagc ccgcagagcg gcataaggac   120
gacagcaggg gtcttgtgct tcctgggtac aagtacctcg gacccttcag cggactcgac   180
aagggagagc cggtcaacga ggcagacgcc gcggccctcg agcacgacaa agcctacgac   240
cggcagctcg acagcggaga caacccgtac ctcaagtaca ccacgccga cgcggagttt   300
caggagcgcc ttaaagaaga tacgtctttt gggggcaacc tcggacgagc agtcttccag   360
gcgaaaaaga gggttcttga acctctgggc ctggttgagg aacctgttaa gacggctccg   420
ggaaaaaaga ggccggtaga gcactctcct gtggagccag actcctcctc gggaaccgga   480
aaggcgggcc agcagcctgc aagaaaaaga ttgaattttg gtcagactgg agacgcagac   540
tcagtacctg accccagcc tctcggacag ccaccagcag cccctctgg tctgggaact   600
aatacgatgg ctacaggcag tggcgcacca atggcagaca ataacgaggg cgccgacgga   660
gtgggtaatt cctcgggaaa ttggcattgc gattccacat ggatgggcga cagagtcatc   720
accaccagca cccgaacctg ggccctgccc acctacaaca accacctcta caaacaaatt   780
tccagccaat caggagcctc gaacgacaat cactactttg gctacagcac cccttggggg   840
tattttgact tcaacagatt ccactgccac ttttcaccac gtgactggca agactcatc   900
aacaacaact ggggattccg acccaagaga ctcaacttca agctctttaa cattcaagtc   960
aaagaggtca cgcagaatga cggtacgacg acgattgcca ataaccttac cagcacggtt  1020
caggtgttta ctgactcggt gtaccagctc ccgtacgtcc tcggctcggc gcatcaagga  1080
tgcctcccgc cgttcccagc ggacgtcttc atggtgccac agtatggata cctcaccctg  1140
aacaacggga gtcaggcagt aggacgctct tcattttact gcctggagta ctttccttct  1200
cagatgctgc gtaccggaaa caactttacc ttcagctaca cttttgagga cgttcctttc  1260
cacagcagct acgctcacag ccagagtctg gaccgtctca tgaatcctct catcgaccag  1320
tacctgtatt acttgagcag aacaaacact ccaagtggaa ccaccacgca gtcaaggctt  1380
cagttttctc aggccggagc gagtgacatt cggaccagt ctaggaactg gcttcctgga  1440
ccctgttacc gccagcagcg agtatcaaag acatctgagg ataacaacaa cagtgaatac  1500
tcgtggactg gagctaccaa gtaccacctc aatggcagag actctctggt gaatccgggc  1560
ccggccatgg caagccacaa ggacgatgaa gaaaagtttt tccctcagag cggggttctc  1620
atctttggga agcaaggctc agagaaaaca gatgtggaca ttgaaaaggt catgattaca  1680
gacgaagagg aaatcaggac aaccaatccc gtggctacgg agcagtatgg ttctgtatct  1740
accaacctcc agagaggcaa cagacaagca gctaccgcag aggtcaacac acaaggcgtt  1800
cttccaggca tggtctggca ggacagagat gtgtaccttc agggccat ctgggcaaag  1860
attccacaca cggacggaca ttttcacccc tctcccctca tgggtggatt cggacttaaa  1920
caccctcctc acagattct catcaagaac acccgggtac ctgcgaatcc ttcgaccacc  1980
ttcagtgcgg caaagtttgc ttccttcatc acacagtact ccacgggaca ggtcagcgtg  2040
gagatcgagt gggagctgca gaaggaaaac agcaaacgct ggaatcccga aattcagtac  2100
acttccaact acaacaagtc tgttaatgtg gggaatactg tggacactaa tggcgtgtat  2160
tcagagcctc gccccattgg caccagatac ctgactcgta atctgtaa            2208
```

<210> SEQ ID NO 23
<211> LENGTH: 735
<212> TYPE: PRT

<213> ORGANISM: adeno-associated virus-2

<400> SEQUENCE: 23

```
Met Ala Ala Asp Gly Tyr Leu Pro Asp Trp Leu Glu Asp Thr Leu Ser
  1               5                  10                  15
Glu Gly Ile Ser Gln Trp Trp Lys Leu Lys Pro Gly Pro Pro Pro Pro
             20                  25                  30
Lys Pro Ala Glu Arg His Lys Asp Asp Ser Arg Gly Leu Val Leu Pro
         35                  40                  45
Gly Tyr Lys Tyr Leu Gly Pro Phe Ser Gly Leu Asp Lys Gly Glu Pro
     50                  55                  60
Val Asn Glu Ala Asp Ala Ala Leu Glu His Asp Lys Ala Tyr Asp
 65                  70                  75                  80
Arg Gln Leu Asp Ser Gly Asp Asn Pro Tyr Leu Lys Tyr Asn His Ala
                 85                  90                  95
Asp Ala Glu Phe Gln Glu Arg Leu Lys Glu Asp Thr Ser Phe Gly Gly
            100                 105                 110
Asn Leu Gly Arg Ala Val Phe Gln Ala Lys Lys Arg Val Leu Glu Pro
        115                 120                 125
Leu Gly Leu Val Glu Glu Pro Val Lys Thr Ala Pro Gly Lys Lys Arg
    130                 135                 140
Pro Val Glu His Ser Pro Val Glu Pro Asp Ser Ser Ser Gly Thr Gly
145                 150                 155                 160
Lys Ala Gly Gln Gln Pro Ala Arg Lys Arg Leu Asn Phe Gly Gln Thr
                165                 170                 175
Gly Asp Ala Asp Ser Val Pro Asp Pro Gln Pro Leu Gly Gln Pro Pro
            180                 185                 190
Ala Ala Pro Ser Gly Leu Gly Thr Asn Thr Met Ala Thr Gly Ser Gly
        195                 200                 205
Ala Pro Met Ala Asp Asn Asn Glu Gly Ala Asp Gly Val Gly Asn Ser
    210                 215                 220
Ser Gly Asn Trp His Cys Asp Ser Thr Trp Met Gly Asp Arg Val Ile
225                 230                 235                 240
Thr Thr Ser Thr Arg Thr Trp Ala Leu Pro Thr Tyr Asn Asn His Leu
                245                 250                 255
Tyr Lys Gln Ile Ser Ser Gln Ser Gly Ala Ser Asn Asp Asn His Tyr
            260                 265                 270
Phe Gly Tyr Ser Thr Pro Trp Gly Tyr Phe Asp Phe Asn Arg Phe His
        275                 280                 285
Cys His Phe Ser Pro Arg Asp Trp Gln Arg Leu Ile Asn Asn Asn Trp
    290                 295                 300
Gly Phe Arg Pro Lys Arg Leu Asn Phe Lys Leu Phe Asn Ile Gln Val
305                 310                 315                 320
Lys Glu Val Thr Gln Asn Asp Gly Thr Thr Thr Ile Ala Asn Asn Leu
                325                 330                 335
Thr Ser Thr Val Gln Val Phe Thr Asp Ser Val Tyr Gln Leu Pro Tyr
            340                 345                 350
Val Leu Gly Ser Ala His Gln Gly Cys Leu Pro Pro Phe Pro Ala Asp
        355                 360                 365
Val Phe Met Val Pro Gln Tyr Gly Tyr Leu Thr Leu Asn Asn Gly Ser
    370                 375                 380
Gln Ala Val Gly Arg Ser Ser Phe Tyr Cys Leu Glu Tyr Phe Pro Ser
385                 390                 395                 400
```

```
Gln Met Leu Arg Thr Gly Asn Asn Phe Thr Phe Ser Tyr Thr Phe Glu
                405                 410                 415
Asp Val Pro Phe His Ser Ser Tyr Ala His Ser Gln Ser Leu Asp Arg
            420                 425                 430
Leu Met Asn Pro Leu Ile Asp Gln Tyr Leu Tyr Tyr Leu Ser Arg Thr
        435                 440                 445
Asn Thr Pro Ser Gly Thr Thr Thr Gln Ser Arg Leu Gln Phe Ser Gln
    450                 455                 460
Ala Gly Ala Ser Asp Ile Arg Asp Gln Ser Arg Asn Trp Leu Pro Gly
465                 470                 475                 480
Pro Cys Tyr Arg Gln Gln Arg Val Ser Lys Thr Ser Glu Asp Asn Asn
                485                 490                 495
Asn Ser Glu Tyr Ser Trp Thr Gly Ala Thr Lys Tyr His Leu Asn Gly
            500                 505                 510
Arg Asp Ser Leu Val Asn Pro Gly Pro Ala Met Ala Ser His Lys Asp
        515                 520                 525
Asp Glu Glu Lys Phe Phe Pro Gln Ser Gly Val Leu Ile Phe Gly Lys
    530                 535                 540
Gln Gly Ser Glu Lys Thr Asp Val Asp Ile Glu Lys Val Met Ile Thr
545                 550                 555                 560
Asp Glu Glu Glu Ile Arg Thr Thr Asn Pro Val Ala Thr Glu Gln Tyr
                565                 570                 575
Gly Ser Val Ser Thr Asn Leu Gln Arg Gly Asn Arg Gln Ala Ala Thr
            580                 585                 590
Ala Glu Val Asn Thr Gln Gly Val Leu Pro Gly Met Val Trp Gln Asp
        595                 600                 605
Arg Asp Val Tyr Leu Gln Gly Pro Ile Trp Ala Lys Ile Pro His Thr
    610                 615                 620
Asp Gly His Phe His Pro Ser Pro Leu Met Gly Gly Phe Gly Leu Lys
625                 630                 635                 640
His Pro Pro Pro Gln Ile Leu Ile Lys Asn Thr Pro Val Pro Ala Asn
                645                 650                 655
Pro Ser Thr Thr Phe Ser Ala Ala Lys Phe Ala Ser Phe Ile Thr Gln
            660                 665                 670
Tyr Ser Thr Gly Gln Val Ser Val Glu Ile Glu Trp Glu Leu Gln Lys
        675                 680                 685
Glu Asn Ser Lys Arg Trp Asn Pro Glu Ile Gln Tyr Thr Ser Asn Tyr
    690                 695                 700
Asn Lys Ser Val Asn Val Asp Phe Thr Val Asp Thr Asn Gly Val Tyr
705                 710                 715                 720
Ser Glu Pro Arg Pro Ile Gly Thr Arg Tyr Leu Thr Arg Asn Leu
                725                 730                 735
```

<210> SEQ ID NO 24
<211> LENGTH: 2208
<212> TYPE: DNA
<213> ORGANISM: adeno-associated virus-2

<400> SEQUENCE: 24

```
atggctgccg atggttatct tccagattgg ctcgaggaca ctctctctga aggaataaga      60
cagtggtgga agctcagacc tggcccacca ccaccaaagc ccgcagagcg gcataaggac     120
gacagcaggg gtcttgtgct tcctgggtac aagtacctcg gacccttcaa cggactcgac     180
aagggagagc cggtcaacga ggcagacgcc gcggccctcg agcacgacaa agcctacgac     240
```

```
cggcagctcg acagcggaga caacccgtac ctcaagtaca accacgccga cgcggagttt    300
caggagcgcc ttaaagaaga tacgtctttt gggggcaacc tcggacgagc agtcttccag    360
gcgaaaaaga gggttcttga acctctgggc ctggttgagg aacctgttaa gacggctccg    420
ggaaaaaaga ggccgtagag cactctcct gtggagccag actcctcctc gggaaccgga    480
aaggcgggcc agcagcctgc aagaaaaaga ttgaattttg gtcagactgg agacgcagac    540
tcagtacctg accccagcc tctcggacag ccaccagcag cccctctgg tctgggaact    600
aatacgatgg ctacaggcag tggcgcacca atggcagaca atgacgaggg cgccgacgga    660
gtgggtaatt cctcgggaaa ttggcattgc gattccacat ggatgggcga cagagtcatc    720
accaccagca cccgaacctg ggccctgccc acctacaaca accacctcta caagcaaatt    780
tccagccaat caggagcctc gaacgacaat cactactttg ctacagcac cccttggggg    840
tattttgact tcaacagatt ccactgccac ttttcaccac gtgactggca agactcatc    900
aacaacaact ggggattccg acccaagaga ctcaacttca agctctttaa cattcaagtc    960
aaagaggtca cgcagaatga cggtacgacg acgattgcca taaccttac cagcacggtt   1020
caggtgttta ctgactcgga gtaccagctc ccgtacgtcc tcagctcggc gcatcaagga   1080
tgcctcccgc cgttcccagc agacgtcttc atggtgccac agtatggata cctcaccctg   1140
aacaacggga gtcaggcagt aggacgctct tcattttact gcctggagta ctttcctcct   1200
cagatgctgc gtaccggaaa caactttacc ttcagctaca cttttgagga cgttcctttc   1260
cacagcagct acgctcacag ccagagtctg gaccgtctca tgaatcctct catcgaccag   1320
tacctgtatt acttgagcag aacaaacact ccaagtggaa ccaccacgca gtcaaggctt   1380
cagttttctc aggccggagc gagtgacatt cgggaccagt ctaggaactg gcttcctgga   1440
ccctgttacc gccagcagcg agtatcaaag acatctgcgg ataacaacaa cagtgaatac   1500
tcgtggactg gagctaccaa gtaccacctc aatggcagag actctctggt gaatccgggc   1560
ccggccatgg caagccacaa ggacgatgaa gaaaagtttt tccctcagag cggggttctc   1620
atctttggga agcaaggctc agagaaaaca aatgtggaca ttgaaaaggt catgattaca   1680
gacgaagagg aaatcaggac aaccaatccc gtggctacgg agcagtatgg ttctgtatct   1740
accaacctcc agagaggcaa cagacaagca gctaccgaag atgtcaacac tcaaggcgtt   1800
cttccaggca tggtctggca ggacagagat gtgtaccttc aggggcccat ctgggcaaag   1860
attccacaca cggacggaca ttttcacccc tctcccctca tgggtggatt cggacttaaa   1920
caccctcctc cacagattct catcaagaac cccggtac ctgcgaatcc ttcgaccacc   1980
ttcagtgcgg caaagtttgc ttccttcatc acacagtact ccacgggaca ggtcagcgtg   2040
gagatcgagt gggagctaca gaaggaaaac agcaaacgct ggaatcccga aattcagtac   2100
acttccaact acaacaagtc tgttaatgtg gactttactg tggacactaa tggcgtgtat   2160
tcagagcctc gccccattgg caccagatac ctgactcgta atctgtaa            2208
```

<210> SEQ ID NO 25
<211> LENGTH: 735
<212> TYPE: PRT
<213> ORGANISM: adeno-associated virus-2

<400> SEQUENCE: 25

Met Ala Ala Asp Gly Tyr Leu Pro Asp Trp Leu Glu Asp Thr Leu Ser
1               5                   10                  15

Glu Gly Ile Arg Gln Trp Trp Lys Leu Arg Pro Gly Pro Pro Pro Pro
            20                  25                  30

```
Lys Pro Ala Glu Arg His Lys Asp Asp Ser Arg Gly Leu Val Leu Pro
         35                  40                  45

Gly Tyr Lys Tyr Leu Gly Pro Phe Asn Gly Leu Asp Lys Gly Glu Pro
 50                  55                  60

Val Asn Glu Ala Asp Ala Ala Leu Glu His Asp Lys Ala Tyr Asp
 65              70                  75                  80

Arg Gln Leu Asp Ser Gly Asp Asn Pro Tyr Leu Lys Tyr Asn His Ala
             85                  90                  95

Asp Ala Glu Phe Gln Glu Arg Leu Lys Glu Asp Thr Ser Phe Gly Gly
                100                 105                 110

Asn Leu Gly Arg Ala Val Phe Gln Ala Lys Lys Arg Val Leu Glu Pro
            115                 120                 125

Leu Gly Leu Val Glu Glu Pro Val Lys Thr Ala Pro Gly Lys Lys Arg
130                 135                 140

Pro Val Glu His Ser Pro Val Glu Pro Asp Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
            195                 200                 205

Ala Pro Met Ala Asp Asn Asp Glu Gly Ala Asp Gly Val Gly Asn Ser
210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
            275                 280                 285

Cys His Phe Ser Pro Arg Asp Trp Gln Arg Leu Ile Asn Asn Asn Trp
290                 295                 300

Gly Phe Arg Pro Lys Arg Leu Asn Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Ser Ser Ala His Gln Gly Cys Leu Pro Pro Phe Pro Ala Asp
            355                 360                 365

Val Phe Met Val Pro Gln Tyr Gly Tyr Leu Thr Leu Asn Asn Gly Ser
370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
                405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Ser Arg Thr
            435                 440                 445
```

```
Asn Thr Pro Ser Gly Thr Thr Thr Gln Ser Arg Leu Gln Phe Ser Gln
        450                 455                 460
Ala Gly Ala Ser Asp Ile Arg Asp Gln Ser Arg Asn Trp Leu Pro Gly
465                 470                 475                 480
Pro Cys Tyr Arg Gln Gln Arg Val Ser Lys Thr Ser Ala Asp Asn Asn
                485                 490                 495
Asn Ser Glu Tyr Ser Trp Thr Gly Ala Thr Lys Tyr His Leu Asn Gly
            500                 505                 510
Arg Asp Ser Leu Val Asn Pro Gly Pro Ala Met Ala Ser His Lys Asp
        515                 520                 525
Asp Glu Glu Lys Phe Phe Pro Gln Ser Gly Val Leu Ile Phe Gly Lys
530                 535                 540
Gln Gly Ser Glu Lys Thr Asn Val Asp Ile Glu Lys Val Met Ile Thr
545                 550                 555                 560
Asp Glu Glu Glu Ile Arg Thr Thr Asn Pro Val Ala Thr Glu Gln Tyr
                565                 570                 575
Gly Ser Val Ser Thr Asn Leu Gln Arg Gly Asn Arg Gln Ala Ala Thr
            580                 585                 590
Glu Asp Val Asn Thr Gln Gly Val Leu Pro Gly Met Val Trp Gln Asp
        595                 600                 605
Arg Asp Val Tyr Leu Gln Gly Pro Ile Trp Ala Lys Ile Pro His Thr
610                 615                 620
Asp Gly His Phe His Pro Ser Pro Leu Met Gly Gly Phe Gly Leu Lys
625                 630                 635                 640
His Pro Pro Pro Gln Ile Leu Ile Lys Asn Thr Pro Val Pro Ala Asn
                645                 650                 655
Pro Ser Thr Thr Phe Ser Ala Ala Lys Phe Ala Ser Phe Ile Thr Gln
            660                 665                 670
Tyr Ser Thr Gly Gln Val Ser Val Glu Ile Glu Trp Glu Leu Gln Lys
        675                 680                 685
Glu Asn Ser Lys Arg Trp Asn Pro Glu Ile Gln Tyr Thr Ser Asn Tyr
690                 695                 700
Asn Lys Ser Val Asn Val Asp Phe Thr Val Asp Thr Asn Gly Val Tyr
705                 710                 715                 720
Ser Glu Pro Arg Pro Ile Gly Thr Arg Tyr Leu Thr Arg Asn Leu
                725                 730                 735

<210> SEQ ID NO 26
<211> LENGTH: 2208
<212> TYPE: DNA
<213> ORGANISM: adeno-associated virus-2

<400> SEQUENCE: 26
atggctgccg atggttatct tccagattgg ctcgaggaca ctctctctga aggaataaga       60
cagtggtgga agctcaaacc tggcccacca ccaccaaagc ccgcagagcg gcataaggac      120
gacagcaggg gtcttgtgct tcctgagtac aagtacctcg gacccttcaa cggactcgac      180
aagggagagc cggtcaacga ggcagacgcc gcggccctcg agcacgacaa agcctacgac      240
cggcagctcg acagcggaga caacccgtac ctcaagtaca accacgccga cgcggagttt      300
caggagcgcc ttaaagaaga tacgtctttt ggggggcaacc tcggacgagc agtcttccag      360
gcgaaaaaga gggttcttga acctctgggc ctggttgagg aacctgttaa gacggctccg      420
ggaaaaaaga ggccggtaga gcactctcct gtggagccag actcctcctc gggaaccgga      480
aaggcgggcc agcagcctgc aagaaaaaga ttgaattttg gtcagactgg agacgcagac      540
```

```
tcagtacctg accccagcc tctcggacag ccaccagcag ccccccctgg tctgggaact    600
aatacgatgg ctacaggcag tggcgcacca atggcagaca ataacgaggg cgccgacgga    660
gtgggtaatt cctcgggaaa ttggcattgc gattccacat ggatgggcga cagagtcatc    720
accaccagca cccgaacctg ggccctgccc acctacaaca accacctcta caacaaaatt    780
tccagccaat caggagcctc gaacgacaat cactactttg ctacagcac cccttggggg    840
tattttgact tcaacagatt ccactgccac ttttcaccac gtgactggca agactcatc    900
aacaacaact ggggattccg acccaagaga ctcaacttca gctctttaa cattcaagtc    960
aaagaggtca cgcagaatga cggtacgacg acgattgcca ataaccttcc cagcacggta   1020
caggtgttta ctgactcgga gtaccagctc ccgtacgtcc tcggctcggc catcaagga   1080
tgcctcccgc cgttcccagc agacgtcttc atggtgccac agtatggata cctcaccctg   1140
aacaacggga gtcaggcagt aggacgctct tcatttact gcctggagta ctttccttct   1200
cagatgctgc gtaccggaag caactttacc ttcagctaca cttttgagga cgttcctttc   1260
cacagcagct acgctcacag ccagagtctg accgtctca tgaatcctct catcgaccag   1320
tacctgtatt acttgagcag aacaaacact ccaagtggaa ccaccacgca gtcaaggctt   1380
cagtttctc aggccggagc gagtgacatt cgggaccagt ctaggaactg gcttcctgga   1440
ccctgttacc gccagcagcg agtatcaaag acatctgagg ataacaacaa cagtgaatac   1500
tcgtggactg gagctaccaa gtaccacctc aatggcagag actctctggt gaatccgggc   1560
ccggccatgg caagccacaa ggacgatgaa gaaaagtttt tcctcagag cggggttctc   1620
atccttggga agcaaggctc agagaaaaca atgtggaca ttgaaaaggt catgattaca   1680
gacgaagagg aaatcaggac aaccaatccc gtggctacgg agcagtatgg ttctgtatct   1740
accaacctcc agagaggcaa cagacaagca gctaccgcag atgtcaacac acaaggcgtt   1800
cttccaggca tggtctggca ggacagagat gtgtaccttc aggggcccat ctgggcaaag   1860
attccacaca cggacggaca ttttcacccc tctcccctca tgggtggatt cggacttaaa   1920
caccctcctc acagattct catcaagaac accccggtac ctgcgaatcc ttcgaccacc   1980
ttcagtgcgg caaagtttgc ttccttcatc acacagtatt ccacgggaca ggtcagcgtg   2040
gagatcgagt ggaagctgca gaaggaaaac agcaaacgct ggaatccga aattcagtac   2100
acttccaact acaacaagtc tgttaatgtg gagtttactg tggacactaa tggcgtgtat   2160
tcagagcctc gccccattgg caccagatac ctgactcgta atctgtaa             2208
```

<210> SEQ ID NO 27
<211> LENGTH: 735
<212> TYPE: PRT
<213> ORGANISM: adeno-associated virus-2

<400> SEQUENCE: 27

```
Met Ala Ala Asp Gly Tyr Leu Pro Asp Trp Leu Glu Asp Thr Leu Ser
 1               5                  10                  15

Glu Gly Ile Arg Gln Trp Trp Lys Leu Lys Pro Gly Pro Pro Pro Pro
            20                  25                  30

Lys Pro Ala Glu Arg His Lys Asp Asp Ser Arg Gly Leu Val Leu Pro
        35                  40                  45

Glu Tyr Lys Tyr Leu Gly Pro Phe Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80
```

-continued

```
Arg Gln Leu Asp Ser Gly Asp Asn Pro Tyr Leu Lys Tyr Asn His Ala
                85              90               95

Asp Ala Glu Phe Gln Glu Arg Leu Lys Glu Asp Thr Ser Phe Gly Gly
            100             105             110

Asn Leu Gly Arg Ala Val Phe Gln Ala Lys Lys Arg Val Leu Glu Pro
        115             120             125

Leu Gly Leu Val Glu Pro Val Lys Thr Ala Pro Gly Lys Lys Arg
    130             135             140

Pro Val Glu His Ser Pro Val Glu Pro Asp Ser Ser Gly Thr Gly
145             150             155             160

Lys Ala Gly Gln Gln Pro Ala Arg Lys Arg Leu Asn Phe Gly Gln Thr
                165             170             175

Gly Asp Ala Asp Ser Val Pro Asp Pro Gln Pro Leu Gly Gln Pro Pro
            180             185             190

Ala Ala Pro Pro Gly Leu Gly Thr Asn Thr Met Ala Thr Gly Ser Gly
        195             200             205

Ala Pro Met Ala Asp Asn Asn Glu Gly Ala Asp Gly Val Gly Asn Ser
    210             215             220

Ser Gly Asn Trp His Cys Asp Ser Thr Trp Met Gly Asp Arg Val Ile
225             230             235             240

Thr Thr Ser Thr Arg Thr Trp Ala Leu Pro Thr Tyr Asn Asn His Leu
                245             250             255

Tyr Lys Gln Ile Ser Ser Gln Ser Gly Ala Ser Asn Asp Asn His Tyr
            260             265             270

Phe Gly Tyr Ser Thr Pro Trp Gly Tyr Phe Asp Phe Asn Arg Phe His
        275             280             285

Cys His Phe Ser Pro Arg Asp Trp Gln Arg Leu Ile Asn Asn Asn Trp
    290             295             300

Gly Phe Arg Pro Lys Arg Leu Asn Phe Lys Leu Phe Asn Ile Gln Val
305             310             315             320

Lys Glu Val Thr Gln Asn Asp Gly Thr Thr Thr Ile Ala Asn Asn Leu
                325             330             335

Pro Ser Thr Val Gln Val Phe Thr Asp Ser Glu Tyr Gln Leu Pro Tyr
            340             345             350

Val Leu Gly Ser Ala His Gln Gly Cys Leu Pro Pro Phe Pro Ala Asp
        355             360             365

Val Phe Met Val Pro Gln Tyr Gly Tyr Leu Thr Leu Asn Asn Gly Ser
    370             375             380

Gln Ala Val Gly Arg Ser Ser Phe Tyr Cys Leu Glu Tyr Phe Pro Ser
385             390             395             400

Gln Met Leu Arg Thr Gly Asn Asn Phe Thr Phe Ser Tyr Thr Phe Glu
                405             410             415

Asp Val Pro Phe His Ser Ser Tyr Ala His Ser Gln Ser Leu Asp Arg
            420             425             430

Leu Met Asn Pro Leu Ile Asp Gln Tyr Leu Tyr Tyr Leu Ser Arg Thr
        435             440             445

Asn Thr Pro Ser Gly Thr Thr Thr Gln Ser Arg Leu Gln Phe Ser Gln
    450             455             460

Ala Gly Ala Ser Asp Ile Arg Asp Gln Ser Arg Asn Trp Leu Pro Gly
465             470             475             480

Pro Cys Tyr Arg Gln Gln Arg Val Ser Lys Thr Ser Ala Asp Asn Asn
                485             490             495
```

```
Asn Ser Glu Tyr Ser Trp Thr Gly Ala Thr Lys Tyr His Leu Asn Gly
                500                 505                 510
Arg Asp Ser Leu Val Asn Pro Gly Pro Ala Met Ala Ser His Lys Asp
            515                 520                 525
Asp Glu Glu Lys Phe Phe Pro Gln Ser Gly Val Leu Ile Phe Gly Lys
        530                 535                 540
Gln Gly Ser Glu Lys Thr Asn Val Asp Ile Glu Lys Val Met Ile Thr
545                 550                 555                 560
Asp Glu Glu Glu Ile Arg Thr Thr Asn Pro Val Ala Thr Glu Gln Tyr
                565                 570                 575
Gly Ser Val Ser Thr Asn Leu Gln Arg Gly Asn Arg Gln Ala Ala Thr
            580                 585                 590
Ala Asp Val Asn Thr Gln Gly Val Leu Pro Gly Met Val Trp Gln Asp
        595                 600                 605
Arg Asp Val Tyr Leu Gln Gly Pro Ile Trp Ala Lys Ile Pro His Thr
610                 615                 620
Asp Gly His Phe His Pro Ser Pro Leu Met Gly Gly Phe Gly Leu Lys
625                 630                 635                 640
His Pro Pro Pro Gln Ile Leu Ile Lys Asn Thr Pro Val Pro Ala Asn
                645                 650                 655
Pro Ser Thr Thr Phe Ser Ala Ala Lys Phe Ala Ser Phe Ile Thr Gln
            660                 665                 670
Tyr Ser Thr Gly Gln Val Ser Val Glu Ile Glu Trp Glu Leu Gln Lys
        675                 680                 685
Glu Asn Ser Lys Arg Trp Asn Pro Glu Ile Gln Tyr Thr Ser Asn Tyr
690                 695                 700
Asn Lys Ser Val Asn Val Asp Phe Thr Val Asp Thr Asn Gly Val Tyr
705                 710                 715                 720
Ser Glu Pro Arg Pro Ile Gly Thr Arg Tyr Leu Thr Arg Asn Leu
                725                 730                 735

<210> SEQ ID NO 28
<211> LENGTH: 2208
<212> TYPE: DNA
<213> ORGANISM: adeno-associated virus-2

<400> SEQUENCE: 28
atggctgccg atggttatct tccagattgg ctcgaggaca ctctctctga aggaataaga      60
cagtggtggg agctcaaacc tggcccacca ccaccaaagc ccgcagagcg gcataaggac     120
gacagcaggg gtcttgtgct tcctgggtac aagtacctcg gacccttcaa cggactcgac     180
aagggagagc cggtcaacga ggcagacgcc gcggccctcg agcacgacaa agcctacgac     240
cggcagctcg acagcggaga caacccgtac cccaagtaca accacgccga cgcggagttt     300
caggagcgcc ttaaagaaga tacgtctttt gggggcaacc tcggacgagc agtcttccag     360
gcgaaaaaaa gggttcttga acctctgggc ctggttgagg aacctgttac gacggctccg     420
ggaaaaaaga ggccggtaga gcactctcct gtggagccag actcctcctc gggaaccgga     480
aaggcgggcc agcagcctgc aagaaaaaga ttgaattttg gtcagactgg agacgcagac     540
tcagtacctg acccctgcc tctcggacag ccaccagcag cccctctgg tctgggaact     600 aatacgatgg ctacaggcag tggcgcacca atggcagaca ataacgaggg cgccgacgga     660
gtgggtaatt cctcgggaaa ttggcattgc gattccacat ggatgggcga cagagtcatc     720
accaccagca cccgaacctg ggccctgccc gcctacaaca accacctcta caaacaaatt     780
```

```
tccagccaat caggagcctc gaacgacaat cactactttg gctacagcac cccttggggg    840
tattttgact tcaacagatt ccactgcctc ttttcaccac gtgactggca aagactcatc    900
aacaacaact ggggactccg acccaagaga ctcaacttca agctctttaa cattcaagtc    960
aaagaggtca cgcagaatga cggtacgacg acgattgcca ataaccttac cagcacggtt   1020
caggtgttta ctgactcgga gtaccagctc ccgtacgtcc tcggctcggc gcatcaagga   1080
tgcctcccgc cgttcccagc agacgtcttc atggtgccac agtatggata cctcacccctg 1140
aacaacggga gtcaggcagt aggacgcact tcattttact gcctggagta ctttcctcct   1200
cagatgctgc gtaccggaaa caactttacc ttcagctaca cttttgagga cgttcctttc   1260
cacagcagct acgctcacag ccagagtctg gaccgtctca tgaatcctct catcgaccag   1320
tacctgtatt acttgagcag aacaaacact ccaagtggaa ccaccacgca gtcaaggctt   1380
cagttttctc aggccggagc gagtgacatt cgggaccagt ctaggaactg gcttcctgga   1440
ccctgttacc gccagcagcg agtatcaaag acatctgagg ataacaacaa cagtgaatac   1500
tcgtggactg gagttaccaa gtaccacctc aatggcagag actctctggt gaatccgggc   1560
ccggccatgg caagccacaa ggacgatgaa gaaaagtttt ttcctcagag cggggttctc   1620
atctttggga agcaaggctc agagaaaaca aatgtggaca ttgaaaagat catgattaca   1680
gacgaagagg aaatcaggac aaccaatccc gtggctacgg agcagtatgg ttctgtatct   1740
accaacctcc agagaggcaa cagacaagca gctaccgcag atgtcaacac acaaggcgtt   1800
cttccaggca tggtctggca ggacagagat gtgtaccttc aggggcccat ctgggcaaag   1860
attccacaca cggacggaca ttttcacccc tctcccctca gggtggatt cggacttaaa    1920
caccctcctc acagattct catcaagaac gccccggtac ctgcgaatcc ttcgaccacc    1980
ttcagtgcgg caaagtttgc ttccttcatc acacagtact ccacgggaca ggtcagcgtg   2040
gagatcgagt gggagctgca gaaggaaaac agcaaacgct ggaatccga aattcagtac    2100
acttccaact acaacaagtc tgttaatgtg gactttactg tggacactaa tggcgtgtat   2160
tcagagcctc gccccattgg caccagatac ctgactcgta atctgtaa                2208
```

<210> SEQ ID NO 29
<211> LENGTH: 735
<212> TYPE: PRT
<213> ORGANISM: adeno-associated virus-2

<400> SEQUENCE: 29

```
Met Ala Ala Asp Gly Tyr Leu Pro Asp Trp Leu Glu Asp Thr Leu Ser
 1               5                  10                  15

Glu Gly Ile Arg Gln Trp Trp Glu Leu Lys Pro Gly Pro Pro Pro Pro
             20                  25                  30

Lys Pro Ala Glu Arg His Lys Asp Asp Ser Arg Gly Leu Val Leu Pro
         35                  40                  45

Gly Tyr Lys Tyr Leu Gly Pro Phe Asn Gly Leu Asp Lys Gly Glu Pro
     50                  55                  60

Val Asn Glu Ala Asp Ala Ala Leu Glu His Asp Lys Ala Tyr Asp
 65                  70                  75                  80

Arg Gln Leu Asp Ser Gly Asp Asn Pro Tyr Pro Lys Tyr Asn His Ala
                 85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125
```

-continued

```
Leu Gly Leu Val Glu Glu Pro Val Thr Thr Ala Pro Gly Lys Lys Arg
    130                 135                 140
Pro Val Glu His Ser Pro Val Glu Pro Asp Ser Ser Ser Gly Thr Gly
145                 150                 155                 160
Lys Ala Gly Gln Gln Pro Ala Arg Lys Arg Leu Asn Phe Gly Gln Thr
                165                 170                 175
Gly Asp Ala Asp Ser Val Pro Asp Pro Leu Pro Leu Gly Gln Pro Pro
            180                 185                 190
Ala Ala Pro Ser Gly Leu Gly Thr Asn Thr Met Ala Thr Gly Ser Gly
        195                 200                 205
Ala Pro Met Ala Asp Asn Asn Glu Gly Ala Asp Gly Val Gly Asn Ser
210                 215                 220
Ser Gly Asn Trp His Cys Asp Ser Thr Trp Met Gly Asp Arg Val Ile
225                 230                 235                 240
Thr Thr Ser Thr Arg Thr Trp Ala Leu Pro Ala Tyr Asn Asn His Leu
                245                 250                 255
Tyr Lys Gln Ile Ser Ser Gln Ser Gly Ala Ser Asn Asp Asn His Tyr
                260                 265                 270
Phe Gly Tyr Ser Thr Pro Trp Gly Tyr Phe Asp Phe Asn Arg Phe His
            275                 280                 285
Cys Leu Phe Ser Pro Arg Asp Trp Gln Arg Leu Ile Asn Asn Asn Trp
        290                 295                 300
Gly Leu Arg Pro Lys Arg Leu Asn Phe Lys Leu Phe Asn Ile Gln Val
305                 310                 315                 320
Lys Glu Val Thr Gln Asn Asp Gly Thr Thr Thr Ile Ala Asn Asn Leu
                325                 330                 335
Thr Ser Thr Val Gln Val Phe Thr Asp Ser Glu Tyr Gln Leu Pro Tyr
            340                 345                 350
Val Leu Gly Ser Ala His Gln Gly Cys Leu Pro Pro Phe Pro Ala Asp
        355                 360                 365
Val Phe Met Val Pro Gln Tyr Gly Tyr Leu Thr Leu Asn Asn Gly Ser
    370                 375                 380
Gln Ala Val Gly Arg Thr Ser Phe Tyr Cys Leu Glu Tyr Phe Pro Ser
385                 390                 395                 400
Gln Met Leu Arg Thr Gly Asn Asn Phe Thr Phe Ser Tyr Thr Phe Glu
                405                 410                 415
Asp Val Pro Phe His Ser Ser Tyr Ala His Ser Gln Ser Leu Asp Arg
            420                 425                 430
Leu Met Asn Pro Leu Ile Asp Gln Tyr Leu Tyr Tyr Leu Ser Arg Thr
        435                 440                 445
Asn Thr Pro Ser Gly Thr Thr Thr Gln Ser Arg Leu Gln Phe Ser Gln
    450                 455                 460
Ala Gly Ala Ser Asp Ile Arg Asp Gln Ser Arg Asn Trp Leu Pro Gly
465                 470                 475                 480
Pro Cys Tyr Arg Gln Gln Arg Val Ser Lys Thr Ser Glu Asp Asn Asn
                485                 490                 495
Asn Ser Glu Tyr Ser Trp Thr Gly Val Thr Lys Tyr His Leu Asn Gly
            500                 505                 510
Arg Asp Ser Leu Val Asn Pro Gly Pro Ala Met Ala Ser His Lys Asp
        515                 520                 525
Asp Glu Glu Lys Phe Phe Pro Gln Ser Gly Val Leu Ile Phe Gly Lys
    530                 535                 540
```

Gln Gly Ser Glu Lys Thr Asn Val Asp Ile Glu Lys Ile Met Ile Thr
545                 550                 555                 560

Asp Glu Glu Ile Arg Thr Thr Asn Pro Val Ala Thr Glu Gln Tyr
            565                 570                 575

Gly Ser Val Ser Thr Asn Leu Gln Arg Gly Asn Arg Gln Ala Ala Thr
            580                 585                 590

Ala Asp Val Asn Thr Gln Gly Val Leu Pro Gly Met Val Trp Gln Asp
            595                 600                 605

Arg Asp Val Tyr Leu Gln Gly Pro Ile Trp Ala Lys Ile Pro His Thr
            610                 615                 620

Asp Gly His Phe His Pro Ser Pro Leu Met Gly Gly Phe Gly Leu Lys
625                 630                 635                 640

His Pro Pro Pro Gln Ile Leu Ile Lys Asn Ala Pro Val Pro Ala Asn
                645                 650                 655

Pro Ser Thr Thr Phe Ser Ala Ala Lys Phe Ala Ser Phe Ile Thr Gln
            660                 665                 670

Tyr Ser Thr Gly Gln Val Ser Val Glu Ile Glu Trp Glu Leu Gln Lys
            675                 680                 685

Glu Asn Ser Lys Arg Trp Asn Pro Glu Ile Gln Tyr Thr Ser Asn Tyr
690                 695                 700

Asn Lys Ser Val Asn Val Asp Phe Thr Val Asp Thr Asn Gly Val Tyr
705                 710                 715                 720

Ser Glu Pro Arg Pro Ile Gly Thr Arg Tyr Leu Thr Arg Asn Leu
                725                 730                 735

<210> SEQ ID NO 30
<211> LENGTH: 2208
<212> TYPE: DNA
<213> ORGANISM: adeno-associated virus-2

<400> SEQUENCE: 30
atggctgccg atggttatct tccagattgg ctcgaggaca ctctctctga aggaataaga        60
cagtggtgga agctcaaacc tggcccacca ccaccaaagc ccgcagagcg gcataaggac       120
gacagcaggg gtcttgcgct tcctgggtac aagtacctcg gacccttcaa cggactcgac       180
aagggagagc cggtcaacga ggcagacgcc gcggccctcg agcacgacaa agcctacgac       240
cggcagctcg acagcggaga caacccgtac ctcaagtaca accacgccga cgcggagttt       300
caggagcgcc ttaaagaaga tacgtctttt gggggcaacc tcggacgagc agtcttccag       360
gcgaaaaaga gggttcttga acctctgggc ctggttgagg aacctgttaa gacggctccg       420
ggaaaaaaga ggccggtaga gcactctcct gtggagccag actcctcctc gggaaccgga       480
aaggcgggcc agcagcctgc aagaaaaaga ttgaattttg gtcagactgg agacgcagac       540
tcagtacctg acccccagcc tctcggacag ccaccagcag ccccccctgg tctgggaact       600
aatacgatgg ctacaggcag tggcgcacca atggcagaca ataacgaggg cgccgacgga       660
gtgggtaatt cctcgggaaa ttggcattgc gattccacat ggatgggcga cagagtcatc       720
accaccagca cccgaacctg gcccctgccc acctacaaca accacctcta caaacaaatt       780
tccagccaat caggagcctc gaacgacaat cactactttg gctacagcac cccttggggg       840
tattttgact tcaacagatt ccactgccac ttttcaccac gtgactggca aagactcatc       900
aacaacaact ggggattccg acccagaga ctcaacttca agctctttaa cattcaagtc       960
aaagaggtca cgcagaatga cggtacgacg acgattgcca ataacctta cagcacggtt      1020 caggtgttta ctgactcgga gtaccagctc ccgtacgtcc tcggctcggc gcatcaagga      1080

```
tgcctcccgc cgttcccagc agacgtcttc atggtgccac agtatggata cctcaccctg   1140
aacaacggga gtcaggcagt aggacgctct tcattttact gcctggagta ctttccttct   1200
cagatgctac gtaccggaaa caactttacc ttcagctaca cttttgagga cgttcctttc   1260
cacagcagct acgctcacag ccagagtctg gaccgtctca tgaatcctct catcgaccag   1320
tacctgtatt acttgagcag aacaaacact ccaagtggaa ccaccacgca gtcaaggctt   1380
cagttttctc aggccggagc gagtgacatt cgggaccagt ctaggaactg gcttcctgga   1440
ccctgttacc gccagcagcg agtatcaaag acatctgcgg ataacaacaa cagtgaatac   1500
tcgtggactg gagctaccaa gtaccactcc aatggcagag actctctggt gaatccgggc   1560
ccggccatgg caagccacaa ggacgatgaa gaaaagtttt tccctcagag cggggttctc   1620
atctttggga agcaaggctc agagaaaaca aatgtggaca ttgaaaaggt catgattaca   1680
gacgaagagg aaatcaggac aaccaatccc gtggctacgg agcagtatgg ttctgtatct   1740
accaacctcc agagaggcaa cagacaagca gctaccgaag atgtcaacac tcaaggcgtt   1800
cttccaggca tggtctggca ggacagagat gtgtaccttc agggccccat ctgggcaaag   1860
attccacaca cggacggaca ttttcacccc tctcccctca tgggtggatt cggacttaaa   1920
caccctcctc cacagattct catcaagaac accccggtac ctgcgaatcc ttcgaccacc   1980
ttcagtgcgg caaagtttgc ttccttcatc acacagtact ccacgggaca ggtcagcgtg   2040
gagatcgagt gggagctgca gaaggaaaac agcaaacgct ggaatcccga aattcagtac   2100
acttctaact acaacaagtc tgttaatgtg gactttactg tggacactaa tggcgtgtat   2160
tcagagcctc gccccattgg caccagatac ctgactcgta atctgtaa               2208
```

<210> SEQ ID NO 31
<211> LENGTH: 735
<212> TYPE: PRT
<213> ORGANISM: adeno-associated virus-2

<400> SEQUENCE: 31

```
Met Ala Ala Asp Gly Tyr Leu Pro Asp Trp Leu Glu Asp Thr Leu Ser
 1               5                  10                  15

Glu Gly Ile Arg Gln Trp Trp Lys Leu Lys Pro Gly Pro Pro Pro
            20                  25                  30

Lys Pro Ala Glu Arg His Lys Asp Asp Ser Arg Gly Leu Ala Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
    130                 135                 140

Pro Val Glu His Ser Pro Val Glu Pro Asp Ser Ser Ser Gly Thr Gly
145                 150                 155                 160

Lys Ala Gly Gln Gln Pro Ala Arg Lys Arg Leu Asn Phe Gly Gln Thr
                165                 170                 175
```

```
Gly Asp Ala Asp Ser Val Pro Asp Pro Gln Pro Leu Gly Gln Pro Pro
            180                 185                 190

Ala Ala Pro Pro Gly Leu Gly Thr Asn Thr Met Ala Thr Gly Ser Gly
            195                 200                 205

Ala Pro Met Ala Asp Asn Asn Glu Gly Ala Asp Gly Val Gly Asn Ser
            210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
                260                 265                 270

Phe Gly Tyr Ser Thr Pro Trp Gly Tyr Phe Asp Phe Asn Arg Phe His
            275                 280                 285

Cys His Phe Ser Pro Arg Asp Trp Gln Arg Leu Ile Asn Asn Asn Trp
            290                 295                 300

Gly Phe Arg Pro Lys Arg Leu Asn Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
            355                 360                 365

Val Phe Met Val Pro Gln Tyr Gly Tyr Leu Thr Leu Asn Asn Gly Ser
            370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
                405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Ser Arg Thr
            435                 440                 445

Asn Thr Pro Ser Gly Thr Thr Thr Gln Ser Arg Leu Gln Phe Ser Gln
450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
                485                 490                 495

Asn Ser Glu Tyr Ser Trp Thr Gly Ala Thr Lys Tyr His Leu Asn Gly
            500                 505                 510

Arg Asp Ser Leu Val Asn Pro Gly Pro Ala Met Ala Ser His Lys Asp
515                 520                 525

Asp Glu Glu Lys Phe Phe Pro Gln Ser Gly Val Leu Ile Phe Gly Lys
            530                 535                 540

Gln Gly Ser Glu Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
                565                 570                 575

Gly Ser Val Ser Thr Asn Leu Gln Arg Gly Asn Arg Gln Ala Ala Thr
            580                 585                 590
```

```
Glu Asp Val Asn Thr Gln Gly Val Leu Pro Gly Met Val Trp Gln Asp
            595                 600                 605
Arg Asp Val Tyr Leu Gln Gly Pro Ile Trp Ala Lys Ile Pro His Thr
        610                 615                 620
Asp Gly His Phe His Pro Ser Pro Leu Met Gly Gly Phe Gly Leu Lys
625                 630                 635                 640
His Pro Pro Pro Gln Ile Leu Ile Lys Asn Thr Pro Val Pro Ala Asn
                645                 650                 655
Pro Ser Thr Thr Phe Ser Ala Ala Lys Phe Ala Ser Phe Ile Thr Gln
            660                 665                 670
Tyr Ser Thr Gly Gln Val Ser Val Glu Ile Glu Trp Glu Leu Gln Lys
        675                 680                 685
Glu Asn Ser Lys Arg Trp Asn Pro Glu Ile Gln Tyr Thr Ser Asn Tyr
    690                 695                 700
Asn Lys Ser Val Asn Val Asp Phe Thr Val Asp Thr Asn Gly Val Tyr
705                 710                 715                 720
Ser Glu Pro Arg Pro Ile Gly Thr Arg Tyr Leu Thr Arg Asn Leu
                725                 730                 735

<210> SEQ ID NO 32
<211> LENGTH: 2208
<212> TYPE: DNA
<213> ORGANISM: adeno-associated virus-2

<400> SEQUENCE: 32
atggctgccg atggttatct tccagattgg ctcgaggaca ctctctctga gggaataaga     60
cagtggtgga agctcaaacc tggcccacca ctaccaaagc ccgcagagcg gcataaggac    120
gacagcaggg gtcttgtgct tcctgggtac aagtacctcg acccttcaa cggactcgac    180 aagggagagc cggtcaacga ggcagacgcc gcggccctcg agcacgacaa agcctacgac    240
cggcagctcg acagcggaga caacccgtac ctcaagtaca accacgccga cgcggagtct    300
caggagcgcc ttaaagaaga tacgtctttt gggggcaacc tcggacgagc agtcttccag    360
gcgaaaaaga gggttcttga acctctgggc ctggttgagg aacctgttaa gacggctccg    420
ggaaaaaaga ggccggtaga gcactctcct gtggagccag actcctcctc gggacccgga    480
aaggcgggcc agcagcctgc aagaaaaaga ttgaattttg gtcagactgg agacgcagac    540
tcagtacctg accccagcc tctcggacag ccaccagcag cccctctgg tctgggaact    600 aatacgatgg ctacaggcag tggcgcacca atggcagaca ataacgaggg cgccgacgga    660
gtgggtaatt cctcgggaaa ttggcattgc gattccacat ggatgggcga cagagtcatc    720
accaccagca cccgaacctg gccctgccc acctacaaca accacctcta caaacaaact    780
tccagccaat caggagcctc gaacgacaat cactactttg ctacagcac cccttggggg    840 tattttgact tcaacaggtt ccactgccac ttttcaccac gtgactggca aagactcatc    900
aacaacaact gggatttccg acccaagaga ctcaacttca gctctttaa cattcaagtc    960 aaagaggtca cgcagaatga cggtacgacg acgattgcca ataaccttac cagcacggtt   1020
caggtgttta ctgactcgga gtaccagctc ccgtacgtcc tcggctcggc gcatcaagga   1080
tgcctcccgc cgttcccagc agacgtcttc atggtgccac agtatggata cctcaccctg   1140
aacaacggga gtcaggcagt aggacgctct tcattttact gcctggagta ctttccttct   1200
cagatgctgc gtaccggaaa caactttacc ttcagctaca cttttgagga cgttcctttc   1260
cacagcagct acgctcacag ccagagtctg gaccgtctca tgaatcctct catcgaccag   1320
```

```
tacctgtatt acttgagcag aacaaacact ccaagtggaa ccaccacgca gtcagggctt   1380
cagttttctc aggccggagc gagtgacatt cgggaccagt ctaggaactg gcttcctgga   1440
ccctgttacc gccagcagcg agtatcaaag acatctgcgg ataacaacaa cagtgaatac   1500
tcgtggactg gagctaccaa gtaccacctc aatggcagag actctctggt gaatccgggc   1560
ccgaccatgg caagccacaa ggacgatgaa gaaaagtttt tccctcagag cggggttctc   1620
atctttggga agcaaggctc agagaaaaca aatgtggaca ttgaaaaggt catgattaca   1680
gacgaagagg aaatcaggac aaccaatccc gtggctacgg agcagtatgg ttctgtgtct   1740
accaacctcc agagaggcaa cagacaagca gctaccgcag atgtcaacac acaaggcgtt   1800
cttccaggca tggtctggca ggacagagat gtgtaccttc aggggcccat ctgggcaaag   1860
attccacaca cggacggaca ttttcacccc tctcccctca tgggtggatt cggacttaaa   1920
caccctcctc acagattctc catcaagaac accccggtac ctgcgaatcc ttcgaccacc   1980
ttcagtgtgg caaagtttgc ttccttcatc acacagtact ccacgggaca ggtcagcgtg   2040
gggatcgagt gggagctgca gaaggaaaac agcaaacgca gaatcccga aattcagtac   2100 acttccaact acaacaagtc tgttaatgtg gactttactg tggacactaa tggcgtgtat   2160
tcagagcctc gccccattgg caccagatac ctgactcgta atctgtaa                2208

<210> SEQ ID NO 33
<211> LENGTH: 735
<212> TYPE: PRT
<213> ORGANISM: adeno-associated virus-2

<400> SEQUENCE: 33

Met Ala Ala Asp Gly Tyr Leu Pro Asp Trp Leu Glu Asp Thr Leu Ser
  1               5                  10                  15

Glu Gly Ile Arg Gln Trp Trp Lys Leu Lys Pro Gly Pro Pro Leu Pro
                 20                  25                  30

Lys Pro Ala Glu Arg His Lys Asp Asp Ser Arg Gly Leu Val Leu Pro
             35                  40                  45

Gly Tyr Lys Tyr Leu Gly Pro Phe Asn Gly Leu Asp Lys Gly Glu Pro
         50                  55                  60

Val Asn Glu Ala Asp Ala Ala Ala Leu Glu His Asp Lys Ala Tyr Asp
 65                  70                  75                  80

Arg Gln Leu Asp Ser Gly Asp Asn Pro Tyr Leu Lys Tyr Asn His Ala
                 85                  90                  95

Asp Ala Glu Ser Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
    130                 135                 140

Pro Val Glu His Ser Pro Val Glu Pro Asp Ser Ser Ser Gly Pro Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
        195                 200                 205

Ala Pro Met Ala Asp Asn Asn Glu Gly Ala Asp Gly Val Gly Asn Ser
    210                 215                 220
```

-continued

```
Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
            245                 250                 255

Tyr Lys Gln Thr Ser Ser Gln Ser Gly Ala Ser Asn Asp Asn His Tyr
        260                 265                 270

Phe Gly Tyr Ser Thr Pro Trp Gly Tyr Phe Asp Phe Asn Arg Phe His
    275                 280                 285

Cys His Phe Ser Pro Arg Asp Trp Gln Arg Leu Ile Asn Asn Asn Trp
290                 295                 300

Gly Phe Arg Pro Lys Arg Leu Asn Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
        355                 360                 365

Val Phe Met Val Pro Gln Tyr Gly Tyr Leu Thr Leu Asn Asn Gly Ser
370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
                405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Ser Arg Thr
        435                 440                 445

Asn Thr Pro Ser Gly Thr Thr Thr Gln Ser Gly Leu Gln Phe Ser Gln
450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
                485                 490                 495

Asn Ser Glu Tyr Ser Trp Thr Gly Ala Thr Lys Tyr His Leu Asn Gly
            500                 505                 510

Arg Asp Ser Leu Val Asn Pro Gly Pro Thr Met Ala Ser His Lys Asp
        515                 520                 525

Asp Glu Glu Lys Phe Phe Pro Gln Ser Gly Val Leu Ile Phe Gly Lys
530                 535                 540

Gln Gly Ser Glu Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
                565                 570                 575

Gly Ser Val Ser Thr Asn Leu Gln Arg Gly Asn Arg Gln Ala Ala Thr
            580                 585                 590

Ala Asp Val Asn Thr Gln Gly Val Leu Pro Gly Met Val Trp Gln Asp
        595                 600                 605

Arg Asp Val Tyr Leu Gln Gly Pro Ile Trp Ala Lys Ile Pro His Thr
610                 615                 620

Asp Gly His Phe His Pro Ser Pro Leu Met Gly Gly Phe Gly Leu Lys
625                 630                 635                 640
```

```
His Pro Pro Pro Gln Ile Leu Ile Lys Asn Thr Pro Val Pro Ala Asn
                645                 650                 655

Pro Ser Thr Thr Phe Ser Val Ala Lys Phe Ala Ser Phe Ile Thr Gln
        660                 665                 670

Tyr Ser Thr Gly Gln Val Ser Val Gly Ile Glu Trp Glu Leu Gln Lys
    675                 680                 685

Glu Asn Ser Lys Arg Arg Asn Pro Glu Ile Gln Tyr Thr Ser Asn Tyr
690                 695                 700

Asn Lys Ser Val Asn Val Asp Phe Thr Val Asp Thr Asn Gly Val Tyr
705                 710                 715                 720

Ser Glu Pro Arg Pro Ile Gly Thr Arg Tyr Leu Thr Arg Asn Leu
                725                 730                 735

<210> SEQ ID NO 34
<211> LENGTH: 2208
<212> TYPE: DNA
<213> ORGANISM: adeno-associated virus-2

<400> SEQUENCE: 34
atggccgccg atggttatct tccagattgg ctcgaggaca ctctctctga aggaataaga      60
cagtggttga agctcaaacc tggcccacca ccaccaaagc cgcagagcg gcataaggac      120 gacagcaggg gtcttgtgct tcctgggtac aagtacctcg acccttcaa cggactcgac      180 aagggagagc cggtcaacga ggcagacgcc gcggccctcg agcacgacaa agcctacgac      240
cggcagctcg acagcggaga caacccgtac ctcaagtaca accacgccga cgcggagttt      300
caggagcgcc ttaaagaaga tacgtctttt ggggggcaacc tcggacgagc agtcttccag      360
gcgaaaaaga gggttcttga acctctgggc ctggttgagg aacctgttaa gacggctccg      420
ggaaaaaaga ggccggtaga gcactctcct gtggagccag actcctcctc gggaaccgga      480
aaggcgggcc agcagcctgc aagaaaaaga ttgaattttg gtcagactgg agacgcagac      540
tcagtacctg accccagcc tctcggacag ccaccagcag cccctctgg tctgggaact      600 aatacgatgg ctacaggcag tggcgcacca atggcagaca taacgaggg cgccgacgga      660 gtgggtaatt cctcgggaaa ttggcattgc ggttccacat ggatgggcga tagagtcatc      720
accaccagca cccgaacctg ggccctgccc acctacaaca accacctcta caaacaaatt      780
tccagccaat caggagcctc gaacgacaat cactactttg ctacagcac ccttgggggg      840 tactttgact tcaacagatt ccactgccac tttcaccac gtgactggca agactcatc      900 aacaacaact ggggattccg acccaagaga ctcaacttca gctctttaa cattcaagtc      960 aaagagttca cgcagaatga cggtacgacg acgattgcca ataaccttac cagcacggtt      1020
caggtgttta ctgactcgga gtacccgctc ccgtacgtcc tcggctcggc gcatcaagga      1080
tgcctcccgc cgttcccagc agacgtcttc atggtgccac agtatggtta cctcaccctg      1140
aacaacggga gtcaggcagt aggacgctct tcattttact gcctggagta ctttcctct      1200 cagatgctgc gtaccgaaaa cgactttacc ttcagctaca cttttgagga cgttcctttc      1260
cacagcagct acgctcacag ccagagtctg gaccgtctca tgaatcctct cattgaccag      1320
tacctgtatt acttgagcag aacaaacact ccaagtggaa ccaccacgca gtcaaggctt      1380
cagttttctc aggccggagc gagtgacatt cgggaccagt ctaggaactg gcttcctgga      1440
ccctgttacc gccagcagcg agtatcaaag acatctgcgg ataacaacaa cagtgaatac      1500
tcgtggactg gagctaccaa gtaccacctc aatggcagag actctctggt gaatccggc      1560 ccggccatgg caagccacaa ggacgatgaa gaaaagtttt tcctcagag cggggttctc      1620
```

-continued

```
atctttggga agcaaggctc agagaaaaca aatgtggaca ttgaaaaggt catgattaca    1680
gacgaagagg aaatcaggac aaccaatccc gtggctacgg agcagtatgg ttctgtatct    1740
accaacctcc agagaggcaa cagacaagcg gctaccgcag atgtcaacac acaaggcgtt    1800
cttccaggca tggtctggca agacagagat gtgtaccttc aggggcccat ctgggcaaag    1860
attccacaca cggacggaca ttttcacccc tctcccctca tgggtggatt cggacttaaa    1920
cacccccctc cacagattct catcaagaac accccggtac ctgcgaatcc ttcgaccacc    1980
ttcagtgcgg caaagtttgc ttccttcatc acacagtact ccacgggaca ggtcagcgtg    2040
gagatcgagt gggagctgca gaaggaaaac agcaaacgct ggaatcccga aattcagtac    2100
acttccaact acaacaagtc tgttaatgtg gactttactg tggacactaa tggcgtgtat    2160
tcagagcctc gccccattgg caccagatac ctgactcgta atctgtaa                2208
```

<210> SEQ ID NO 35
<211> LENGTH: 735
<212> TYPE: PRT
<213> ORGANISM: adeno-associated virus-2

<400> SEQUENCE: 35

```
Met Ala Ala Asp Gly Tyr Leu Pro Asp Trp Leu Glu Asp Thr Leu Ser
 1               5                  10                  15

Glu Gly Ile Arg Gln Trp Leu Lys Leu Lys Pro Gly Pro Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
    130                 135                 140

Pro Val Glu His Ser Pro Val Glu Pro Asp Ser Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
        195                 200                 205

Ala Pro Met Ala Asp Asn Asn Glu Gly Ala Asp Gly Val Gly Asn Ser
    210                 215                 220

Ser Gly Asn Trp His Cys Gly Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Phe Ser Gln Ser Gly Ala Ser Asn Asp Asn His Tyr
            260                 265                 270
```

```
Phe Gly Tyr Ser Thr Pro Trp Gly Tyr Phe Asp Phe Asn Arg Phe His
            275                 280                 285
Cys His Phe Ser Pro Arg Asp Trp Gln Arg Leu Ile Asn Asn Asn Trp
    290                 295                 300
Gly Phe Arg Pro Lys Arg Leu Asn Phe Lys Leu Phe Asn Ile Gln Val
305                 310                 315                 320
Lys Glu Phe Thr Gln Asn Asp Gly Thr Thr Ile Ala Asn Asn Leu
                325                 330                 335
Thr Ser Thr Val Gln Val Phe Thr Asp Ser Glu Tyr Pro Leu Pro Tyr
                340                 345                 350
Val Leu Gly Ser Ala His Gln Gly Cys Leu Pro Pro Phe Pro Ala Asp
            355                 360                 365
Val Phe Met Val Pro Gln Tyr Gly Tyr Leu Thr Leu Asn Asn Gly Ser
370                 375                 380
Gln Ala Val Gly Arg Ser Ser Phe Tyr Cys Leu Glu Tyr Phe Pro Ser
385                 390                 395                 400
Gln Met Leu Arg Thr Glu Asn Asp Phe Thr Phe Ser Tyr Thr Phe Glu
                405                 410                 415
Asp Val Pro Phe His Ser Ser Tyr Ala His Ser Gln Ser Leu Asp Arg
                420                 425                 430
Leu Met Asn Pro Leu Ile Asp Gln Tyr Leu Tyr Tyr Leu Ser Arg Thr
            435                 440                 445
Asn Thr Pro Ser Gly Thr Thr Thr Gln Ser Arg Leu Gln Phe Ser Gln
            450                 455                 460
Ala Gly Ala Ser Asp Ile Arg Asp Gln Ser Arg Asn Trp Leu Pro Gly
465                 470                 475                 480
Pro Cys Tyr Arg Gln Gln Arg Val Ser Lys Thr Ser Ala Asp Asn Asn
                485                 490                 495
Asn Ser Glu Tyr Ser Trp Thr Gly Ala Thr Lys Tyr His Leu Asn Gly
                500                 505                 510
Arg Asp Ser Leu Val Asn Pro Gly Pro Ala Met Ala Ser His Lys Asp
            515                 520                 525
Asp Glu Glu Lys Phe Phe Pro Gln Ser Gly Val Leu Ile Phe Gly Lys
530                 535                 540
Gln Gly Ser Glu Lys Thr Asn Val Asp Ile Glu Lys Val Met Ile Thr
545                 550                 555                 560
Asp Glu Glu Glu Ile Arg Thr Thr Asn Pro Val Ala Thr Glu Gln Tyr
                565                 570                 575
Gly Ser Val Ser Thr Asn Leu Gln Arg Gly Asn Arg Gln Ala Ala Thr
                580                 585                 590
Ala Asp Val Asn Thr Gln Gly Val Leu Pro Gly Met Val Trp Gln Asp
            595                 600                 605
Arg Asp Val Tyr Leu Gln Gly Pro Ile Trp Ala Lys Ile Pro His Thr
610                 615                 620
Asp Gly His Phe His Pro Ser Pro Leu Met Gly Gly Phe Gly Leu Lys
625                 630                 635                 640
His Pro Pro Pro Gln Ile Leu Ile Lys Asn Thr Pro Val Pro Ala Asn
                645                 650                 655
Pro Ser Thr Thr Phe Ser Ala Ala Lys Phe Ala Ser Phe Ile Thr Gln
                660                 665                 670
Tyr Ser Thr Gly Gln Val Ser Val Glu Ile Glu Trp Glu Leu Gln Lys
            675                 680                 685
```

| | | | | | | | | | | | | | |
|---|---|---|---|---|---|---|---|---|---|---|---|---|---|
|Glu|Asn|Ser|Lys|Arg|Trp|Asn|Pro|Glu|Ile|Gln|Tyr|Thr|Ser|Asn|Tyr|
| |690| | | |695| | | |700| | | | | | |

| | | | | | | | | | | | | | | | |
|---|---|---|---|---|---|---|---|---|---|---|---|---|---|---|---|
|Asn|Lys|Ser|Val|Asn|Val|Asp|Phe|Thr|Val|Asp|Thr|Asn|Gly|Val|Tyr|
|705| | | | |710| | | | |715| | | | |720|

| | | | | | | | | | | | |
|---|---|---|---|---|---|---|---|---|---|---|---|
|Ser|Glu|Pro|Arg|Pro|Ile|Gly|Thr|Arg|Tyr|Leu|Thr|Arg|Asn|Leu|
| | | |725| | | | |730| | | | |735| |

<210> SEQ ID NO 36
<211> LENGTH: 2208
<212> TYPE: DNA
<213> ORGANISM: adeno-associated virus-2

<400> SEQUENCE: 36

```
atggctgccg atggttatct tccagattgg ctcgaggaca ctctctctga aggaataaga      60
cagtggttga agctcaaacc tggcccacca ccaccaaagc ccgcagagcg cataaggac     120
gacagcaggg gtcttgtgct tcctgggtac aagtacctcg gacccttcaa cggactcgac    180
aagggagagc cggtcaacga ggcagacgcc gcggccctcg agcacgacaa agcctacgac    240
cggcagctcg acagcggaga caacccgtac ctcaagtaca accacgccga cgcggagttt    300
caggagcgcc ttaaagaaga tacgtctttt gggggcaacc tcggacgagc agtcttccag    360
gcgaaaaaga gggttcttga acctctgggc ctggttgagg aacctgttaa gacggctccg    420
ggaaaaaaga ggccggtaga gcactctcct gtggagccag actcctcctc gggaaccgga    480
aaggcgggcc agcagcctgc aagaaaaaga ttgaattttg gtcagactgg agacgcagac    540
tcagtacctg accccagcc tctcggacag ccaccagcag ctcccactgg tctgggaact    600
aatacgatgg ctacaggcag tggcgcacca atggcagaca ataacgaggg cgccgacgga    660
gtgggtaatt cctcgggaaa ttggcattgc ggttccacat ggatgggcga cagagtcatc    720
accaccagca cccgaacctg ggccctgccc acctacaaca accacctcta caaacaaatt    780
ttcagccaat caggagcctc gaacgacaat cactactttg ctacagcac ccttggggg     840
tactttgact tcaacagatt ccactgccac ttttcaccac gtgactggca agactcatc    900
aacaacaact ggggattccg acccaagaga ctcaacttca gctctttaa cattcaagtc    960
aaagaggtca cgcagaatga cggtacgacg acgattgcca taaccttac cagcacggtt   1020
caggtgttta ctgactcgga gtacccgctc ccgtacgtcc tcggctcggc gcatcaagga   1080
tgcctcccgc cgttcccagc agacgtcttc atggtgccac agtatggtta cctcaccctg   1140
aacaacggga gtcaggcagt aggacgctct tcatttact gcctggagta ctttccttct   1200
cagatgctgc gtaccgaaaa cgactttacc ttcagctaca cttttgagga cgttcctttc   1260
cacagcagct acgctcacag ccagagtctg gaccgtctca tgaatcctct catcgaccag   1320
tacctgtatt acttgagcag aacaaacact ccaagtggaa ccaccacgca gtcaaggctt   1380
cagtttctc aggccggagc gagtgacatt cgggaccagt ctaggaactg gcttcctgga   1440
ccctgttacc gccagcagcg agtatcaaag acatctgcgg ataacaacaa cagtgaatac   1500
tcgtggactg gagctaccaa gtaccacctc aatggcagag actctctggt gaatccgggc   1560
ccggccatgg caagcacaa ggacgatgaa gaaaagtttt tcctcagag cggggttctc   1620
atctttggga agcaaggctc agagaaaaca atgtggaca ttgaaaaggt catgattaca   1680
gacgaagagg aaatcaggac aaccgatccc gtggctacgg agcagtatgg ttcagtatct   1740
accaacctcc agagaggcaa cagacaagca gctaccgcag atgtcgacac acaaggcgtt   1800
cttccaggca tggtctggca ggacagagat gtgtaccttc aggggcccat ctgggcaaag   1860
```

-continued

```
attccacaca cggacggaca ttttcacccc tctcccctca tgggtggatt cggacttaaa    1920
caccctcctc cacagattct catcaagaac accccggtac ctgcgaatcc ttcgaccacc    1980
ttcagtgcgg caaagtttgc ttccttcatc acacagtact ccacgggaca ggtcagcgtg    2040
gagatcgagt gggagctgca gaaggaaaac agcaaacgct ggaatcccga aattcagtac    2100
acttccaact acaacaagtc tgttaatgtg gactttactg tggacactaa tggcgtgtat    2160
tcagagcctc gcccccattgg caccagatac ctgactcgta atctgtaa            2208

<210> SEQ ID NO 37
<211> LENGTH: 735
<212> TYPE: PRT
<213> ORGANISM: adeno-associated virus-2

<400> SEQUENCE: 37

Met Ala Ala Asp Gly Tyr Leu Pro Asp Trp Leu Glu Asp Thr Leu Ser
 1               5                  10                  15

Glu Gly Ile Arg Gln Trp Leu Lys Leu Lys Pro Gly Pro Pro Pro Pro
                20                  25                  30

Lys Pro Ala Glu Arg His Lys Asp Asp Ser Arg Gly Leu Val Leu Pro
            35                  40                  45

Gly Tyr Lys Tyr Leu Gly Pro Phe Asn Gly Leu Asp Lys Gly Glu Pro
        50                  55                  60

Val Asn Glu Ala Asp Ala Ala Ala Leu Glu His Asp Lys Ala Tyr Asp
 65                  70                  75                  80

Arg Gln Leu Asp Ser Gly Asp Asn Pro Tyr Leu Lys Tyr Asn His Ala
                 85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
    130                 135                 140

Pro Val Glu His Ser Pro Val Glu Pro Asp Ser Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Thr Gly Leu Gly Thr Asn Thr Met Ala Thr Gly Ser Gly
        195                 200                 205

Ala Pro Met Ala Asp Asn Asn Glu Gly Ala Asp Gly Val Gly Asn Ser
    210                 215                 220

Ser Gly Asn Trp His Cys Gly Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Phe Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
    290                 295                 300

Gly Phe Arg Pro Lys Arg Leu Asn Phe Lys Leu Phe Asn Ile Gln Val
305                 310                 315                 320
```

```
Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Pro Leu Pro Tyr
                340                 345                 350

Val Leu Gly Ser Ala His Gln Gly Cys Leu Pro Pro Phe Pro Ala Asp
                355                 360                 365

Val Phe Met Val Pro Gln Tyr Gly Tyr Leu Thr Leu Asn Asn Gly Ser
            370                 375                 380

Gln Ala Val Gly Arg Ser Ser Phe Tyr Cys Leu Glu Tyr Phe Pro Ser
385                 390                 395                 400

Gln Met Leu Arg Thr Glu Asn Asp Phe Thr Phe Ser Tyr Thr Phe Glu
                405                 410                 415

Asp Val Pro Phe His Ser Ser Tyr Ala His Ser Gln Ser Leu Asp Arg
                420                 425                 430

Leu Met Asn Pro Leu Ile Asp Gln Tyr Leu Tyr Tyr Leu Ser Arg Thr
            435                 440                 445

Asn Thr Pro Ser Gly Thr Thr Thr Gln Ser Arg Leu Gln Phe Ser Gln
            450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
                485                 490                 495

Asn Ser Glu Tyr Ser Trp Thr Gly Ala Thr Lys Tyr His Leu Asn Gly
            500                 505                 510

Arg Asp Ser Leu Val Asn Pro Gly Pro Ala Met Ala Ser His Lys Asp
            515                 520                 525

Asp Glu Glu Lys Phe Phe Pro Gln Ser Gly Val Leu Ile Phe Gly Lys
            530                 535                 540

Gln Gly Ser Glu Lys Thr Asn Val Asp Ile Glu Lys Val Met Ile Thr
545                 550                 555                 560

Asp Glu Glu Glu Ile Arg Thr Thr Asp Pro Val Ala Thr Glu Gln Tyr
                565                 570                 575

Gly Ser Val Ser Thr Asn Leu Gln Arg Gly Asn Arg Gln Ala Ala Thr
            580                 585                 590

Ala Asp Val Asp Thr Gln Gly Val Leu Pro Gly Met Val Trp Gln Asp
            595                 600                 605

Arg Asp Val Tyr Leu Gln Gly Pro Ile Trp Ala Lys Ile Pro His Thr
            610                 615                 620

Asp Gly His Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asn
                645                 650                 655

Pro Ser Thr Thr Phe Ser Ala Ala Lys Phe Ala Ser Phe Ile Thr Gln
            660                 665                 670

Tyr Ser Thr Gly Gln Val Ser Val Glu Ile Glu Trp Glu Leu Gln Lys
            675                 680                 685

Glu Asn Ser Lys Arg Trp Asn Pro Glu Ile Gln Tyr Thr Ser Asn Tyr
            690                 695                 700

Asn Lys Ser Val Asn Val Asp Phe Thr Val Asp Thr Asn Gly Val Tyr
705                 710                 715                 720

Ser Glu Pro Arg Pro Ile Gly Thr Arg Tyr Leu Thr Arg Asn Leu
                725                 730                 735
```

<210> SEQ ID NO 38
<211> LENGTH: 2208
<212> TYPE: DNA
<213> ORGANISM: adeno-associated virus-2

<400> SEQUENCE: 38

| | | | | | |
|---|---|---|---|---|---|
| atggctgccg | atggttatct | tccagattgg | ctcgaggaca | ctctctctga | aggaataaga | 60 |
| cagtggtgga | agctcaaacc | tggcccacca | ccaccaaagc | ccgcagagcg | gcataaggac | 120 |
| gacagcaggg | gtcttgtgct | tcctgggtac | aagtacctcg | gacccttcaa | cggactcgac | 180 |
| aagggagagc | cggtcaacga | ggcagacgcc | gcggccctcg | agcacgacaa | agcctacgac | 240 |
| cggcagctcg | acagcggaga | caacccgtac | ctcaagtaca | accacgccga | cgcggagttt | 300 |
| caggagcgcc | ttaaagaaga | tacgtctttt | gggggcaacc | tcggacgagc | agtcttccag | 360 |
| gcgaaaaaga | gggttcttga | acctctgggc | ctggttgagg | aacctgttaa | gacggctccg | 420 |
| ggaaaaaaga | ggccggtaga | gcactctcct | gtggagccag | actcctcctc | gggaaccgga | 480 |
| aaggcgggcc | agcagcctgc | aagaaaaaga | ttgaattttg | gtcagactgg | agacgcagac | 540 |
| tcagtacctg | acccccagcc | tctcggacag | ccaccagcag | ccccctctgg | tctgggaact | 600 |
| aatacgatgg | ctacaggcag | tggcgcacca | atggcagaca | ataacgaggg | cgccgacgga | 660 |
| gtgggtaatt | cctcgggaaa | ttggcattgc | gattccacat | gggtgggcga | cagagtcatc | 720 |
| accaccagca | cccgaacctg | ggcctgtgcc | acctacaaca | accacctcta | caaacaaatt | 780 |
| tccagccaat | caggagcctc | gaacgacaat | cactactttg | gctacagcac | cccttggggg | 840 |
| tattttgact | tcaacagatt | ccactgccac | ttttcaccac | gtgactggca | agactcatc | 900 |
| aacaacaact | ggggattccg | acccaagaga | ctcaacttca | agctctttaa | cattcaagtc | 960 |
| aaagaggtca | cgcagaatga | cggtacgacg | acgattgcca | ataaccttac | cagcacggtt | 1020 |
| caggtgttta | ctgactcgga | gtaccagctc | ccgtacgtcc | tcggctcggc | gcatcaagga | 1080 |
| tgcctcccgc | cgttcccagc | agacgtcttc | atggtgccac | agtatggata | cctcaccctg | 1140 |
| aacaacggga | gtcaggcagt | aggacgctct | tcatttact | gcctggagta | ctttccttct | 1200 |
| cggatgctgc | gtaccggaaa | caactttacc | ttcagctaca | cttttgagga | cgttcctttc | 1260 |
| cacagcagct | acgctcacag | ccagagtctg | gaccgtctca | tgaatcctca | catcgaccag | 1320 |
| tacctgtatt | acttgagcag | aacaaacact | ccaagtggaa | ccaccacgca | gtcaaggctt | 1380 |
| cagttttctc | aggccggagc | gagtgacatt | cgggaccagt | ctaggaactg | gcttcctgga | 1440 |
| ccctgttacc | gccagcagcg | agtatcaaag | acatctgcgg | ataacaacaa | cagtgaatac | 1500 |
| tcgtggactg | gagctaccaa | gtaccacctc | aatggcagag | actctctggt | gaatccgggc | 1560 |
| ccggccatgg | caagccacaa | ggacgatgaa | gaaaagtttt | tccctcagag | cggggttctc | 1620 |
| atctttggga | agcaaggctc | agagaaaaca | aatgtggaca | ttgaaaaggt | catgattaca | 1680 |
| gacgaagagg | aaatcaggac | aaccaatccc | gtggctacgg | agcagtatgg | ttctgtatct | 1740 |
| accaccctcc | agagaggcaa | cagacaagca | gctaccgcag | atgtcaacac | acaaggcgtt | 1800 |
| cttccaggca | tggtctggca | ggacagagat | gtgtaccttc | aggggcccat | ctgggcaaag | 1860 |
| attccacaca | cggacggaca | ttttcacccc | tctcccctca | tgggtggatt | cggacttaaa | 1920 |
| caccctcctc | cacagattct | catcaagaac | accccggtac | ctgcgaatcc | ttcgaccgcc | 1980 |
| ttcagtgcgg | caaagtttgc | ttccttcatc | acacagtact | ccacgggaca | ggtcagcgtg | 2040 |
| gagatcgagt | gggagctgca | gaaggaaaac | agcaaacgct | ggaatccgga | aattcagtac | 2100 |
| acttccaact | acaacaagtc | tgttaatgtg | gactttactg | tggacactaa | tggcgtgtat | 2160 | tcagagcctc gccccattgg caccagatac ctgactcgta atctgtaa                    2208

<210> SEQ ID NO 39
<211> LENGTH: 735
<212> TYPE: PRT
<213> ORGANISM: adeno-associated virus-2

<400> SEQUENCE: 39

```
Met Ala Ala Asp Gly Tyr Leu Pro Asp Trp Leu Glu Asp Thr Leu Ser
 1               5                  10                  15

Glu Gly Ile Arg Gln Trp Trp Lys Leu Lys Pro Gly Pro Pro Pro Pro
             20                  25                  30

Lys Pro Ala Glu Arg His Lys Asp Asp Ser Arg Gly Leu Val Leu Pro
         35                  40                  45

Gly Tyr Lys Tyr Leu Gly Pro Phe Asn Gly Leu Asp Lys Gly Glu Pro
     50                  55                  60

Val Asn Glu Ala Asp Ala Ala Leu Glu His Asp Lys Ala Tyr Asp
 65                  70                  75                  80

Arg Gln Leu Asp Ser Gly Asp Asn Pro Tyr Leu Lys Tyr Asn His Ala
                 85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
    130                 135                 140

Pro Val Glu His Ser Pro Val Glu Pro Asp Ser Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Thr Trp Val Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
    290                 295                 300

Gly Phe Arg Pro Lys Arg Leu Asn Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
        355                 360                 365
```

```
Val Phe Met Val Pro Gln Tyr Gly Tyr Leu Thr Leu Asn Asn Gly Ser
        370                 375                 380

Gln Ala Val Gly Arg Ser Ser Phe Tyr Cys Leu Glu Tyr Phe Pro Ser
385                 390                 395                 400

Arg Met Leu Arg Thr Gly Asn Asn Phe Thr Phe Ser Tyr Thr Phe Glu
                405                 410                 415

Asp Val Pro Phe His Ser Ser Tyr Ala His Ser Gln Ser Leu Asp Arg
            420                 425                 430

Leu Met Asn Pro His Ile Asp Gln Tyr Leu Tyr Tyr Leu Ser Arg Thr
        435                 440                 445

Asn Thr Pro Ser Gly Thr Thr Thr Gln Ser Arg Leu Gln Phe Ser Gln
450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
                485                 490                 495

Asn Ser Glu Tyr Ser Trp Thr Gly Ala Thr Lys Tyr His Leu Asn Gly
            500                 505                 510

Arg Asp Ser Leu Val Asn Pro Gly Pro Ala Met Ala Ser His Lys Asp
        515                 520                 525

Asp Glu Glu Lys Phe Phe Pro Gln Ser Gly Val Leu Ile Phe Gly Lys
530                 535                 540

Gln Gly Ser Glu Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
                565                 570                 575

Gly Ser Val Ser Thr Asp Leu Gln Arg Gly Asn Arg Gln Ala Ala Thr
            580                 585                 590

Ala Asp Val Asn Thr Gln Gly Val Leu Pro Gly Met Val Trp Gln Asp
        595                 600                 605

Arg Asp Val Tyr Leu Gln Gly Pro Ile Trp Ala Lys Ile Pro His Thr
610                 615                 620

Asp Gly His Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asn
                645                 650                 655

Pro Ser Thr Ala Phe Ser Ala Ala Lys Phe Ala Ser Phe Ile Thr Gln
            660                 665                 670

Tyr Ser Thr Gly Gln Val Ser Val Glu Ile Glu Trp Glu Leu Gln Lys
        675                 680                 685

Glu Asn Ser Lys Arg Trp Asn Pro Glu Ile Gln Tyr Thr Ser Asn Tyr
690                 695                 700

Asn Lys Ser Val Asn Val Asp Phe Thr Val Asp Thr Asn Gly Val Tyr
705                 710                 715                 720

Ser Glu Pro Arg Pro Ile Gly Thr Arg Tyr Leu Thr Arg Asn Leu
                725                 730                 735

<210> SEQ ID NO 40
<211> LENGTH: 2208
<212> TYPE: DNA
<213> ORGANISM: adeno-associated virus-2

<400> SEQUENCE: 40
atggctgccg atggttatct tccagattgg ctcgaggaca ctctctctga aggaataaga     60
```

```
cagtggtgga agctcaaacc tggcccacca ccaccaaagc ccgcagagcg gcataaggac    120
gacagcaggg gtcttgtgct tcctgggtac aagtacctcg gacccttcaa cggactcgac    180
aagggagagc cggtcaacga ggcagacgcc gcggccctcg agcacgacaa agcctacgac    240
cggcagctcg acagcggaga caacccgtac ctcaagtaca accacgccga cgcggagttt    300
caggagcgcc ttaaagaaga tacgtctttt gggggcaacc tcggacgagc agtcttccag    360
gcgaaaaaga gggttcttga acctctgggc ctggttgagg aacctgttaa gacggctccg    420
ggaaaaaaga ggccggtaga gcactctcct gtggagccag actcctcctc gggaaccgga    480
aaggcgggcc agcagcctgc aagaaaaaga ttgaattttg gtcagactgg agacgcagac    540
tcagtacctg accccagcc tctcggacag ccaccagcag ccccctctgg tctgggaact    600
aatacgatgg ctacaggcag tggcgcacca atggcagaca taacgagggg cgccgacgga    660
gtgggtaatt cctcgggaaa ttggcattgc gattccacat ggatgggcga cagagtcatc    720
accaccagca cccgaacctg ggcctgcccc acctacaaca accacctcta cgaacaaatt    780
tccagccaat caggagcctc gaacgacaat cactactttg gctacagcac cccttggggg    840
tattttgact tcaacagatt ccactgccac ttttcaccac gtgactggca agactcatc    900 aacaacaact ggggattccg acccaagaga ctcaacttca agccctttaa cattcaagtc    960
aaaggggtca cgcagaatga cggtacgacg acgattgcca ataaccttac cagcacggtt   1020 caggtgtttta ctgactcgga gtaccagctc ccgtacgtcc tcggctcggc gcatcaagga   1080
tgcctcccgc cgttcccagc agacgtcttc atggtgccac agtatggata cctcaccctg   1140
aacaacggga gtcaggcagt aggacgctct tcatttttact gcctggagta ctttcccttct   1200 cagatgctgc gtaccggaaa caactttacc ttcagctaca cttttgagga cgttcctttc   1260
cacagcagct acgctcacag ccagagtctg gaccgtctca tgaatcctct catcgaccag   1320
tacctgtatt acttgagcag aacaaacact ccaagtggaa ctaccacgca gtcaaggctt   1380
cagttttctc aggccggagc gagtgacatt cgggaccagt ctaggaactg gcttcctgga   1440
ccctgttacc gccagcagcg agtatcaaag acatctgcgg ataacaacaa cagtgaatac   1500
tcgtggactg gagctaccaa gtaccacctc aatggcagag actctctggt gaatccgggc   1560
ccggccatgg caagccacaa ggacgatgaa gaaaagttttt ttcctcagag cggggttctc   1620
atctttggga agcaaggctc agagaaaaca aatgtggaca ttgaaaaggt catgattaca   1680
gacgaagagg aaatcaggac aaccaatccc gtggctacgg agcagtatgg ttctgtatct   1740
accaacctcc agagaggcaa cagacaagca gctaccgcag atgtcaacac acaaggcgtt   1800
cttccaggca tgatctggca ggacagagat gtgtaccttc aggggcccat ctgggcaaag   1860
attccacaca cggacggaca ttttcacccc tctcccctca tgggtggatt cggacttaaa   1920
caccctcctc cacagattct catcaagaac acccccggtac ctgcgaatcc ttcgaccacc   1980
ttcagtgcgg caaagtttgc ttccttcatc acacagtact ccacgggaca ggtcagcgtg   2040
gagatcgagt gggagctgca gaaggaaaac agcaaacgct ggaatcccga aattcagtac   2100
acttccaact acaacaagtc tgttaatgtg gactttactg tggacactaa tggcgtgtat   2160
tcagagcctc gccccattgg caccagatac ctgactcgta atctgtaa              2208
```

<210> SEQ ID NO 41
<211> LENGTH: 735
<212> TYPE: PRT
<213> ORGANISM: adeno-associated virus-2

<400> SEQUENCE: 41

```
Met Ala Ala Asp Gly Tyr Leu Pro Asp Trp Leu Glu Asp Thr Leu Ser
1               5                   10                  15
Glu Gly Ile Arg Gln Trp Trp Lys Leu Lys Pro Gly Pro Pro Pro Pro
            20                  25                  30
Lys Pro Ala Glu Arg His Lys Asp Asp Ser Arg Gly Leu Val Leu Pro
        35                  40                  45
Gly Tyr Lys Tyr Leu Gly Pro Phe Asn Gly Leu Asp Lys Gly Glu Pro
50                  55                  60
Val Asn Glu Ala Asp Ala Ala Leu Glu His Asp Lys Ala Tyr Asp
65                  70                  75                  80
Arg Gln Leu Asp Ser Gly Asp Asn Pro Tyr Leu Lys Tyr Asn His Ala
                85                  90                  95
Asp Ala Glu Phe Gln Glu Arg Leu Lys Glu Asp Thr Ser Phe Arg Gly
            100                 105                 110
Asn Leu Gly Arg Ala Val Phe Gln Ala Lys Lys Arg Val Leu Glu Pro
        115                 120                 125
Leu Gly Leu Val Glu Glu Pro Val Lys Thr Ala Pro Gly Lys Lys Arg
130                 135                 140
Pro Val Glu His Ser Pro Val Glu Pro Asp Ser Ser Ser Gly Thr Gly
145                 150                 155                 160
Lys Ala Gly Gln Gln Pro Ala Arg Lys Arg Leu Asn Phe Gly Gln Thr
                165                 170                 175
Gly Asp Ala Asp Ser Val Pro Asp Pro Gln Pro Leu Gly Gln Pro Pro
            180                 185                 190
Ala Ala Pro Ser Gly Leu Gly Thr Asn Thr Met Ala Thr Gly Ser Gly
        195                 200                 205
Ala Pro Met Ala Asp Asn Asn Glu Gly Ala Asp Gly Val Gly Asn Ser
210                 215                 220
Ser Gly Asn Trp His Cys Asp Ser Thr Trp Met Gly Asp Arg Val Ile
225                 230                 235                 240
Thr Thr Ser Thr Arg Thr Trp Ala Leu Pro Thr Tyr Asn Asn His Leu
                245                 250                 255
Tyr Glu Gln Ile Ser Ser Gln Ser Gly Ala Ser Asn Asp Asn His Tyr
            260                 265                 270
Phe Gly Tyr Ser Thr Pro Trp Gly Tyr Phe Asp Phe Asn Arg Phe His
        275                 280                 285
Cys His Phe Ser Pro Arg Asp Trp Gln Arg Leu Ile Asn Asn Asn Trp
290                 295                 300
Gly Phe Arg Pro Lys Arg Leu Asn Phe Lys Pro Phe Asn Ile Gln Val
305                 310                 315                 320
Lys Gly Val Thr Gln Asn Asp Gly Thr Thr Thr Ile Ala Asn Asn Leu
                325                 330                 335
Thr Ser Thr Val Gln Val Phe Thr Asp Ser Glu Tyr Gln Leu Pro Tyr
            340                 345                 350
Val Leu Gly Ser Ala His Gln Gly Cys Leu Pro Pro Phe Pro Ala Asp
        355                 360                 365
Val Phe Met Val Pro Gln Tyr Gly Tyr Leu Thr Leu Asn Asn Gly Ser
370                 375                 380
Gln Ala Val Gly Arg Ser Ser Phe Tyr Cys Leu Glu Tyr Phe Pro Ser
385                 390                 395                 400
Gln Met Leu Arg Thr Gly Asn Asn Phe Thr Phe Ser Tyr Thr Phe Glu
                405                 410                 415
```

```
Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Ser Arg Thr
        435                 440                 445

Asn Thr Pro Ser Gly Thr Thr Thr Gln Ser Arg Leu Gln Phe Ser Gln
    450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
                485                 490                 495

Asn Ser Glu Tyr Ser Trp Thr Gly Ala Thr Lys Tyr His Leu Asn Gly
            500                 505                 510

Arg Asp Ser Leu Val Asn Pro Gly Pro Ala Met Ala Ser His Lys Asp
        515                 520                 525

Asp Glu Glu Lys Phe Phe Pro Gln Ser Gly Val Leu Ile Phe Gly Lys
    530                 535                 540

Gln Gly Ser Glu Lys Thr Asp Val Asp Ile Glu Lys Val Met Ile Thr
545                 550                 555                 560

Asp Glu Glu Ile Arg Thr Thr Asn Pro Val Ala Thr Glu Gln Tyr
                565                 570                 575

Gly Ser Val Ser Thr Asn Leu Gln Arg Gly Asn Arg Gln Ala Ala Thr
            580                 585                 590

Ala Asp Val Asn Thr Gln Gly Val Leu Pro Gly Met Ile Trp Gln Asp
        595                 600                 605

Arg Asp Val Tyr Leu Gln Gly Pro Ile Trp Ala Lys Ile Pro His Thr
    610                 615                 620

Asp Gly His Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asn
                645                 650                 655

Pro Ser Thr Thr Phe Ser Ala Ala Lys Phe Ala Ser Phe Ile Thr Gln
            660                 665                 670

Tyr Ser Thr Gly Gln Val Ser Val Glu Ile Glu Trp Glu Leu Gln Lys
        675                 680                 685

Glu Asn Ser Lys Arg Trp Asn Pro Glu Ile Gln Tyr Thr Ser Asn Tyr
    690                 695                 700

Asn Lys Ser Val Asn Val Asp Phe Thr Val Asp Thr Asn Gly Val Tyr
705                 710                 715                 720

Ser Glu Pro Arg Pro Ile Gly Thr Arg Tyr Leu Thr Arg Asn Leu
                725                 730                 735

<210> SEQ ID NO 42
<211> LENGTH: 725
<212> TYPE: PRT
<213> ORGANISM: adeno-associated virus-5

<400> SEQUENCE: 42

Met Ala Ala Asp Gly Tyr Leu Pro Asp Trp Leu Glu Asp Thr Leu Ser
 1               5                  10                  15

Glu Gly Ile Arg Gln Trp Trp Lys Leu Lys Pro Gly Pro Pro Pro Pro
                20                  25                  30

Lys Pro Ala Glu Arg His Lys Asp Asp Ser Arg Gly Leu Val Leu Pro
            35                  40                  45

Gly Tyr Lys Tyr Leu Gly Pro Phe Asn Gly Leu Asp Lys Gly Glu Pro
```

-continued

```
                50                  55                  60
Val Asn Glu Ala Asp Ala Ala Leu Glu His Asp Lys Ala Tyr Asp
 65                  70                  75                  80

Arg Gln Leu Asp Ser Gly Asp Asn Pro Tyr Leu Lys Tyr Asn His Ala
                 85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Phe Gly Leu Val Glu Glu Gly Ala Lys Thr Ala Pro Thr Gly Lys Arg
130                 135                 140

Ile Asp Asp His Phe Pro Lys Arg Lys Lys Ala Arg Thr Glu Glu Asp
145                 150                 155                 160

Ser Lys Pro Ser Thr Ser Ser Asp Ala Glu Ala Gly Pro Ser Gly Ser
                165                 170                 175

Gln Gln Leu Gln Ile Pro Ala Gln Pro Ala Ser Ser Leu Gly Ala Asp
            180                 185                 190

Thr Met Ser Ala Gly Gly Gly Pro Leu Gly Asp Asn Asn Gln Gly
        195                 200                 205

Ala Asp Gly Val Gly Asn Ala Ser Gly Asp Trp His Cys Asp Ser Thr
210                 215                 220

Trp Met Gly Asp Arg Val Val Thr Lys Ser Thr Arg Thr Trp Val Leu
225                 230                 235                 240

Pro Ser Tyr Asn Asn His Gln Tyr Arg Glu Ile Lys Ser Gly Ser Val
                245                 250                 255

Asp Gly Ser Asn Ala Asn Ala Tyr Phe Gly Tyr Ser Thr Pro Trp Gly
            260                 265                 270

Tyr Phe Asp Phe Asn Arg Phe His Ser His Trp Ser Pro Arg Asp Trp
        275                 280                 285

Gln Arg Leu Ile Asn Asn Tyr Trp Gly Phe Arg Pro Arg Ser Leu Arg
290                 295                 300

Val Lys Ile Phe Asn Ile Gln Val Lys Glu Val Thr Val Gln Asp Ser
305                 310                 315                 320

Thr Thr Thr Ile Ala Asn Asn Leu Thr Ser Thr Val Gln Val Phe Thr
                325                 330                 335

Asp Asp Asp Tyr Gln Leu Pro Tyr Val Val Gly Asn Gly Thr Glu Gly
            340                 345                 350

Cys Leu Pro Ala Phe Pro Pro Gln Val Phe Thr Leu Pro Gln Tyr Gly
        355                 360                 365

Tyr Ala Thr Leu Asn Arg Asp Asn Thr Glu Asn Pro Thr Glu Arg Ser
370                 375                 380

Ser Phe Phe Cys Leu Glu Tyr Phe Pro Ser Lys Met Leu Arg Thr Gly
385                 390                 395                 400

Asn Asn Phe Glu Phe Thr Tyr Asn Phe Glu Glu Val Pro Phe His Ser
                405                 410                 415

Ser Phe Ala Pro Ser Gln Asn Leu Phe Lys Leu Ala Asn Pro Leu Val
            420                 425                 430

Asp Gln Tyr Leu Tyr Arg Phe Val Ser Thr Asn Asn Thr Gly Gly Val
        435                 440                 445

Gln Phe Asn Lys Asn Leu Ala Gly Arg Tyr Ala Asn Thr Tyr Lys Asn
450                 455                 460

Trp Phe Pro Gly Pro Met Gly Arg Thr Gln Gly Trp Asn Leu Gly Ser
465                 470                 475                 480
```

```
Gly Val Asn Arg Ala Ser Val Ser Ala Phe Ala Thr Thr Asn Arg Met
                485                 490                 495

Glu Leu Glu Gly Ala Ser Tyr Gln Val Pro Gln Pro Asn Gly Met
            500                 505                 510

Thr Asn Asn Leu Gln Gly Ser Asn Thr Tyr Ala Leu Glu Asn Thr Met
            515                 520                 525

Ile Phe Asn Ser Gln Pro Ala Asn Pro Gly Thr Thr Ala Thr Tyr Leu
            530                 535                 540

Glu Gly Asn Met Leu Ile Thr Ser Glu Ser Glu Thr Gln Pro Val Asn
545                 550                 555                 560

Arg Val Ala Tyr Asn Val Gly Gly Gln Met Ala Thr Asn Asn Gln Ser
                565                 570                 575

Ser Thr Thr Ala Pro Thr Thr Gly Thr Tyr Asn Leu Gln Glu Ile Val
            580                 585                 590

Pro Gly Ser Val Trp Met Glu Arg Asp Val Tyr Leu Gln Gly Pro Ile
            595                 600                 605

Trp Ala Lys Ile Pro Glu Thr Gly Ala His Phe His Pro Ser Pro Ala
            610                 615                 620

Met Gly Gly Phe Gly Leu Lys His Pro Pro Met Met Leu Ile Lys
625                 630                 635                 640

Asn Thr Pro Val Pro Gly Asn Ile Thr Ser Phe Ser Asp Val Pro Val
                645                 650                 655

Ser Ser Phe Ile Thr Gln Tyr Ser Thr Gly Gln Val Thr Val Glu Met
            660                 665                 670

Glu Trp Glu Leu Lys Lys Glu Asn Ser Lys Arg Trp Asn Pro Glu Ile
            675                 680                 685

Gln Tyr Thr Asn Asn Tyr Asn Asp Pro Gln Phe Val Asp Phe Ala Pro
            690                 695                 700

Asp Ser Thr Gly Glu Tyr Arg Thr Thr Arg Pro Ile Gly Thr Arg Tyr
705                 710                 715                 720

Leu Thr Arg Pro Leu
            725

<210> SEQ ID NO 43
<211> LENGTH: 724
<212> TYPE: PRT
<213> ORGANISM: adeno-associated virus-5

<400> SEQUENCE: 43

Met Ser Phe Val Asp His Pro Pro Asp Trp Leu Glu Glu Val Gly Glu
1               5                   10                  15

Gly Leu Arg Glu Phe Leu Gly Leu Glu Ala Gly Pro Pro Lys Pro Lys
            20                  25                  30

Pro Asn Gln Gln His Gln Asp Gln Ala Arg Gly Leu Val Leu Pro Gly
            35                  40                  45

Tyr Asn Tyr Leu Gly Pro Gly Asn Gly Leu Asp Arg Gly Glu Pro Val
            50                  55                  60

Asn Arg Ala Asp Glu Val Ala Arg Glu His Asp Ile Ser Tyr Asn Glu
65                  70                  75                  80

Gln Leu Glu Ala Gly Asp Asn Pro Tyr Leu Lys Tyr Asn His Ala Asp
                85                  90                  95

Ala Glu Phe Gln Glu Lys Leu Ala Asp Asp Thr Ser Phe Gly Gly Asn
            100                 105                 110

Leu Gly Lys Ala Val Phe Gln Ala Lys Lys Arg Val Leu Glu Pro Phe
```

```
                115                 120                 125
Gly Leu Val Glu Glu Gly Ala Lys Thr Ala Pro Thr Gly Lys Arg Ile
130                 135                 140

Asp Asp His Phe Pro Lys Arg Lys Lys Ala Arg Thr Glu Glu Asp Ser
145                 150                 155                 160

Lys Pro Ser Thr Ser Ser Asp Ala Glu Ala Gly Pro Ser Gly Ser Gln
                165                 170                 175

Gln Leu Gln Ile Pro Ala Gln Pro Ala Ser Ser Leu Gly Ala Asp Thr
                180                 185                 190

Met Ser Ala Gly Gly Gly Pro Leu Gly Asp Asn Asn Gln Gly Ala
                195                 200                 205

Asp Gly Val Gly Asn Ala Ser Gly Asp Trp His Cys Asp Ser Thr Trp
210                 215                 220

Met Gly Asp Arg Val Val Thr Lys Ser Thr Arg Thr Trp Val Leu Pro
225                 230                 235                 240

Ser Tyr Asn Asn His Gln Tyr Arg Glu Ile Lys Ser Gly Ser Val Asp
                245                 250                 255

Gly Ser Asn Ala Asn Ala Tyr Phe Gly Tyr Ser Thr Pro Trp Gly Tyr
                260                 265                 270

Phe Asp Phe Asn Arg Phe His Ser His Trp Ser Pro Arg Asp Trp Gln
                275                 280                 285

Arg Leu Ile Asn Asn Tyr Trp Gly Phe Arg Pro Arg Ser Leu Arg Val
290                 295                 300

Lys Ile Phe Asn Ile Gln Val Lys Glu Val Thr Val Gln Asp Ser Thr
305                 310                 315                 320

Thr Thr Ile Ala Asn Asn Leu Thr Ser Thr Val Gln Val Phe Thr Asp
                325                 330                 335

Asp Asp Tyr Gln Leu Pro Tyr Val Val Gly Asn Gly Thr Glu Gly Cys
                340                 345                 350

Leu Pro Ala Phe Pro Pro Gln Val Phe Thr Leu Pro Gln Tyr Gly Tyr
                355                 360                 365

Ala Thr Leu Asn Arg Asp Asn Thr Glu Asn Pro Thr Glu Arg Ser Ser
370                 375                 380

Phe Phe Cys Leu Glu Tyr Phe Pro Ser Lys Met Leu Arg Thr Gly Asn
385                 390                 395                 400

Asn Phe Glu Phe Thr Tyr Asn Phe Glu Glu Val Pro Phe His Ser Ser
                405                 410                 415

Phe Ala Pro Ser Gln Asn Leu Phe Lys Leu Ala Asn Pro Leu Val Asp
                420                 425                 430

Gln Tyr Leu Tyr Arg Phe Val Ser Thr Asn Asn Thr Gly Gly Val Gln
                435                 440                 445

Phe Asn Lys Asn Leu Ala Gly Arg Tyr Ala Asn Thr Tyr Lys Asn Trp
450                 455                 460

Phe Pro Gly Pro Met Gly Arg Thr Gln Gly Trp Asn Leu Gly Ser Gly
465                 470                 475                 480

Val Asn Arg Ala Ser Val Ser Ala Phe Ala Thr Thr Asn Arg Met Glu
                485                 490                 495

Leu Glu Gly Ala Ser Tyr Gln Val Pro Pro Gln Pro Asn Gly Met Thr
                500                 505                 510

Asn Asn Leu Gln Gly Ser Asn Thr Tyr Ala Leu Glu Asn Thr Met Ile
                515                 520                 525

Phe Asn Ser Gln Pro Ala Asn Pro Gly Thr Thr Ala Thr Tyr Leu Glu
530                 535                 540
```

-continued

```
Gly Asn Met Leu Ile Thr Ser Glu Ser Glu Thr Gln Pro Val Asn Arg
545                 550                 555                 560

Val Ala Tyr Asn Val Gly Gly Gln Met Ala Thr Asn Asn Gln Ser Ser
                565                 570                 575

Thr Thr Ala Pro Ala Thr Gly Thr Tyr Asn Leu Gln Glu Ile Val Pro
            580                 585                 590

Gly Ser Val Trp Met Glu Arg Asp Val Tyr Leu Gln Gly Pro Ile Trp
        595                 600                 605

Ala Lys Ile Pro Glu Thr Gly Ala His Phe His Pro Ser Pro Ala Met
    610                 615                 620

Gly Gly Phe Gly Leu Lys His Pro Pro Met Met Leu Ile Lys Asn
625                 630                 635                 640

Thr Pro Val Pro Gly Asn Ile Thr Ser Phe Ser Asp Val Pro Val Ser
                645                 650                 655

Ser Phe Ile Thr Gln Tyr Ser Thr Gly Gln Val Thr Val Glu Met Glu
            660                 665                 670

Trp Glu Leu Lys Lys Glu Asn Ser Lys Arg Trp Asn Pro Glu Ile Gln
        675                 680                 685

Tyr Thr Asn Asn Tyr Asn Asp Pro Gln Phe Val Asp Phe Ala Pro Asp
    690                 695                 700

Ser Thr Gly Glu Tyr Arg Thr Thr Arg Pro Ile Gly Thr Arg Tyr Leu
705                 710                 715                 720

Thr Arg Pro Leu

<210> SEQ ID NO 44
<211> LENGTH: 735
<212> TYPE: PRT
<213> ORGANISM: adeno-associated virus-2

<400> SEQUENCE: 44

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
    130                 135                 140

Pro Val Glu His Ser Pro Val Glu Pro Asp Ser Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Glu Pro Pro
            180                 185                 190
```

```
Ala Thr Pro Ala Ala Val Gly Pro Thr Thr Met Ala Ser Gly Gly
            195                 200                 205

Ala Pro Met Ala Asp Asn Asn Glu Gly Ala Asp Gly Val Gly Asn Ala
        210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Ala Ser Thr Gly Ala Ser Asn Asp Asn His
                260                 265                 270

Tyr Phe Gly Tyr Ser Thr Pro Trp Gly Tyr Phe Asp Phe Asn Arg Phe
            275                 280                 285

His Cys His Phe Ser Pro Arg Asp Trp Gln Arg Leu Ile Asn Asn Asn
        290                 295                 300

Trp Gly Phe Arg Pro Lys Arg Leu Asn Phe Lys Leu Phe Asn Ile Gln
305                 310                 315                 320

Val Lys Glu Val Thr Gln Asn Asp Gly Thr Thr Ile Ala Asn Asn
                325                 330                 335

Leu Thr Ser Thr Val Gln Val Phe Thr Asp Ser Glu Tyr Gln Leu Pro
            340                 345                 350

Tyr Val Leu Gly Ser Ala His Gln Gly Cys Leu Pro Pro Phe Pro Ala
        355                 360                 365

Asp Val Phe Met Ile Pro Gln Tyr Gly Tyr Leu Thr Leu Asn Asn Gly
    370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
                405                 410                 415

Glu Asp Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Asn Arg
        435                 440                 445

Thr Gln Asn Gln Ser Gly Ser Ala Gln Asp Lys Ala Leu Leu Phe Ser
    450                 455                 460

Arg Gly Ser Pro Ala Gly Met Ser Val Gln Pro Lys Asn Trp Leu Pro
465                 470                 475                 480

Gly Pro Cys Tyr Arg Gln Gln Arg Val Ser Lys Thr Lys Thr Asp Asn
                485                 490                 495

Asn Asn Ser Asn Phe Thr Trp Thr Gly Ala Ser Lys Tyr Asn Leu Asn
            500                 505                 510

Gly Arg Glu Ser Ile Ile Asn Pro Gly Thr Ala Met Ala Ser His Lys
        515                 520                 525

Asp Asp Lys Asp Lys Phe Phe Pro Met Ser Gly Val Met Ile Phe Gly
    530                 535                 540

Lys Glu Ser Ala Gly Ala Ser Asn Thr Ala Leu Asp Asn Val Met Ile
545                 550                 555                 560

Thr Asp Glu Glu Glu Ile Lys Ala Thr Asn Pro Val Ala Thr Glu Arg
                565                 570                 575

Phe Gly Thr Val Ala Val Asn Phe Gln Ser Ser Ser Thr Asp Pro Ala
            580                 585                 590

Thr Gly Asp Val His Val Met Gly Ala Leu Pro Gly Met Val Trp Gln
        595                 600                 605
```

```
Asp Arg Asp Val Tyr Leu Gln Gly Pro Ile Trp Ala Lys Ile Pro His
    610                 615                 620

Thr Asp Gly His Phe His Pro Ser Pro Leu Met Gly Gly Phe Gly Leu
625                 630                 635                 640

Lys His Pro Pro Gln Ile Leu Ile Lys Asn Thr Pro Val Pro Ala
            645                 650                 655

Asn Pro Pro Ala Glu Phe Ser Ala Thr Lys Phe Ala Ser Phe Ile Thr
        660                 665                 670

Gln Tyr Ser Thr Gly Gln Val Ser Val Glu Ile Glu Trp Glu Leu Gln
            675                 680                 685

Lys Glu Asn Ser Lys Arg Trp Asn Pro Glu Val Gln Tyr Thr Ser Asn
    690                 695                 700

Tyr Ala Lys Ser Ala Asn Val Asp Phe Thr Val Asp Asn Asn Gly Leu
705                 710                 715                 720

Tyr Thr Glu Pro Arg Pro Ile Gly Thr Arg Tyr Leu Thr Arg Pro
                725                 730                 735

<210> SEQ ID NO 45
<211> LENGTH: 739
<212> TYPE: PRT
<213> ORGANISM: adeno-associated virus-2

<400> SEQUENCE: 45

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
130                 135                 140

Pro Val Glu His Ser Pro Val Glu Pro Asp Ser Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255
```

```
Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
            275                 280                 285

Cys His Phe Ser Pro Arg Asp Trp Gln Arg Leu Ile Asn Asn Asn Trp
            290                 295                 300

Gly Phe Arg Pro Lys Arg Leu Asn Phe Lys Leu Phe Asn Ile Gln Val
305                 310                 315                 320

Lys Glu Val Thr Gln Asn Asp Gly Thr Thr Ile Ala Asn Asn Leu
            325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
            355                 360                 365

Val Phe Met Val Pro Gln Tyr Gly Tyr Leu Thr Leu Asn Asn Gly Ser
            370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
            405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Ser Arg Thr
            435                 440                 445

Asn Thr Pro Ser Gly Thr Thr Thr Gln Ser Gly Leu Gln Phe Ser Gln
            450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
            485                 490                 495

Asn Ser Glu Tyr Ser Trp Thr Gly Ala Thr Lys Tyr His Leu Asn Gly
            500                 505                 510

Arg Asp Ser Leu Val Asn Pro Gly Pro Ala Met Ala Ser His Lys Asp
            515                 520                 525

Asp Glu Glu Lys Phe Phe Pro Gln Ser Gly Val Leu Ile Phe Gly Lys
            530                 535                 540

Gln Gly Ser Glu Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
            565                 570                 575

Gly Ser Val Ser Thr Asn Leu Gln Arg Gly Asn Arg Gln Ala Ala Thr
            580                 585                 590

Ala Asp Val Asn Thr Gln Gly Val Leu Pro Gly Met Val Trp Gln Asp
            595                 600                 605

Arg Asp Val Tyr Leu Gln Gly Pro Ile Trp Ala Lys Ile Pro His Thr
            610                 615                 620

Asp Gly His Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asn
            645                 650                 655

Pro Ser Thr Thr Phe Ser Ala Ala Lys Phe Ala Ser Phe Ile Thr Gln
            660                 665                 670
```

```
Tyr Ser Thr Gly Gln Val Ser Val Glu Ile Glu Trp Glu Leu Gln Lys
            675                 680                 685

Glu Asn Ser Lys Arg Trp Asn Pro Glu Ile Gln Tyr Thr Ser Asn Tyr
        690                 695                 700

Asn Lys Ser Val Asn Val Asp Phe Thr Val Asp Thr Asn Gly Val Tyr
705                 710                 715                 720

Ser Glu Pro Arg Pro Ile Gly Thr Arg Tyr Leu Thr Arg Asn Leu Leu
                725                 730                 735

Leu Ala Ala

<210> SEQ ID NO 46
<211> LENGTH: 740
<212> TYPE: PRT
<213> ORGANISM: adeno-associated virus-2

<400> SEQUENCE: 46

Met Ala Ala Asp Gly Tyr Leu Pro Asp Trp Leu Glu Asp Thr Leu Ser
 1               5                  10                  15

Glu Gly Ile Arg Gln Trp Trp Lys Leu Lys Pro Gly Pro Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
 50                  55                  60

Val Asn Ala Ala Asp Ala Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
130                 135                 140

Pro Val Glu His Ser Pro Val Glu Pro Asp Ser Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
        195                 200                 205

Ala Pro Met Ala Asp Asn Asn Glu Gly Ala Asp Gly Val Gly Asn Ser
210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
290                 295                 300
```

```
Gly Phe Arg Pro Lys Arg Leu Asn Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
        355                 360                 365

Val Phe Met Val Pro Gln Tyr Gly Tyr Leu Thr Leu Asn Asn Gly Ser
    370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
                405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Ser Arg Thr
        435                 440                 445

Asn Thr Pro Ser Gly Thr Thr Thr Gln Ser Gly Leu Gln Phe Ser Gln
    450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
                485                 490                 495

Asn Ser Glu Tyr Ser Trp Thr Gly Ala Thr Lys Tyr His Leu Asn Gly
            500                 505                 510

Arg Asp Ser Leu Val Asn Pro Gly Pro Ala Met Ala Ser His Lys Asp
        515                 520                 525

Asp Glu Glu Lys Phe Phe Pro Gln Ser Gly Val Leu Ile Phe Gly Lys
    530                 535                 540

Gln Gly Ser Glu Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
                565                 570                 575

Gly Ser Val Ser Thr Asn Leu Gln Arg Gly Asn Arg Gln Ala Ala Thr
            580                 585                 590

Ala Asp Val Asn Thr Gln Gly Val Leu Pro Gly Met Val Trp Gln Asp
        595                 600                 605

Arg Asp Val Tyr Leu Gln Gly Pro Ile Trp Ala Lys Ile Pro His Thr
    610                 615                 620

Asp Gly His Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asn
                645                 650                 655

Pro Ser Thr Thr Phe Ser Ala Ala Lys Phe Ala Ser Phe Ile Thr Gln
            660                 665                 670

Tyr Ser Thr Gly Gln Val Ser Val Glu Ile Glu Trp Glu Leu Gln Lys
        675                 680                 685

Glu Asn Ser Lys Arg Trp Asn Pro Glu Ile Gln Tyr Thr Ser Asn Tyr
    690                 695                 700

Asn Lys Ser Val Asn Val Asp Phe Thr Val Asp Thr Asn Gly Val Tyr
705                 710                 715                 720

Ser Glu Pro Arg Pro Ile Gly Thr Arg Tyr Leu Thr Arg Asn Leu Leu
```

```
                    725                 730                 735

Leu Ala Ala Ala
            740

<210> SEQ ID NO 47
<211> LENGTH: 741
<212> TYPE: PRT
<213> ORGANISM: adeno-associated virus-2

<400> SEQUENCE: 47

Met Ala Ala Asp Gly Tyr Leu Pro Asp Trp Leu Glu Asp Thr Leu Ser
  1               5                  10                  15

Glu Gly Ile Arg Glu Trp Trp Ala Leu Lys Pro Gly Ala Pro Lys Pro
             20                  25                  30

Lys Ala Asn Gln Gln Lys Gln Asp Asp Gly Arg Gly Leu Val Leu Pro
         35                  40                  45

Gly Tyr Lys Tyr Leu Gly Pro Phe Asn Gly Leu Asp Lys Gly Glu Pro
     50                  55                  60

Val Asn Glu Ala Asp Ala Ala Leu Glu His Asp Lys Ala Tyr Asp
 65                  70                  75                  80

Gln Gln Leu Gln Ala Gly Asp Asn Pro Tyr Leu Arg Tyr Asn His Ala
                 85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
    130                 135                 140

Pro Val Glu His Ser Pro Val Glu Pro Asp Ser Ser Ser Gly Thr Gly
145                 150                 155                 160

Lys Ser Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
    290                 295                 300

Gly Phe Arg Pro Lys Arg Leu Asn Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350
```

```
Val Leu Gly Ser Ala His Gln Gly Cys Leu Pro Phe Pro Ala Asp
            355                 360                 365

Val Phe Met Val Pro Gln Tyr Gly Tyr Leu Thr Leu Asn Asn Gly Ser
370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
            405                 410                 415

Asp Val Pro Phe His Ser Ser Tyr Ala His Ser Gln Ser Leu Asp Arg
        420                 425                 430

Leu Met Asn Pro Leu Ile Asp Gln Tyr Leu Tyr Tyr Leu Ser Arg Thr
            435                 440                 445

Asn Thr Pro Ser Gly Thr Thr Thr Gln Ser Gly Leu Gln Phe Ser Gln
        450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
            485                 490                 495

Asn Ser Glu Tyr Ser Trp Thr Gly Ala Thr Lys Tyr His Leu Asn Gly
        500                 505                 510

Arg Asp Ser Leu Val Asn Pro Gly Pro Ala Met Ala Ser His Lys Asp
    515                 520                 525

Asp Glu Glu Lys Phe Phe Pro Gln Ser Gly Val Leu Ile Phe Gly Lys
530                 535                 540

Gln Gly Ser Glu Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
                565                 570                 575

Gly Ser Val Ser Thr Asn Leu Gln Arg Gly Asn Leu Ala Asn His Asn
            580                 585                 590

Asn Thr Thr Asn Ala Arg Gln Ala Ala Thr Ala Asp Val Asn Thr Gln
            595                 600                 605

Gly Val Leu Pro Gly Met Val Trp Gln Asp Arg Asp Val Tyr Leu Gln
610                 615                 620

Gly Pro Ile Trp Ala Lys Ile Pro His Thr Asp Gly His Phe His Pro
625                 630                 635                 640

Ser Pro Leu Met Gly Gly Phe Gly Leu Lys His Pro Pro Pro Gln Ile
            645                 650                 655

Leu Ile Lys Asn Thr Pro Val Pro Ala Asn Pro Ser Thr Thr Phe Ser
            660                 665                 670

Ala Ala Lys Phe Ala Ser Phe Ile Thr Gln Tyr Ser Thr Gly Gln Val
            675                 680                 685

Ser Val Glu Ile Glu Trp Glu Leu Gln Lys Glu Asn Ser Lys Arg Trp
690                 695                 700

Asn Pro Glu Ile Gln Tyr Thr Ser Asn Tyr Asn Lys Ser Ile Asn Val
705                 710                 715                 720

Asp Phe Thr Val Asp Thr Asn Gly Val Tyr Ser Glu Pro Arg Pro Ile
                725                 730                 735

Gly Thr Arg Tyr Leu
            740

<210> SEQ ID NO 48
<211> LENGTH: 734
<212> TYPE: PRT
```

<213> ORGANISM: adeno-associated virus-2

<400> SEQUENCE: 48

```
Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
    130                 135                 140

Pro Val Glu His Ser Pro Val Glu Pro Asp Ser Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
    290                 295                 300

Gly Phe Arg Pro Lys Arg Leu Asn Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
        355                 360                 365

Val Phe Met Val Pro Gln Tyr Gly Tyr Leu Thr Leu Asn Asn Gly Ser
    370                 375                 380

Gln Ala Val Gly Arg Ser Ser Phe Tyr Cys Leu Glu Tyr Phe Pro Ser
385                 390                 395                 400
```

-continued

```
Gln Met Leu Arg Thr Gly Asn Asn Phe Thr Phe Ser Tyr Thr Phe Glu
                405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Ser Arg Thr
        435                 440                 445

Asn Thr Pro Ser Gly Thr Thr Thr Gln Ser Gly Leu Gln Phe Ser Gln
    450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
                485                 490                 495

Asn Ser Glu Tyr Ser Trp Thr Gly Ala Thr Met Tyr His Leu Asn Gly
            500                 505                 510

Arg Asp Ser Leu Val Asn Pro Gly Pro Ala Met Ala Ser His Lys Asp
        515                 520                 525

Asp Glu Glu Lys Phe Phe Pro Gln Ser Gly Val Leu Ile Phe Gly Lys
    530                 535                 540

Gln Gly Ser Glu Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
                565                 570                 575

Gly Ser Val Ser Thr Asn Leu Gln Arg Gly Asn Arg Gln Ala Ala Thr
            580                 585                 590

Ala Asp Val Asn Thr Gln Gly Val Leu Pro Gly Met Val Trp Gln Asp
        595                 600                 605

Arg Asp Val Tyr Leu Gln Gly Pro Ile Trp Ala Lys Ile Pro His Thr
    610                 615                 620

Asp Gly His Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asn
                645                 650                 655

Pro Ser Thr Thr Phe Ser Ala Ala Lys Phe Ala Ser Phe Ile Thr Gln
            660                 665                 670

Tyr Ser Thr Gly Gln Val Ser Val Glu Ile Glu Trp Glu Leu Gln Lys
        675                 680                 685

Glu Asn Ser Lys Arg Trp Asn Pro Glu Ile Gln Tyr Thr Ser Asn Tyr
    690                 695                 700

Asn Lys Ser Ile Asn Val Asp Phe Thr Val Asp Thr Asn Gly Val Tyr
705                 710                 715                 720

Ser Glu Pro Arg Pro Ile Gly Thr Arg Tyr Leu Thr Arg Asn
                725                 730

<210> SEQ ID NO 49
<211> LENGTH: 734
<212> TYPE: PRT
<213> ORGANISM: adeno-associated virus-2

<400> SEQUENCE: 49

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro
                20                  25                  30

Lys Pro Ala Glu Arg His Lys Asp Asp Ser Arg Gly Leu Val Leu Pro
            35                  40                  45
```

```
Gly Tyr Lys Tyr Leu Gly Pro Phe Asn Gly Leu Asp Lys Gly Glu Pro
     50                  55                  60

Val Asn Glu Ala Asp Ala Ala Leu Glu His Asp Lys Ala Tyr Asp
 65                  70                  75                  80

Arg Gln Leu Asp Ser Gly Asp Asn Pro Tyr Leu Lys Tyr Asn His Ala
                 85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
    130                 135                 140

Pro Val Glu His Ser Pro Val Glu Pro Asp Ser Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
    290                 295                 300

Gly Phe Arg Pro Lys Arg Leu Asn Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
        355                 360                 365

Val Phe Met Val Pro Gln Tyr Gly Tyr Leu Thr Leu Asn Asn Gly Ser
    370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
                405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Ser Arg Thr
        435                 440                 445

Asn Thr Pro Ser Gly Thr Thr Thr Gln Ser Gly Leu Gln Phe Ser Gln
    450                 455                 460
```

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
            485                 490                 495

Asn Ser Glu Tyr Ser Trp Thr Gly Ala Thr Lys Tyr His Leu Asn Gly
        500                 505                 510

Arg Asp Ser Leu Val Asn Pro Gly Pro Ala Met Ala Ser His Lys Asp
    515                 520                 525

Asp Glu Glu Lys Phe Phe Pro Gln Ser Gly Val Leu Ile Phe Gly Lys
530                 535                 540

Gln Gly Ser Glu Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
                565                 570                 575

Gly Ser Val Ser Thr Asn Leu Gln Arg Gly Asn Arg Gln Ala Ala Thr
            580                 585                 590

Ala Asp Val Asn Thr Gln Gly Val Leu Pro Gly Met Val Trp Gln Asp
        595                 600                 605

Arg Asp Val Tyr Leu Gln Gly Pro Ile Trp Ala Lys Ile Pro His Thr
610                 615                 620

Asp Gly His Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asn
                645                 650                 655

Pro Ser Thr Thr Phe Ser Glu Ala Lys Phe Ala Ser Phe Ile Thr Gln
            660                 665                 670

Tyr Ser Thr Gly Gln Val Ser Val Glu Ile Glu Trp Glu Leu Gln Lys
        675                 680                 685

Glu Asn Ser Lys Arg Trp Asn Pro Glu Ile Gln Tyr Thr Ser Asn Tyr
690                 695                 700

Asn Lys Ser Val Asn Val Asp Phe Thr Val Asp Thr Asn Gly Val Tyr
705                 710                 715                 720

Ser Glu Pro Arg Pro Ile Gly Thr Arg Tyr Leu Thr Arg Asn
                725                 730

<210> SEQ ID NO 50
<211> LENGTH: 725
<212> TYPE: PRT
<213> ORGANISM: adeno-associated virus-2

<400> SEQUENCE: 50

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

```
Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
    130                 135                 140

Pro Val Glu His Ser Pro Val Glu Pro Asp Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
                180                 185                 190

Ala Ala Pro Ser Gly Leu Gly Thr Asn Thr Met Ala Thr Gly Ser Gly
            195                 200                 205

Ala Pro Met Ala Asp Asn Asn Glu Gly Ala Asp Gly Val Gly Asn Ser
        210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
                260                 265                 270

Phe Gly Tyr Ser Thr Pro Trp Gly Tyr Phe Asp Phe Asn Arg Phe His
            275                 280                 285

Cys His Phe Ser Pro Arg Asp Trp Gln Arg Leu Ile Asn Asn Asn Trp
        290                 295                 300

Gly Phe Arg Pro Lys Arg Leu Asn Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
        355                 360                 365

Val Phe Met Val Pro Gln Tyr Gly Tyr Leu Thr Leu Asn Asn Gly Ser
    370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
                405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Ser Arg Thr
        435                 440                 445

Asn Thr Pro Ser Gly Thr Thr Thr Gln Ser Gly Leu Gln Phe Ser Gln
    450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
                485                 490                 495

Asn Ser Glu Tyr Ser Trp Thr Gly Ala Thr Lys Tyr His Leu Asn Gly
            500                 505                 510

Arg Asp Ser Leu Val Asn Pro Gly Pro Ala Met Ala Ser His Lys Asp
        515                 520                 525
```

```
Asp Glu Glu Lys Phe Phe Pro Gln Ser Gly Val Leu Ile Phe Gly Lys
            530                 535                 540

Gln Gly Ser Glu Lys Thr Asn Val Asp Ile Glu Lys Val Met Ile Thr
545                 550                 555                 560

Asp Glu Glu Ile Arg Thr Thr Asn Pro Val Ala Thr Glu Gln Tyr
                565                 570                 575

Gly Ser Val Ser Thr Asn Leu Gln Arg Gly Asn Arg Gln Ala Ala Thr
                580                 585                 590

Ala Asp Val Asn Thr Gln Gly Val Leu Pro Gly Met Val Trp Gln Asp
                595                 600                 605

Arg Asp Val Tyr Leu Gln Gly Pro Ile Trp Ala Lys Ile Pro His Thr
            610                 615                 620

Asp Gly His Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asn
                645                 650                 655

Pro Ser Thr Thr Phe Ser Ala Ala Lys Phe Ala Ser Phe Ile Thr Gln
                660                 665                 670

Tyr Ser Thr Gly Gln Val Ser Val Glu Ile Glu Trp Glu Leu Gln Lys
            675                 680                 685

Glu Asn Ser Lys Arg Trp Asn Pro Glu Ile Gln Tyr Thr Ser Asn Tyr
690                 695                 700

Asn Lys Ser Val Asn Val Asp Phe Thr Val Asp Thr Asn Gly Val Tyr
705                 710                 715                 720

Ser Glu Pro Arg Pro
                725

<210> SEQ ID NO 51
<211> LENGTH: 737
<212> TYPE: PRT
<213> ORGANISM: adeno-associated virus-2

<400> SEQUENCE: 51

Met Ala Ser Asp Gly Tyr Leu Pro Asp Trp Leu Glu Asp Asn Leu Ser
1                   5                   10                  15

Glu Gly Ile Arg Glu Trp Trp Asp Leu Lys Pro Gly Ala Pro Lys Pro
                20                  25                  30

Lys Ala Asn Gln Gln Lys Gln Asp Asp Gly Arg Gly Leu Val Leu Pro
            35                  40                  45

Gly Tyr Lys Tyr Leu Gly Pro Phe Asn Gly Leu Asp Lys Gly Glu Pro
        50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
                100                 105                 110

Asn Leu Gly Arg Ala Val Phe Gln Ala Lys Lys Arg Val Leu Glu Pro
            115                 120                 125

Phe Gly Leu Val Glu Glu Gly Ala Lys Thr Ala Pro Gly Lys Lys Arg
        130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175
```

```
Gly Asp Ser Glu Ser Val Pro Asp Pro Gln Pro Leu Gly Glu Pro Pro
            180                 185                 190

Ala Thr Pro Ala Ala Val Gly Pro Thr Thr Met Ala Ser Gly Gly Gly
            195                 200                 205

Ala Pro Met Ala Asp Asn Asn Glu Gly Ala Asp Gly Val Gly Asn Ala
            210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Ala Ser Thr Gly Ala Ser Asn Asp Asn His
            260                 265                 270

Tyr Phe Gly Tyr Ser Thr Pro Trp Gly Tyr Phe Asp Phe Asn Arg Phe
            275                 280                 285

His Cys His Phe Ser Pro Arg Asp Trp Gln Arg Leu Ile Asn Asn Asn
            290                 295                 300

Trp Gly Phe Arg Pro Lys Arg Leu Asn Phe Lys Leu Phe Asn Ile Gln
305                 310                 315                 320

Val Lys Glu Val Thr Thr Asn Asp Gly Thr Thr Thr Ile Ala Asn Asn
                325                 330                 335

Leu Thr Ser Thr Val Gln Val Phe Thr Asp Ser Glu Tyr Gln Leu Pro
            340                 345                 350

Tyr Val Leu Gly Ser Ala His Gln Gly Cys Leu Pro Pro Phe Pro Ala
            355                 360                 365

Asp Val Phe Met Val Pro Gln Tyr Gly Tyr Leu Thr Leu Asn Asn Gly
            370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
                405                 410                 415

Glu Asp Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Ser Arg
            435                 440                 445

Thr Asn Thr Pro Ser Gly Thr Thr Thr Gln Ser Gly Leu Gln Phe Ser
450                 455                 460

Gln Ala Gly Ala Ser Asp Ile Arg Asp Gln Ser Arg Asn Trp Leu Pro
465                 470                 475                 480

Gly Pro Cys Tyr Arg Gln Gln Arg Val Ser Lys Thr Ser Ala Asp Asn
                485                 490                 495

Asn Asn Ser Glu Tyr Ser Trp Thr Gly Ala Thr Lys Tyr His Leu Asn
            500                 505                 510

Gly Arg Asp Ser Leu Val Asn Pro Gly Pro Ala Met Ala Ser His Lys
            515                 520                 525

Asp Asp Glu Glu Lys Phe Phe Pro Gln Ser Gly Val Leu Ile Phe Gly
            530                 535                 540

Lys Gln Gly Ser Glu Lys Thr Asn Val Asp Ile Glu Lys Val Met Ile
545                 550                 555                 560

Thr Asp Glu Glu Glu Ile Arg Thr Thr Asn Pro Val Ala Thr Glu Gln
                565                 570                 575

Tyr Gly Ser Val Ser Thr Asn Leu Gln Arg Gly Asn Arg Gln Ala Ala
            580                 585                 590
```

```
Thr Ala Asp Val Asn Thr Gln Gly Val Leu Pro Gly Met Val Trp Gln
            595                 600                 605

Asp Arg Asp Val Tyr Leu Gln Gly Pro Ile Trp Ala Lys Ile Pro His
    610                 615                 620

Thr Asp Gly His Phe His Pro Ser Pro Leu Met Gly Gly Phe Gly Leu
625                 630                 635                 640

Lys His His Pro Pro Gln Ile Leu Ile Lys Asn Thr Pro Val Pro Ala
                645                 650                 655

Asn Pro Ser Thr Thr Phe Ser Ala Ala Lys Phe Ala Ser Phe Ile Thr
            660                 665                 670

Gln Tyr Ser Thr Gly Gln Val Ser Val Glu Ile Glu Trp Glu Leu Gln
    675                 680                 685

Lys Glu Asn Ser Lys Arg Trp Asn Pro Glu Ile Gln Tyr Thr Ser Asn
    690                 695                 700

Tyr Asn Lys Ser Val Asn Val Asp Phe Thr Val Asp Thr Asn Gly Val
705                 710                 715                 720

Tyr Ser Glu Pro Arg Pro Ile Gly Thr Arg Tyr Leu Thr Arg Asn Leu
                725                 730                 735

Leu

<210> SEQ ID NO 52
<211> LENGTH: 707
<212> TYPE: PRT
<213> ORGANISM: adeno-associated virus-2

<400> SEQUENCE: 52

Met Ala Ala Asp Gly Tyr Leu Pro Asp Trp Leu Glu Asp Thr Leu Ser
  1               5                  10                  15

Glu Gly Ile Arg Gln Trp Trp Lys Leu Lys Pro Gly Pro Pro Pro Pro
                 20                  25                  30

Lys Pro Ala Glu Arg His Lys Asp Asp Ser Arg Gly Leu Val Leu Pro
             35                  40                  45

Gly Tyr Lys Tyr Leu Gly Pro Phe Asn Gly Leu Asp Lys Gly Glu Pro
     50                  55                  60

Val Asn Glu Ala Asp Ala Ala Ala Leu Glu His Asp Lys Ala Tyr Asp
 65                  70                  75                  80

Arg Gln Leu Asp Ser Gly Asp Asn Pro Tyr Leu Lys Tyr Asn His Ala
                 85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
    130                 135                 140

Pro Val Glu His Ser Pro Val Glu Pro Asp Ser Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
        195                 200                 205

Ala Pro Met Ala Asp Asn Asn Glu Gly Ala Asp Gly Val Gly Asn Ser
    210                 215                 220
```

-continued

```
Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
            245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
            275                 280                 285

Cys His Phe Ser Pro Arg Asp Trp Gln Arg Leu Ile Asn Asn Asn Trp
290                 295                 300

Gly Phe Arg Pro Lys Arg Leu Asn Phe Lys Leu Phe Asn Ile Gln Val
305                 310                 315                 320

Lys Glu Val Thr Gln Asn Asp Gly Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
            355                 360                 365

Val Phe Met Val Pro Gln Tyr Gly Tyr Leu Thr Leu Asn Asn Gly Ser
370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
            405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Ser Arg Thr
435                 440                 445

Asn Thr Pro Ser Gly Thr Thr Thr Gln Ser Gly Leu Gln Phe Ser Gln
450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
            485                 490                 495

Asn Ser Glu Tyr Ser Trp Thr Gly Ala Thr Lys Tyr His Leu Asn Gly
            500                 505                 510

Arg Asp Ser Leu Val Asn Pro Gly Pro Ala Met Ala Ser His Lys Asp
            515                 520                 525

Asp Glu Glu Lys Phe Phe Pro Gln Ser Gly Val Leu Ile Phe Gly Lys
530                 535                 540

Gln Gly Ser Glu Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
            565                 570                 575

Gly Ser Cys Ile Tyr Gln Pro Pro Glu Arg Gln Gln Thr Ser Ser Tyr
            580                 585                 590

Arg Arg Cys Gln His Thr Arg Arg Ser Ser Arg His Gly Leu Ala Gly
            595                 600                 605

Gln Arg Cys Val Pro Ser Gly Ala His Leu Gly Lys Asp Ser Thr His
            610                 615                 620

Gly Arg Thr Phe Ser Pro Leu Ser Pro His Gly Trp Ile Arg Thr Thr
625                 630                 635                 640

Pro Ser Ser Thr Asp Ser His Gln Glu His Pro Gly Thr Cys Glu Ser
```

```
                    645                 650                 655
Phe Asp His Leu Gln Cys Gly Lys Val Cys Phe Leu His His Thr Val
                660                 665                 670

Leu His Gly Thr Gly Gln Arg Gly Asp Arg Val Arg Ala Ala Glu Gly
            675                 680                 685

Lys Gln Gln Thr Leu Glu Ser Arg Asn Ser Val His Phe Gln Leu Gln
        690                 695                 700

Gln Val Cys
705

<210> SEQ ID NO 53
<211> LENGTH: 739
<212> TYPE: PRT
<213> ORGANISM: adeno-associated virus-2

<400> SEQUENCE: 53

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
    130                 135                 140

Pro Val Glu His Ser Pro Val Glu Pro Asp Ser Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
    290                 295                 300
```

-continued

```
Gly Phe Arg Pro Lys Arg Leu Asn Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
                340                 345                 350

Val Leu Gly Ser Ala His Gln Gly Cys Leu Pro Pro Phe Pro Ala Asp
                355                 360                 365

Val Phe Met Val Pro Gln Tyr Gly Tyr Leu Thr Leu Asn Asn Gly Ser
            370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
                405                 410                 415

Asp Val Pro Phe His Ser Ser Tyr Ala His Ser Gln Ser Leu Asp Arg
                420                 425                 430

Leu Met Asn Pro Leu Ile Asp Gln Tyr Leu Tyr Tyr Leu Ser Arg Thr
            435                 440                 445

Asn Thr Pro Ser Gly Thr Thr Thr Gln Ser Gly Leu Gln Phe Ser Gln
450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
                485                 490                 495

Asn Ser Glu Tyr Ser Trp Thr Gly Ala Thr Lys Tyr His Leu Asn Gly
            500                 505                 510

Arg Asp Ser Leu Val Asn Pro Gly Pro Ala Met Ala Ser His Lys Asp
                515                 520                 525

Asp Glu Glu Lys Phe Phe Pro Gln Ser Gly Val Leu Ile Phe Gly Lys
            530                 535                 540

Gln Gly Ser Glu Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
                565                 570                 575

Gly Ser Val Ser Thr Asn Leu Gln Arg Gly Asn Arg Gln Ala Ala Thr
                580                 585                 590

Ala Asp Val Asn Thr Gln Gly Val Leu Pro Gly Met Val Trp Gln Asp
            595                 600                 605

Arg Asp Val Tyr Leu Gln Gly Pro Ile Trp Ala Lys Ile Pro His Thr
610                 615                 620

Asp Gly His Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asn
                645                 650                 655

Pro Ser Thr Thr Phe Ser Ala Ala Lys Phe Ala Ser Phe Ile Thr Gln
            660                 665                 670

Tyr Ser Thr Gly Gln Val Ser Val Glu Ile Glu Trp Glu Leu Gln Lys
                675                 680                 685

Glu Asn Ser Lys Arg Trp Asn Pro Glu Ile Gln Tyr Thr Ser Asn Tyr
            690                 695                 700

Asn Lys Ser Val Asn Val Asp Phe Thr Val Asp Thr Asn Gly Val Tyr
705                 710                 715                 720

Ser Glu Pro Arg Pro Ile Gly Thr Arg Tyr Leu Thr Arg Asn Leu Leu
```

Leu Ala Ala

<210> SEQ ID NO 54
<211> LENGTH: 734
<212> TYPE: PRT
<213> ORGANISM: adeno-associated virus-2

<400> SEQUENCE: 54

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
130                 135                 140

Pro Val Glu His Ser Pro Val Glu Pro Asp Ser Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Ser Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
    290                 295                 300

Gly Phe Arg Pro Lys Arg Leu Asn Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp

```
                     355                 360                 365
Val Phe Met Val Pro Gln Tyr Gly Tyr Leu Thr Leu Asn Asn Gly Ser
370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
                405                 410                 415

Asp Val Pro Phe His Ser Ser Tyr Ala His Ser Gln Ser Leu Asp Arg
                420                 425                 430

Leu Met Asn Pro Leu Ile Asp Gln Tyr Leu Tyr Tyr Leu Ser Arg Thr
                435                 440                 445

Asn Thr Pro Ser Gly Thr Thr Thr Gln Ser Arg Leu Gln Phe Ser Gln
                450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
                485                 490                 495

Asn Ser Glu Tyr Ser Trp Thr Gly Ala Thr Lys Tyr His Leu Asn Gly
                500                 505                 510

Arg Asp Ser Leu Val Asn Pro Gly Pro Ala Met Ala Ser His Lys Asp
                515                 520                 525

Asp Glu Glu Lys Phe Phe Pro Gln Ser Gly Val Leu Ile Phe Gly Lys
                530                 535                 540

Gln Gly Ser Glu Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
                565                 570                 575

Gly Ser Val Ser Thr Asn Leu Gln Arg Gly Asn Arg Gln Ala Ala Thr
                580                 585                 590

Ala Asp Val Asn Thr Gln Gly Val Leu Pro Gly Met Val Trp Gln Asp
                595                 600                 605

Arg Asp Val Tyr Leu Gln Gly Pro Ile Trp Ala Lys Ile Pro His Thr
610                 615                 620

Asp Gly His Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asn
                645                 650                 655

Pro Ser Thr Thr Phe Ser Ala Ala Lys Phe Ala Ser Phe Ile Thr Gln
                660                 665                 670

Tyr Ser Thr Gly Gln Val Ser Val Glu Ile Glu Trp Glu Leu Gln Lys
                675                 680                 685

Glu Asn Ser Lys Arg Trp Asn Pro Glu Ile Gln Tyr Thr Ser Asn Tyr
                690                 695                 700

Asn Lys Ser Ile Asn Val Asp Phe Thr Val Asp Thr Asn Gly Val Tyr
705                 710                 715                 720

Ser Glu Pro Arg Pro Ile Gly Thr Arg Tyr Leu Thr Arg Asn
                725                 730

<210> SEQ ID NO 55
<211> LENGTH: 730
<212> TYPE: PRT
<213> ORGANISM: adeno-associated virus-2

<400> SEQUENCE: 55
```

-continued

```
Met Ala Ser Asp Gly Tyr Leu Pro Asp Trp Leu Glu Asp Asn Leu Ser
 1               5                  10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
 50                  55                  60

Val Asn Ala Ala Asp Ala Ala Leu Glu His Asp Lys Ala Tyr Asp
 65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Phe Gly Leu Val Glu Glu Gly Ala Lys Thr Ala Pro Gly Lys Lys Arg
 130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Thr Pro Ala Ala Val Gly Pro Thr Thr Met Ala Ser Gly Gly Gly
        195                 200                 205

Ala Pro Met Ala Asp Asn Asn Glu Gly Ala Asp Gly Val Gly Asn Ala
 210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Ala Ser Thr Gly Ala Ser Asn Asp Asn His
            260                 265                 270

Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
 290                 295                 300

Trp Gly Phe Arg Pro Lys Arg Leu Asn Phe Lys Leu Phe Asn Ile Gln
305                 310                 315                 320

Val Lys Glu Val Thr Thr Asn Asp Gly Val Thr Thr Ile Ala Asn Asn
                325                 330                 335

Leu Thr Ser Thr Val Gln Val Phe Ser Asp Ser Glu Tyr Gln Leu Pro
            340                 345                 350

Tyr Val Leu Gly Ser Ala His Gln Gly Cys Leu Pro Pro Phe Pro Ala
        355                 360                 365

Asp Val Phe Met Ile Pro Gln Tyr Gly Tyr Leu Thr Leu Asn Asn Gly
 370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
                405                 410                 415

Glu Asp Val Pro Phe His Ser Ser Tyr Ala His Ser Gln Ser Leu Asp
```

420                 425                 430

Arg Leu Met Asn Pro Leu Ile Asp Gln Tyr Leu Tyr Tyr Leu Asn Arg
            435                 440                 445

Thr Gln Asn Gln Ser Gly Ser Ala Gln Asn Asn Asp Leu Leu Phe Ser
450                 455                 460

Arg Gly Ser Pro Ala Gly Met Ser Val Gln Pro Lys Asn Trp Leu Pro
465                 470                 475                 480

Gly Pro Cys Tyr Arg Gln Gln Arg Val Ser Lys Thr Lys Thr Asp Asn
                485                 490                 495

Asn Asn Ser Asn Phe Thr Trp Thr Gly Ala Ser Lys Tyr Asn Leu Asn
            500                 505                 510

Gly Arg Glu Ser Ile Ile Asn Pro Gly Thr Ala Met Ala Ser His Lys
        515                 520                 525

Asp Asp Lys Asp Lys Phe Phe Pro Met Ser Gly Val Met Ile Phe Gly
    530                 535                 540

Lys Glu Ser Ala Gly Ala Ser Asn Thr Ala Leu Asp Asn Val Met Ile
545                 550                 555                 560

Thr Asp Glu Glu Glu Ile Lys Ala Thr Asn Pro Val Ala Thr Glu Arg
                565                 570                 575

Phe Gly Thr Val Ala Val Asn Leu Gln Ser Ser Ser Thr Asp Pro Ala
            580                 585                 590

Thr Gly Asp Val His Val Met Gly Ala Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly His Phe His Pro Ser Pro Leu Met Gly Gly Phe Gly Leu
625                 630                 635                 640

Lys Asn Pro Pro Pro Gln Ile Leu Ile Lys Asn Thr Pro Val Pro Ala
                645                 650                 655

Asn Pro Pro Ala Glu Phe Ser Ala Thr Lys Phe Ala Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Val Gln Tyr Thr Ser Asn
    690                 695                 700

Tyr Ala Lys Ser Ala Asn Val Asp Phe Thr Val Asp Asn Asn Gly Leu
705                 710                 715                 720

Tyr Thr Glu Pro Arg Pro Ile Gly Thr Arg
                725                 730

<210> SEQ ID NO 56
<211> LENGTH: 735
<212> TYPE: PRT
<213> ORGANISM: adeno-associated virus-2
<220> FEATURE:
<221> NAME/KEY: VARIANT
<222> LOCATION: 239
<223> OTHER INFORMATION: Xaa = Any Amino Acid

<400> SEQUENCE: 56

Met Ala Ser Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Gly Arg Gly Leu Val Leu Pro
        35                  40                  45

```
Gly Tyr Lys Tyr Leu Gly Pro Phe Asn Gly Leu Asp Lys Gly Glu Pro
 50                  55                  60

Val Asn Ala Ala Asp Ala Ala Leu Glu His Asp Lys Ala Tyr Asp
 65                  70                  75                  80

Gln Gln Leu Lys Ala Gly Asp Pro Tyr Leu Arg Tyr Asn His Ala
                 85                  90                  95

Asp Ala Glu Phe Gln Glu Arg Leu Gln Glu Asp Thr Ser Phe Gly Gly
                100                 105                 110

Asn Leu Gly Arg Ala Val Phe Gln Ala Lys Lys Arg Val Leu Glu Pro
            115                 120                 125

Phe Gly Leu Val Glu Glu Gly Ala Lys Thr Ala Pro Gly Lys Lys Arg
            130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Thr Pro Ala Ala Val Gly Pro Thr Thr Met Ala Ser Gly Gly Gly
            195                 200                 205

Ala Pro Met Ala Asp Asn Asn Glu Gly Ala Asp Gly Val Gly Asn Ala
210                 215                 220

Ser Gly Asn Trp His Cys Asp Ser Thr Trp Leu Gly Asp Arg Xaa Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Ala Ser Thr Gly Ala Ser Asn Asp Asn His
                260                 265                 270

Tyr Phe Gly Tyr Ser Thr Pro Trp Gly Tyr Phe Asp Phe Asn Arg Phe
            275                 280                 285

His Cys His Phe Ser Pro Arg Asp Trp Gln Arg Leu Ile Asn Asn Asn
290                 295                 300

Trp Gly Phe Arg Pro Lys Arg Leu Asn Phe Lys Leu Phe Asn Ile Gln
305                 310                 315                 320

Val Lys Glu Val Thr Thr Asn Asp Gly Val Thr Thr Ile Ala Asn Asn
                325                 330                 335

Leu Thr Ser Thr Val Gln Val Phe Ser Asp Ser Glu Tyr Gln Leu Pro
            340                 345                 350

Tyr Val Leu Gly Ser Ala His Gln Gly Cys Leu Pro Pro Phe Pro Ala
            355                 360                 365

Asp Val Phe Met Ile Pro Gln Tyr Gly Tyr Leu Thr Leu Asn Asn Gly
            370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
                405                 410                 415

Glu Asp Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Asn Arg
            435                 440                 445

Thr Gln Asn Gln Ser Gly Ser Ala Gln Asn Asn Asp Leu Leu Phe Ser
            450                 455                 460
```

Arg Gly Ser Pro Ala Gly Met Ser Val Gln Pro Lys Asn Trp Leu Pro
465                 470                 475                 480

Gly Pro Cys Tyr Arg Gln Gln Arg Val Ser Lys Thr Lys Thr Asp Asn
            485                 490                 495

Asn Asn Ser Asn Phe Thr Trp Thr Gly Ala Ser Lys Tyr Asn Leu Asn
        500                 505                 510

Gly Arg Glu Ser Ile Ile Asn Pro Gly Thr Ala Met Ala Ser His Lys
    515                 520                 525

Asp Asp Lys Asp Lys Phe Phe Pro Met Ser Gly Val Met Ile Phe Gly
530                 535                 540

Lys Glu Ser Ala Gly Ala Ser Asn Thr Ala Leu Asp Asn Val Met Ile
545                 550                 555                 560

Thr Asp Glu Glu Glu Ile Lys Ala Thr Asn Pro Val Ala Thr Glu Arg
                565                 570                 575

Phe Gly Thr Val Ala Val Asn Leu Gln Ser Ser Ser Thr Asp Pro Ala
            580                 585                 590

Thr Gly Asp Val His Val Met Gly Ala Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly His Phe His Pro Ser Pro Leu Met Gly Gly Phe Gly Leu
625                 630                 635                 640

Lys Asn Pro Pro Pro Gln Ile Leu Ile Lys Asn Thr Pro Val Pro Ala
                645                 650                 655

Asn Pro Pro Ala Glu Phe Ser Ala Thr Lys Phe Ala Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Val Gln Tyr Thr Ser Asn
    690                 695                 700

Tyr Ala Lys Ser Ala Asn Val Asp Phe Thr Val Asp Asn Asn Gly Leu
705                 710                 715                 720

Tyr Thr Glu Pro Arg Pro Ile Gly Thr Arg Tyr Leu Thr Arg Pro
                725                 730                 735

<210> SEQ ID NO 57
<211> LENGTH: 734
<212> TYPE: PRT
<213> ORGANISM: adeno-associated virus-2

<400> SEQUENCE: 57

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro Pro
            20                  25                  30

Lys Pro Ala Glu Arg His Lys Asp Asp Ser Arg Gly Leu Val Leu Pro
        35                  40                  45

Gly Cys Lys Tyr Leu Gly Pro Phe Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

-continued

```
Asn Leu Gly Arg Ala Val Phe Gln Ala Lys Lys Arg Val Leu Glu Pro
            115                 120                 125
Leu Gly Leu Val Glu Glu Pro Val Lys Thr Ala Pro Gly Lys Lys Arg
        130                 135                 140
Pro Val Glu His Ser Pro Val Glu Pro Asp Ser Ser Gly Thr Gly
145                 150                 155                 160
Lys Ala Gly Gln Gln Pro Ala Arg Lys Arg Leu Asn Phe Gly Gln Thr
                165                 170                 175
Gly Asp Ala Asp Ser Val Pro Asp Pro Gln Pro Leu Gly Gln Pro Pro
            180                 185                 190
Ala Ala Pro Ser Gly Leu Gly Thr Asn Thr Met Ala Thr Gly Ser Gly
        195                 200                 205
Ala Pro Met Ala Asp Asn Asn Glu Gly Ala Asp Gly Val Gly Asn Ser
210                 215                 220
Ser Gly Asn Trp His Cys Asp Ser Thr Trp Met Gly Asp Arg Val Ile
225                 230                 235                 240
Thr Thr Ser Thr Arg Thr Trp Ala Leu Pro Thr Tyr Asn Asn His Leu
                245                 250                 255
Tyr Lys Gln Ile Ser Ser Gln Ser Gly Ala Ser Asn Asp Asn His Tyr
            260                 265                 270
Phe Gly Tyr Ser Thr Pro Trp Gly Tyr Phe Asp Phe Asn Arg Phe His
        275                 280                 285
Cys His Phe Ser Pro Arg Asp Trp Gln Arg Leu Ile Asn Asn Asn Trp
    290                 295                 300
Gly Phe Arg Pro Lys Arg Leu Asn Phe Lys Leu Phe Asn Ile Gln Val
305                 310                 315                 320
Lys Glu Val Thr Gln Asn Asp Gly Thr Thr Thr Ile Ala Asn Asn Leu
                325                 330                 335
Thr Ser Thr Val Gln Val Phe Ser Asp Ser Glu Tyr Gln Leu Pro Tyr
            340                 345                 350
Val Leu Gly Ser Ala His Gln Gly Cys Leu Pro Pro Phe Pro Ala Asp
        355                 360                 365
Val Phe Met Ile Pro Gln Tyr Gly Tyr Leu Thr Leu Asn Asn Gly Ser
    370                 375                 380
Gln Ala Val Gly Arg Ser Ser Phe Tyr Cys Leu Glu Tyr Phe Pro Ser
385                 390                 395                 400
Gln Met Leu Arg Thr Gly Asn Asn Phe Thr Phe Asn Tyr Thr Phe Glu
                405                 410                 415
Asp Val Pro Phe His Ser Ser Tyr Ala His Ser Gln Ser Leu Asp Arg
            420                 425                 430
Leu Met Asn Pro Leu Ile Asp Gln Tyr Leu Tyr Tyr Leu Asn Arg Thr
        435                 440                 445
Gln Asn Gln Ser Gly Ser Ala Gln Asn Asn Asp Leu Leu Phe Ser Arg
    450                 455                 460
Gly Ser Pro Ala Gly Met Ser Val Gln Pro Lys Asn Trp Leu Pro Gly
465                 470                 475                 480
Pro Cys Tyr Arg Gln Gln Arg Val Ser Lys Thr Lys Thr Asp Asn Asn
                485                 490                 495
Asn Ser Asn Phe Thr Trp Thr Gly Ala Ser Lys Tyr Asn Leu Asn Gly
            500                 505                 510
Arg Glu Ser Ile Ile Asn Pro Gly Thr Ala Met Ala Ser His Lys Asp
        515                 520                 525
```

```
Asp Lys Asp Lys Phe Phe Pro Met Ser Gly Val Met Ile Phe Gly Lys
    530                 535                 540

Glu Ser Ala Gly Ala Ser Asn Thr Ala Leu Asp Asn Val Met Ile Thr
545                 550                 555                 560

Asp Glu Glu Ile Lys Ala Thr Asn Pro Val Ala Thr Glu Arg Phe
                565                 570                 575

Gly Thr Val Ala Val Asn Leu Gln Ser Ser Thr Asp Pro Ala Thr
            580                 585                 590

Gly Asp Val His Val Met Gly Ala Leu Pro Gly Met Val Trp Gln Asp
                595                 600                 605

Arg Asp Val Tyr Leu Gln Gly Pro Ile Trp Ala Lys Ile Pro His Thr
610                 615                 620

Asp Gly His Phe His Pro Ser Pro Leu Met Gly Gly Phe Gly Leu Lys
625                 630                 635                 640

Asn Pro Pro Pro Gln Ile Leu Ile Lys Asn Thr Pro Val Pro Ala Asn
                645                 650                 655

Pro Pro Ala Glu Phe Ser Ala Thr Lys Phe Ala Ser Phe Ile Thr Gln
                660                 665                 670

Tyr Ser Thr Gly Gln Val Ser Val Glu Ile Glu Trp Glu Leu Gln Lys
            675                 680                 685

Glu Asn Ser Lys Arg Trp Asn Pro Glu Val Gln Tyr Thr Ser Asn Tyr
690                 695                 700

Ala Lys Ser Ala Asn Val Asp Phe Thr Val Asp Asn Asn Gly Leu Tyr
705                 710                 715                 720

Thr Glu Pro Arg Pro Ile Gly Thr Arg Tyr Leu Thr Arg Pro
                725                 730

<210> SEQ ID NO 58
<211> LENGTH: 733
<212> TYPE: PRT
<213> ORGANISM: adeno-associated virus-2

<400> SEQUENCE: 58

Met Ala Ser Asp Gly Tyr Leu Pro Asp Trp Leu Glu Asp Asn Leu Ser
  1               5                  10                  15

Glu Gly Ile Arg Glu Trp Trp Asp Leu Lys Pro Gly Ala Pro Lys Pro
                20                  25                  30

Lys Ala Asn Gln Gln Lys Gln Asp Asp Gly Arg Gly Leu Val Leu Pro
            35                  40                  45

Gly Tyr Lys Tyr Leu Gly Pro Phe Asn Gly Leu Asp Lys Gly Glu Pro
        50                  55                  60

Val Asn Ala Ala Asp Ala Ala Ala Leu Glu His Asp Lys Ala Tyr Asp
 65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Leu Ala Lys Lys Arg Val Leu Glu Pro
        115                 120                 125

Phe Gly Leu Val Glu Glu Gly Ala Lys Thr Ala Pro Gly Lys Lys Arg
    130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175
```

-continued

```
Gly Asp Ser Glu Ser Val Pro Asp Pro Gln Pro Leu Gly Glu Pro Pro
            180                 185                 190

Ala Thr Pro Ala Ala Val Gly Pro Thr Thr Met Ala Ser Gly Gly Gly
        195                 200                 205

Ala Pro Met Ala Asp Asn Asn Glu Gly Ala Asp Gly Val Gly Asn Ala
    210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Ala Ser Thr Gly Ala Ser Asn Asp Asn His
            260                 265                 270

Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
    290                 295                 300

Trp Gly Phe Arg Pro Lys Arg Leu Asn Phe Lys Leu Phe Asn Ile Gln
305                 310                 315                 320

Val Lys Glu Val Thr Thr Asn Asp Gly Val Thr Thr Ile Ala Asn Asn
                325                 330                 335

Leu Thr Ser Thr Val Gln Val Phe Ser Asp Ser Glu Tyr Gln Leu Pro
            340                 345                 350

Tyr Val Leu Gly Ser Ala His Gln Gly Cys Leu Pro Pro Phe Pro Ala
        355                 360                 365

Asp Val Phe Met Ile Pro Gln Tyr Gly Tyr Leu Thr Leu Asn Asn Gly
    370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
                405                 410                 415

Glu Asp Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Asn Arg
        435                 440                 445

Thr Gln Asn Gln Ser Gly Ser Ala Gln Asn Asn Asp Leu Leu Phe Ser
    450                 455                 460

Arg Gly Ser Pro Ala Gly Met Ser Val Gln Pro Lys Asn Trp Leu Pro
465                 470                 475                 480

Gly Pro Cys Tyr Arg Gln Gln Arg Val Ser Lys Thr Lys Thr Asp Asn
                485                 490                 495

Asn Asn Ser Asn Phe Thr Trp Thr Gly Ala Ser Lys Tyr Asn Leu Asn
            500                 505                 510

Gly Arg Glu Ser Ile Ile Asn Pro Gly Thr Ala Met Ala Ser His Lys
        515                 520                 525

Asp Asp Lys Asp Lys Phe Phe Pro Met Ser Gly Val Met Ile Phe Gly
    530                 535                 540

Lys Glu Ser Ala Gly Ala Ser Asn Thr Ala Leu Asp Asn Val Met Ile
545                 550                 555                 560

Thr Asp Glu Glu Glu Ile Lys Ala Thr Asn Pro Val Ala Thr Glu Arg
                565                 570                 575

Phe Gly Thr Val Ala Val Asn Leu Gln Ser Ser Ser Thr Asp Pro Ala
            580                 585                 590
```

```
Thr Gly Asp Val His Val Met Gly Ala Leu Pro Gly Met Val Trp Gln
            595                 600                 605
Asp Arg Asp Val Tyr Leu Gln Gly Pro Ile Trp Ala Lys Ile Pro His
    610                 615                 620
Thr Asp Gly His Phe His Pro Ser Pro Leu Met Gly Gly Phe Gly Leu
625                 630                 635                 640
Lys Asn Pro Pro Gln Ile Leu Ile Lys Asn Thr Pro Val Pro Ala
                645                 650                 655
Asn Pro Pro Ala Glu Phe Ser Ala Thr Lys Phe Ala Ser Phe Ile Thr
                660                 665                 670
Gln Tyr Ser Thr Gly Gln Val Ser Val Glu Ile Glu Trp Glu Leu Gln
        675                 680                 685
Lys Glu Asn Ser Lys Arg Trp Asn Pro Glu Val Gln Tyr Thr Ser Asn
    690                 695                 700
Tyr Ala Lys Ser Ala Asn Val Asp Phe Thr Val Asp Asn Asn Gly Leu
705                 710                 715                 720
Tyr Thr Glu Pro Arg Pro Ile Gly Thr Arg Tyr Leu Thr
                725                 730

<210> SEQ ID NO 59
<211> LENGTH: 738
<212> TYPE: PRT
<213> ORGANISM: adeno-associated virus-2

<400> SEQUENCE: 59

Met Ala Ala Asp Gly Tyr Leu Pro Asp Trp Leu Glu Asp Thr Leu Ser
 1               5                  10                  15
Glu Gly Ile Arg Gln Trp Trp Lys Leu Lys Pro Gly Pro Pro Pro
                20                  25                  30
Lys Pro Ala Glu Arg His Lys Asp Asp Ser Arg Gly Leu Val Leu Pro
            35                  40                  45
Gly Tyr Lys Tyr Leu Gly Pro Phe Asn Gly Leu Asp Lys Gly Glu Pro
        50                  55                  60
Val Asn Glu Ala Asp Ala Ala Ala Leu Glu His Asp Lys Ala Tyr Asp
65                  70                  75                  80
Arg Gln Leu Asp Gly Asp Asn Pro Tyr Leu Lys Tyr Asn His Ala
                85                  90                  95
Asp Ala Glu Phe Gln Glu Arg Leu Lys Glu Asp Thr Ser Phe Gly Gly
                100                 105                 110
Asn Leu Gly Arg Ala Val Phe Gln Ala Lys Lys Arg Val Leu Glu Pro
            115                 120                 125
Leu Gly Leu Val Glu Glu Pro Val Lys Thr Ala Pro Gly Lys Lys Arg
        130                 135                 140
Pro Val Glu His Ser Pro Val Glu Pro Asp Ser Ser Gly Thr Gly
145                 150                 155                 160
Lys Ala Gly Gln Gln Pro Ala Arg Lys Arg Leu Asn Phe Gly Gln Thr
                165                 170                 175
Gly Asp Ala Asp Ser Val Pro Asp Pro Gln Pro Leu Gly Gln Pro Pro
                180                 185                 190
Ala Ala Pro Ser Gly Leu Gly Thr Asn Thr Met Ala Thr Gly Ser Gly
            195                 200                 205
Ala Pro Met Ala Asp Asn Asn Glu Gly Ala Asp Gly Val Gly Asn Ser
        210                 215                 220
Ser Gly Asn Trp His Cys Asp Ser Thr Trp Met Gly Asp Arg Val Ile
225                 230                 235                 240
```

```
Thr Thr Ser Thr Arg Thr Trp Ala Leu Pro Thr Tyr Asn Asn His Leu
            245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
            275                 280                 285

Cys His Phe Ser Pro Arg Asp Trp Gln Arg Leu Ile Asn Asn Asn Trp
            290                 295                 300

Gly Phe Arg Pro Lys Arg Leu Asn Phe Lys Leu Phe Asn Ile Gln Val
305                 310                 315                 320

Lys Glu Val Thr Gln Asn Asp Gly Thr Thr Ile Ala Asn Asn Leu
            325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
            355                 360                 365

Val Phe Met Val Pro Gln Tyr Gly Tyr Leu Thr Leu Asn Asn Gly Ser
            370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
            405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Ser Arg Thr
            435                 440                 445

Asn Thr Pro Ser Gly Thr Thr Thr Gln Ser Gly Leu Gln Phe Ser Gln
            450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
            485                 490                 495

Asn Ser Glu Tyr Ser Trp Thr Gly Ala Thr Lys Tyr His Leu Asn Gly
            500                 505                 510

Arg Asp Ser Leu Val Asn Pro Gly Pro Ala Met Ala Ser His Lys Asp
            515                 520                 525

Asp Glu Glu Lys Phe Phe Pro Gln Ser Gly Val Leu Ile Phe Gly Lys
            530                 535                 540

Gln Gly Ser Glu Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
            565                 570                 575

Gly Ser Val Ser Thr Asn Leu Gln Arg Gly Asn Arg Gln Ala Ala Thr
            580                 585                 590

Ala Asp Val Asn Thr Gln Gly Val Leu Pro Gly Met Val Trp Gln Asp
            595                 600                 605

Arg Asp Val Tyr Leu Gln Gly Pro Ile Trp Ala Lys Ile Pro His Thr
            610                 615                 620

Asp Gly His Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asn
            645                 650                 655
```

-continued

```
Pro Ser Thr Thr Phe Ser Ala Ala Lys Phe Ala Ser Phe Ile Thr Gln
            660             665             670

Tyr Ser Thr Gly Gln Val Ser Val Glu Ile Glu Trp Glu Leu Gln Lys
        675             680             685

Glu Asn Ser Lys Arg Trp Asn Pro Glu Ile Gln Tyr Thr Ser Asn Tyr
    690             695             700

Asn Lys Ser Val Asn Val Asp Phe Thr Val Asp Thr Asn Gly Val Tyr
705             710             715             720

Ser Glu Pro Arg Pro Ile Gly Thr Arg Tyr Leu Thr Arg Asn Leu Leu
            725             730             735

Arg Pro
```